(12) United States Patent
Zagar et al.

(10) Patent No.: US 6,175,007 B1
(45) Date of Patent: Jan. 16, 2001

(54) SUBSTITUTED AROMATIC PHOSHONIC ACID DERIVATIVES

(75) Inventors: Cyrill Zagar, Ludwigshafen; Elisabeth Heistracher, Mannheim; Olaf Menke, Altleiningen; Gerhard Hamprecht, Weinheim; Markus Menges, Mannheim; Peter Schäfer, Ottersheim; Karl-Otto Westphalen, Speyer; Ulf Misslitz, Neustadt; Helmut Walter, Obrigheim, all of (DE)

(73) Assignee: BASF Aktiengesellschaft, Ludwigshafen (DE)

( * ) Notice: Under 35 U.S.C. 154(b), the term of this patent shall be extended for 0 days.

(21) Appl. No.: 09/117,665

(22) PCT Filed: Feb. 17, 1997

(86) PCT No.: PCT/EP97/00733

§ 371 Date: Aug. 4, 1998

§ 102(e) Date: Aug. 4, 1998

(87) PCT Pub. No.: WO97/30060

PCT Pub. Date: Aug. 21, 1997

(30) Foreign Application Priority Data

Feb. 16, 1996 (DE) ................................. 196 05 765

(51) Int. Cl.$^7$ ..................... C07D 273/00; A01N 47/04
(52) U.S. Cl. .................. 544/242; 544/66; 504/243
(58) Field of Search .................. 544/66, 242; 504/243

(56) References Cited

U.S. PATENT DOCUMENTS 4,560,752 * 12/1985 Lee ............................................ 544/66
5,356,863 * 10/1994 Satow et al. ........................... 504/243

OTHER PUBLICATIONS

Juzo et al., Chem Abs., 115:207989$^r$, 1991.

* cited by examiner

Primary Examiner—Mukund J. Shah
Assistant Examiner—Pavanaram K Sripada
(74) Attorney, Agent, or Firm—Keil & Weinkauf

(57) ABSTRACT

Phosphonic acid compounds I

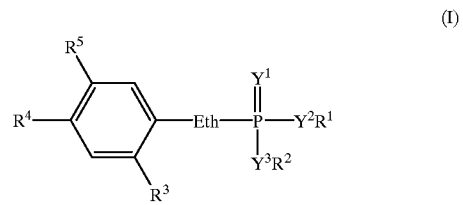

wherein
Eth is optionally substituted 1,2-ethynediyl, ethanediyl or ethene-1,2-diyl;
$Y^1$ is oxygen or sulfur;
$Y^2$ is oxygen, sulfur or —N($R^6$)—;
$Y^3$ is oxygen, sulfur or —N($R^7$)—;
$R^1$, $R^2$, $R^6$ and $R^7$ are hydrogen or
  optionally substituted alkyl, alkenyl, alkynyl, cycloalkyl, phenyl or heterocyclyl, or
$R^1$ and $R^2$, $R^1$ and $R^6$, $R^2$ and $R^7$ together are optionally substituted 1,2-ethanediyl, 1,3-propylene, tetramethylene, pentamethylene or ethyleneoxyethylene, or
$R^1$ and $R^2$ together are optionally substituted 1,2-phenylene;
$R^3$ is cyano, halogen, alkyl, haloalkyl, alkoxy or haloalkoxy;
$R^4$ is hydrogen or halogen, and
$R^5$ is a heterocycle $\Phi^1$ to $\Phi^{22}$ as defined in the specification, their manufacture and intermediates therefore. The phosphonic acid compounds are effective against unwanted plants and act as desiccants and defoliants.

24 Claims, No Drawings

SUBSTITUTED AROMATIC PHOSHONIC ACID DERIVATIVES

This application is a 371 of PCT/EP97/00733 filed on Feb. 17, 1997.

The present invention relates to novel substituted aromatic phosphonic acid derivatives of the formula I

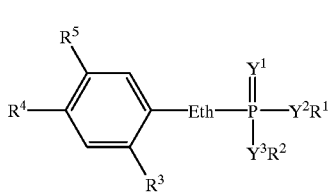

where the variables have the following meanings:

Eth is 1,2-ethynediyl or an ethane- or ethene-1,2-diyl chain, each of which can be unsubstituted or have attached to it one or two of the following substituents: halogen, cyano, carboxyl, $C_1$–$C_4$-alkyl, $C_1$–$C_4$-haloalkyl, $C_1$–$C_4$-alkoxy, $C_1$–$C_4$-haloalkoxy, ($C_1$–$C_4$-alkoxy)carbonyl and/or di($C_1$–$C_4$-alkyl)amino, it being possible for the ethane-1, 2-diyl chain, if desired, additionally to have attached to it a hydroxyl, amino or $C_1$–$C_4$-alkylamino group;

$Y^1$ is oxygen or sulfur;

$Y^2$ is oxygen, sulfur or —N($R^6$)—;

$Y^3$ is oxygen, sulfur or —N($R^7$)—;

$R^1$, $R^2$, $R^6$ and $R^7$ independently of one another are hydrogen, $C_1$–$C_6$-alkyl, $C_1$–$C_6$-haloalkyl, hydroxy-$C_1$–$C_4$-alkyl, cyano-$C_1$–$C_4$-alkyl, $C_1$–$C_4$-alkoxy-$C_1$–$C_4$-alkyl, $C_1$–$C_4$-haloalkoxy-$C_1$–$C_4$-alkyl, $C_3$–$C_4$-alkenyloxy-$C_1$–$C_4$-alkyl, $C_3$–$C_4$-alkynyloxy-$C_1$–$C_4$-alkyl, $C_3$–$C_8$-cycloalkoxy-$C_1$–$C_4$-alkyl, amino-$C_1$–$C_4$-alkyl, $C_1$–$C_4$-alkylamino-$C_1$–$C_4$-alkyl, di($C_1$–$C_4$-alkyl)amino-$C_1$–$C_4$-alkyl, $C_1$–$C_4$-alkylthio-$C_1$–$C_4$-alkyl, $C_1$–$C_4$-haloalkylthio-$C_1$–$C_4$-alkyl, $C_3$–$C_4$-alkenylthio-$C_1$–$C_4$-alkyl, $C_3$–$C_4$-alkynylthio-$C_1$–$C_4$-alkyl, $C_1$–$C_4$-alkylsulfinyl-$C_1$–$C_4$-alkyl, $C_1$–$C_4$-haloalkylsulfinyl-$C_1$–$C_4$-alkyl, $C_3$–$C_4$-alkenylsulfinyl-$C_1$–$C_4$-alkyl, $C_3$–$C_4$-alkynyl-sulfinyl-$C_1$–$C_4$-alkyl, $C_1$–$C_4$-alkylsulfonyl-$C_1$–$C_4$-alkyl, $C_1$–$C_4$-haloalkylsulfonyl-$C_1$–$C_4$-alkyl, $C_3$–$C_4$-alkenylsulfonyl-$C_1$–$C_4$-alkyl, $C_3$–$C_4$-alkynylsulfonyl-$C_1$–$C_4$-alkyl, $C_3$–$C_6$-alkenyl, $C_3$–$C_6$-haloalkenyl, cyano-$C_3$–$C_6$-alkenyl, $C_3$–$C_6$-alkynyl, $C_3$–$C_6$-haloalkynyl, cyano-$C_3$–$C_6$-alkynyl, hydroxycarbonyl-$C_1$–$C_4$-alkyl, ($C_1$–$C_4$-alkoxy)carbonyl-$C_1$–$C_4$-alkyl, ($C_1$–$C_4$-alkyl-thio)carbonyl-$C_1$–$C_4$-alkyl, aminocarbonyl-$C_1$–$C_4$-alkyl, ($C_1$–$C_4$-alkyl)aminocarbonyl-$C_1$–$C_4$-alkyl, di($C_1$–$C_4$-alkyl)amino-carbonyl-$C_1$–$C_4$-alkyl, $C_3$–$C_8$-cycloalkyl, $C_3$–$C_8$-cycloalkyl-$C_1$–$C_4$-alkyl, phenyl, phenyl-$C_1$–$C_4$-alkyl or 3- to 7-membered heterocyclyl or heterocyclyl-$C_1$–$C_4$-alkyl, it being possible for all heterocycles, if desired, to contain a carbonyl or thiocarbonyl ring member, and it being possible for all cycloalkyl, phenyl and heterocyclyl rings to be unsubstituted or to have attached to them one to four substituents, in each case selected from the group consisting of halogen, cyano, nitro, amino, hydroxyl, carboxyl, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfonyl, $C_1$–$C_4$-haloalkylsulfonyl, ($C_1$–$C_4$-alkyl)carbonyl, ($C_1$–$C_4$-haloalkyl)carbonyl, ($C_1$–$C_4$-alkoxy)carbonyl, ($C_1$–$C_4$-alkyl)carbonyloxy, ($C_1$–$C_4$-haloalkyl)carbonyloxy and di($C_1$–$C_4$-alkyl)amino, or $R^1$ and $R^2$ or $R^1$ and $R^6$ and/or $R^2$ and $R^7$ in each case together form a 1,2-ethanediyl, 1,3-propylene, tetramethylene, pentamethylene or ethyleneoxyethylene chain which, if desired, can be substituted by one to four $C_1$–$C_4$-alkyl and/or one or two ($C_1$–$C_4$-alkoxy)carbonyl groups, or $R^1$ and $R^2$ together are 1,2-phenylene which can be unsubstituted or have attached to it one to three substituents, in each case selected from the group consisting of cyano, nitro, halogen, $C_1$–$C_4$-alkyl, $C_1$–$C_4$-haloalkyl, $C_1$–$C_4$-alkoxy and $C_1$–$C_4$-haloalkoxy;

$R^3$ is cyano, halogen, $C_1$–$C_4$-alkyl, $C_1$–$C_4$-haloalkyl, $C_1$–$C_4$-alkoxy or $C_1$–$C_4$-haloalkoxy;

$R^4$ is hydrogen or halogen;

$R^5$ is one of the following heterocycles $\Phi^1$ to $\Phi^{20}$:

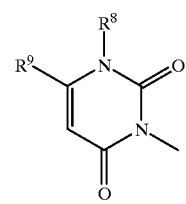

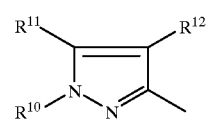

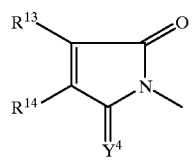

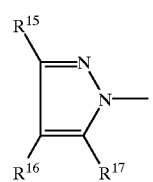

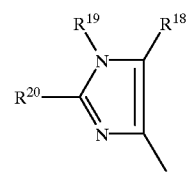

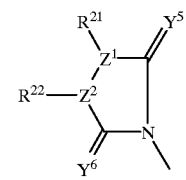

-continued
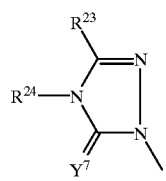
Φ⁷
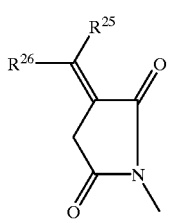
Φ⁸
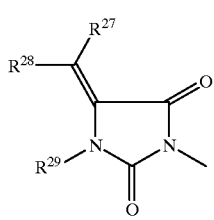
Φ⁹
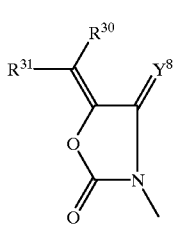
Φ¹⁰
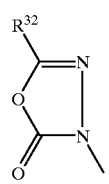
Φ¹¹
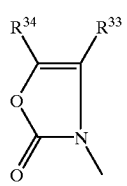
Φ¹²
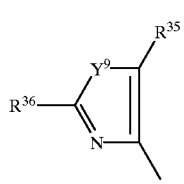
Φ¹³
-continued
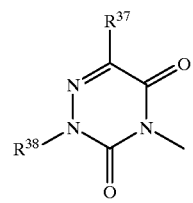
Φ¹⁴
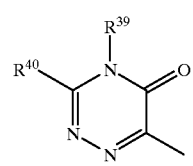
Φ¹⁵
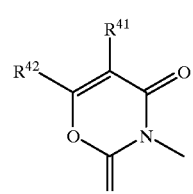
Φ¹⁶
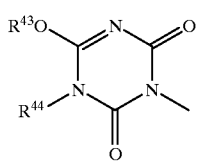
Φ¹⁷
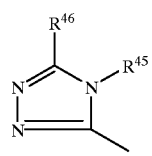
Φ¹⁸
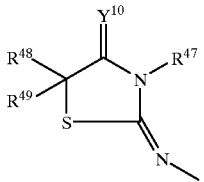
Φ¹⁹
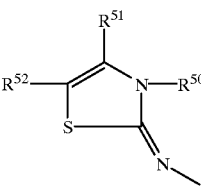
Φ²⁰
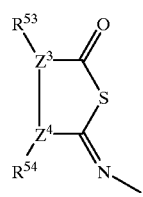
Φ²¹

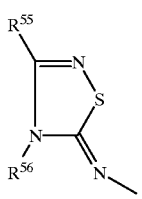

where
R$^8$ is hydrogen, amino, C$_1$–C$_4$-alkyl or C$_1$–C$_4$-haloalkyl;
R$^9$ is cyano, C$_1$–C$_4$-alkyl, C$_1$–C$_4$-haloalkyl, C$_1$–C$_4$-alkylsulfonyl or C$_1$–C$_4$-haloalkylsulfonyl;
R$^{10}$ is C$_1$–C$_4$-alkyl or C$_1$–C$_4$-haloalkyl;
R$^{11}$ is cyano, C$_1$–C$_4$-alkyl, C$_1$–C$_4$-haloalkyl, C$_1$–C$_4$-alkoxy, C$_1$–C$_4$-haloalkoxy, C$_1$–C$_4$-alkylthio, C$_1$–C$_4$-haloalkylthio, C$_1$–C$_4$-alkylsulfinyl, C$_1$–C$_4$-haloalkylsulfinyl, C$_1$–C$_4$-alkylsulfonyl or C$_1$–C$_4$-haloalkylsulfonyl, or
R$^{10}$ and R$^{11}$ together with the ring atoms linking them are a 5- to 7-membered heterocycle which has one or two hetero atoms and which can be unsubstituted or have attached to it one or two C$_1$–C$_4$-alkyl radicals;
R$^{12}$ is hydrogen, cyano, halogen, C$_1$–C$_4$-alkyl or C$_1$–C$_4$-haloalkyl;
Y$^4$ is oxygen, sulfur or methylene;
R$^{13}$, R$^{14}$, R$^{25}$, R$^{26}$, R$^{27}$, R$^{28}$, R$^{30}$ and R$^{31}$ independently of one another are hydrogen or C$_1$–C$_4$-alkyl, or
R$^{13}$ and R$^{14}$ together with the ring atoms linking them are a 5- to 7-membered carbo- or heterocyclic ring, it being possible for the ring, if desired, additionally to have attached to it one or two halogen and/or C$_1$–C$_4$-alkyl radicals or a further, fused 3- to 6-membered carbo- or heterocyclic ring;
R$^{15}$ and R$^{16}$ independently of one another are hydrogen, halogen, C$_1$–C$_4$-alkyl or C$_1$–C$_4$-haloalkyl, or
R$^{15}$ and R$^{16}$ together with the ring atoms linking them are a 5- to 7-membered carbo- or heterocyclic ring which, if desired, can additionally have attached to it one or two C$_1$–C$_4$-alkyl radicals;
R$^{17}$ is halogen or C$_1$–C$_4$-alkyl;
R$^{18}$, R$^{33}$ and R$^{35}$ independently of one another are halogen;
R$^{19}$, R$^{20}$, R$^{29}$, R$^{37}$, R$^{38}$, R$^{39}$, R$^{40}$, R$^{41}$, R$^{42}$, R$^{44}$, R$^{55}$ and R$^{57}$ independently of one another are hydrogen, C$_1$–C$_4$-alkyl or C$_1$–C$_4$-halo-alkyl, or
R$^{19}$ and R$^{20}$ and/or R$^{39}$ and R$^{40}$ and/or R$^{41}$ and R$^{42}$ and/or R$^{55}$ and R$^{56}$ together with the ring atoms linking them are a 5- to 7-membered ring which, if desired, can additionally have attached to it one or two C$_1$–C$_4$-alkyl or C$_1$–C$_4$-haloalkyl radicals;
Y$^5$, Y$^6$, Y$^7$, Y$^9$ and Y$^{10}$ independently of one another are oxygen or sulfur;
Z$^1$, Z$^2$, Z$^3$ and Z$^4$ independently of one another are nitrogen or CH;
R$^{21}$ and R$^{22}$ and/or R$^{23}$ and R$^{24}$ and/or R$^{53}$ and R$^{54}$ together with the ring atoms linking them are a 5- to 7-membered ring which, if desired, can additionally have attached to it one or two C$_1$–C$_4$-alkyl radicals;
R$^{32}$, R$^{34}$, R$^{48}$, R$^{49}$ and R$^{52}$ independently of one another are hydrogen, C$_1$–C$_4$-alkyl, C$_3$–C$_6$-cycloalkyl or C$_1$–C$_4$-haloalkyl;
Y$^8$ is oxygen or =NH;
R$^{36}$ is hydrogen, C$_1$–C$_4$-alkyl, C$_1$–C$_4$-haloalkyl or C$_1$–C$_4$-haloalkoxy;
R$^{43}$ is C$_1$–C$_4$-alkyl; and
R$^{45}$, R$^{46}$, R$^{47}$, R$^{50}$ and R$^{51}$ independently of one another are C$_1$–C$_4$-alkyl, C$_1$–C$_4$-haloalkyl or C$_3$–C$_6$-cycloalkyl, and the agriculturally useful salts of the compounds I,
with the exception of those compounds I where R$^4$ is hydrogen and R$^5$ is Φ$^2$.

Furthermore, the invention relates to
the use of the compounds I as herbicides or for the desiccation/defoliation of plants,
herbicidal compositions and compositions for the desiccation/defoliation of plants which comprise the compounds I as active substances,
processes for the preparation of the compounds I and of herbicidal compositions and compositions for the desiccation/defoliation of plants using the compounds I,
methods of controlling undesirable vegetation and of desiccating/defoliating plants using the compounds I,
intermediates of the formulae XXVIII, XXXI, XXXII, XXXIIIa, XXXV and XL and processes for their preparation.

The herbicidal activity of diethyl 1-chloro-2-[2,4-dichloro-5-(4-difluoromethyl-4,5-dihydro-3-methyl-5-oxo-1H-1,2,4-triazol-1-yl)phenyl]ethylphosphonate has already been mentioned by G. Theodoridis, J. T. Bahr, B. L. Davidson, S. E. Hart, F. W. Hotzman, K. M. Poss & S. F. Tutt in ACS Symp. Ser. 584, 90 (1995).

JP 03/151 367 describes 3-phenylpyrazoles of the formula

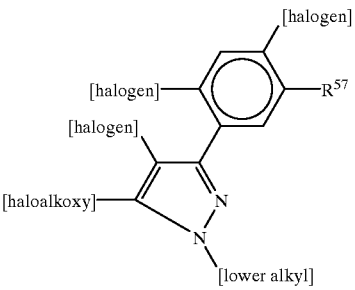

where R$^{57}$ is, inter alia, dialkoxyphosphinylalkyl as being herbicides.

WO 95/32188 furthermore discloses herbicidally active 3-phenylpyrazoles of the formula

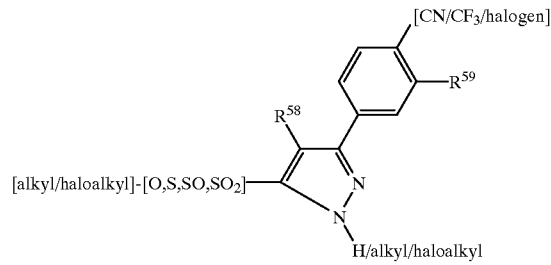

where the alkyl/haloalkyl substituents are in each case C$_1$–C$_4$ and
R$^{58}$ is hydrogen, nitro, halogen, carboxyl or an ester or acid amide radical and
R$^{59}$ is —CH$_2$—CH$_2$—P(O)(OR$^{60}$)$_2$ or —CH=CH—P(O)(OR$^{60}$)$_2$ where R$^{60}$=hydrogen or a specific organic radical.

Phenyluracils of the general formula

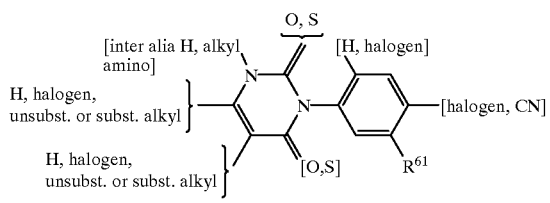

where the radical $R^{61}$ is, inter alia, dialkoxy(thio)phosphoryl which is linked to the aromatic directly or via a chain, come under the general formulae of uracils which
together with other herbicides are suitable for the selective control of weeds in rice growing (according to DE-A 44 37 197);
are suitable for the semi- and non-selective control of weeds (according to DE-A 44 32 888);
together with certain other herbicides show a synergistic herbicidal activity (according to DE-A 44 31 219).

U.S. Pat. No. 5,434,288 teaches certain benzene derivatives as phospholipase A2 inhibitors. Given a suitable choice of substituents, some of the present compounds I formally also come under the broad definition of these compounds.

Moreover, given a suitable choice of substituents, some compounds of the formula I formally come under the general formulae of
supported catalysts for the preparation of acetic acid which are described in DE-A 41 21 959;
antithrombic, antiaggregatory and tumor-inhibitory active ingredients which are described in EP-A 537 696 and in DE-A 41 24 942;
active ingredients described in FR-A 2 729 142 as antiarrhythmic substances;
intermediates mentioned in EP-A 421 436 for the preparation of certain NMDA receptor inhibitors.

Furthermore, EP-A 426 112 describes photographic silver halide materials which comprise organic phosphorus compounds. These compounds, which are very broadly defined, formally also encompass some of the present aromatic phosphonic acid derivatives when the substituents are chosen appropriately.

Since the herbicidal properties of the abovementioned herbicides are not always entirely satisfactory with regard to the harmful plants, it is an object of the present invention to provide novel herbicidally active compounds with which undesirable plants can be controlled specifically better than this was possible to date. The object also extends to providing novel compounds which act as desiccants/defoliants.

We have found that this object is achieved by the present substituted aromatic phosphonic acid derivatives of the formula I and by their herbicidal activity.

We have furthermore found herbicidal compositions which comprise the compounds I and which have a very good herbicidal activity. Moreover, we have found processes for preparing these compositions and method of controlling undesirable vegetation using the compounds I.

Furthermore, it has been found that the compounds I are also suitable for the desiccation/defoliation of parts of plants, suitable examples being crop plants such as cotton, potatoes, oilseed rape, sunflowers, soybeans or field beans, in particular cotton. Accordingly, we have found compositions for the desiccation and/or defoliation of plants, processes for the preparation of these compositions, and methods of desiccating and/or defoliating plants using the compounds I.

Depending on the substitution pattern, the compounds of the formula I can contain one or more chiral centers, in which case they exist as enantiomer or diastereomer mixtures. E/Z isomers are also possible depending on the meaning of Eth. The invention relates to the pure enantiomers or the diastereomers and also to mixtures of these.

Agriculturally useful salts are to be understood as meaning mainly the salts of I with those cations and acid addition salts of I with those acids which do not adversely affect the herbicidal or desiccant/defoliant activity of I.

Thus, suitable cations are, in particular, the ions of the alkali metals, preferably sodium and potassium, of the alkaline earth metals, preferably calcium, magnesium and barium, and of the transition metals, preferably manganese, copper, zinc and iron, and the ammonium ion which may have attached to it a $C_1$–$C_4$-alkyl, phenyl or benzyl substituent and, if desired, additionally one to three further $C_1$–$C_4$-alkyl radicals, preferably diisopropylammonium, tetramethylammonium, tetrabutylammonium, trimethylbenzylammonium, furthermore phosphonium ions, preferably tri($C_1$–$C_4$-alkyl)-phosphonium, sulfonium ions, preferably tri($C_1$–$C_4$-alkyl)-sulfonium, and sulfoxonium ions, preferably tri($C_1$–$C_4$-alkyl)-sulfoxonium.

Anions of useful acid addition salts are mainly fluoride, chloride, bromide, hydrogen sulfate, sulfate, dihydrogen phosphate, hydrogen phosphate, phosphate, nitrate, hydrogen carbonate, carbonate, hexafluorosilicate, hexafluorophosphate, benzoate, oxalate, dodecylbenzenesulfonate, and the anions of $C_1$–$C_4$-alkanoic acids, preferably formate, acetate, propionate and butyrate.

The organic moieties given for the substituents $R^1$ to $R^3$, $R^6$ to $R^{17}$, $R^{19}$, $R^{20}$, $R^{25}$ to $R^{32}$, $R^{34}$, $R^{36}$ to $R^{52}$, $R^{55}$ and $R^{56}$ or as radicals on cycloalkyl, phenyl or heterocyclyl rings or on ethylene, ethene-1,2-diyl, 1,3-propylene, tetramethylene, pentamethylene or ethyleneoxy ethylene chains are collective terms for individual enumerations of every single group member. All carbon chains, i.e. all alkyl, haloalkyl, hydroxyalkyl, cyanoalkyl, aminoalkyl, hydroxycarbonylalkyl, aminocarbonylalkyl, alkoxy, haloalkoxy, alkylthio, haloalkylthio, alkylsulfinyl, halosulfinyl, alkylsulfonyl, haloalkylsulfonyl, alkylamino, dialkylamino, alkenyl, haloalkenyl, cyanoalkenyl, alkenyloxy, alkenylthio, alkenylsulfinyl, alkenylsulfonyl, alkynyl, haloalkynyl, cyanoalkynyl, alkynyloxy, alkynylthio, alkynylsulfinyl and alkynylsulfonyl moieties, can be straight-chain or branched. Halogenated substituents preferably have attached to them one to five identical or different halogen atoms.

The meaning halogen is in each case fluorine, bromine, chlorine or iodine, in particular fluorine or chlorine.

Other examples of meanings are:
$C_1$–$C_4$-alkyl is: methyl, ethyl, n-propyl, 1-methylethyl, n-butyl, 1-methylpropyl, 2-methylpropyl or 1,1-dimethylethyl, in particular methyl or ethyl;
$C_1$–$C_4$-haloalkyl is: a $C_1$–$C_4$-alkyl radical as mentioned above which is partially or fully substituted by fluorine, chlorine, bromine and/or iodine, i.e. chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fdluoroethyl, 2-chloro-2,2-difluoroethyl, 2,2-dichloro-2-fluoroethyl, 2,2, 2-trichloroethyl, pentafluoroethylp 2-fluoropropyl, 3-fluoropropyl, 2,2-difluoropropyl, 2,3-difluoropropyl, 2-chloropropyl, 3-choropropyl, 2,3-dichioropropyl, 2-bromopropyl, 3-bromopropyl, 3,3l3-trifluoropropyl, 3,3,23-trichloropropyl, 2,2,3,3,13- pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl, in particular chloromethyl, fluoromethyl, difluoromethyl, trifluoromethyl, 2-fluoroethyl, 2-chloroethyl or 2,2,2-trifluoroethyl;

$C_1$–$C_6$-alkyl is: $C_1$–$C_4$-alkyl as mentioned above, and also, for example, n-pentyl, 1-methylbutyl, 2-methylbutyl, 3-methylbutyl, 2,2-dimethyapropyl, 1-ethylpropyl, n-hexyl, 1,1-dimethyipropyl, 1, 2-dimethylpropyl, 1-m ethylpentyl, 2-methylpentyl, 3-methyl pentyl, 4-methyl pentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethyipropyl, 1,2,2-trimethyipropyl, 1-ethyl-1-methylpropyl or 1-ethyl-2-methylpropyl, in particular methyl, ethyl, n-propyl, 1-methylethyl, n-butyl, 1,1-dimethylethyl, n-pentyl or n-hexyl;

$C_1$–$C_6$-haloalkyl is: a $C_2$–$C_6$-alkyl radical as mentioned above which is partially or fully substituted by fluorine, chlorine, bromine and/or iodine, i.e. one of the radicals mentioned under $C_1$–$C_4$-haloalkyl, or 5-fluoro-1-pentyl, 5-chloro-1 -pentyl, 5-bromo-4-pentyl, 5-iodo-1-pentyl, 5,5, 5-trichloro-1-pentyl, undecafluoropentyl, 6-fluoro-1-hexyl, 6-chloro-1-hexyl, 6-bromo-1-hexyl, 6-iodo-1-hexyl, 6,6,6-trichloro-1-hexyl or dodecafluorohexyl, in particular chloromethyl, fluoromethyl, difluoromethyl, trifluoromethyl, 2-fluoroethyl, 2-chloroethyl or 2,2,2-trifluoroethyl;

hydroxy-$C_1$–$C_4$-alkyl is: e.g. hydroxymethyl, 2-hydroxyeth-1-yl, 2-hydroxyprop-1-yl, 3-hydroxyprop-1-yl, 1-hydroxyprop-2-yl, 2-hydroxybut-1-yl, 3-hydroxybut-1-yl, 4-hydroxybut-1-yl, 1-hydroxybut-2-yl, 1-hydroxybut-3-yl, 2-hydroxybut-3-yl, 1-hydroxy-2-methylprop-3-yl, 2-hydroxy-2-methylprop-3-yl or 2-hydroxymethylprop-2-yl, in particular 2-hydroxyethyl;

cyano-$C_1$–$C_4$-alkyl is: cyanomethyl, 1-cyanoeth-1-yl, 2-cyanoeth-1-yl, 1-cyanoprop-1-yl, 2-cyanoprop-1-yl, 3-cyanoprop-1-yl, 1-cyanoprop-2-yl, 2-cyanoprop-2-yl, 1-cyanobut- 1-yl, 2-cyanobut-1-yl, 3-cyanobut-1-yl, 4-cyanobut-1-yl, 1-cyanobut-2-yl, 2-cyanobut-2-yl, 1-cyanobut-3-yl, 2-cyanobut-3-yl, 1-cyano-2-methylprop-3-yl, 2-cyano-2-methylprop-3-yl, 3-cyano-2-methylprop-3-yl or 2-cyanomethylprop-2-yl, in particular cyanomethyl or 2-cyanoethyl;

amino-$C_1$–$C_4$-alkyl is: e.g. aminomethyl, 2-aminoethyl, 2-aminoprop-1-yl, 3-aminoprop-1-yl, 2-aminobut-1-yl, 3-aminobut-1-yl, 4-aminobut-1-yl, 1-aminobut-2-yl, 3-aminobut-2-yl, 4-aminobut-2-yl, 1-(aminomethyl)eth-1-yl, 1-(aminomethyl)-1-(methyl)eth-1-yl or 1-(aminomethyl)prop-1-yl, in particular aminomethyl or 2-aminoethyl;

hydroxycarbonyl-$C_1$–$C_4$-alkyl is: hydroxycarbonylmethyl, 1-(hydroxycarbonyl)ethyl, 2-(hydroxycarbonyl)ethyl, 1-(hydroxycarbonyl)prop-1-yl, 2-(hydroxycarbonyl) prop-1-yl, 3-(hydroxycarbonyl)prop-1-yl, 1-(hydroxycarbonyl)but-1-yl, 2-(hydroxycarbonyl)but-1-yl, 3-(hydroxycarbonyl)but-1-yl, 4-(hydroxycarbonyl) but-1-yl, 1-(hydroxycarbonyl)but-2-yl, 2-(hydroxycarbonyl)but-2-yl, 3-(hydroxycarbonyl)but-2-yl, 4-(hydroxycarbonyl)but-2-yl, 1-(hydroxycarbonylmethyl)eth-1-yl, 1-(hydroxycarbonylmethyl)-1-(methyl)eth-1-yl or 1-(hydroxycarbonylmethyl)prop-1-yl, in particular hydroxycarbonylmethyl or 2-(hydroxycarbonyl)ethyl;

aminocarbonyl-$C_1$–$C_4$-alkyl is: aminocarbonylmethyl, 1-(aminocarbonyl)ethyl, 2-(aminocarbonyl)ethyl, 1-(aminocarbonyl)prop-1-yl, 2-(aminocarbonyl)prop-1-yl, 3-(aminocarbonyl)prop-1-yl, 1-(aminocarbonyl)but-1-yl, 2-(aminocarbonyl)but-1-yl, 3-(aminocarbonyl)but-1-yl, 4-(aminocarbonyl)but-1-yl, 1-(aminocarbonyl)but-2-yl, 2-(aminocarbonyl)but-2-yl, 3-(aminocarbonyl)but-2-yl, 4-(aminocarbonyl)but-2-yl, 1-(aminocarbonylmethyl) eth-1-yl, 1-(aminocarbonylmethyl)-1-(methyl)eth-1-yl or 1-(aminocarbonylmethyl)prop-1-yl, in particular aminocarbonylmethyl or 2-(aminocarbonyl)ethyl;

phenyl-$C_1$–$C_4$-alkyl is: benzyl, 1-phenylethyl, 2-phenylethyl, 1-phenylprop-1-yl, 2-phenylprop-1-yl, 3-phenylprop-1-yl, 1-phenylbut-1-yl, 2-phenylbut-1-yl, 3-phenylbut-1-yl, 4-phenylbut-1-yl, 1-phenylbut-2-yl, 2-phenylbut-2-yl, 3-phenylbut-2-yl, 4-phenylbut-2-yl, 1-(phenylmethyl)eth-1-yl, 1-(phenylmethyl)-1-(methyl) eth-1-yl or 1-(phenylmethyl)prop-1-yl, in particular benzyl or 2-phenylethyl;

heterocyclyl-$C_1$–$C_4$-alkyl is: heterocyclylmethyl, 1-heterocyclylethyl, 2-heterocyclylethyl, 1-heterocyclylprop-1-yl, 2-heterocyclylprop-1-yl, 3-heterocyclylprop-1-yl, 1-heterocyclylbut-1-yl, 2-heterocyclylbut-1-yl, 4-heterocyclylbut-1-yl, 1-heterocyclylbut-2-yl, 2-heterocyclylbut-2-yl, 3-heterocyclylbut-2-yl, 3-heterocyclylbut-2-yl, 4-heterocyclylbut-2-yl, 1-(heterocyclyl-methyl)eth-1-yl, 1-(heterocyclylmethyl)-1-(methyl)eth-1-yl or 1-(heterocyclylmethyl)-prop-1-yl, in particular heterocyclylmethyl or 2-heterocyclylethyl or 3-heterocyclylpropyl; in particular 3-oxetanylmethyl, 2-(1,3-oxazolin-2-on-3-yl)ethyl and 3-(2-pyridyl)propyl are especially preferred;

($C_1$–$C_4$-alkyl)carbonyl is: CO—$CH_3$, CO—$C_2H_5$, n-propylcarbonyl, CO—$CH(CH_3)_2$, n-butylcarbonyl, 1-methylpropylcarbonyl, 2-methylpropylcarbonyl or CO—$C(CH_3)_3$, in particular CO—$CH_3$;

($C_1$–$C_4$-haloalkyl)carbonyl is: a ($C_1$–$C_4$-alkyl)carbonyl radical as mentioned above which is partially or fully substituted by fluorine, chlorine, bromine and/or iodine, i.e. chloroacetyl, dichloroacetyl, trichloroacetyl, fluoroacetyl, difluoroacetyl, CO—$CF_3$, chlorofluoroacetyl, dichlorofluoroacetyl, chlorodifluoroacetyl, 2-fluoroethylcarbonyl, 2-chloroethylcarbonyl, 2-bromoethylcarbonyl, 2-iodoethylcarbonyl, 2,2-difluoroethylcarbonyl, 2,2,2-trifluoroethylcarbonyl, 2-chloro-2-fluoroethylcarbonyl, 2-chloro-2,2-difluoroethylcarbonyl, 2,2-dichloro-2-fluoroethylcarbonyl, 2,2,2-trichloroethylcarbonyl, pentafluoroethylcarbonyl, 2-fluoropropylcarbonyl, 3-fluoropropylcarbonyl, 2,2-difluoropropylcarbonyl, 2,3-difluoropropylcarbonyl, 2-chloropropylcarbonyl, 3-chloropropylcarbonyl, 2,3-dichloropropylcarbonyl, 2-bromopropylcarbonyl, 3-bromopropylcarbonyl, 3,3,3-trifluoropropylcarbonyl, 3,3,3-trichloropropylcarbonyl, 2,2,3,3,3-pentafluoropropylcarbonyl, heptafluoropropylcarbonyl, 1-(fluoromethyl)-2-fluoroethylcarbonyl, 1-(chloromethyl)-2-chloroethylcarbonyl, 1-(bromomethyl)-2-bromoethylcarbonyl, 4-fluorobutylcarbonyl, 4-chlorobutylcarbonyl, 4-bromobutylcarbonyl or nonafluorobutylcarbonyl, in particular CO—$CF_3$;

($C_1$–$C_4$-alkyl)carbonyloxy is: acetyloxy, ethylcarbonyloxy, n-propylcarbonyloxy, 1-methylethylcarbonyloxy, n-butylcarbonyloxy, 1-methylpropylcarbonyloxy, 2-methylpropylcarbonyloxy or 1,1-dimethylethylcarbonyloxy, in particular acetyloxy;

($C_1$–$C_4$-haloalkyl)carbonyloxy is: a ($C_1$–$C_4$-alkyl) carbonyloxy radical as mentioned above which is partially or fully substituted by fluorine, chlorine, bromine and/or iodine, e.g. chloroacetyloxy, dichloroacetyloxy, trichloroacetyloxy, fluoroacetyloxy, difluoroacetyloxy, trifluoroacetyloxy, chlorofluoroacetyloxy, dichlorofluoroacetyloxy, chlorodifluoroacetyloxy, 2-fluoroethylcarbonyloxy, 2-chloroethylcarbonyloxy, 2-bromoethylcarbonyloxy, 2-iodoethylcarbonyloxy, 2,2-difluoroethylcarbonyloxy, 2,2,2-trifluoroethylcarbonyloxy, 2-chloro-2-fluoroethylcarbonyloxy, 2-chloro-2,2-difluoroethylcarbonyloxy, 2,2-dichloro-2-fluoroethylcarbonyloxy, 2,2,2-trichloroethylcarbonyloxy, pentafluoroethylcarbonyloxy, 2-fluoropropylcarbonyloxy, 3-fluoropropylcarbonyloxy, 2,2-difluoropropylcarbonyloxy, 2,3-difluoropropylcarbonyloxy, 2-chloro-1S propylcarbonyloxy, 3-chloropropylcarbonyloxy, 2,3-dichloropropylcarbonyloxy, 2-bromopropylcarbonyloxy, 3-bromopropylcarbonyloxy, 3,3,3-trifluoropropylcarbonyloxy, 3,3,3-trichloropropylcarbonyloxy, 2,2,3,3,3-pentafluoropropylcarbonyloxy, heptafluoropropylcarbonyloxy, 1-(fluoromethyl)-2-fluoroethylcarbonyloxy, 1-(chloromethyl)-2-chloroethylcarbonyloxy, 1-(bromomethyl)-2-bromoethylcarbonyloxy, 4-fluorobutylcarbonyloxy, 4-chlorobutylcarbonyloxy, 4-bromobutyl or nonafluorobutyl, in particular trifluoroacetoxy;

$C_1$–$C_4$-alkoxy is: methoxy, ethoxy, n-propoxy, 1-methylethoxy, n-butoxy, 1-methylpropoxy, 2-methylpropoxy or 1,1-dimethylethoxy, in particular methoxy or ethoxy;

$C_1$–$C_4$-haloalkoxy is: a $C_1$–$C_4$-alkoxy radical as mentioned above which is partially or fully substituted by fluorine, chlorine, bromine and/or iodine, e.g. chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy or nonafluorobutoxy, in particular 2-chloroethoxy or 2,2,2-trifluoroethoxy;

($C_1$–$C_4$-alkoxy)carbonyl is: CO—OCH$_3$, CO—OC$_2$H$_5$, n-propoxycarbonyl, CO—OCH(CH$_3$) 2, n-butoxycarbonyl, 1-methylpropoxycarbonyl, CO—OCH$_2$—CH(CH$_3$)$_2$ or CO—OC(CH$_3$)$_3$, in particular CO—OCH$_3$ or CO—OC$_2$H$_5$;

$C_1$–$C_6$-alkylthio is: SCH$_3$, SC$_2$HS, n-propylthio, SCH(CH$_3$)$_2$, n-butylthio, 1-methylpropylthio, 2-methylpropylthio or SC(CH$_3$)$_3$, in particular SCH$_3$ or SC$_2$H$_5$;

$C_1$–$C_4$-alkylamino is: methylamino, ethylamino, n-propylamino, 1-methylethylamino, n-butylamino, 1-methylpropylamino, 2-methylpropylamino or 1,1-dimethylethylamino, in particular methylamino or ethylamino;

di($C_1$–$C_4$-alkyl)amino is: N,N-dimethylamino, N,N-diethylamino, N,N-dipropylamino, N,N-di(1-methylethyl)amino, N,N-dibutylamino, N,N-di(1-methylpropyl)amino, N,N-di(2-methylpropyl)amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino or N-(1,1-dimethylethyl)-N-(2-methylpropyl)amino, in particular N,N-dimethylamino or N,N-diethylamino;

$C_1$–$C_4$-alkoxy-$C_1$–$C_4$-alkyl is: $C_1$–$C_4$-alkyl substituted by $C_1$–$C_4$-alkoxy as mentioned above, e.g. methoxymethyl, ethoxymethyl, n-propoxymethyl, (1-methylethoxy)methyl, n-butoxymethyl, (1-methylpropoxy)methyl, (2-methylpropoxy)methyl, (1,1-dimethylethoxy)methyl, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl or 4-(1,1-dimethylethoxy)butyl, in particular methoxymethyl or 2-methoxyethyl;

($C_1$–$C_4$-alkoxy)carbonyl-$C_1$–$C_4$-alkyl is: $C_1$–$C_4$-alkylsubstituted by ($C_1$–$C_4$-alkoxy)carbonyl as mentioned above, e.g. methoxycarbonylmethyl, ethoxycarbonylmethyl, 1-(methoxycarbonyl)ethyl or 2-(methoxycarbonyl)ethyl;

$C_1$–$C_4$-alkylthio-$C_1$–$C_4$-alkyl is: $C_1$–$C_4$-alkyl substituted by $C_1$–$C_4$-alkylthio as mentioned above, e.g. methylthiomethyl, ethylthiomethyl, n-propylthiomethyl, (1-methylethylthio)methyl, n-butylthiomethyl, (1-methylpropylthio)methyl, (2-methylpropylthio) methyl, (1,1-dimethylethylthio)methyl, 2-methylthioethyl, 2-ethylthioethyl, 2-(n-propylthio)ethyl, 2-(1-methylethylthio)ethyl, 2-(n-butylthio)ethyl, 2-(1-methyl-propylthio)ethyl, 2-(2-methylpropylthio)ethyl, r-2-(1,1-dimethylethylthio)ethyl, 2-(methylthio)propyl, 3-(methylthio)propyl, 2-(ethylthio)propyl, 3-(ethylthio)propyl, 3-(propylthio)propyl, 3-(butylthio) propyl, 4-(methylthio)butyl, 4-(ethylthio)butyl, 4-(n-propylthio)butyl or 4-(n-butylthio)butyl, in particular 2-(methylthio)ethyl;

($C_1$–$C_4$-alkylthio)carbonyl-$C_1$–$C_4$-alkyl is: $C_1$–$C_4$-alkyl substituted by ($C_1$–$C_4$-alkylthio)carbonyl, such as (methylthio)carbonyl, (ethylthio)carbonyl, (n-propylthio)carbonyl, (1-methylethylthio)carbonyl, (n-butylthio)carbonyl, (1-methylpropylthio)carbonyl, (2-methylpropylthio)carbonyl and (1,1-dimethylethylthio)carbonyl, preferably (methylthio)carbonyl or (ethylthio)carbonyl, e.g. (methylthio)carbonylmethyl, (ethylthio)carbonylmethyl, 1-[methylthio)carbonyl]ethyl or 2-[(methylthio)carbonyl]ethyl;

$C_1$–$C_4$-haloalkylthio-$C_1$–$C_4$-alkyl is: $C_1$–$C_4$-alkyl as mentioned above which has attached to it a $C_1$–$C_4$-alkylthio group which is partially or fully substituted by fluorine, chlorine and/or bromine, e.g. difluoromethylthio, trifluoromethylthio, chlorodifluoromethylthio, bromodifluoromethylthio, 2-fluoroethylthio, 2-chloroethylthio, 2-bromoethylthio, 2-iodoethylthio, 2,2-difluoroethylthio, 2,2,2-trifluoroethylthio, 2,2,2-trichloroethylthio, 2-chloro-2-fluoroethylthio, 2-chloro-2,2-difluoroethylthio, 2,2-dichloro-2-fluoroethylthio, pentafluoroethylthio, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, (chloromethyl)-2-chloroethylthio, 1-(bromomethyl)-2-bromoethylthio, 4-fluorobutylthio, 4-chlorobutylthio or 4-bromobutylthio, e.g. difluoromethylthiomethyl;

$C_1$–$C_4$-alkylamino-$C_1$–$C_4$-alkyl is: $C_1$–$C_4$-alkyl which is substituted by $C_1$–$C_4$-alkylamino as mentioned above, e.g. methylaminomethyl, ethylaminomethyl, n-propylaminomethyl, (1-methylethylamino)methyl, n-butylaminomethyl, (1-methylpropylamino)methyl, (2-methylpropylamino)methyl, (1,1-dimethylethylamino)methyl, 2-methylaminoethyl, 2-ethylaminoethyl, 2-(n-propylamino)ethyl, 2-(1-methylethylamino)ethyl, 2-(n-butylamino)ethyl, 2-(1-methylpropylamino)ethyl, 2-(2-methylpropylamino)ethyl, 2-(1,1-dimethylethylamino)ethyl, 2-(methylamino)propyl, 3-(methylamino)propyl, 2-(ethylamino)propyl, 3-(ethylamino)propyl, 3-(propylamino)propyl, 3-(butylamino)propyl, 4-(methylamino)butyl, 4-(ethylamino)butyl, 4-(n-propylamino)butyl or 4-(n-butylamino)butyl, in particular 2-(methylamino)ethyl;

$C_1$–$C_4$-alkylaminocarbonyl-$C_1$–$C_4$-alkyl is: $C_1$–$C_4$-alkyl which is substituted by $C_1$–$C_4$-alkylaminocarbonyl, such as methylaminocarbonyl, ethylaminocarbonyl, n-propylaminocarbonyl, 1-methylethylaminocarbonyl, n-butylaminocarbonyl, 1-methylpropylaminocarbonyl, 2-methylpropylaminocarbonyl or 1,1-dimethylethylaminocarbonyl, preferably methylaminocarbonyl or ethylaminocarbonyl, e.g. (methylaminocarbonyl)methyl, (ethylaminocarbonyl)methyl, 1-(methylaminocarbonyl)ethyl or 2-(methylaminocarbonyl)ethyl;

di-($C_1$–$C_4$-alkyl)amino-$C_1$–$C_4$-alkyl: $C_1$–$C_4$-alkyl which is substituted by di($C_1$–$C_4$-alkyl)amino as mentioned above, e.g. dimethylaminomethyl or diethylaminomethyl;

di($C_1$–$C_4$-alkyl)aminocarbonyl-$C_1$–$C_4$-alkyl is: $C_1$–$C_4$-alkyl which is substituted by di($C_1$–$C_4$-alkyl)aminocarbonyl, such as N,N-dimethylaminocarbonyl, N,N-diethylaminocarbonyl, N,N-dipropylaminocarbonyl, N,N-di(1-methylethyl)aminocarbonyl, N,N-dibutylaminocarbonyl, N,N-di(1-methylpropyl)aminocarbonyl, N,N-di(2-methylpropyl)aminocarbonyl, N,N-di(1,1-dimethylethyl)aminocarbonyl, N-ethyl-N-methylaminocarbonyl, N-methyl-N-propylaminocarbonyl, N-methyl-N-(1-methylethyl)aminocarbonyl, N-butyl-N-methylaminocarbonyl, N-methyl-N-(1-methylpropyl)aminocarbonyl, N-methyl-N-(2-methylpropyl)aminocarbonyl, N-(1,1-dimethylethyl)-N-methylaminocarbonyl, N-ethyl-N-propylaminocarbonyl, N-ethyl-N-(1-methylethyl)aminocarbonyl, N-butyl-N-ethylaminocarbonyl, N-ethyl-N-(1-methylpropyl)aminocarbonyl, N-ethyl-N-(2-methylpropyl)aminocarbonyl, N-ethyl-N-(1,1-dimethylethyl)aminocarbonyl, N-(1-methylethyl)-N-propylaminocarbonyl, N-butyl-N-propylaminocarbonyl, N-(1-methylpropyl)-N-propylaminocarbonyl, N-(2-methylpropyl)-N-propylaminocarbonyl, N-(1,1-dimethylethyl)-N-propylaminocarbonyl, N-butyl-N-(1-methylethyl)aminocarbonyl, N-(1-methylethyl)-N-methylpropyl)aminocarbonyl, N-(1-methylethyl)-N-(2-methylpropyl)aminocarbonyl, N-(1,1-dimethylethyl)-N-(1-methylethyl)aminocarbonyl, N-butyl-N-(1-methylpropyl)aminocarbonyl, N-butyl-N-(2-methylpropyl)aminocarbonyl, N-butyl-N-(1,1-dimethylethyl)aminocarbonyl, N-(1-methylpropyl)-N-(2-methylpropyl)aminocarbonyl, N-(1,1-dimethylethyl)-N-(1-methylpropyl)aminocarbonyl or N-(1,1-dimethylethyl)-N-(2-methylpropyl)aminocarbonyl, preferably N,N-dimethylaminocarbonyl or N,N-diethylaminocarbonyl, e.g. dimethylaminocarbonylmethyl, diethylaminocarbonylmethyl, 1-(dimethylaminocarbonyl)ethyl or 2-(dimethylaminocarbonyl)ethyl;

$C_1$–$C_4$-alkylsulfinyl-$C_1$–$C_4$-alkyl is: $C_1$–$C_4$-alkyl which is substituted by methylsulfinyl, ethylsulfinyl, n-propylsulfinyl, 1-methylethylsulfinyl, n-butylsulfinyl, 1-methylpropylsulfinyl, 2-methylpropylsulfinyl or 1,1-dimethylethylsulfinyl, preferably methylsulfinyl, for example methylsulfinylmethyl or 2-methylsulfinylethyl;

$C_1$–$C_4$-haloalkylsulfinyl-$C_1$–$C_4$-alkyl is: $C_1$–$C_4$-alkyl as mentioned above which has attached to it a $C_1$–$C_4$-alkylsulfinyl group which is partially or fully substituted by fluorine, chlorine and/or bromine, e.g. difluoromethylsulfinyl, trifluoromethylsulfinyl, chlorodifluoromethylsulfinyl, bromodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2,2,2-trichloroethylsulfinyl, 2-chloro-2-fluoroethylsulfinyl, 2-chloro-2,2-difluoroethylsulfinyl, 2,2-dichloro-2-fluoroethylsulfinyl, pentafluoroethylsulfinyl, 2-fluoropropylsulfinyl, 3-fluoropropylsulfinyl, 2-chloropropylsulfinyl, 3-chloropropylsulfinyl, 2-bromopropylsulfinyl, 3-bromopropylsulfinyl, 2,2-difluoropropylsulfinyl, 2,3-difluoropropylsulfinyl, 2,3-dichloropropylsulfinyl, 3,3,3-trifluoropropylsulfinyl, 3,3,3-trichloropropylsulfinyl, 2,2,3,3,3-pentafluoropropylsulfinyl, heptafluoropropylsulfinyl, 1-(fluoromethyl)-2-fluoroethylsulfinyl, 1-(chloromethyl)-2-chloroethylsulfinyl, 1-(bromomethyl)-2-bromoethylsulfinyl, 4-fluorobutylsulfinyl, 4-chlorobutylsulfinyl or 4-bromobutylsulfinyl, for example difluoromethylsulfinylmethyl;

$C_1$–$C_4$-alkylsulfonyl is: $SO_2$—$CH_3$, $SO_2$–$C_2H_5$, n-propylsulfonyl, $SO_2$—$CH(CH_3)_2$, n-butylsulfonyl, 1-methylpropylsulfonyl, 2-methylpropylsulfonyl or $SO_2$—$C(CH_3)$, in particular $SO_2$—$CH_3$ or $SO_2$–$C_2H_5$;

$C_1$–$C_4$-alkylsulfonyl-$C_1$–$C_4$-alkyl is: $C_1$–$C_4$-alkyl which is substituted by $C_1$–$C_4$-alkylsulfonyl as mentioned above, preferably methylsulfonyl, for example methylsulfonylmethyl or 2-methylsulfonylethyl;

$C_1$–$C_4$-haloalkylsulfonyl-$C_1$–$C_4$-alkyl is: $C_1$–$C_4$-alkyl as mentioned above which has attached to it a $C_1$–$C_4$-alkylsulfonyl group which is partially or fully substituted by fluorine, chlorine and/or bromine, e.g. difluoromethylsulfonyl, trifluoromethylsulfonyl, chlorodifluoromethylsulfonyl, bromodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2,2,2-trichloroethylsulfonyl, 2-chloro-2-fluoroethylsulfonyl, 2-chloro-2,2-difluoroethylsulfonyl, 2,2-dichloro-2-fluoroethylsulfonyl, pentafluoroethylsulfonyl, 2-fluoropropylsulfonyl, 3-fluoropropylsulfonyl, 2-chloropropylsulfonyl, 3-chloropropylsulfonyl, 2-bromopropylsulfonyl, 3-bromopropylsulfonyl, 2,2-difluoropropylsulfonyl, 2,3-difluoropropylsulfonyl, 2,3-dichloropropylsulfonyl, 3,3,3-trifluoropropylsulfonyl, 3,3,3-trichloropropylsulfonyl, 2,2,3,3,3-pentafluoropropylsulfonyl, heptafluoropropylsulfonyl, 1-(fluoromethyl)-2-fluoroethylsulfonyl, 1-(chloromethyl)-2-chloroethylsulfonyl, 1-(bromomethyl)-2-bromoethylsulfonyl, 4-fluorobutylsulfonyl, 4-chlorobutylsulfonyl or 4-bromobutylsulfonyl, for example 2-chloroethylsulfonyl;

$C_3$–$C_6$-alkenyl is: e.g. prop-2-en-1-yl, n-buten-4-yl, 1-methylprop-2-en-1-yl, 2-methylprop-2-en-1-yl, 2-buten-1-yl, n-penten-3-yl, n-penten-4-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-2-en-1-yl, 1-ethylprop-2-en-1-yl, n-hex-3-en-1-yl, n-hex-4-en-1-yl, n-hex-5-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-2-en-1-yl, 1,2-dimethylbut-3-en-1-yl, 1,3-dimethylbut-2-en-1-yl, 1,3-dimethylbut-3-en-1-yl, 2,2-dimethylbut-3-en-1-yl, 2,3-dimethylbut-2-en-1-yl, 2,3-dimethylbut-3-en-1-yl, 3,3-dimethylbut-2-en-1-yl, 1-ethylbut-2-en-1-yl, 1-ethylbut-3-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl or 1-ethyl-2-methylprop-2-en-1-yl, in particular prop-2-en-1-yl or n-buten-4-yl;

$C_3$–$C_6$-haloalkenyl is: $C_3$–$C_6$-alkenyl as mentioned above which is partially or fully substituted by fluorine, chlorine and/or bromine, e.g. 2-chloroallyl, 3-chloroallyl, 2,3-dichloroallyl, 3,3-dichloroallyl, 2,3,3-trichloroallyl, 2,3-dichlorobut-2-enyl, 2-bromoallyl, 3-bromoallyl, 2,3-dibromoallyl, 3,3-dibromoallyl, 2,3,3-tribromoallyl or 2,3-dibromobut-2-enyl, in particular 2-chloroallyl or 3,3-dichloroallyl;

cyano-$C_3$–$C_6$-alkenyl is: e.g. 3-cyanoallyl, 4-cyanobut-2-enyl, 4-cyanobut-3-enyl or 5-cyanopent-4-enyl, preferably 3-cyanoallyl or 4-cyanobut-2-enyl, in particular 3-cyanoallyl;

$C_3$–$C_4$-alkenyloxy-$C_1$–$C_4$-alkyl is: $C_1$–$C_4$-alkyl which is substituted by $C_3$–$C_4$-alkenyloxy, such as prop-2-enyloxy, n-but-2-enyloxy, n-but-3-enyloxy, 1-methylprop-2-enyloxy or 2-methylprop-2-enyloxy, preferably allyloxy, 2-methylprop-2-en-1-yloxy, but-1-en-3-yloxy, but-1-en-4-yloxy or but-2-en-1-yloxy, for example allyloxymethyl, 2-allyloxyethyl or but-1-en-4-yloxymethyl;

$C_3$–$C_4$-alkenylthio-$C_1$–$C_4$-alkyl is: $C_1$–$C_4$-alkyl which is substituted by $C_3$–$C_4$-alkenylthio, such as prop-2-enylthio, n-but-2-enylthio, n-but-3-enylthio, 1-methylprop-2-enylthio or 2-methylprop-2-enylthio, preferably allylthio, 2-methylprop-2-en-1-ylthio, but-1-en-3-ylthio, but-1-en-4-ylthio or but-2-en-1-ylthio, for example allylthiomethyl, 2-allylthioethyl or but-1-en-4-ylthiomethyl; $C_3$–$C_4$-alkenylsulfinyl-$C_1$–$C_4$-alkyl is: $C_1$–$C_4$-alkyl which is substituted by $C_3$–$C_4$-alkenylsulfinyl, such as prop-2-enylsulfinyl, n-but-2-enylsulfinyl, n-but-3-enylsulfinyl, 1-methylprop-2-enylsulfinyl or 2-methylprop-2-enylsulfinyl, preferably allylsulfinyl, 2-methylprop-2-en-1-ylsulfinyl, but-1-en-3-ylsulfinyl, but-1-en-4-ylsulfinyl or but-2-en-1-ylsulfinyl, for example allylsulfinylmethyl, 2-allylsulfinylethyl or but-1-en-4-ylsulfinylmethyl;

$C_3$–$C_4$-alkenylsulfonyl-$C_1$–$C_4$-alkyl is: $C_1$–$C_4$-alkyl which is substituted by $C_3$–$C_4$-alkenylsulfonyl, such as prop-2-enylsulfonyl, n-but-2-enylsulfonyl, n-but-3-enylsulfonyl, 1-methylprop-2-enylsulfonyl or 2-methylprop-2-enylsulfonyl, preferably allylsulfonyl, 2-methylprop-2-en-1-ylsulfonyl, but-1-en-3-ylsulfonyl, but-1-en-4-ylsulfonyl or but-2-en-1-ylsulfonyl, for example allylsulfonylmethyl, 2-allylsulfonylethyl or but-1-en-4-ylsulfonylmethyl;

$C_3$–$C_6$-alkynyl is: e.g. propargyl, n-but-1-yn-3-yl, n-but-1-yn-4-yl, n-but-2-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-3-yl, 3-methylpent-1-yn-4-yl, 3-methylpent-1-yn-5-yl, 4-methylpent-2-yn-4-yl or 4-methylpent-2-yn-5-yl, in particular propargyl;

$C_3$–$C_6$-haloalkynyl is: $C_3$–$C_6$-alkynyl as mentioned above which is partially or fully substituted by fluorine, chlorine and/or bromine, e.g. 1,1-difluoroprop-2-yn-1-yl, 4-fluorobut-2-yn-1-yl, 4-chlorobut-2-yn-1-yl, 1,1-difluorobut-2-yn-1-yl, 5-fluoropent-3-yn-1-yl or 6-fluorohex-4-yn-1-yl;

cyano-$C_3$–$C_6$-alkynyl is: e.g. 3-cyanopropargyl;

$C_3$–$C_4$-alkynyloxy-$C_1$–$C_4$-alkyl is: $C_1$–$C_4$-alkyl which is substituted by $C_3$–$C_4$-alkynyloxy, such as prop-2-ynyloxy, n-but-2-ynyloxy, n-but-3-ynyloxy or 1-methylprop-2-ynyloxy, preferably propargyloxy, but-1-yn-3-yloxy, but-1-yn-4-yloxy or but-2-yn-1-yloxy, for example propargyloxymethyl or 2-propargyloxyethyl;

$C_3$–$C_4$-alkynylthio-$C_1$–$C_4$-alkyl is: $C_1$–$C_4$-alkyl which is substituted by $C_3$–$C_4$-alkynylthio, such as prop-2-ynylthio, n-but-2-ynylthio, n-but-3-ynylthio or 1-methylprop-2-ynylthio, preferably propargylthio, but-1-yn-3-ylthio, but-1-yn-4-ylthio or but-2-yn-1-ylthio, for example propargylthiomethyl or 2-propargylthioethyl;

$C_3$–$C_4$-alkynylsulfinyl-$C_1$–$C_4$-alkyl is: $C_1$–$C_4$-alkyl which is substituted by $C_3$–$C_4$-alkynylsulfinyl, such as prop-2-ynylsulfinyl, n-but-2-ynylsulfinyl, n-but-3-ynylsulfinyl and 1-methylprop-2-ynylsulfinyl, preferably propargylsulfinyl, but-1-yn-3-ylsulfinyl, but-1-yn-4-ylsulfinyl or but-2-yn-1-ylsulfinyl, for example propargylsulfinylmethyl or 2-propargylsulfinylethyl;

$C_3$–$C_4$-alkynylsulfonyl-$C_1$–$C_4$-alkyl is: $C_1$–$C_4$-alkyl which is substituted by $C_3$–$C_4$-alkynylsulfonyl, such as prop-2-ynylsulfonyl, n-but-2-ynylsulfonyl, n-but-3-ynylsulfonyl and 1-methylprop-2-ynylsulfonyl, preferably propargylsulfonyl, but-1-yn-3-ylsulfonyl, but-1-yn-4-ylsulfonyl or but-2-yn-1-ylsulfonyl, for example propargylsulfonylmethyl or 2-propargylsulfonylethyl;

$C_3$–$C_6$-cycloalkyl is: cyclopropyl, cyclobutyl, cyclopentyl or cyclohexyl, in particular cyclopentyl or cyclohexyl;

$C_3$–$C_8$-cycloalkyl is: cyclopropyl, cyclobutyl, cyclopentyl, cyclohexyl, cycloheptyl or cyclooctyl, in particular cyclopentyl or cyclohexyl;

$C_3$–$C_8$-cycloalkyl-$C_1$–$C_4$-alkyl is: cyclopropylmethyl, cyclobutylmethyl, cyclopentylmethyl, cyclohexylmethyl, cycloheptylmethyl, cyclooctylmethyl, 1-(cyclopropyl)ethyl, 1-(cyclobutyl)ethyl, 1-(cyclopentyl)ethyl, 1-(cyclohexyl)ethyl, 1-(cycloheptyl)ethyl, 1-(cyclooctyl)ethyl, 2-(cyclopropyl)ethyl, 2-(cyclobutyl)ethyl, 2-(cyclopentyl)ethyl, 2-(cyclohexyl)ethyl, 2-(cycloheptyl)ethyl, 2-(cyclooctyl)ethyl, 3-(cyclopropyl)propyl, 3-(cyclobutyl)propyl, 3-(cyclopentyl)propyl, 3-(cyclohexyl)propyl, 3-(cycloheptyl)propyl, 3-(cyclooctyl)propyl, 4-(cyclopropyl)butyl, 4-(cyclobutyl)butyl, 4-(cyclopentyl)butyl, 4-(cyclohexyl)butyl, 4-(cycloheptyl)butyl or 4-(cyclooctyl)butyl, in particular cyclopentylmethyl or cyclohexylmethyl;

$C_3$–$C_8$-cycloalkoxy-$C_1$–$C_4$-alkyl is: cyclopropyloxymethyl, cyclobutyloxymethyl, cyclopentyloxymethyl, cyclohexyloxymethyl, cycloheptyloxymethyl, cyclooctyloxymethyl, 1-(cyclopropyloxy)ethyl, 1-(cyclobutyloxy)ethyl, 1-(cyclopentyloxy)ethyl, 1-(cyclohexyloxy)ethyl, 1-(cycloheptyloxy)ethyl, 1-(cyclooctyloxy)ethyl, 2-(cyclopropyloxy)ethyl, 2-(cyclobutyloxy)ethyl, 2-(cyclopentyloxy)ethyl, 2-(cyclohexyloxy)ethyl, 2-(cycloheptyloxy)ethyl, 2-(cyclooctyloxy)ethyl, 3-(cyclopropyloxy)propyl, 3-(cyclobutyloxy)propyl, 3-(cyclopentyloxy)propyl, 3-(cyclohexyloxy)propyl, 3-(cycloheptyloxy)propyl, 3-(cyclooctyloxy)propyl, 4-(cyclopropyloxy)butyl, 4-(cyclobutyloxy)butyl, 4-(cyclopentyloxy)butyl, 4-(cyclohexyloxy)butyl, 4-(cycloheptyloxy)butyl or 4-(cyclooctyloxy)butyl, in particular cyclopentyloxymethyl, cyclohexyloxymethyl or 2-(cyclopentyloxy)ethyl.

3- to 7-membered heterocyclyl is to be understood as meaning not only saturated or partially or fully unsaturated but also aromatic heterocycles having one to three hetero atoms selected from a group consisting of
one to three nitrogen atoms,
one or two oxygen and
one or two sulfur atoms.

Examples of saturated heterocycles which can contain a carbonyl or thiocarbonyl ring member are:
oxiranyl, thiiranyl, aziridin-1-yl, aziridin-2-yl, diaziridin-1-yl, diaziridin-3-yl, oxetan-2-yl, oxetan-3-yl, thietan-2-yl, thietan-3-yl, azetidin-1-yl, azetidin-2-yl, azetidin-3-yl, tetrahydrofuran-2-yl, tetrahydrofuran-3-yl, tetrahydrothiophen-2-yl, tetrahydrothiophen-3-yl, pyrrolidin-1-yl, pyrrolidin-2-yl, pyrrolidin-3-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-oxazolidin-2-yl, 1,3-oxazolidin-3-yl, 1,3-oxazolidin-4-yl, 1,3-oxazolidin-5-yl, 1,2-oxazolidin-2-yl, 1,2-oxazolidin-3-yl, 1,2-oxazolidin-4-yl, 1,2-oxazolidin-5-yl, 1,3-dithiolan-2-yl; 1,3-dithiolan-4-yl, pyrrolidin-1-yl, pyrrolidin-2-yl, pyrrolidin-5-yl, tetrahydropyrazol-1-yl, tetrahydropyrazol-3-yl, tetrahydropyrazol-4-yl, tetrahydropyran-2-yl, tetrahydropyran-3-yl, tetrahydropyran-4-yl, tetrahydrothiopyran-2-yl, tetrahydrothiopyran-3-yl, tetrahydropyran-4-yl, piperidin-1-yl, piperidin-2-yl, piperidin-3-yl, piperidin-4-yl, 1,3-dioxan-2-yl, 1,3-dioxan-4-yl, 1,3-dioxan-5-yl, 1,4-dioxan-2-yl, 1,3-oxathian-2-yl, 1,4-oxathian-4-yl, 1,3-oxathian-5-yl, 1,3-oxathian-6-yl, 1,4-oxathian-2-yl, 1,4-oxathian-3-yl, morpholin-2-yl, morpholin-3-yl, morpholin-4-yl, hexahydropyridazin-1-yl, hexahydropyridazin-3-yl, hexahydropyridazin-4-yl, hexahydropyrimidin-1-yl, hexahydropyrimidin-2-yl, hexahydropyrimidin-4-yl, hexahydropyrimidin-5-yl, piperazin-1-yzi piperazin-2-yl, piperazin-3-yl, hexahydro-1,3,5-triazin-1-yl, hexahydro-1, 3, 5-triazin-2-yl, oxepan-2-yl, oxepan-3-yl, oxepan-4-yl, thiepan-2-yl, thiepan-3-yl, thiepan-4-yl, 1,3-dioxepan-2-yl, 1,3-dioxepan-4-yl, 1,3-dioxepan-5-yl, 1,3-dioxepan-6-yl, 1,3-dithiepan-2-yl, 1,3-dithiepan-2-yl, 1,3-dithiepan-2-yl, 1,3-dithiepan-2-yl, 1,4-dioxepan-2-yl, 1, 4-dioxepan-7-yl, hexahydroazepin-1-yl, hexahydroazepin-2-yl, hexahydroazepin-3-yl, hexahydroazepin-4-yl, hexahydro-1,3-diazepin-1-yl, hexahydro-1,3-diazepin-2-yl, hexahydro-1,3-diazepin-4-yl, hexahydro-1,4-diazepin-1-yl and hexahydro-1,4-diazepin-2-yl;

Examples of unsaturated heterocycles which can contain a carbonyl or thiocarbonyl ring member are:
dihydrofuran-2-yl, 1,2-oxazolin-3-yl, 1, 2-oxazolin-5-yl, 1,3-oxazolin-2-yl;

Amongst the heteroaromatics, the 5- and 6-membered ones are preferred, e.g. furyl, such as 2-furyl and 3-furyl, thienyl, such as 2-thienyl and 3-thienyl, pyrrolyl, such as 2-pyrrolyl and 3-pyrrolyl, isoxazolyl, such as 3-isoxazolyl, 4-isoxazolyl and 5-isoxazolyl, isothiazolyl, such as 3-isothiazolyl, 4-isothiazolyl and 5-isothiazolyl, pyrazolyl, such as 3-pyrazolyl, 4-pyrazolyl and 5-pyrazolyl, oxazolyl, such as 2-oxazolyl, 4-oxazolyl and 5-oxazolyl, thiazolyl, such as 2-thiazolyl, 4-thiazolyl and 5-thiazolyl, imidazolyl, such as 2-imnidazolyl and 4-jimidazolyl, oxadiazolyl, such as oxadiazol-3-yl, 1,2,4-oxadiazol-5-yl and 1,3,4-oxadiazol-2-yl, thiadiazolyl, such as 1,2,4-thiadiazol-3-yl, 1,2,4-thiadiazol-5-yl and 1,3,4-thiadiazol-2-yl, triazolyl, such as 1,2,4-triazol-1-yl, 1,2,4-triazol-3-yl and 1,2,4-triazol-4-yl, pyridinyl, such as 2-pyridinyl, 3-pyridinyl and 4-pyridinyl, pyridazinyl, such as 3-pyridazinyl and 4-pyridazinyl, pyrimidinyl, such as 2-pyrimidinyl, 4-pyrimidinyl and 5-pyrimidinyl, furthermore 2-pyrazinyl, 1,3,5-triazin-2-yl and 1,2,4-triazin-3-yl, in particular pyridyl, pyrimidyl, furanyl and thienyl.

All phenyl and heterocyclic rings are preferably unsubstituted or have attached to them a cyano, nitro, halogen, $C_1$–$C_4$-alkyl, $C_1$–$C_4$-haloalkyl, $C_1$–$C_4$-alkoxy, $C_1$–$C_4$-haloalkoxy, ($C_1$–$C_4$-alkyl)carbonyl, ($C_1$–$C_4$-alkoxy)carbonyl or ($C_1$–$C_4$-alkyl)carbonyloxy substituent.

Preferred with a view to the use of the substituted aromatic phosphonic acid derivatives I as herbicides or for the desiccation/defoliation of plants are those compounds I where the substituents have the following meanings, in each case alone or in is combination:

Eth is —$CH_2$—CH(halogen)—, —$CH_2$—CH(CN)—, —$CH_2$—CH(COO$CH_3$)—, —CH=CH—, —CH=C(halogen)—, —CH=C(CN)—, —CH=C($CH_3$)—, —CH=C(COO$CH_3$)— or —C≡C—, in particular —$CH_2$—CH(halogen)— or —CH=C(halogen)—, particularly preferably —CH=C(halogen)—;

$Y^1$ is oxygen;
$Y^2$ is oxygen;
$Y^3$ is oxygen;
$R^1$, $R^2$, $R^6$, $R^7$ independently of one another are hydrogen, $C_1-C_6$-alkyl, $C_1-C_6$-haloalkyl, hydroxy-$C_1-C_4$-alkyl, cyano-$C_1-C_4$-alkyl, $C_1-C_4$-alkoxy-$C_1-C_4$-alkyl, di($C_1-C_4$-alkyl)-amino-$C_1-C_4$-alkyl, $C_1-C_4$-alkylthio-$C_1-C_4$-alkyl, $C_1-C_4$-alkyl-sulfonyl-$C_1-C_4$-alkyl, $C_1-C_4$-haloalkylsulfonyl-$C_1-C_4$-alkyl, $C_3-C_6$-alkenyl, $C_3-C_6$-haloalkenyl, $C_3-C_6$-alkynyl, hydroxycarbonyl-$C_1-C_4$-alkyl, ($C_1-C_4$-alkoxy)carbonyl-$C_1-C_4$-alkyl, aminocarbonyl-$C_1-C_4$-alkyl, ($C_1-C_4$-alkyl)aminocarbonyl-$C_1-C_4$-alkyl, di($C_1-C_4$-alkyl)aminocarbonyl-$C_1-C_4$-alkyl, $C_3-C_8$-cycloalkyl, $C_3-C_8$-cycloalkyl-$C_1-C_4$-alkyl, phenyl, phenyl-$C_1-C_4$-alkyl or 3- to 7-membered heterocyclyl or heterocyclyl-$C_1-C_4$-alkyl, it being possible for all heterocycles, if desired, to contain a carbonyl or thiocarbonyl ring member, and it being possible for all cycloalkyl, phenyl and heterocyclyl rings to be unsubstituted or to have attached to them one to four substituents, in each case selected from the group consisting of halogen, nitro, amino, hydroxyl, carboxyl, $C_1-C_4$-alkyl, $C_1-C_4$-haloalkyl, $C_1-C_4$-alkoxy, $C_1-C_4$-alkylsulfonyl, ($C_1-C_4$-alkyl)carbonyl, ($C_1-C_4$-alkoxy) carbonyl and di ($C_1-C_4$-alkyl)amino, or $R^1$ and $R^2$ or $R^1$ and $R^6$ and/or $R^2$ and $R^7$ in each case together form a 1,2-ethanediyl, 1,3-propylene, tetramethylene, pentamethylene or ethyleneoxyethylene chain which, if desired, can be substituted by one to four $C_1-C_4$-alkyl and/or one or two ($C_1-C_4$-alkoxy) carbonyl groups, $R^1$, $R^2$ h $R^6$, $R^7$ are, in particular, in each case hydrogen, $C_1-C_6$-alkyl, $C_1-C_6$-haloalkyl, $C_3-C_6$-alkenyl, $C_3-C_6$-haloalkenyl, $C_3-C_6$-alkynyl, ($C_3-C_4$-alkoxy)carbonyl-$C_1-C_4$-alkyl, $C_3-C_8$-cycloalkyl, $C_3-C_8$-cycloalkyl-$C_1-C_4$-alkyl, phenyl, phenyl-$C_1-C_4$-alkyl or 3- to 7-membered heterocyclyl or heterocyclyl-$C_1-C_4$-alkyl or $R^1$ and $R^2$ or $R^1$ and $R^6$ and/or $R^2$ and $R^7$ in each case together form a 1, 2-ethanediyl or 1,3-propylene chain;

$R^1$, $R^2$, $R^6$, $R^7$ is particularly preferably in each case hydrogen, $C_1-C_6$-alkyl, $C_3-C_6$-alkenyl, $C_3-C_6$-alkynyl, $C_3$-CB-cycloalkyl, phenyl or phenyl-Cl-$c_4$-alkyl, or $R^1$ and $R^2$ together form a 1,3-propylene chain;

$R^3$ is cyano, halogen or $C_1-C_4$-haloalkyl, in particular halogen, particularly preferably chlorine;

$R^4$ is hydrogen, fluorine or chlorine, in particular fluorine or chlorine, particularly preferably fluorine;

$R^5$ is one of the following heterocycles $\Phi^1$ to $\Phi^5$, $\Phi^7$, $\Phi^{20}$, $\Phi^{21}$ and $\Phi^{22}$:

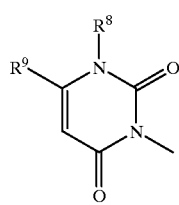

$\Phi^1$

-continued

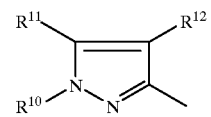

$\Phi^2$

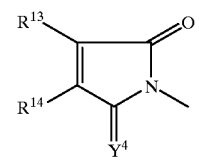

$\Phi^3$

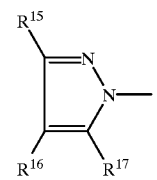

$\Phi^4$

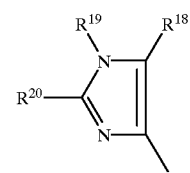

$\Phi^5$

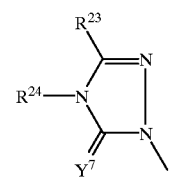

$\Phi^7$

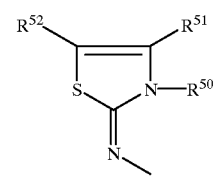

$\Phi^{20}$

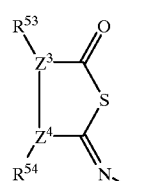

$\Phi^{21}$

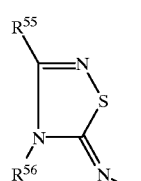

$\Phi^{22}$ where $R^8$ is methyl;
$R^9$ is $C_1-C_4$-haloalkyl, in particular trifluoromethyl;
$R^{10}$ is $C_1-C_4$-alkyl, in particular methyl;

$R^{11}$ is $C_1$–$C_4$-haloalkyl, in particular trifluoromethyl, or $C_1$–$C_4$-haloalkoxy, in particular difluoromethoxy;

$R^{12}$ is halogen, in particular chlorine, or $C_1$–$C_4$-haloalkyl, in particular trifluoromethyl;

$Y^4$ is oxygen;

$R^{13}$ and $R^{14}$ independently of one another are $C_1$–$C_4$-alkyl, in particular methyl, or $R^{13}$ and $R^{14}$ together with the ring atoms linking them are a 6-membered carbocyclic ring;

$R^{15}$ and $R^{16}$ together with the ring atoms linking them are a 6-membered carbocyclic ring;

$R^{17}$ is halogen, in particular chlorine;

$R^{18}$ is chlorine or bromine, in particular chlorine;

$R^{19}$ is halomethyl, in particular difluoromethyl;

$R^{20}$ is $C_1$–$C_4$-alkyl, in particular methyl;

$R^{23}$ and $R^{24}$ together with the ring atoms linking them are a 6-membered ring;

$Y^7$ is oxygen;

$R^{50}$ is $C_1$–$C_4$-alkyl, in particular methyl;

$R^{51}$ is $C_1$–$C_4$-haloalkyl, in particular trifluoromethyl;

$R^{52}$ is hydrogen;

$R^{53}$ and $R^{54}$ together with the ring atoms linking them are a 6-membered ring;

$Z^3$, $Z^4$ independently of one another are nitrogen;

$R^{55}$ and $R^{56}$ together with the ring atoms linking them are a 5- or 6-membered ring which, if desired, can additionally have attached to it one or two $C_1$–$C_4$-alkyl substituents;

$R^5$ is especially preferably 1-methyl-6-trifluoromethyl-2,4 (1H,3H)-pyrimidinedion-3-yl, 4-chloro-5-difluoromethoxy-1-methyl-1H-pyrazol-3-yl, 4-chloro-1-methyl-5-trifluoromethyl-1H-pyrazol-3-yl, 1-methyl-4,5-di(trifluoromethyl)-1H-pyrazol-3-yl, 1,3,4,5,6,7-hexahydro-1,3-dioxo-2H-isoindol-2-yl, 3,4-dimethyl-1H-pyrrol-2,5-dion-1-yl, 3-chloro-4,5,6,7-tetrahydro-2H-indazol-2-yl, 5-chloro-1-difluoromethyl-2-methyl-1H-imidazol-4-yl, 5,6,7,8-tetrahydro-1,2,4-triazolo[4,3-a]pyridin-3(2H)-on-2-yl, (3-methyl-4-trifluoromethyl-2(3H)-thiazolylidene)amino, (tetrahydro-3-oxo-1H,3H-[1,3,4]thiadiazolo-[3,4-a]pyridazin-1-ylidene)amino or (6,7-dihydro-6,6-dimethyl-3H,5H-pyrrolo[2,1-c][1,2,4]thiadiazol-3-ylidene)amino.

Very especially preferred are the compounds IAa listed in Table 1 below ($\triangleq$ I where $R^3$=chlorine; Eth=—$CH_2$—$CH_2$—; $R^5$=heterocycle $\Phi^1$ where $R^8$=$CH_3$ and $R^9$=$CF_3$):

TABLE 1

IAa

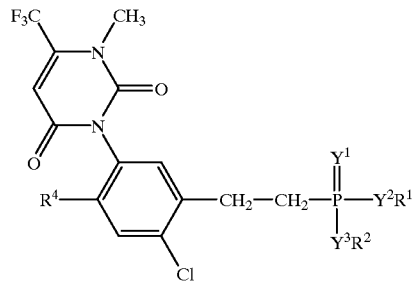

| No. | $R^4$ | —P(=$Y^1$)($Y^2R^1$)($Y^3R^2$) |
|---|---|---|
| IAa.1 | H | —P(=O)(OH)$_2$ |
| IAa.2 | H | —P(=O)(OCH$_3$)$_2$ |
| IAa.3 | H | —P(=O)(OC$_2$H$_5$)$_2$ |
| IAa.4 | H | —P(=O)[O-(n-C$_3$H$_7$)]$_2$ |
| IAa.5 | H | —P(=O)(OCH(CH$_3$)$_2$)$_2$ |
| IAa.6 | H | —P(=O)[O-(n-C$_4$H$_9$)]$_2$ |

TABLE 1-continued

IAa

| No. | $R^4$ | —P(=$Y^1$)($Y^2R^1$)($Y^3R^2$) |
|---|---|---|
| IAa.7 | H | —P(=O)[OCH$_2$—CH(CH$_3$)$_2$]$_2$ |
| IAa.8 | H | —P(=O)[OCH(CH$_3$)—C$_2$H$_5$]$_2$ |
| IAa.9 | H | —P(=O)(OCH$_2$—CF$_3$)$_2$ |
| IAa.10 | H | —P(=O)(OCH$_2$—CH$_2$—OH)$_2$ |
| IAa.11 | H | —P(=O)(OCH$_2$—CH$_2$—CN)$_2$ |
| IAa.12 | H | —P(=O)(OCH$_2$—CH$_2$—OCH$_3$)$_2$ |
| IAa.13 | H | —P(=O)(OCH$_2$—CH$_2$—OC$_2$H$_5$)$_2$ |
| IAa.14 | H | —P(=O)(OCH$_2$—CH$_2$—OCF$_3$)$_2$ |
| IAa.15 | H | —P(=O)(OCH$_2$—CH$_2$—OCH$_2$—CH=CH$_2$)$_2$ |
| IAa.16 | H | —P(=O)(OCH$_2$—CH$_2$—OCH$_2$—C≡CH)$_2$ |
| IAa.17 | H | —P(=O)(OCH$_2$—CH$_2$—O-cyclopentyl)$_2$ |
| IAa.18 | H | —P(=O)(OCH$_2$—CH$_2$—NH$_2$)$_2$ |
| IAa.19 | H | —P(=O)(OCH$_2$—CH$_2$—NH—CH$_3$)$_2$ |
| IAa.20 | H | —P(=O)[OCH$_2$—CH$_2$—N(CH$_3$)$_2$]$_2$ |
| IAa.21 | H | —P(=O)(OCH$_2$—CH$_2$—SCH$_3$)$_2$ |
| IAa.22 | H | —P(=O)(OCH$_2$—CH$_2$—SC$_2$H$_5$)$_2$ |
| IAa.23 | H | —P(=O)(OCH$_2$—CH$_2$—SCF$_3$)$_2$ |
| IAa.24 | H | —P(=O)(OCH$_2$—CH$_2$—SCH$_2$—CH=CH$_2$)$_2$ |
| IAa.25 | H | —P(=O)(OCH$_2$—CH$_2$—SCH$_2$—C≡CH)$_2$ |
| IAa.26 | H | —P(=O)(OCH$_2$—CH$_2$—SO—CH$_3$)$_2$ |
| IAa.27 | H | —P(=O)(OCH$_2$—CH$_2$—SO—C$_2$H$_5$)$_2$ |
| IAa.28 | H | —P(=O)(OCH$_2$—SO$_2$—CH$_3$)$_2$ |
| IAa.29 | H | —P(=O)(OCH$_2$—SO$_2$—C$_2$H$_5$)$_2$ |
| IAa.30 | H | —P(=O)(OCH$_2$—CH$_2$—SO$_2$—CH$_3$)$_2$ |
| IAa.31 | H | —P(=O)(OCH$_2$—CH$_2$—SO$_2$—C$_2$H$_5$)$_2$ |
| IAa.32 | H | —P(=O)(OCH$_2$—CH=CH$_2$)$_2$ |
| IAa.33 | H | —P(=O)(OCH$_2$—CH=CH—CH$_3$)$_2$ |
| IAa.34 | H | —P(=O)(OCH$_2$—CH$_2$—CH=CH$_2$)$_2$ |
| IAa.35 | H | —P(=O)(OCH$_2$—CH=CH—Cl)$_2$ |
| IAa.36 | H | —P(=O)(OCH$_2$—C≡CH)$_2$ |
| IAa.37 | H | —P(=O)[OCH(CH$_3$)—C≡CH]$_2$ |
| IAa.38 | H | —P(=O)(OCH$_2$—CO—OCH$_3$)$_2$ |
| IAa.39 | H | —P(=O)(OCH$_2$—CO—OC$_2$H$_5$)$_2$ |
| IAa.40 | H | —P(=O)[OCH(CH$_3$)—CO—OCH$_3$]$_2$ |
| IAa.41 | H | —P(=O)[OCH(CH$_3$)—CO—OC$_2$H$_5$]$_2$ |
| IAa.42 | H | —P(=O)(OCH$_2$—CO—NH$_2$)$_2$ |
| IAa.43 | H | —P(=O)(OCH$_2$—CO—NH—CH$_3$)$_2$ |
| IAa.44 | H | —P(=O)[OCH$_2$—CO—N(CH$_3$)$_2$]$_2$ |
| IAa.45 | H | —P(=O)[OCH(CH$_3$)—CO—NH$_2$]$_2$ |
| IAa.46 | H | —P(=O)[OCH(CH$_3$)—CO—NH—CH$_3$]$_2$ |
| IAa.47 | H | —P(=O)[OCH(CH$_3$)—CO—N(CH$_3$)$_2$]$_2$ |
| IAa.48 | H | —P(=O)(O-cyclopropyl)$_2$ |
| IAa.49 | H | —P(=O)(O-cyclobutyl)$_2$ |
| IAa.50 | H | —P(=O)(O-cyclopentyl)$_2$ |
| IAa.51 | H | —P(=O)(O-cyclohexyl)$_2$ |
| IAa.52 | H | —P(=O)(OCH$_2$-cyclopropyl)$_2$ |
| IAa.53 | H | —P(=O)(OCH$_2$-cyclobutyl)$_2$ |
| IAa.54 | H | —P(=O)(OCH$_2$-cyclopentyl)$_2$ |
| IAa.55 | H | —P(=O)(OCH$_2$-cyclohexyl)$_2$ |
| IAa.56 | H | —P(=O)(O-phenyl)$_2$ |
| IAa.57 | H | —P(=O)(OCH$_2$-phenyl)$_2$ |
| IAa.58 | H | —P(=O)(O-oxetan-3-yl)$_2$ |
| IAa.59 | H | —P(=O)(O-tetrahydrofuran-2-yl)$_2$ |
| IAa.60 | H | —P(=O)(O-tetrahydrofuran-3-yl)$_2$ |
| IAa.61 | H | —P(=O)(O-tetrahydropyran-2-yl)$_2$ |
| IAa.62 | H | —P(=O)(O-tetrahydropyran-3-yl)$_2$ |
| IAa.63 | H | —P(=O)(O-tetrahydropyran-4-yl)$_2$ |
| IAa.64 | H | —P(=O)(OCH$_2$-oxiran-2-yl)$_2$ |
| IAa.65 | H | —P(=O)(OCH$_2$-oxetan-3-yl)$_2$ |
| IAa.66 | H | —P(=O)(OCH$_2$-tetrahydrofuran-2-yl)$_2$ |
| IAa.67 | H | —P(=O)(OCH$_2$-tetrahydrofuran-3-yl)$_2$ |

TABLE 1-continued

IAa

F₃C, CH₃ on pyrimidine-2,4-dione ring; N-aryl substituted with R⁴, Cl, and —CH₂—CH₂—P(=Y¹)(Y²R¹)(Y³R²)

| No. | R⁴ | —P(=Y¹)(Y²R¹)(Y³R²) |
|---|---|---|
| IAa.68 | H | —P(=O)(OCH₂-pyrrolidin-1-yl)₂ |
| IAa.69 | H | —P(=O)[OCH₂-(2-pyrrolidon-1-yl)]₂ |
| IAa.70 | H | —P(=O)(OCH₂-tetrahydropyran-2-yl)₂ |
| IAa.71 | H | —P(=O)(OCH₂-tetrahydropyran-3-yl)₂ |
| IAa.72 | H | —P(=O)(OCH₂-tetrahydropyran-4-yl)₂ |
| IAa.73 | H | —P(=O)(OCH₂-piperidin-1-yl)₂ |
| IAa.74 | H | —P(=O)(OCH₂-morpholin-4-yl)₂ |
| IAa.75 | H | —P(=O)(OH)(OCH₃) |
| IAa.76 | H | —P(=O)(OH)(OC₂H₅) |
| IAa.77 | H | —P(=O)(OH)[O-[n-C₃H₇]] |
| IAa.78 | H | —P(=O)(OH)[OCH(CH₃)₂] |
| IAa.79 | H | —P(=O)(OH)[O-(n-C₄H₉)] |
| IAa.80 | H | —P(=O)(OH)[OCH₂—CH(CH₃)₂] |
| IAa.81 | H | —P(=O)(OH)[OCH(CH₃)—C₂H₅] |
| IAa.82 | H | —P(=O)(OH)(OCH₂—CF₃) |
| IAa.83 | H | —P(=O)(OH)(OCH₂—CH₂—OH) |
| IAa.84 | H | —P(=O)(OH)(OCH₂—CH₂—CN) |
| IAa.85 | H | —P(=O)(OH)(OCH₂—CH₂—OCH₃) |
| IAa.86 | H | —P(=O)(OH)(OCH₂—CH₂—OC₂H₅) |
| IAa.87 | H | —P(=O)(OH)(OCH₂—CH₂—OCF₃) |
| IAa.88 | H | —P(=O)(OH)(OCH₂—CH₂—OCH₂—CH=CH₂) |
| IAa.89 | H | —P(=O)(OH)(OCH₂—CH₂—OCH₂—C≡CH) |
| IAa.90 | H | —P(=O)(OH)(OCH₂—CH₂—O-cyclopentyl) |
| IAa.91 | H | —P(=O)(OH)(OCH₂—CH₂—NH₂) |
| IAa.92 | H | —P(=O)(OH)(OCH₂—CH₂—NH—CH₃) |
| IAa.93 | H | —P(=O)(OH)[OCH₂—CH₂—N(CH₃)₂] |
| IAa.94 | H | —P(=O)(OH)(OCH₂—CH₂—SCH₃) |
| IAa.95 | H | —P(=O)(OH)(OCH₂—CH₂—SC₂H₅) |
| IAa.96 | H | —P(=O)(OH)(OCH₂—CH₂—SCF₃) |
| IAa.97 | H | —P(=O)(OH)(OCH₂—CH₂—SCH₂—CH=CH₂) |
| IAa.98 | H | —P(=O)(OH)(OCH₂—CH₂—SCH₂—C≡CH) |
| IAa.99 | H | —P(=O)(OH)(OCH₂—CH₂—SO—CH₃) |
| IAa.100 | H | —P(=O)(OH)(OCH₂—CH₂—SO—C₂H₅) |
| IAa.101 | H | —P(=O)(OH)(OCH₂—SO₂—CH₃) |
| IAa.102 | H | —P(=O)(OH)(OCH₂—SO₂—C₂H₅) |
| IAa.103 | H | —P(=O)(OH)(OCH₂—CH₂—SO₂—CH₃) |
| IAa.104 | H | —P(=O)(OH)(OCH₂—CH₂—SO₂—C₂H₅) |
| IAa.105 | H | —P(=O)(OH)(OCH₂—CH=CH₂) |
| IAa.106 | H | —P(=O)(OH)(OCH₂—CH=CH—CH₃) |
| IAa.107 | H | —P(=O)(OH)(OCH₂—CH₂—CH=CH₂) |
| IAa.108 | H | —P(=O)(OH)(OCH₂—CH=CH—Cl) |
| IAa.109 | H | —P(=O)(OH)(OCH₂—C≡CH) |
| IAa.110 | H | —P(=O)(OH)[OCH(CH₃)—C≡CH] |
| IAa.111 | H | —P(=O)(OH)(OCH₂—CO—OCH₃) |
| IAa.112 | H | —P(=O)(OH)(OCH₂—CO—OC₂H₅) |
| IAa.113 | H | —P(=O)(OH)[OCH(CH₃)—CO—OCH₃] |
| IAa.114 | H | —P(=O)(OH)[OCH(CH₃)—CO—OC₂H₅] |
| IAa.115 | H | —P(=O)(OH)(OCH₂—CO—NH₂) |
| IAa.116 | H | —P(=O)(OH)(OCH₂—CO—NH—CH₃) |
| IAa.117 | H | —P(=O)(OH)[OCH₂—CO—N(CH₃)₂] |
| IAa.118 | H | —P(=O)(OH)[OCH(CH₃)—CO—NH₂] |
| IAa.119 | H | —P(=O)(OH)[OCH(CH₃)—CO—NH—CH₃] |
| IAa.120 | H | —P(=O)(OH)[OCH(CH₃)—CO—N(CH₃)₂] |
| IAa.121 | H | —P(=O)(OH)(O-cyclopropyl) |
| IAa.122 | H | —P(=O)(OH)(O-cyclobutyl) |
| IAa.123 | H | —P(=O)(OH)(O-cyclopentyl) |
| IAa.124 | H | —P(=O)(OH)(O-cyclohexyl) |
| IAa.125 | H | —P(=O)(OH)(OCH₂-cyclopropyl) |
| IAa.126 | H | —P(=O)(OH)(OCH₂-cyclobutyl) |
| IAa.127 | H | —P(=O)(OH)(OCH₂-cyclopentyl) |
| IAa.128 | H | —P(=O)(OH)(OCH₂-cyclohexyl) |
| IAa.129 | H | —P(=O)(OH)(O-phenyl) |
| IAa.130 | H | —P(=O)(OH)(OCH₂-phenyl) |
| IAa.131 | H | —P(=O)(OH)(O-oxetan-3-yl) |
| IAa.132 | H | —P(=O)(OH)(O-tetrahydrofuran-2-yl) |
| IAa.133 | H | —P(=O)(OH)(O-tetrahydrofuran-3-yl) |
| IAa.134 | H | —P(=O)(OH)(O-tetrahydropyran-2-yl) |
| IAa.135 | H | —P(=O)(OH)(O-tetrahydropyran-3-yl) |
| IAa.136 | H | —P(=O)(OH)(O-tetrahydropyran-4-yl) |
| IAa.137 | H | —P(=O)(OH)(OCH₂-oxiran-2-yl) |
| IAa.138 | H | —P(=O)(OH)(OCH₂-oxetan-3-yl) |
| IAa.139 | H | —P(=O)(OH)(OCH₂-tetrahydrofuran-2-yl) |
| IAa.140 | H | —P(=O)(OH)(OCH₂-tetrahydrofuran-3-yl) |
| IAa.141 | H | —P(=O)(OH)(OCH₂-pyrrolidin-1-yl) |
| IAa.142 | H | —P(=O)(OH)[OCH₂-(2-pyrrolidon-1-yl)] |
| IAa.143 | H | —P(=O)(OH)(OCH₂-tetrahydropyran-2-yl) |
| IAa.144 | H | —P(=O)(OH)(OCH₂-tetrahydropyran-3-yl) |
| IAa.145 | H | —P(=O)(OH)(OCH₂-tetrahydropyran-4-yl) |
| IAa.146 | H | —P(=O)(OH)(OCH₂-piperidin-1-yl) |
| IAa.147 | H | —P(=O)(OH)(OCH₂-morpholin-4-yl) |
| IAa.148 | H | —P(=O)(OCH₃)(OC₂H₅) |
| IAa.149 | H | —P(=O)(OCH₃)[O-(n-C₃H₇)] |
| IAa.150 | H | —P(=O)(OCH₃)[OCH(CH₃)₂] |
| IAa.151 | H | —P(=O)(OCH₃)[O-(n-C₄H₉)] |
| IAa.152 | H | —P(=O)(OCH₃)[OCH₂—CH(CH₃)₂] |
| IAa.153 | H | —P(=O)(OCH₃)[OCH(CH₃)—C₂H₅] |
| IAa.154 | H | —P(=O)(OCH₃)(OCH₂—CF₃) |
| IAa.155 | H | —P(=O)(OCH₃)(OCH₂—CH₂—OH) |
| IAa.156 | H | —P(=O)(OCH₃)(OCH₂—CH₂—CN) |
| IAa.157 | H | —P(=O)(OCH₃)(OCH₂—CH₂—OCH₃) |
| IAa.158 | H | —P(=O)(OCH₃)(OCH₂—CH₂—OC₂H₅) |
| IAa.159 | H | —P(=O)(OCH₃)(OCH₂—CH₂—OCF₃) |
| IAa.160 | H | —P(=O)(OCH₃)(OCH₂—CH₂—OCH₂—CH=CH₂) |
| IAa.161 | H | —P(=O)(OCH₃)(OCH₂—CH₂—OCH₂—C≡CH) |
| IAa.162 | H | —P(=O)(OCH₃)(OCH₂—CH₂—O-cyclopentyl) |
| IAa.163 | H | —P(=O)(OCH₃)(OCH₂—CH₂—NH₂) |
| IAa.164 | H | —P(=O)(OCH₃)(OCH₂—CH₂—NH—CH₃) |
| IAa.165 | H | —P(=O)(OCH₃)[OCH₂—CH₂—N(CH₃)₂] |
| IAa.166 | H | —P(=O)(OCH₃)(OCH₂—CH₂—SCH₃) |
| IAa.167 | H | —P(=O)(OCH₃)(OCH₂—CH₂—SC₂H₅) |
| IAa.168 | H | —P(=O)(OCH₃)(OCH₂—CH₂—SCF₃) |
| IAa.169 | H | —P(=O)(OCH₃)(OCH₂—CH₂—SCH₂—CH=CH₂) |
| IAa.170 | H | —P(=O)(OCH₃)(OCH₂—CH₂—SCH₂—C≡CH) |
| IAa.171 | H | —P(=O)(OCH₃)(OCH₂—CH₂—SO—CH₃) |
| IAa.172 | H | —P(=O)(OCH₃)(OCH₂—CH₂—SO—C₂H₅) |
| IAa.173 | H | —P(=O)(OCH₃)(OCH₂—SO₂—CH₃) |
| IAa.174 | H | —P(=O)(OCH₃)(OCH₂—SO₂—C₂H₅) |
| IAa.175 | H | —P(=O)(OCH₃)(OCH₂—CH₂—SO₂—CH₃) |
| IAa.176 | H | —P(=O)(OCH₃)(OCH₂—CH₂—SO₂—C₂H₅) |
| IAa.177 | H | —P(=O)(OCH₃)(OCH₂—CH=CH₂) |
| IAa.178 | H | —P(=O)(OCH₃)(OCH₂—CH=CH—CH₃) |
| IAa.179 | H | —P(=O)(OCH₃)(OCH₂—CH₂—CH=CH₂) |
| IAa.180 | H | —P(=O)(OCH₃)(OCH₂—CH=CH—Cl) |
| IAa.181 | H | —P(=O)(OCH₃)(OCH₂—C≡CH) |
| IAa.182 | H | —P(=O)(OCH₃)[OCH(CH₃)—C≡CH] |
| IAa.183 | H | —P(=O)(OCH₃)(OCH₂—CO—OCH₃) |
| IAa.184 | H | —P(=O)(OCH₃)(OCH₂—CO—OC₂H₅) |
| IAa.185 | H | —P(=O)(OCH₃)[OCH(CH₃)—CO—OCH₃] |
| IAa.186 | H | —P(=O)(OCH₃)[OCH(CH₃)—CO—OC₂H₅] |
| IAa.187 | H | —P(=O)(OCH₃)(OCH₂—CO—NH₂) |
| IAa.188 | H | —P(=O)(OCH₃)(OCH₂—CO—NH—CH₃) |
| IAa.189 | H | —P(=O)(OCH₃)[OCH₂—CO—N(CH₃)₂] |

TABLE 1-continued

IAa

| No. | R⁴ | —P(=Y¹)(Y²R¹)(Y³R²) |
|---|---|---|
| IAa.190 | H | —P(=O)(OCH₃)[OCH(CH₃)—CO—NH₂] |
| IAa.191 | H | —P(=O)(OCH₃)[OCH(CH₃)—CO—NH—CH₃] |
| IAa.192 | H | —P(=O)(OCH₃)[OCH(CH₃)—CO—N(CH₃)₂] |
| IAa.193 | H | —P(=O)(OCH₃)(O-cyclopropyl) |
| IAa.194 | H | —P(=O)(OCH₃)(O-cyclobutyl) |
| IAa.195 | H | —P(=O)(OCH₃)(O-cyclopentyl) |
| IAa.196 | H | —P(=O)(OCH₃)(O-cyclohexyl) |
| IAa.197 | H | —P(=O)(OCH₃)(OCH₂-cyclopropyl) |
| IAa.198 | H | —P(=O)(OCH₃)(OCH₂-cyclobutyl) |
| IAa.199 | H | —P(=O)(OCH₃)(OCH₂-cyclopentyl) |
| IAa.200 | H | —P(=O)(OCH₃)(OCH₂-cyclohexyl) |
| IAa.201 | H | —P(=O)(OCH₃)(O-phenyl) |
| IAa.202 | H | —P(=O)(OCH₃)(OCH₂-phenyl) |
| IAa.203 | H | —P(=O)(OCH₃)(O-oxetan-3-yl) |
| IAa.204 | H | —P(=O)(OCH₃)(O-tetrahydrofuran-2-yl) |
| IAa.205 | H | —P(=O)(OCH₃)(O-tetrahydrofuran-3-yl) |
| IAa.206 | H | —P(=O)(OCH₃)(O-tetrahydropyran-2-yl) |
| IAa.207 | H | —P(=O)(OCH₃)(O-tetrahydropyran-3-yl) |
| IAa.208 | H | —P(=O)(OCH₃)(O-tetrahydropyran-4-yl) |
| IAa.209 | H | —P(=O)(OCH₃)(OCH₂-oxiran-2-yl) |
| IAa.210 | H | —P(=O)(OCH₃)(OCH₂-oxetan-3-yl) |
| IAa.211 | H | —P(=O)(OCH₃)(OCH₂-tetrahydrofuran-2-yl) |
| IAa.212 | H | —P(=O)(OCH₃)(OCH₂-tetrahydrofuran-3-yl) |
| IAa.213 | H | —P(=O)(OCH₃)(OCH₂-pyrrolidin-1-yl) |
| IAa.214 | H | —P(=O)(OCH₃)[OCH₂-(2-pyrrolidon-1-yl)] |
| IAa.215 | H | —P(=O)(OCH₃)(OCH₂-tetrahydropyran-2-yl) |
| IAa.216 | H | —P(=O)(OCH₃)(OCH₂-tetrahydropyran-3-yl) |
| IAa.217 | H | —P(=O)(OCH₃)(OCH₂-tetrahydropyran-4-yl) |
| IAa.218 | H | —P(=O)(OCH₃)(OCH₂-piperidin-1-yl) |
| IAa.219 | H | —P(=O)(OCH₃)(OCH₂-morpholin-4-yl) |
| IAa.220 | H | —P(=O)(OC₂H₅)[O-(n-C₃H₇)] |
| IAa.221 | H | —P(=O)(OC₂H₅)[OCH(CH₃)₂] |
| IAa.222 | H | —P(=O)(OC₂H₅)[O-(n-C₄H₉)] |
| IAa.223 | H | —P(=O)(OC₂H₅)[OCH₂—CH(CH₃)₂] |
| IAa.224 | H | —P(=O)(OC₂H₅)[OCH(CH₃)—C₂H₅] |
| IAa.225 | H | —P(=O)(OC₂H₅)(OCH₂—CF₃) |
| IAa.226 | H | —P(=O)(OC₂H₅)(OCH₂—CH₂—OH) |
| IAa.227 | H | —P(=O)(OC₂H₅)(OCH₂—CH₂—CN) |
| IAa.228 | H | —P(=O)(OC₂H₅)(OCH₂—CH₂—OCH₃) |
| IAa.229 | H | —P(=O)(OC₂H₅)(OCH₂—CH₂—OC₂H₅) |
| IAa.230 | H | —P(=O)(OC₂H₅)(OCH₂—CH₂—OCF₃) |
| IAa.231 | H | —P(=O)(OC₂H₅)(OCH₂—CH₂—OCH₂—CH=CH₂) |
| IAa.232 | H | —P(=O)(OC₂H₅)(OCH₂—CH₂—OCH₂—C≡CH) |
| IAa.233 | H | —P(=O)(OC₂H₅)(OCH₂—CH₂—O-cyclopentyl) |
| IAa.234 | H | —P(=O)(OC₂H₅)(OCH₂—CH₂—NH₂) |
| IAa.235 | H | —P(=O)(OC₂H₅)(OCH₂—CH₂—NH—CH₃) |
| IAa.236 | H | —P(=O)(OC₂H₅)[OCH₂—CH₂—N(CH₃)₂] |
| IAa.237 | H | —P(=O)(OC₂H₅)(OCH₂—CH₂—SCH₃) |
| IAa.238 | H | —P(=O)(OC₂H₅)(OCH₂—CH₂—SC₂H₅) |
| IAa.239 | H | —P(=O)(OC₂H₅)(OCH₂—CH₂—SCF₃) |
| IAa.240 | H | —P(=O)(OC₂H₅)(OCH₂—CH₂—SCH₂—CH=CH₂) |
| IAa.241 | H | —P(=O)(OC₂H₅)(OCH₂—CH₂—SCH₂—C≡CH) |
| IAa.242 | H | —P(=O)(OC₂H₅)(OCH₂—CH₂—SO—CH₃) |
| IAa.243 | H | —P(=O)(OC₂H₅)(OCH₂—CH₂—SO—C₂H₅) |
| IAa.244 | H | —P(=O)(OC₂H₅)(OCH₂—CH₂—SO₂—CH₃) |
| IAa.245 | H | —P(=O)(OC₂H₅)(OCH₂—CH₂—SO₂—C₂H₅) |
| IAa.246 | H | —P(=O)(OC₂H₅)(OCH₂—CH₂—SO₂—CH₃) |
| IAa.247 | H | —P(=O)(OC₂H₅)(OCH₂—CH₂—SO₂—C₂H₅) |
| IAa.248 | H | —P(=O)(OC₂H₅)(OCH₂—CH=CH₂) |
| IAa.249 | H | —P(=O)(OC₂H₅)(OCH₂—CH=CH—CH₃) |
| IAa.250 | H | —P(=O)(OC₂H₅)(OCH₂—CH₂—CH=CH₂) |
| IAa.251 | H | —P(=O)(OC₂H₅)(OCH₂—CH=CH—Cl) |
| IAa.252 | H | —P(=O)(OC₂H₅)(OCH₂—C≡CH) |
| IAa.253 | H | —P(=O)(OC₂H₅)[OCH(CH₃)—C≡CH] |
| IAa.254 | H | —P(=O)(OC₂H₅)(OCH₂—CO—OCH₃) |
| IAa.255 | H | —P(=O)(OC₂H₅)(OCH₂—CO—OC₂H₅) |
| IAa.256 | H | —P(=O)(OC₂H₅)[OCH(CH₃)—CO—OCH₃] |
| IAa.257 | H | —P(=O)(OC₂H₅)[OCH(CH₃)—CO—OC₂H₅] |
| IAa.258 | H | —P(=O)(OC₂H₅)(OCH₂—CO—NH₂) |
| IAa.259 | H | —P(=O)(OC₂H₅)(OCH₂—CO—NH—CH₃) |
| IAa.260 | H | —P(=O)(OC₂H₅)[OCH₂—CO—N(CH₃)₂] |
| IAa.261 | H | —P(=O)(OC₂H₅)[OCH(CH₃)—CO—NH₂] |
| IAa.262 | H | —P(=O)(OC₂H₅)[OCH(CH₃)—CO—NH—CH₃] |
| IAa.263 | H | —P(=O)(OC₂H₅)[OCH(CH₃)—CO—N(CH₃)₂] |
| IAa.264 | H | —P(=O)(OC₂H₅)(O-cyclopropyl) |
| IAa.265 | H | —P(=O)(OC₂H₅)(O-cyclobutyl) |
| IAa.266 | H | —P(=O)(OC₂H₅)(O-cyclopentyl) |
| IAa.267 | H | —P(=O)(OC₂H₅)(O-cyclohexyl) |
| IAa.268 | H | —P(=O)(OC₂H₅)(OCH₂-cyclopropyl) |
| IAa.269 | H | —P(=O)(OC₂H₅)(OCH₂-cyclobutyl) |
| IAa.270 | H | —P(=O)(OC₂H₅)(OCH₂-cyclopentyl) |
| IAa.271 | H | —P(=O)(OC₂H₅)(OCH₂-cyclohexyl) |
| IAa.272 | H | —P(=O)(OC₂H₅)(O-phenyl) |
| IAa.273 | H | —P(=O)(OC₂H₅)(OCH₂-phenyl) |
| IAa.274 | H | —P(=O)(OC₂H₅)(O-oxetan-3-yl) |
| IAa.275 | H | —P(=O)(OC₂H₅)(O-tetrahydrofuran-2-yl) |
| IAa.276 | H | —P(=O)(OC₂H₅)(O-tetrahydrofuran-3-yl) |
| IAa.277 | H | —P(=O)(OC₂H₅)(O-tetrahydropyran-2-yl) |
| IAa.278 | H | —P(=O)(OC₂H₅)(O-tetrahydropyran-3-yl) |
| IAa.279 | H | —P(=O)(OC₂H₅)(O-tetrahydropyran-4-yl) |
| IAa.280 | H | —P(=O)(OC₂H₅)(OCH₂-oxiran-2-yl) |
| IAa.281 | H | —P(=O)(OC₂H₅)(OCH₂-oxetan-3-yl) |
| IAa.282 | H | —P(=O)(OC₂H₅)(OCH₂-tetrahydrofuran-2-yl) |
| IAa.283 | H | —P(=O)(OC₂H₅)(OCH₂-tetrahydrofuran-3-yl) |
| IAa.284 | H | —P(=O)(OC₂H₅)(OCH₂-pyrrolidin-1-yl) |
| IAa.285 | H | —P(=O)(OC₂H₅)[OCH₂-(2-pyrrolidon-1-yl)] |
| IAa.286 | H | —P(=O)(OC₂H₅)(OCH₂-tetrahydropyran-2-yl) |
| IAa.287 | H | —P(=O)(OC₂H₅)(OCH₂-tetrahydropyran-3-yl) |
| IAa.288 | H | —P(=O)(OC₂H₅)(OCH₂-tetrahydropyran-4-yl) |
| IAa.289 | H | —P(=O)(OC₂H₅)(OCH₂-piperidin-1-yl) |
| IAa.290 | H | —P(=O)(OC₂H₅)(OCH₂-morpholin-4-yl) |
| IAa.291 | H | —P(=O)(1,2-phenylenedioxy) |
| IAa.292 | H | —P(=O)(O—CH₂—CH₂—O) |
| IAa.293 | H | —P(=O)[O—CH(CH₃)—CH₂—O] |
| IAa.294 | H | —P(=O)(O—CH(CH₃)—CH(CH₃)—O) |
| IAa.295 | H | —P(=O)[O—CH(COOCH₃)—CH(COOCH₃)—O] |
| IAa.296 | H | —P(=O)(O—CH₂—CH₂—CH₂—O) |
| IAa.297 | H | —P(=O)[O—CH₂—C(CH₃)₂—CH₂—O] |
| IAa.298 | H | —P(=O)(O—CH₂—CH₂—CH₂—CH₂—O) |
| IAa.299 | H | —P(=S)(OH)₂ |
| IAa.300 | H | —P(=S)(OCH₃)₂ |
| IAa.301 | H | —P(=S)(OC₂H₅)₂ |
| IAa.302 | H | —P(=S)[O-(n-C₃H₇)]₂ |
| IAa.303 | H | —P(=S)[O-(n-C₄H₉)]₂ |
| IAa.304 | H | —P(=S)(O—CH₂—CH₂—CH₂—O) |
| IAa.305 | H | —P(=O)(NH₂)₂ |
| IAa.306 | H | —P(=O)(NH—CH₃)₂ |
| IAa.307 | H | —P(=O)[N(CH₃)₂]₂ |
| IAa.308 | H | —P(=O)(NH—C₂H₅)₂ |
| IAa.309 | H | —P(=O)[N(C₂H₅)₂]₂ |
| IAa.310 | H | —P(=O)(NH—CH₂—CH=CH₂)₂ |
| IAa.311 | H | —P(=O)(NH—CH₂—C≡CH)₂ |

TABLE 1-continued

IAa

Structure: F$_3$C and CH$_3$ substituted pyrimidine-2,4-dione with N-phenyl group bearing R$^4$, Cl, and —CH$_2$—CH$_2$—P(=Y$^1$)(Y$^2$R$^1$)(Y$^3$R$^2$) substituents.

| No. | R$^4$ | —P(=Y$^1$)(Y$^2$R$^1$)(Y$^3$R$^2$) |
|---|---|---|
| IAa.312 | H | —P(=O)(NH-cyclopropyl)$_2$ |
| IAa.313 | H | —P(=O)(NH—CH$_2$-cyclopentyl)$_2$ |
| IAa.314 | H | —P(=O)(NH-phenyl)$_2$ |
| IAa.315 | H | —P(=O)(NH—CH$_2$-phenyl)$_2$ |
| IAa.316 | H | —P(=O)(pyrrolidin-1-yl)$_2$ |
| IAa.317 | H | —P(=O)(2-methoxycarbonylpyrrolidin-1-yl)$_2$ |
| IAa.318 | H | —P(=O)(NH—CH$_2$—CO—OCH$_3$)$_2$ |
| IAa.319 | H | —P(=O)[N(CH$_3$)—CH$_2$—CO—OCH$_3$]$_2$ |
| IAa.320 | H | —P(=O)(NH—CH$_2$—CO—OC$_2$H$_5$)$_2$ |
| IAa.321 | H | —P(=O)[N(CH$_3$)—CH$_2$—CO—OC$_2$H$_5$]$_2$ |
| IAa.322 | H | —P(=O)[NH—CH(CH$_3$)—CO—OCH$_3$]$_2$ |
| IAa.323 | H | —P(=O)(OH)(NH$_2$) |
| IAa.324 | H | —P(=O)(OH)(NH—CH$_3$) |
| IAa.325 | H | —P(=O)(OH)[N(CH$_3$)$_2$] |
| IAa.326 | H | —P(=O)(OH)(NH—C$_2$H$_5$) |
| IAa.327 | H | —P(=O)(OH)[N(C$_2$H$_5$)$_2$] |
| IAa.328 | H | —P(=O)(OH)(NH—CH$_2$—CH=CH$_2$) |
| IAa.329 | H | —P(=O)(OH)(NH—CH$_2$—C≡CH) |
| IAa.330 | H | —P(=O)(OH)(NH-cyclopropyl) |
| IAa.331 | H | —P(=O)(OH)(NH—CH$_2$-cyclopentyl) |
| IAa.332 | H | —P(=O)(OH)(NH-phenyl) |
| IAa.333 | H | —P(=O)(OH)(NH—CH$_2$-phenyl) |
| IAa.334 | H | —P(=O)(OH)(pyrrolidin-1-yl) |
| IAa.335 | H | —P(=O)(OH)(2-methoxycarbonylpyrrolidin-1-yl) |
| IAa.336 | H | —P(=O)(OH)(NH—CH$_2$—CO—OCH$_3$) |
| IAa.337 | H | —P(=O)(OH)[N(CH$_3$)—CH$_2$—CO—OCH$_3$] |
| IAa.338 | H | —P(=O)(OH)(NH—CH$_2$—CO—OC$_2$H$_5$) |
| IAa.339 | H | —P(=O)(OH)[N(CH$_3$)—CH$_2$—CO—OC$_2$H$_5$] |
| IAa.340 | H | —P(=O)(OH)[NH—CH(CH$_3$)—CO—OCH$_3$] |
| IAa.341 | H | —P(=O)(OCH$_3$)(NH$_2$) |
| IAa.342 | H | —P(=O)(OCH$_3$)(NH—CH$_3$) |
| IAa.343 | H | —P(=O)(OCH$_3$)[N(CH$_3$)$_2$] |
| IAa.344 | H | —P(=O)(OCH$_3$)(NH—C$_2$H$_5$) |
| IAa.345 | H | —P(=O)(OCH$_3$)[N(C$_2$H$_5$)$_2$] |
| IAa.346 | H | —P(=O)(OCH$_3$)(NH—CH$_2$—CH=CH$_2$) |
| IAa.347 | H | —P(=O)(OCH$_3$)(NH—CH$_2$—C≡CH) |
| IAa.348 | H | —P(=O)(OCH$_3$)(NH-cyclopropyl) |
| IAa.349 | H | —P(=O)(OCH$_3$)(NH—CH$_2$-cyclopentyl) |
| IAa.350 | H | —P(=O)(OCH$_3$)(NH-phenyl) |
| IAa.351 | H | —P(=O)(OCH$_3$)(NH—CH$_2$-phenyl) |
| IAa.352 | H | —P(=O)(OCH$_3$)(pyrrolidin-1-yl) |
| IAa.353 | H | —P(=O)(OCH$_3$)(2-methoxycarbonylpyrrolidin-1-yl) |
| IAa.354 | H | —P(=O)(OCH$_3$)(NH—CH$_2$—CO—OCH$_3$) |
| IAa.355 | H | —P(=O)(OCH$_3$)[N(CH$_3$)—CH$_2$—CO—OCH$_3$] |
| IAa.356 | H | —P(=O)(OCH$_3$)(NH—CH$_2$—CO—OC$_2$H$_5$) |
| IAa.357 | H | —P(=O)(OCH$_3$)[N(CH$_3$)—CH$_2$—CO—OC$_2$H$_5$] |
| IAa.358 | H | —P(=O)(OCH$_3$)[NH—CH(CH$_3$)—CO—OCH$_3$] |
| IAa.359 | H | —P(=O)(OC$_2$H$_5$)(NH$_2$) |
| IAa.360 | H | —P(=O)(OC$_2$H$_5$)(NH—CH$_3$) |
| IAa.361 | H | —P(=O)(OC$_2$H$_5$)[N(CH$_3$)$_2$] |
| IAa.362 | H | —P(=O)(OC$_2$H$_5$)(NH—C$_2$H$_5$) |
| IAa.363 | H | —P(=O)(OC$_2$H$_5$)[N(C$_2$H$_5$)$_2$] |
| IAa.364 | H | —P(=O)(OC$_2$H$_5$)(NH—CH$_2$—CH=CH$_2$) |
| IAa.365 | H | —P(=O)(OC$_2$H$_5$)(NH—CH$_2$—C≡CH) |
| IAa.366 | H | —P(=O)(OC$_2$H$_5$)(NH-cyclopropyl) |
| IAa.367 | H | —P(=O)(OC$_2$H$_5$)(NH—CH$_2$-cyclopentyl) |
| IAa.368 | H | —P(=O)(OC$_2$H$_5$)(NH-phenyl) |
| IAa.369 | H | —P(=O)(OC$_2$H$_5$)(NH—CH$_2$-phenyl) |
| IAa.370 | H | —P(=O)(OC$_2$H$_5$)(pyrrolidin-1-yl) |
| IAa.371 | H | —P(=O)(OC$_2$H$_5$)(2-methoxycarbonylpyrrolidin-1-yl) |
| IAa.372 | H | —P(=O)(OC$_2$H$_5$)(NH—CH$_2$—CO—OCH$_3$) |
| IAa.373 | H | —P(=O)(OC$_2$H$_5$)[N(CH$_3$)—CH$_2$—CO—OCH$_3$] |
| IAa.374 | H | —P(=O)(OC$_2$H$_5$)(NH—CH$_2$—CO—OC$_2$H$_5$) |
| IAa.375 | H | —P(=O)(OC$_2$H$_5$)[N(CH$_3$)—CH$_2$—CO—OC$_2$H$_5$] |
| IAa.376 | H | —P(=O)(OC$_2$H$_5$)[NH—CH(CH$_3$)—CO—OCH$_3$] |
| IAa.377 | H | —P(=O)[N(CH$_3$)$_2$](OCH$_3$) |
| IAa.378 | H | —P(=O)[N(CH$_3$)$_2$](OC$_2$H$_5$) |
| IAa.379 | H | —P(=O)[N(CH$_3$)$_2$][O-(n-C$_3$H$_7$)] |
| IAa.380 | H | —P(=O)[N(CH$_3$)$_2$][OCH(CH$_3$)$_2$] |
| IAa.381 | H | —P(=O)[N(CH$_3$)$_2$][O-(n-C$_4$H$_9$)] |
| IAa.382 | H | —P(=O)[N(CH$_3$)$_2$](OCH$_2$—CH=CH$_2$) |
| IAa.383 | H | —P(=O)[N(CH$_3$)$_2$](OCH$_2$—C≡CH) |
| IAa.384 | H | —P(=O)[N(CH$_3$)$_2$](O-cyclohexyl) |
| IAa.385 | H | —P(=O)[N(CH$_3$)$_2$](OCH$_2$-cyclohexyl) |
| IAa.386 | H | —P(=O)[N(CH$_3$)$_2$](O-phenyl) |
| IAa.387 | H | —P(=O)[N(CH$_3$)$_2$](OCH$_2$-phenyl) |
| IAa.388 | H | —P(=O)[N(CH$_3$)$_2$](O-tetrahydrofuran-2-yl) |
| IAa.389 | H | —P(=O)[N(CH$_3$)$_2$](OCH$_2$-oxetan-3-yl) |
| IAa.390 | H | —P(=O)[N(CH$_3$)$_2$](OCH$_2$—CF$_3$) |
| IAa.391 | H | —P(=O)[N(CH$_3$)$_2$](OCH$_2$—CO—OCH$_3$) |
| IAa.392 | H | —P(=O)[N(CH$_3$)$_2$](OCH$_2$—CO—OC$_2$H$_5$) |
| IAa.393 | H | —P(=O)(NH—CH$_2$—CH$_2$—O) |
| IAa.394 | H | —P(=O)(NH—CH$_2$—CH$_2$—NH) |
| IAa.395 | H | —P(=O)[N(CH$_3$)—CH$_2$—CH$_2$—N(CH$_3$)] |
| IAa.396 | H | —P(=O)(NH—CH$_2$—CH$_2$—CH$_2$—O) |
| IAa.397 | H | —P(=O)(NH—CH$_2$—CH$_2$—CH$_2$—NH) |
| IAa.398 | H | —P(=O)[N(CH$_3$)—CH$_2$—CH$_2$—CH$_2$—N(CH$_3$)] |
| IAa.399 | H | —P(=O)[O—CH$_2$—CH(CH$_3$)—CH$_2$—O] |
| IAa.400 | H | —P(=O)(NH—CH$_2$—CH$_2$—CH$_2$—NH) |
| IAa.401 | H | —P(=O)[N(CH$_3$)—CH$_2$—C(CH$_3$)$_2$—CH$_2$—N(CH$_3$)] |
| IAa.402 | H | —P(=O)[NH—CH$_2$—CH$_2$—CH$_2$—CH$_2$—O] |
| IAa.403 | H | —P(=O)[NH—CH$_2$—CH$_2$—CH$_2$—CH$_2$—NH] |
| IAa.404 | H | —P(=S)(NH$_2$)$_2$ |
| IAa.405 | H | —P(=S)(NH—CH$_3$)$_2$ |
| IAa.406 | H | —P(=S)[N(CH$_3$)$_2$]$_2$ |
| IAa.407 | H | —P(=S)(NH—C$_2$H$_5$)$_2$ |
| IAa.408 | H | —P(=S)[N(C$_2$H$_5$)$_2$]$_2$ |
| IAa.409 | H | —P(=S)(NH—CH$_2$—CH$_2$—O) |
| IAa.410 | H | —P(=S)(NH—CH$_2$—CH$_2$—NH) |
| IAa.411 | H | —P(=S)[N(CH$_3$)—CH$_2$—CH$_2$—CH$_2$—N(CH$_3$)] |
| IAa.412 | H | —P(=O)(SCH$_3$)$_2$ |
| IAa.413 | H | —P(=O)(SC$_2$H$_5$)$_2$ |
| IAa.414 | H | —P(=O)[S-(n-C$_3$H$_7$)]$_2$ |
| IAa.415 | H | —P(=O)[SCH(CH$_3$)$_2$]$_2$ |
| IAa.416 | H | —P(=O)[S-(n-C$_4$H$_9$)]$_2$ |
| IAa.417 | H | —P(=O)(SCH$_2$—CH=CH$_2$)$_2$ |
| IAa.418 | H | —P(=O)(S-phenyl)$_2$ |
| IAa.419 | H | —P(=O)(SCH$_2$-phenyl)$_2$ |
| IAa.420 | H | —P(=O)(SCH$_2$—CO—OCH$_3$)$_2$ |
| IAa.421 | H | —P(=O)(SCH$_2$—CO—OC$_2$H$_5$)$_2$ |
| IAa.422 | H | —P(=O)(S—CH$_2$—CH$_2$—CH$_2$—S) |
| IAa.423 | H | —P(=O)(S—CH$_2$—CH$_2$—CH$_2$—O) |
| IAa.424 | H | —P(=S)(SCH$_3$)$_2$ |
| IAa.425 | H | —P(=S)(SC$_2$H$_5$)$_2$ |
| IAa.426 | H | —P(=S)[S-(n-C$_3$H$_7$)]$_2$ |
| IAa.427 | H | —P(=S)[S-n-C$_4$H$_9$]$_2$ |
| IAa.428 | H | —P(=S)(S—CH$_2$—CH$_2$—CH$_2$—S) |
| IAa.429 | H | —P(=S)(S—CH$_2$—CH$_2$—CH$_2$—O) |
| IAa.430 | Cl | —P(=O)(OH)$_2$ |
| IAa.431 | Cl | —P(=O)(OCH$_3$)$_2$ |
| IAa.432 | Cl | —P(=O)(OC$_2$H$_5$)$_2$ |
| IAa.433 | Cl | —P(=O)(O-(n-C$_3$H$_7$)]$_2$ |

TABLE 1-continued

IAa

| No. | $R^4$ | $-P(=Y^1)(Y^2R^1)(Y^3R^2)$ |
|---|---|---|
| IAa.434 | Cl | $-P(=O)[OCH(CH_3)_2]_2$ |
| IAa.435 | Cl | $-P(=O)(O-(n-C_4H_9)]_2$ |
| IAa.436 | Cl | $-P(=O)[OCH_2-CH(CH_3)_2]_2$ |
| IAa.437 | Cl | $-P(=O)[OCH(CH_3)-C_2H_5]_2$ |
| IAa.438 | Cl | $-P(=O)(OCH_2-CF_3)_2$ |
| IAa.439 | Cl | $-P(=O)(OCH_2-CH_2-OH)_2$ |
| IAa.440 | Cl | $-P(=O)(OCH_2-CH_2-CN)_2$ |
| IAa.441 | Cl | $-P(=O)(OCH_2-CH_2-OCH_3)_2$ |
| IAa.442 | Cl | $-P(=O)(OCH_2-CH_2-OC_2H_5)_2$ |
| IAa.443 | Cl | $-P(=O)(OCH_2-CH_2-OCF_3)_2$ |
| IAa.444 | Cl | $-P(=O)(OCH_2-CH_2-OCH_2-CH=CH_2)_2$ |
| IAa.445 | Cl | $-P(=O)(OCH_2-CH_2-OCH_2-C\equiv CH)_2$ |
| IAa.446 | Cl | $-P(=O)(OCH_2-CH_2-O-cyclopentyl)_2$ |
| IAa.447 | Cl | $-P(=O)(OCH_2-CH_2-NH_2)_2$ |
| IAa.448 | Cl | $-P(=O)(OCH_2-CH_2-NH-CH_3)_2$ |
| IAa.449 | Cl | $-P(=O)[OCH_2-CH_2-N(CH_3)_2]_2$ |
| IAa.450 | Cl | $-P(=O)(OCH_2-CH_2-SCH_3)_2$ |
| IAa.451 | Cl | $-P(=O)(OCH_2-CH_2-SC_2H_5)_2$ |
| IAa.452 | Cl | $-P(=O)(OCH_2-CH_2-SCF_3)_2$ |
| IAa.453 | Cl | $-P(=O)(OCH_2-CH_2-SCH_2-CH=CH_2)_2$ |
| IAa.454 | Cl | $-P(=O)(OCH_2-CH_2-SCH_2-C\equiv CH)_2$ |
| IAa.455 | Cl | $-P(=O)(OCH_2-CH_2-SO-CH_3)_2$ |
| IAa.456 | Cl | $-P(=O)(OCH_2-CH_2-SO-C_2H_5)_2$ |
| IAa.457 | Cl | $-P(=O)(OCH_2-SO_2-CH_3)_2$ |
| IAa.458 | Cl | $-P(=O)(OCH_2-SO_2-C_2H_5)_2$ |
| IAa.459 | Cl | $-P(=O)(OCH_2-CH_2-SO_2-CH_3)_2$ |
| IAa.460 | Cl | $-P(=O)(OCH_2-CH_2-SO_2-C_2H_5)_2$ |
| IAa.461 | Cl | $-P(=O)(OCH_2CH=CH_2)_2$ |
| IAa.462 | Cl | $-P(=O)(OCH_2-CH=CH-CH_3)_2$ |
| IAa.463 | Cl | $-P(=O)(OCH_2-CH_2-CH=CH_2)_2$ |
| IAa.464 | Cl | $-P(=O)(OCH_2-CH=CH-Cl)_2$ |
| IAa.465 | Cl | $-P(=O)(OCH_2-C\equiv CH)_2$ |
| IAa.466 | Cl | $-P(=O)[OCH(CH_3)-C\equiv CH]_2$ |
| IAa.467 | Cl | $-P(=O)(OCH_2-CO-OCH_3)_2$ |
| IAa.468 | Cl | $-P(=O)(OCH_2-CO-OC_2H_5)_2$ |
| IAa.469 | Cl | $-P(=O)[OCH(CH_3)-CO-OCH_3]_2$ |
| IAa.470 | Cl | $-P(=O)[OCH(CH_3)-CO-OC_2H_5]_2$ |
| IAa.471 | Cl | $-P(=O)(OCH_2-CO-NH_2)_2$ |
| IAa.472 | Cl | $-P(=O)(OCH_2-CO-NH-CH_3)_2$ |
| IAa.473 | Cl | $-P(=O)[OCH_2-CO-N(CH_3)_2]_2$ |
| IAa.474 | Cl | $-P(=O)[OCH(CH_3)-CO-NH_2]_2$ |
| IAa.475 | Cl | $-P(=O)[OCH(CH_3)-CO-NH-CH_3]_2$ |
| IAa.476 | Cl | $-P(=O)[OCH(CH_3)-CO-N(CH_3)_2]_2$ |
| IAa.477 | Cl | $-P(=O)(O-cyclopropyl)_2$ |
| IAa.478 | Cl | $-P(=O)(O-cyclobutyl)_2$ |
| IAa.479 | Cl | $-P(=O)(O-cyclopentyl)_2$ |
| IAa.480 | Cl | $-P(=O)(O-cyclohexyl)_2$ |
| IAa.481 | Cl | $-P(=O)(OCH_2-cyclopropyl)_2$ |
| IAa.482 | Cl | $-P(=O)(OCH_2-cyclobutyl)_2$ |
| IAa.483 | Cl | $-P(=O)(OCH_2-cyclopentyl)_2$ |
| IAa.484 | Cl | $-P(=O)(OCH_2-cyclohexyl)_2$ |
| IAa.485 | Cl | $-P(=O)(O-phenyl)_2$ |
| IAa.486 | Cl | $-P(=O)(OCH_2-phenyl)_2$ |
| IAa.487 | Cl | $-P(=O)(O-oxetan-3-yl)_2$ |
| IAa.488 | Cl | $-P(=O)(O-tetrahydrofuran-2-yl)_2$ |
| IAa.489 | Cl | $-P(=O)(O-tetrahydrofuran-3-yl)_2$ |
| IAa.490 | Cl | $-P(=O)(O-tetrahydropyran-2-yl)_2$ |
| IAa.491 | Cl | $-P(=O)(O-tetrahydropyran-3-yl)_2$ |
| IAa.492 | Cl | $-P(=O)(O-tetrahydropyran-4-yl)_2$ |
| IAa.493 | Cl | $-P(=O)(OCH_2-oxiran-2-yl)_2$ |
| IAa.494 | Cl | $-P(=O)(OCH_2-oxetan-3-yl)_2$ |
| IAa.495 | Cl | $-P(=O)(OCH_2-tetrahydrofuran-2-yl)_2$ |
| IAa.496 | Cl | $-P(=O)(OCH_2-tetrahydrofuran-3-yl)_2$ |
| IAa.497 | Cl | $-P(=O)(OCH_2-pyrrolidin-1-yl)_2$ |
| IAa.498 | Cl | $-P(=O)[OCH_2-(2-pyrrolidon-1-yl)]_2$ |
| IAa.499 | Cl | $-P(=O)(OCH_2-tetrahydropyran-2-yl)_2$ |
| IAa.500 | Cl | $-P(=O)(OCH_2-tetrahydropyran-3-yl)_2$ |
| IAa.501 | Cl | $-P(=O)(OCH_2-tetrahydropyran-4-yl)_2$ |
| IAa.502 | Cl | $-P(=O)(OCH_2-piperidin-1-yl)_2$ |
| IAa.503 | Cl | $-P(=O)(OCH_2-morpholin-4-yl)_2$ |
| IAa.504 | Cl | $-P(=O)(OH)(OCH_3)$ |
| IAa.505 | Cl | $-P(=O)(OH)(OC_2H_5)$ |
| IAa.506 | Cl | $-P(=O)(OH)[O-[n-C_3H_7)]$ |
| IAa.507 | Cl | $-P(=O)(OH)[OCH(CH_3)_2]$ |
| IAa.508 | Cl | $-P(=O)(OH)[O-(n-C_4H_9)]$ |
| IAa.509 | Cl | $-P(=O)(OH)[OCH_2-CH(CH_3)_2]$ |
| IAa.510 | Cl | $-P(=O)(OH)[OCH(CH_3)-C_2H_5]$ |
| IAa.511 | Cl | $-P(=O)(OH)(OCH_2-CF_3)$ |
| IAa.512 | Cl | $-P(=O)(OH)(OCH_2-CH_2-OH)$ |
| IAa.513 | Cl | $-P(=O)(OH)(OCH_2-CH_2-CN)$ |
| IAa.514 | Cl | $-P(=O)(OH)(OCH_2-CH_2-OCH_3)$ |
| IAa.515 | Cl | $-P(=O)(OH)(OCH_2-CH_2-OC_2H_5)$ |
| IAa.516 | Cl | $-P(=O)(OH)(OCH_2-CH_2-OCF_3)$ |
| IAa.517 | Cl | $-P(=O)(OH)(OCH_2-CH_2-OCH_2-CH=CH_2)$ |
| IAa.518 | Cl | $-P(=O)(OH)(OCH_2-CH_2-OCH_2-C\equiv CH)$ |
| IAa.519 | Cl | $-P(=O)(OH)(OCH_2-CH_2-O-cyclopentyl)$ |
| IAa.520 | Cl | $-P(=O)(OH)(OCH_2-CH_2-NH_2)$ |
| IAa.521 | Cl | $-P(=O)(OH)(OCH_2-CH_2-NH-CH_3)$ |
| IAa.522 | Cl | $-P(=O)(OH)[OCH_2-CH_2-N(CH_3)_2]$ |
| IAa.523 | Cl | $-P(=O)(OH)(OCH_2-CH_2-SCH_3)$ |
| IAa.524 | Cl | $-P(=O)(OH)(OCH_2-CH_2-SC_2H_5)$ |
| IAa.525 | Cl | $-P(=O)(OH)(OCH_2-CH_2-SCF_3)$ |
| IAa.526 | Cl | $-P(=O)(OH)(OCH_2-CH_2-SCH_2-CH=CH_2)$ |
| IAa.527 | Cl | $-P(=O)(OH)(OCH_2-CH_2-SCH_2-C\equiv CH)$ |
| IAa.528 | Cl | $-P(=O)(OH)(OCH_2-CH_2-SO-CH_3)$ |
| IAa.529 | Cl | $-P(=O)(OH)(OCH_2-CH_2-SO-C_2H_5)$ |
| IAa.530 | Cl | $-P(=O)(OH)(OCH_2-SO_2-CH_3)$ |
| IAa.531 | Cl | $-P(=O)(OH)(OCH_2-SO_2-C_2H_5)$ |
| IAa.532 | Cl | $-P(=O)(OH)(OCH_2-CH_2-SO_2-CH_3)$ |
| IAa.533 | Cl | $-P(=O)(OH)(OCH_2-CH_2-SO_2-C_2H_5)$ |
| IAa.534 | Cl | $-P(=O)(OH)(OCH_2-CH=CH_2)$ |
| IAa.535 | Cl | $-P(=O)(OH)(OCH_2-CH=CH-CH_3)$ |
| IAa.536 | Cl | $-P(=O)(OH)(OCH_2-CH_2-CH=CH_2)$ |
| IAa.537 | Cl | $-P(=O)(OH)(OCH_2-CH=CH-Cl)$ |
| IAa.538 | Cl | $-P(=O)(OH)(OCH_2-C\equiv CH)$ |
| IAa.539 | Cl | $-P(=O)(OH)[OCH(CH_3)-C\equiv CH]$ |
| IAa.540 | Cl | $-P(=O)(OH)(OCH_2-CO-OCH_3)$ |
| IAa.541 | Cl | $-P(=O)(OH)(OCH_2-CO-OC_2H_5)$ |
| IAa.542 | Cl | $-P(=O)(OH)[OCH(CH_3)-CO-OCH_3]$ |
| IAa.543 | Cl | $-P(=O)(OH)[OCH(CH_3)-CO-OC_2H_5]$ |
| IAa.544 | Cl | $-P(=O)(OH)(OCH_2-CO-NH_2)$ |
| IAa.545 | Cl | $-P(=O)(OH)(OCH_2-CO-NH-CH_3)$ |
| IAa.546 | Cl | $-P(=O)(OH)[OCH_2-CO-N(CH_3)_2]$ |
| IAa.547 | Cl | $-P(=O)(OH)[OCH(CH_3)-CO-NH_2]$ |
| IAa.548 | Cl | $-P(=O)(OH)[OCH(CH_3)-CO-NH-CH_3]$ |
| IAa.549 | Cl | $-P(=O)(OH)[OCH(CH_3)-CO-N(CH_3)_2]$ |
| IAa.550 | Cl | $-P(=O)(OH)(O-cyclopropyl)$ |
| IAa.551 | Cl | $-P(=O)(OH)(O-cyclobutyl)$ |
| IAa.552 | Cl | $-P(=O)(OH)(O-cyclopentyl)$ |
| IAa.553 | Cl | $-P(=O)(OH)(O-cyclohexyl)$ |
| IAa.554 | Cl | $-P(=O)(OH)(OCH_2-cyclopropyl)$ |
| IAa.555 | Cl | $-P(=O)(OH)(OCH_2-cyclobutyl)$ |

TABLE 1-continued

IAa

[Structure: 6-trifluoromethyl-1-methyl-3-(phenyl)pyrimidine-2,4-dione with R⁴ and Cl substituents on phenyl, and —CH₂—CH₂—P(=Y¹)(Y²R¹)(Y³R²) group]

| No. | R⁴ | —P(=Y¹)(Y²R¹)(Y³R²) |
|---|---|---|
| IAa.556 | Cl | —P(=O)(OH)(OCH₂-cyclopentyl) |
| IAa.557 | Cl | —P(=O)(OH)(OCH₂-cyclohexyl) |
| IAa.558 | Cl | —P(=O)(OH)(O-phenyl) |
| IAa.559 | Cl | —P(=O)(OH)(OCH₂-phenyl) |
| IAa.560 | Cl | —P(=O)(OH)(O-oxetan-3-yl) |
| IAa.561 | Cl | —P(=O)(OH)(O-tetrahydrofuran-2-yl) |
| IAa.562 | Cl | —P(=O)(OH)(O-tetrahydrofuran-3-yl) |
| IAa.563 | Cl | —P(=O)(OH)(O-tetrahydropyran-2-yl) |
| IAa.564 | Cl | —P(=O)(OH)(O-tetrahydropyran-3-yl) |
| IAa.565 | Cl | —P(=O)(OH)(O-tetrahydropyran-4-yl) |
| IAa.566 | Cl | —P(=O)(OH)(OCH₂-oxiran-2-yl) |
| IAa.567 | Cl | —P(=O)(OH)(OCH₂-oxetan-3-yl) |
| IAa.568 | Cl | —P(=O)(OH)(OCH₂-tetrahydrofuran-2-yl) |
| IAa.569 | Cl | —P(=O)(OH)(OCH₂-tetrahydrofuran-3-yl) |
| IAa.570 | Cl | —P(=O)(OH)(OCH₂-pyrrolidin-1-yl) |
| IAa.571 | Cl | —P(=O)(OH)[OCH₂-(2-pyrrolidon-1-yl)] |
| IAa.572 | Cl | —P(=O)(OH)(OCH₂-tetrahydropyran-2-yl) |
| IAa.573 | Cl | —P(=O)(OH)(OCH₂-tetrahydropyran-3-yl) |
| IAa.574 | Cl | —P(=O)(OH)(OCH₂-tetrahydropyran-4-yl) |
| IAa.575 | Cl | —P(=O)(OH)(OCH₂-piperidin-1-yl) |
| IAa.576 | Cl | —P(=O)(OH)(OCH₂-morpholin-4-yl) |
| IAa.577 | Cl | —P(=O)(OCH₃)(OC₂H₅) |
| IAa.578 | Cl | —P(=O)(OCH₃)[O-(n-C₃H₇)] |
| IAa.579 | Cl | —P(=O)(OCH₃)[OCH(CH₃)₂] |
| IAa.580 | Cl | —P(=O)(OCH₃)[O-(n-C₄H₉)] |
| IAa.581 | Cl | —P(=O)(OCH₃)[OCH₂—CH(CH₃)₂] |
| IAa.582 | Cl | —P(=O)(OCH₃)[OCH(CH₃)—C₂H₅] |
| IAa.583 | Cl | —P(=O)(OCH₃)(OCH₂—CF₃) |
| IAa.584 | Cl | —P(=O)(OCH₃)(OCH₂—CH₂—OH) |
| IAa.585 | Cl | —P(=O)(OCH₃)(OCH₂—CH₂—CN) |
| IAa.586 | Cl | —P(=O)(OCH₃)(OCH₂—CH₂—OCH₃) |
| IAa.587 | Cl | —P(=O)(OCH₃)(OCH₂—CH₂—OC₂H₅) |
| IAa.588 | Cl | —P(=O)(OCH₃)(OCH₂—CH₂—OCF₃) |
| IAa.589 | Cl | —P(=O)(OCH₃)(OCH₂—CH₂—OCH₂—CH=CH₂) |
| IAa.590 | Cl | —P(=O)(OCH₃)(OCH₂—CH₂—OCH₂—C≡CH) |
| IAa.591 | Cl | —P(=O)(OCH₃)(OCH₂—CH₂—O-cyclopentyl) |
| IAa.592 | Cl | —P(=O)(OCH₃)(OCH₂—CH₂—NH₂) |
| IAa.593 | Cl | —P(=O)(OCH₃)(OCH₂—CH₂—NH—CH₃) |
| IAa.594 | Cl | —P(=O)(OCH₃)[OCH₂—CH₂—N(CH₃)₂] |
| IAa.595 | Cl | —P(=O)(OCH₃)(OCH₂—CH₂—SCH₃) |
| IAa.596 | Cl | —P(=O)(OCH₃)(OCH₂—CH₂—SC₂H₅) |
| IAa.597 | Cl | —P(=O)(OCH₃)(OCH₂—CH₂—SCF₃) |
| IAa.598 | Cl | —P(=O)(OCH₃)(OCH₂—CH₂—SCH₂—CH=CH₂) |
| IAa.599 | Cl | —P(=O)(OCH₃)(OCH₂—CH₂—SCH₂—C≡CH) |
| IAa.600 | Cl | —P(=O)(OCH₃)(OCH₂—CH₂—SO—CH₃) |
| IAa.601 | Cl | —P(=O)(OCH₃)(OCH₂—CH₂—SO—C₂H₅) |
| IAa.602 | Cl | —P(=O)(OCH₃)(OCH₂—SO₂—CH₃) |
| IAa.603 | Cl | —P(=O)(OCH₃)(OCH₂—SO₂—C₂H₅) |
| IAa.604 | Cl | —P(=O)(OCH₃)(OCH₂—CH₂—SO₂—CH₃) |
| IAa.605 | Cl | —P(=O)(OCH₃)(OCH₂—CH₂—SO₂—C₂H₅) |
| IAa.606 | Cl | —P(=O)(OCH₃)(OCH₂—CH=CH₂) |
| IAa.607 | Cl | —P(=O)(OCH₃)(OCH₂—CH=CH—CH₃) |
| IAa.608 | Cl | —P(=O)(OCH₃)(OCH₂—CH₂—CH=CH₂) |
| IAa.609 | Cl | —P(=O)(OCH₃)(OCH₂—CH₂—CH₂—Cl) |
| IAa.610 | Cl | —P(=O)(OCH₃)(OCH₂—C≡CH) |
| IAa.611 | Cl | —P(=O)(OCH₃)[OCH(CH₃)—C≡CH] |
| IAa.612 | Cl | —P(=O)(OCH₃)(OCH₂—CO—OCH₃) |
| IAa.613 | Cl | —P(=O)(OCH₃)(OCH₂—CO—OC₂H₅) |
| IAa.614 | Cl | —P(=O)(OCH₃)[OCH(CH₃)—CO—OCH₃] |
| IAa.615 | Cl | —P(=O)(OCH₃)[OCH(CH₃)—CO—OC₂H₅] |
| IAa.616 | O | —P(=O)(OCH₃)(OCH₂—CO—NH₂) |
| IAa.617 | Cl | —P(=O)(OCH₃)(OCH₂—CO—NH—CH₃) |
| IAa.618 | Cl | —P(=O)(OCH₃)[OCH₂—CO—N(CH₃)₂] |
| IAa.619 | Cl | —P(=O)(OCH₃)[OCH(CH₃)—CO—NH₂] |
| IAa.620 | Cl | —P(=O)(OCH₃)[OCH(CH₃)—CO—NH—CH₃] |
| IAa.621 | Cl | —P(=O)(OCH₃)[OCH(CH₃)—CO—N(CH₃)₂] |
| IAa.622 | Cl | —P(=O)(OCH₃)(O-cyclopropyl) |
| IAa.623 | Cl | —P(=O)(OCH₃)(O-cyclobutyl) |
| IAa.624 | Cl | —P(=O)(OCH₃)(O-cyclopentyl) |
| IAa.625 | Cl | —P(=O)(OCH₃)(O-cyclohexyl) |
| IAa.626 | Cl | —P(=O)(OCH₃)(OCH₂-cyclopropyl) |
| IAa.627 | Cl | —P(=O)(OCH₃)(OCH₂-cyclobutyl) |
| IAa.628 | Cl | —P(=O)(OCH₃)(OCH₂-cyclopentyl) |
| IAa.629 | Cl | —P(=O)(OCH₃)(OCH₂-cyclohexyl) |
| IAa.630 | Cl | —P(=O)(OCH₃)(O-phenyl) |
| IAa.631 | Cl | —P(=O)(OCH₃)(OCH₂-phenyl) |
| IAa.632 | Cl | —P(=O)(OCH₃)(O-oxetan-3-yl) |
| IAa.633 | Cl | —P(=O)(OCH₃)(O-tetrahydrofuran-2-yl) |
| IAa.634 | Cl | —P(=O)(OCH₃)(O-tetrahydrofuran-3-yl) |
| IAa.635 | Cl | —P(=O)(OCH₃)(O-tetrahydropyran-2-yl) |
| IAa.636 | Cl | —P(=O)(OCH₃)(O-tetrahydropyran-3-yl) |
| IAa.637 | Cl | —P(=O)(OCH₃)(O-tetrahydropyran-4-yl) |
| IAa.638 | Cl | —P(=O)(OCH₃)(OCH₂-oxiran-2-yl) |
| IAa.639 | Cl | —P(=O)(OCH₃)(OCH₂-oxetan-3-yl) |
| IAa.640 | Cl | —P(=O)(OCH₃)(OCH₂-tetrahydrofuran-2-yl) |
| IAa.641 | Cl | —P(=O)(OCH₃)(OCH₂-tetrahydrofuran-3-yl) |
| IAa.642 | Cl | —P(=O)(OCH₃)(OCH₂-pyrrolidin-1-yl) |
| IAa.643 | Cl | —P(=O)(OCH₃)[OCH₂—(2-pyrrolidon-1-yl)] |
| IAa.644 | Cl | —P(=O)(OCH₃)(OCH₂-tetrahydropyran-2-yl) |
| IAa.645 | Cl | —P(=O)(OCH₃)(OCH₂-tetrahydropyran-3-yl) |
| IAa.646 | Cl | —P(=O)(OCH₃)(OCH₂-tetrahydropyran-4-yl) |
| IAa.647 | Cl | —P(=O)(OCH₃)(OCH₂-piperidin-1-yl) |
| IAa.648 | Cl | —P(=O)(OCH₃)(OCH₂-morpholin-4-yl) |
| IAa.649 | Cl | —P(=O)(OC₂H₅)[O-(n-C₃H₇)] |
| IAa.650 | Cl | —P(=O)(OC₂H₅)[OCH(CH₃)₂] |
| IAa.651 | Cl | —P(=O)(OC₂H₅)[O-(n-C₄H₉)] |
| IAa.652 | Cl | —P(=O)(OC₂H₅)[OCH₂—CH(CH₃)₂] |
| IAa.653 | Cl | —P(=O)(OC₂H₅)[OCH(CH₃)—C₂H₅] |
| IAa.654 | Cl | —P(=O)(OC₂H₅)(OCH₂—CF₃) |
| IAa.655 | Cl | —P(=O)(OC₂H₅)(OCH₂—CH₂—OH) |
| IAa.656 | Cl | —P(=O)(OC₂H₅)(OCH₂—CH₂—CN) |
| IAa.657 | Cl | —P(=O)(OC₂H₅)(OCH₂—CH₂—OCH₃) |
| IAa.658 | Cl | —P(=O)(OC₂H₅)(OCH₂—CH₂—OC₂H₅) |
| IAa.659 | Cl | —P(=O)(OC₂H₅)(OCH₂—CH₂—OCF₃) |
| IAa.660 | Cl | —P(=O)(OC₂H₅)(OCH₂—CH₂—OCH₂—CH=CH₂) |
| IAa.661 | Cl | —P(=O)(OC₂H₅)(OCH₂—CH₂—OCH₂—C≡CH) |
| IAa.662 | Cl | —P(=O)(OC₂H₅)(OCH₂—CH₂—O-cyclopentyl) |
| IAa.663 | Cl | —P(=O)(OC₂H₅)(OCH₂—CH₂—NH₂) |
| IAa.664 | Cl | —P(=O)(OC₂H₅)(OCH₂—CH₂—NH—CH₃) |
| IAa.665 | Cl | —P(=9)(OC₂H₅)[OCH₂—CH₂—N(CH₃)₂] |
| IAa.666 | Cl | —P(=O)(OC₂H₅)(OCH₂—CH₂—SCH₃) |
| IAa.667 | Cl | —P(=O)(OC₂H₅)(OCH₂—CH₂—SC₂H₅) |
| IAa.668 | Cl | —P(=O)(OC₂H₅)(OCH₂—CH₂—SCF₃) |
| IAa.669 | Cl | —P(=O)(OC₂H₅)(OCH₂—CH₂—SCH₂—CH=CH₂) |
| IAa.670 | Cl | —P(=O)(OC₂H₅)(OCH₂—CH₂—SCH₂—C≡CH) |
| IAa.671 | Cl | —P(=O)(OC₂H₅)(OCH₂—CH₂—SO—CH₃) |
| IAa.672 | Cl | —P(=O)(OC₂H₅)(OCH₂—CH₂—SO—C₂H₅) |
| IAa.673 | Cl | —P(=O)(OC₂H₅)(OCH₂—SO₂—CH₃) |
| IAa.674 | Cl | —P(=O)(OC₂H₅)(OCH₂—SO₂—C₂H₅) |
| IAa.675 | Cl | —P(=O)(OC₂H₅)(OCH₂—CH₂—SO₂—CH₃) |
| IAa.676 | Cl | —P(=O)(OC₂H₅)(OCH₂—CH₂—SO₂—C₂H₅) |
| IAa.677 | Cl | —P(=O)(OC₂H₅)(OCH₂—CH=CH₂) |

TABLE 1-continued

IAa

| No. | R⁴ | —P(=Y¹)(Y²R¹)(Y³R²) |
|---|---|---|
| IAa.678 | Cl | —P(=O)(OC₂H₅)(OCH₂—CH=CH—CH₃) |
| IAa.679 | Cl | —P(=O)(OC₂H₅)(OCH₂—CH₂—CH=CH₂) |
| IAa.680 | Cl | —P(=O)(OC₂H₅)(OCH₂—CH=CH—Cl) |
| IAa.681 | Cl | —P(=O)(OC₂H₅)(OCH₂—C≡CH) |
| IAa.682 | Cl | —P(=O)(OC₂H₅)[OCH(CH₃)—C≡CH] |
| IAa.683 | Cl | —P(=O)(OC₂H₅)(OCH₂—CO—OCH₃) |
| IAa.684 | Cl | —P(=O)(OC₂H₅)(OCH₂—CO—OC₂H₅) |
| IAa.685 | Cl | —P(=O)(OC₂H₅)[OCH(CH₃)—CO—OCH₃] |
| IAa.686 | Cl | —P(=O)(OC₂H₅)[OCH(CH₃)—CO—OC₂H₅] |
| IAa.687 | Cl | —P(=O)(OC₂H₅)(OCH₂—CO—NH₂) |
| IAa.688 | Cl | —P(=O)(OC₂H₅)(OCH₂—CO—NH—CH₃) |
| IAa.689 | Cl | —P(=O)(OC₂H₅)(OCH₂—CO—N(CH₃)₂) |
| IAa.690 | Cl | —P(=O)(OC₂H₅)[OCH(CH₃)—CO—NH₂] |
| IAa.691 | Cl | —P(=O)(OC₂H₅)[OCH(CH₃)—CO—NH—CH₃] |
| IAa.692 | Cl | —P(=O)(OC₂H₅)[OCH(CH₃)—CO—N(CH₃)₂] |
| IAa.693 | Cl | —P(=O)(OC₂H₅)(O-cyclopropyl) |
| IAa.694 | Cl | —P(=O)(OC₂H₅)(O-cyclobutyl) |
| IAa.695 | Cl | —P(=O)(OC₂H₅)(O-cyclopentyl) |
| IAa.696 | Cl | —P(=O)(OC₂H₅)(O-cyclohexyl) |
| IAa.697 | Cl | —P(=O)(OC₂H₅)(OCH₂-cyclopropyl) |
| IAa.698 | Cl | —P(=O)(OC₂H₅)(OCH₂-cyclobutyl) |
| IAa.699 | Cl | —P(=O)(OC₂H₅)(OCH₂-cyclopentyl) |
| IAa.700 | Cl | —P(=O)(OC₂H₅)(OCH₂-cyclohexyl) |
| IAa.701 | Cl | —P(=O)(OC₂H₅)(O-phenyl) |
| IAa.702 | Cl | —P(=O)(OC₂H₅)(OCH₂-phenyl) |
| IAa.703 | Cl | —P(=O)(OC₂H₅)(O-oxetan-3-yl) |
| IAa.704 | Cl | —P(=O)(OC₂H₅)(O-tetrahydrofuran-2-yl) |
| IAa.705 | Cl | —P(=O)(OC₂H₅)(O-tetrahydrofuran-3-yl) |
| IAa.706 | Cl | —P(=O)(OC₂H₅)(O-tetrahydropyran-2-yl) |
| IAa.707 | Cl | —P(=O)(OC₂H₅)(O-tetrahydropyran-3-yl) |
| IAa.708 | Cl | —P(=O)(OC₂H₅)(O-tetrahydropyran-4-yl) |
| IAa.709 | Cl | —P(=O)(OC₂H₅)(OCH₂-oxiran-2-yl) |
| IAa.710 | Cl | —P(=O)(OC₂H₅)(OCH₂-oxetan-3-yl) |
| IAa.711 | Cl | —P(=O)(OC₂H₅)(OCH₂-tetrahydrofuran-2-yl) |
| IAa.712 | Cl | —P(=O)(OC₂H₅)(OCH₂-tetrahydrofuran-3-yl) |
| IAa.713 | Cl | —P(=O)(OC₂H₅)(OCH₂-pyrrolidin-1-yl) |
| IAa.714 | Cl | —P(=O)(OC₂H₅)[OCH₂-(2-pyrrolidon-1-yl)] |
| IAa.715 | Cl | —P(=O)(OC₂H₅)(OCH₂-tetrahydropyran-2-yl) |
| IAa.716 | Cl | —P(=O)(OC₂H₅)(OCH₂-tetrahydropyran-3-yl) |
| IAa.717 | Cl | —P(=O)(OC₂H₅)(OCH₂-tetrahydropyran-4-yl) |
| IAa.718 | Cl | —P(=O)(OC₂H₅)(OCH₂-piperidin-1-yl) |
| IAa.719 | Cl | —P(=O)(OC₂H₅)(OCH₂-morpholin-4-yl) |
| IAa.720 | Cl | —P(=O)(1,2-phenylenedioxy) |
| IAa.721 | Cl | —P(=O)(O—CH₂—CH₂—O) |
| IAa.722 | Cl | —P(=O)[O—CH(CH₃)—CH₂—O] |
| IAa.723 | Cl | —P(=O)[O—CH(CH₃)—CH(CH₃)—O] |
| IAa.724 | Cl | —P(=O)[O—CH(COOCH₃)—CH(COOCH₃)—O] |
| IAa.725 | Cl | —P(=O)(O—CH₂—CH₂—CH₂—O) |
| IAa.726 | Cl | —P(=O)[O—CH₂—C(CH₃)₂—CH₂—O] |
| IAa.727 | Cl | —P(=O)(O—CH₂—CH₂—CH₂—CH₂—O) |
| IAa.728 | Cl | —P(=S)(OH)₂ |
| IAa.729 | Cl | —P(=S)(OCH₃)₂ |
| IAa.730 | Cl | —P(=S)(OC₂H₅)₂ |
| IAa.731 | Cl | —P(=S)[O-(n-C₃H₇)]₂ |
| IAa.732 | Cl | —P(=S)[O-(n-C₄C₉)]₂ |
| IAa.733 | Cl | —P(=S)(O—CH₂—CH₂—O) |
| IAa.734 | Cl | —P(=O)(NH₂)₂ |
| IAa.735 | Cl | —P(=O)(NH—CH₃)₂ |
| IAa.736 | Cl | —P(=O)[N(CH₃)₂]₂ |
| IAa.737 | Cl | —P(=O)(NH—C₂H₅)₂ |
| IAa.738 | Cl | —P(=O)[N(C₂H₅)₂]₂ |
| IAa.739 | Cl | —P(=O)(NH—CH₂—CH=CH₂)₂ |
| IAa.740 | Cl | —P(=O)(NH—CH₂—C≡CH)₂ |
| IAa.741 | Cl | —P(=O)NH-cyclopropyl)₂ |
| IAa.742 | Cl | —P(=O)(NH—CH₂-cyclopentyl)₂ |
| IAa.743 | Cl | —P(=O)(NH-phenyl)₂ |
| IAa.744 | Cl | —P(=O)(NH—CH₂-phenyl)₂ |
| IAa.745 | Cl | —P(=O)(pyrrolidin-1-yl)₂ |
| IAa.746 | Cl | —P(=O)(2-methoxycarbonylpyrrolidin-1-yl)₂ |
| IAa.747 | Cl | —P(=O)(NH—CH₂—CO—OCH₃)₂ |
| IAa.748 | Cl | —P(=O)[N(CH₃)—CH₂—CO—OCH₃]₂ |
| IAa.749 | Cl | —P(=O)(NH—CH₂—CO—OC₂H₅)₂ |
| IAa.750 | Cl | —P(=O)[N(CH₃)—CH₂—CO—OC₂H₅]₂ |
| IAa.751 | Cl | —P(=O)[NH—CH(CH₃)—CO—OCH₃]₂ |
| IAa.752 | Cl | —P(=O)(OH)(NH₂) |
| IAa.753 | Cl | —P(=O)(OH)(NH—CH₃) |
| IAa.754 | Cl | —P(=O)(OH)[N(CH₃)₂] |
| IAa.755 | Cl | —P(=O)(OH)(NH—C₂H₅) |
| IAa.756 | Cl | —P(=O)(OH)[N(C₂H₅)₂] |
| IAa.757 | Cl | —P(=O)(OH)(NH—CH₂—CH=CH₂) |
| IAa.758 | Cl | —P(=O)(OH)(NH—CH₂—C≡CH) |
| IAa.759 | Cl | —P(=O)(OH)(NH-cyclopropyl) |
| IAa.760 | Cl | —P(=O)(OH)(NH—CH₂-cyclopentyl) |
| IAa.761 | Cl | —P(=O)(OH)(NH-phenyl) |
| IAa.762 | Cl | —P(=O)(OH)(NH—CH₂-phenyl) |
| IAa.763 | Cl | —P(=O)(OH)(pyrrolidin-1-yl) |
| IAa.764 | Cl | —P(=O)(OH)(2-methoxycarbonylpyrrolidin-1-yl) |
| IAa.765 | Cl | —P(=O)(OH)(NH—CH₂—CO—OCH₃) |
| IAa.766 | Cl | —P(=O)(OH)[N(CH₃)—CH₂—CO—OCH₃] |
| IAa.767 | Cl | —P(=O)(OH)NH—CH₂—CO—OC₂H₅) |
| IAa.768 | Cl | —P(=O)(OH)[N(CH₃)—CH₂—CO—OC₂H₅] |
| IAa.769 | Cl | —P(=O)(OH)[NH—CH(CH₃)—CO—OCH₃] |
| IAa.770 | Cl | —P(=O)(OCH₃)(NH₂) |
| IAa.771 | Cl | —P(=O)(OCH₃)(NH—CH₃) |
| IAa.772 | Cl | —P(=O)(OCH₃)[N(CH₃)₂] |
| IAa.773 | Cl | —P(=O)(OCH₃)(NH—C₂H₅) |
| IAa.774 | Cl | —P(=O)(OCH₃)[N(C₂H₅)₂] |
| IAa.775 | Cl | —P(=O)(OCH₃)(NH—CH₂—CH=CH₂) |
| IAa.776 | Cl | —P(=O)(OCH₃)(NH—CH₂—C≡CH) |
| IAa.777 | Cl | —P(=O)(OCH₃)(NH-cyclopropyl) |
| IAa.778 | Cl | —P(=O)(OCH₃)(NH—CH₂-cyclopentyl) |
| IAa.779 | Cl | —P(=O)(OCH₃)(NH-phenyl) |
| IAa.780 | Cl | —P(=O)(OCH₃)(NH—CH₂-phenyl) |
| IAa.781 | Cl | —P(=O)(OCH₃)(pyrrolidin-1-yl) |
| IAa.782 | Cl | —P(=O)(OCH₃)(2-methoxycarbonylpyrrolidin-1-yl) |
| IAa.783 | Cl | —P(=O)(OCH₃)(NH—CH₂—CO—OCH₃) |
| IAa.784 | Cl | —P(=O)(OCH₃)[N(CH₃)—CH₂—CO—OCH₃] |
| IAa.785 | Cl | —P(=O)(OCH₃)(NH—CH₂—CO—OC₂H₅) |
| IAa.786 | Cl | —P(=O)(OCH₃)[N(CH₃)—CH₂—CO—OC₂H₅] |
| IAa.787 | Cl | —P(=O)(OCH₃)[NH—CH(CH₃)—CO—OCH₃] |
| IAa.788 | Cl | —P(=O)(OC₂H₅)(NH₂) |
| IAa.789 | Cl | —P(=O)(OC₂H₅)(NH—CH₃) |
| IAa.790 | Cl | —P(=O)(OC₂H₅)[N(CH₃)₂] |
| IAa.791 | Cl | —P(=O)(OC₂H₅)(NH—C₂H₅) |
| IAa.792 | Cl | —P(=O)(OC₂H₅)[N(C₂H₅)₂] |
| IAa.793 | Cl | —P(=O)(OC₂H₅)(NH—CH₂—CH=CH₂) |
| IAa.794 | Cl | —P(=O)(OC₂H₅)(NH—CH₂—C≡CH) |
| IAa.795 | Cl | —P(=O)(OC₂H₅)(NH-cyclopropyl) |
| IAa.796 | Cl | —P(=O)(OC₂H₅)(NH—CH₂-cyclopentyl) |
| IAa.797 | Cl | —P(=O)(OC₂H₅)(NH-phenyl) |
| IAa.798 | Cl | —P(=O)(OC₂H₅)(NH—CH₂-phenyl) |
| IAa.799 | Cl | —P(=O)(OC₂H₅)(pyrrolidin-1-yl) |

TABLE 1-continued

IAa

[Structure: pyrimidinedione with F₃C and CH₃ substituents on the ring, N-linked to a phenyl bearing R⁴ and Cl, with -CH₂-CH₂-P(=Y¹)(Y²R¹)(Y³R²) side chain]

| No. | R⁴ | —P(=Y¹)(Y²R¹)(Y³R²) |
|---|---|---|
| IAa.800 | Cl | —P(=O)(OC₂H₅)(2-methoxycarbonylpyrrolidin-1-yl) |
| IAa.801 | Cl | —P(=O)(OC₂H₅)(NH—CH₂—CO—OCH₃) |
| IAa.802 | Cl | —P(=O)(OC₂H₅)[N(CH₃)—CH₂—CO—OCH₃] |
| IAa.803 | Cl | —P(=O)(OC₂H₅)(NH—CH₂—CO—OC₂H₅) |
| IAa.804 | Cl | —P(=O)(OC₂H₅)[N(CH₃)—CH₂—CO—OC₂H₅] |
| IAa.805 | Cl | —P(=O)(OC₂H₅)[NH—CH(CH₃)—CO—OCH₃] |
| IAa.806 | Cl | —P(=O)[N(CH₃)₂](OCH₃) |
| IAa.807 | Cl | —P(=O)[N(CH₃)₂](OC₂H₅) |
| IAa.808 | Cl | —P(=O)[N(CH₃)₂][O-(n-C₃H₇)] |
| IAa.809 | Cl | —P(=O)[N(CH₃)₂][OCH(CH₃)₂] |
| IAa.810 | Cl | —P(=O)[N(CH₃)₂][O-(n-C₄H₉)] |
| IAa.811 | Cl | —P(=O)[N(CH₃)₂](OCH₂—CH=CH₂) |
| IAa.812 | Cl | —P(=O)[N(CH₃)₂](OCH₂—C≡CH) |
| IAa.813 | Cl | —P(=O)[N(CH₃)₂](O-cyclohexyl) |
| IAa.814 | Cl | —P(=O)[N(CH₃)₂](OCH₂-cyclohexyl) |
| IAa.815 | Cl | —P(=O)[N(CH₃)₂](O-phenyl) |
| IAa.816 | Cl | —P(=O)[N(CH₃)₂](OCH₂-phenyl) |
| IAa.817 | Cl | —P(=O)[N(CH₃)₂](O-tetrahydrofuran-2-yl) |
| IAa.818 | Cl | —P(=O)[N(CH₃)₂](OCH₂-oxetan-3-yl) |
| IAa.819 | Cl | —P(=O)[N(CH₃)₂](OCH₂—CF₃) |
| IAa.820 | Cl | —P(=O)[N(CH₃)₂](OCH₂—CO—OCH₃) |
| IAa.821 | Cl | —P(=O)[N(CH₃)₂](OCH₂—CO—OC₂H₅) |
| IAa.822 | Cl | —P(=O)(NH—CH₂—CH₂—O) |
| IAa.823 | Cl | —P(=O)(NH—CH₂—CH₂—NH) |
| IAa.824 | Cl | —P(=O)[N(CH₃)—CH₂—CH₂—N(CH₃)] |
| IAa.825 | Cl | —P(=O)(NH—CH₂—CH₂—CH₂—O) |
| IAa.826 | Cl | —P(=O)(NH—CH₂—CH₂—CH₂—NH) |
| IAa.827 | Cl | —P(=O)[N(CH₃)—CH₂—CH₂—CH₂—N(CH₃)] |
| IAa.828 | Cl | —P(=O)(O—CH₂—CH(CH₃)—CH₂—O) |
| IAa.829 | Cl | —P(=O)[NH—CH₂—CH₂—CH₂—N(CH₃)] |
| IAa.830 | Cl | —P(=O)[N(CH₃)—CH₂—C(CH₃)₂—CH₂—N(CH₃)] |
| IAa.831 | Cl | —P(=O)[NH—CH₂—CH₂—CH₂—CH₂—O] |
| IAa.832 | Cl | —P(=O)[NH—CH₂—CH₂—CH₂—CH₂—NH] |
| IAa.833 | Cl | —P(=S)(NH₂)₂ |
| IAa.834 | Cl | —P(=S)(NH—CH₃)₂ |
| IAa.835 | Cl | —P(=S)[N(CH₃)₂]₂ |
| IAa.836 | Cl | —P(=S)(NH—C₂H₅)₂ |
| IAa.837 | Cl | —P(=S)[N(C₂H₅)₂]₂ |
| IAa.838 | Cl | —P(=S)(NH—CH₂—CH₂—O) |
| IAa.839 | Cl | —P(=S)(NH—CH₂—CH₂—CH₂—NH) |
| IAa.840 | Cl | —P(=S)[N(CH₃)—CH₂—CH₂—CH₂—N(CH₃)] |
| IAa.841 | Cl | —P(=O)(SCH₃)₂ |
| IAa.842 | Cl | —P(=O)(SC₂H₅)₂ |
| IAa.843 | Cl | —P(=O)[S-(n-C₃H₇)]₂ |
| IAa.844 | Cl | —P(=O)[SCH(CH₃)₂]₂ |
| IAa.845 | Cl | —P(=O)[S-(n-C₄H₉)]₂ |
| IAa.846 | Cl | —P(=O)(SCH₂—CH=CH₂)₂ |
| IAa.847 | Cl | —P(=O)(S-phenyl)₂ |
| IAa.848 | Cl | —P(=O)(SCH₂—phenyl)₂ |
| IAa.849 | Cl | —P(=O)(SCH₂—CO—OCH₃)₂ |
| IAa.850 | Cl | —P(=O)(SCH₂—CO—OC₂H₅)₂ |
| IAa.851 | Cl | —P(=O)(S—CH₂—CH₂—CH₂—S) |
| IAa.852 | Cl | —P(=O)(S—CH₂—CH₂—CH₂—O) |
| IAa.853 | Cl | —P(=S)(SCH₃)₂ |
| IAa.854 | Cl | —P(=S)(SC₂H₅)₂ |
| IAa.855 | Cl | —P(=S)[S-(n-C₃H₇)]₂ |
| IAa.856 | Cl | —P(=S)[S-n-C₄H₉]₂ |
| IAa.857 | Cl | —P(=S)(S—CH₂—CH₂—CH₂—S) |
| IAa.858 | Cl | —P(=S)(S—CH₂—CH₂—CH₂—O) |
| IAa.859 | F | —P(=O)(OH)₂ |
| IAa.860 | F | —P(=O)(OCH₃)₂ |
| IAa.861 | F | —P(=O)(OC₂H₅)₂ |
| IAa.862 | F | —P(=O)[O-(n-C₃H₇)]₂ |
| IAa.863 | F | —P(=O)[OCH(CH₃)₂]₂ |
| IAa.864 | F | —P(=O)[O-(n-C₄H₉)]₂ |
| IAa.865 | F | —P(=O)[OCH₂—CH(CH₃)₂]₂ |
| IAa.866 | F | —P(=O)[OCH(CH₃)—C₂H₅]₂ |
| IAa.867 | F | —P(=O)(OCH₂—CF₃)₂ |
| IAa.868 | F | —P(=O)(OCH₂—CH₂—OH)₂ |
| IAa.869 | F | —P(=O)(OCH₂—CH₂—CN)₂ |
| IAa.870 | F | —P(=O)(OCH₂—CH₂—OCH₃)₂ |
| IAa.871 | F | —P(=O)(OCH₂—CH₂—OC₂H₅)₂ |
| IAa.872 | F | —P(=O)(OCH₂—CH₂—OCF₃)₂ |
| IAa.873 | F | —P(=O)(OCH₂—CH₂—OCH₂—CH=CH₂)₂ |
| IAa.874 | F | —P(=O)(OCH₂—CH₂—OCH₂—C≡CH)₂ |
| IAa.875 | F | —P(=O)(OCH₂—CH₂—O-cyclopentyl)₂ |
| IAa.876 | F | —P(=O)(OCH₂—CH₂—NH₂)₂ |
| IAa.877 | F | —P(=O)(OCH₂—CH₂—NH—CH₃)₂ |
| IAa.878 | F | —P(=O)[OCH₂—CH₂—N(CH₃)₂]₂ |
| IAa.879 | F | —P(=O)(OCH₂—CH₂—SCH₃)₂ |
| IAa.880 | F | —P(=O)(OCH₂—CH₂—SC₂H₅)₂ |
| IAa.881 | F | —P(=O)(OCH₂—CH₂—SCF₃)₂ |
| IAa.882 | F | —P(=O)(OCH₂—CH₂—SCH₂—CH=CH₂)₂ |
| IAa.883 | F | —P(=O)(OCH₂—CH₂—SCH₂—C≡CH)₂ |
| IAa.884 | F | —P(=O)(OCH₂—CH₂—SO—CH₃)₂ |
| IAa.885 | F | —P(=O)(OCH₂—CH₂—SO—C₂H₅)₂ |
| IAa.886 | F | —P(=O)(OCH₂—SO₂—CH₃)₂ |
| IAa.887 | F | —P(=O)(OCH₂—SO₂—C₂H₅)₂ |
| IAa.888 | F | —P(=O)(OCH₂—CH₂—SO₂—CH₃)₂ |
| IAa.889 | F | —P(=O)(OCH₂—CH₂—SO₂—C₂H₅)₂ |
| IAa.890 | F | —P(=O)(OCH₂—CH=CH₂)₂ |
| IAa.891 | F | —P(=O)(OCH₂—CH=CH—CH₃)₂ |
| IAa.892 | F | —P(=O)(OCH₂—CH₂—CH=CH₂)₂ |
| IAa.893 | F | —P(=O)(OCH₂—CH=CH—Cl)₂ |
| IAa.894 | F | —P(=O)(OCH₂—C≡CH)₂ |
| IAa.895 | F | —P(=O)[OCH(CH₃)—C≡CH]₂ |
| IAa.896 | F | —P(=O)(OCH₂—CO—OCH₃)₂ |
| IAa.897 | F | —P(=O)(OCH₂—CO—OC₂H₅)₂ |
| IAa.898 | F | —P(=O)[OCH(CH₃)—CO—OCH₃]₂ |
| IAa.899 | F | —P(=O)[OCH(CH₃)—CO—OC₂H₅]₂ |
| IAa.900 | F | —P(=O)(OCH₂—CO—NH₂)₂ |
| IAa.901 | F | —P(=O)(OCH₂—CO—NH—CH₃)₂ |
| IAa.902 | F | —P(=O)[OCH₂—CO—N(CH₃)₂]₂ |
| IAa.903 | F | —P(=O)[OCH(CH₃)—CO—NH₂]₂ |
| IAa.904 | F | —P(=O)[OCH(CH₃)—CO—NH—CH₃]₂ |
| IAa.905 | F | —P(=O)[OCH(CH₃)—CO—N(CH₃)₂]₂ |
| IAa.906 | F | —P(=O)(O-cyclopropyl)₂ |
| IAa.907 | F | —P(=O)(O-cyclobutyl)₂ |
| IAa.908 | F | —P(=O)(O-cyclopentyl)₂ |
| IAa.909 | F | —P(=O)(O-cyclohexyl)₂ |
| IAa.910 | F | —P(=O)(OCH₂-cyclopropyl)₂ |
| IAa.911 | F | —P(=O)(OCH₂-cyclobutyl)₂ |
| IAa.912 | F | —P(=O)(OCH₂-cyclopentyl)₂ |
| IAa.913 | F | —P(=O)(OCH₂-cyclohexyl)₂ |
| IAa.914 | F | —P(=O)(O-phenyl)₂ |
| IAa.915 | F | —P(=O)(OCH₂-phenyl)₂ |
| IAa.916 | F | —P(=O)(O-oxetan-3-yl)₂ |
| IAa.917 | F | —P(=O)(O-tetrahydrofuran-2-yl)₂ |
| IAa.918 | F | —P(=O)(O-tetrahydrofuran-3-yl)₂ |
| IAa.919 | F | —P(=O)(O-tetrahydropyran-2-yl)₂ |
| IAa.920 | F | —P(=O)(O-tetrahydropyran-3-yl)₂ |
| IAa.921 | F | —P(=O)(O-tetrahydropyran-4-yl)₂ |

TABLE 1-continued

IAa

[Structure: 1-methyl-6-trifluoromethyl pyrimidine-2,4-dione with N-substituted phenyl group bearing R⁴, Cl, and CH₂—CH₂—P(=Y¹)(Y²R¹)(Y³R²) substituents]

| No. | R⁴ | —P(=Y¹)(Y²R¹)(Y³R²) |
|---|---|---|
| IAa.922 | F | —P(=O)(OCH₂-oxiran-2-yl)₂ |
| IAa.923 | F | —P(=O)(OCH₂-oxetan-3-yl)₂ |
| IAa.924 | F | —P(=O)(OCH₂-tetrahydrofuran-2-yl)₂ |
| IAa.925 | F | —P(=O)(OCH₂-tetrahydrofuran-3-yl)₂ |
| IAa.926 | F | —P(=O)(OCH₂-pyrrolidin-1-yl)₂ |
| IAa.927 | F | —P(=O)[OCH₂-(2-pyrrolidon-1-yl)₂ |
| IAa.928 | F | —P(=O)(OCH₂-tetrahydropyran-2-yl)]₂ |
| IAa.929 | F | —P(=O)(OCH₂-tetrahydropyran-3-yl)₂ |
| IAa.930 | F | —P(=O)(OCH₂-tetrahydropyran-4-yl)₂ |
| IAa.931 | F | —P(=O)(OCH₂-piperidin-1-yl)₂ |
| IAa.932 | F | —P(=O)(OCH₂-morpholin-4-yl)₂ |
| IAa.933 | F | —P(=O)(OH)(OCH₃) |
| IAa.934 | F | —P(=O)(OH)(OC₂H₅) |
| IAa.935 | F | —P(=O)(OH)[O-[n-C₃H₇]] |
| IAa.936 | F | —P(=O)(OH)[OCH(CH₃)₂] |
| IAa.937 | F | —P(=O)(OH)[O-(n-C₄H₉)] |
| IAa.938 | F | —P(=O)(OH)[OCH₂—CH(CH₃)₂] |
| IAa.939 | F | —P(=O)(OH)[OCH(CH₃)—C₂H₅] |
| IAa.940 | F | —P(=O)(OH)(OCH₂—CF₃) |
| IAa.941 | F | —P(=O)(OH)(OCH₂—CH₂—OH) |
| IAa.942 | F | —P(=O)(OH)(OCH₂—CH₂—CN) |
| IAa.943 | F | —P(=O)(OH)(OCH₂—CH₂—OCH₃) |
| IAa.944 | F | —P(=O)(OH)(OCH₂—CH₂—OC₂H₅) |
| IAa.945 | F | —P(=O)(OH)(OCH₂—CH₂—OCF₃) |
| IAa.946 | F | —P(=O)(OH)(OCH₂—CH₂—OCH₂—CH=CH₂) |
| IAa.947 | F | —P(=O)(OH)(OCH₂—CH₂—OCH₂—C≡CH) |
| IAa.948 | F | —P(=O)(OH)(OCH₂—CH₂—O-cyclopentyl) |
| IAa.949 | F | —P(=O)(OH)(OCH₂—CH₂—NH₂) |
| IAa.950 | F | —P(=O)(OH)(OCH₂—CH₂—NH—CH₃) |
| IAa.951 | F | —P(=O)(OH)[OCH₂—CH₂—N(CH₃)₂] |
| IAa.952 | F | —P(=O)(OH)(OCH₂—CH₂—SCH₃) |
| IAa.953 | F | —P(=O)(OH)(OCH₂—CH₂—SC₂H₅) |
| IAa.954 | F | —P(=O)(OH)(OCH₂—CH₂—SCF₃) |
| IAa.955 | F | —P(=O)(OH)(OCH₂—CH₂—SCH₂—CH=CH₂) |
| IAa.956 | F | —P(=O)(OH)(OCH₂—CH₂—SCH₂—C≡CH) |
| IAa.957 | F | —P(=O)(OH)(OCH₂—CH₂—SO—CH₃) |
| IAa.958 | F | —P(=O)(OH)(OCH₂—CH₂—SO—C₂H₅) |
| IAa.959 | F | —P(=O)(OH)(OCH₂—SO₂—CH₃) |
| IAa.960 | F | —P(=O)(OH)(OCH₂—SO₂—C₂H₅) |
| IAa.961 | F | —P(=O)(OH)(OCH₂—CH₂—SO₂—CH₃) |
| IAa.962 | F | —P(=O)(OH)(OCH₂—CH₂—SO₂—C₂H₅) |
| IAa.963 | F | —P(=O)(OH)(OCH₂—CH=CH₂) |
| IAa.964 | F | —P(=O)(OH)(OCH₂—CH=CH—CH₃) |
| IAa.965 | F | —P(=O)(OH)(OCH₂—CH₂—CH=CH₂) |
| IAa.966 | F | —P(=O)(OH)(OCH₂—CH=CH—Cl) |
| IAa.967 | F | —P(=O)(OH)(OCH₂—C≡CH) |
| IAa.968 | F | —P(=O)(OH)[OCH(CH₃)—C≡CH] |
| IAa.969 | F | —P(=O)(OH)(OCH₂—CO—OCH₃) |
| IAa.970 | F | —P(=O)(OH)(OCH₂—CO—OC₂H₅) |
| IAa.971 | F | —P(=O)(OH)[OCH(CH₃)—CO—OCH₃] |
| IAa.972 | F | —P(=O)(OH)[OCH(CH₃)—CO—OC₂H₅] |
| IAa.973 | F | —P(=O)(OH)(OCH₂—CO—NH₂) |
| IAa.974 | F | —P(=O)(OH)(OCH₂—CO—NH—CH₃) |
| IAa.975 | F | —P(=O)(OH)[OCH₂—CO—N(CH₃)₂] |
| IAa.976 | F | —P(=O)(OH)[OCH(CH₃)—CO—NH₂] |
| IAa.977 | F | —P(=O)(OH)[OCH(CH₃)—CO—NH—CH₃] |
| IAa.978 | F | —P(=O)(OH)[OCH(CH₃)—CO—N(CH₃)₂] |
| IAa.979 | F | —P(=O)(OH)(O-cyclopropyl) |
| IAa.980 | F | —P(=O)(OH)(O-cyclobutyl) |
| IAa.981 | F | —P(=O)(OH)(O-cyclopentyl) |
| IAa.982 | F | —P(=O)(OH)(O-cyclohexyl) |
| IAa.983 | F | —P(=O)(OH)(OCH₂-cyclopropyl) |
| IAa.984 | F | —P(=O)(OH)(OCH₂-cyclobutyl) |
| IAa.985 | F | —P(=O)(OH)(OCH₂-cyclopentyl) |
| IAa.986 | F | —P(=O)(OH)(OCH₂-cyclohexyl) |
| IAa.987 | F | —P(=O)(OH)(O-phenyl) |
| IAa.988 | F | —P(=O)(OH)(OCH₂-phenyl) |
| IAa.989 | F | —P(=O)(OH)(O-oxetan-3-yl) |
| IAa.990 | F | —P(=O)(OH)(O-tetrahydrofuran-2-yl) |
| IAa.991 | F | —P(=O)(OH)(O-tetrahydrofuran-3-yl) |
| IAa.992 | F | —P(=O)(OH)(O-tetrahydropyran-2-yl) |
| IAa.993 | F | —P(=O)(OH)(O-tetrahydropyran-3-yl) |
| IAa.994 | F | —P(=O)(OH)(O-tetrahydropyran-4-yl) |
| IAa.995 | F | —P(=O)(OH)(OCH₂-oxiran-2-yl) |
| IAa.996 | F | —P(=O)(OH)(OCH₂-oxetan-3-yl) |
| IAa.997 | F | —P(=O)(OH)(OCH₂-tetrahydrofuran-2-yl) |
| IAa.998 | F | —P(=O)(OH)(OCH₂-tetrahydrofuran-3-yl) |
| IAa.999 | F | —P(=O)(OH)(OCH₂-pyrrolidin-1-yl) |
| IAa.1000 | F | —P(=O)(OH)[OCH₂-(2-pyrrolidon-1-yl)] |
| IAa.1001 | F | —P(=O)(OH)(OCH₂-tetrahydropyran-2-yl) |
| IAa.1002 | F | —P(=O)(OH)(OCH₂-tetrahydropyran-3-yl) |
| IAa.1003 | F | —P(=O)(OH)(OCH₂-tetrahydropyran-4-yl) |
| IAa.1004 | F | —P(=O)(OH)(OCH₂-piperidin-1-yl) |
| IAa.1005 | F | —P(=O)(OH)(OCH₂-morpholin-4-yl) |
| IAa.1006 | F | —P(=O)(OCH₃)(OC₂H₅) |
| IAa.1007 | F | —P(=O)(OCH₃)[O-(n-C₃H₇)] |
| IAa.1008 | F | —P(=O)(OCH₃)[OCH(CH₃)₂] |
| IAa.1009 | F | —P(=O)(OCH₃)[O-(n-C₄H₉)] |
| IAa.1010 | F | —P(=O)(OCH₃)[OCH₂—CH(CH₃)₂] |
| IAa.1011 | F | —P(=O)(OCH₃)[OCH(CH₃)—C₂H₅] |
| IAa.1012 | F | —P(=O)(OCH₃)(OCH₂—CF₃) |
| IAa.1013 | F | —P(=O)(OCH₃)(OCH₂—CH₂—OH) |
| IAa.1014 | F | —P(=O)(OCH₃)(OCH₂—CH₂—CN) |
| IAa.1015 | F | —P(=O)(OCH₃)(OCH₂—CH₂—OCH₃) |
| IAa.1016 | F | —P(=O)(OCH₃)(OCH₂—CH₂—OC₂H₅) |
| IAa.1017 | F | —P(=O)(OCH₃)(OCH₂—CH₂—OCF₃) |
| IAa.1018 | F | —P(=O)(OCH₃)(OCH₂—CH₂—OCH₂—CH=CH₂) |
| IAa.1019 | F | —P(=O)(OCH₃)(OCH₂—CH₂—OCH₂—C≡CH) |
| IAa.1020 | F | —P(=O)(OCH₃)(OCH₂—CH₂—O-cyclopentyl) |
| IAa.1021 | F | —P(=O)(OCH₃)(OCH₂—CH₂—NH₂) |
| IAa.1022 | F | —P(=O)(OCH₃)(OCH₂—CH₂—NH—CH₃) |
| IAa.1023 | F | —P(=O)(OCH₃)[OCH₂—CH₂—N(CH₃)₂] |
| IAa.1024 | F | —P(=O)(OCH₃)(OCH₂—CH₂—SCH₃) |
| IAa.1025 | F | —P(=O)(OCH₃)(OCH₂—CH₂—SC₂H₅) |
| IAa.1026 | F | —P(=O)(OCH₃)(OCH₂—CH₂—SCF₃) |
| IAa.1027 | F | —P(=O)(OCH₃)(OCH₂—CH₂—SCH₂—CH=CH₂) |
| IAa.1028 | F | —P(=O)(OCH₃)(OCH₂—CH₂—SCH₂—C≡CH) |
| IAa.1029 | F | —P(=O)(OCH₃)(OCH₂—CH₂—SO—CH₃) |
| IAa.1030 | F | —P(=O)(OCH₃)(OCH₂—CH₂—SO—C₂H₅) |
| IAa.1031 | F | —P(=O)(OCH₃)(OCH₂—SO₂—CH₃) |
| IAa.1032 | F | —P(=O)(OCH₃)(OCH₂—SO₂—C₂H₅) |
| IAa.1033 | F | —P(=O)(OCH₃)(OCH₂—CH₂—SO₂—CH₃) |
| IAa.1034 | F | —P(=O)(OCH₃)(OCH₂—CH₂—SO₂—C₂H₅) |
| IAa.1035 | F | —P(=O)(OCH₃)(OCH₂—CH=CH₂) |
| IAa.1036 | F | —P(=O)(OCH₃)(OCH₂—CH=CH—CH₃) |
| IAa.1037 | F | —P(=O)(OCH₃)(OCH₂—CH₂—CH=CH₂) |
| IAa.1038 | F | —P(=O)(OCH₃)(OCH₂—CH=CH—Cl) |
| IAa.1039 | F | —P(=O)(OCH₃)(OCH₂—C≡CH) |
| IAa.1040 | F | —P(=O)(OCH₃)[OCH(CH₃)—C≡CH] |
| IAa.1041 | F | —P(=O)(OCH₃)(OCH₂—CO—OCH₃) |
| IAa.1042 | F | —P(=O)(OCH₃)(OCH₂—CO—OC₂H₅) |
| IAa.1043 | F | —P(=O)(OCH₃)[OCH(CH₃)—CO—OCH₃] |

TABLE 1-continued

IAa

Structure: F₃C and CH₃ on pyrimidine ring (1-methyl, 6-trifluoromethyl pyrimidine-2,4-dione), N-linked to phenyl ring bearing R⁴, Cl, and —CH₂—CH₂—P(=Y¹)(Y²R¹)(Y³R²)

| No. | R⁴ | —P(=Y¹)(Y²R¹)(Y³R²) |
|---|---|---|
| IAa.1044 | F | —P(=O)(OCH₃)[OCH(CH₃)—CO—OC₂H₅] |
| IAa.1045 | F | —P(=O)(OCH₃)(OCH₂—CO—NH₂) |
| IAa.1046 | F | —P(=O)(OCH₃)(OCH₂—CO—NH—CH₃) |
| IAa.1047 | F | —P(=O)(OCH₃)[OCH₂—CO—N(CH₃)₂] |
| IAa.1048 | F | —P(=O)(OCH₃)[OCH(CH₃)—CO—NH₂] |
| IAa.1049 | F | —P(=O)(OCH₃)[OCH(CH₃)—CO—NH—CH₃] |
| IAa.1050 | F | —P(=O)(OCH₃)[OCH(CH₃)—CO—N(CH₃)₂] |
| IAa.1051 | F | —P(=O)(OCH₃)(O-cyclopropyl) |
| IAa.1052 | F | —P(=O)(OCH₃)(O-cyclobutyl) |
| IAa.1053 | F | —P(=O)(OCH₃)(O-cyclopentyl) |
| IAa.1054 | F | —P(=O)(OCH₃)(O-cyclohexyl) |
| IAa.1055 | F | —P(=O)(OCH₃)(OCH₂-cyclopropyl) |
| IAa.1056 | F | —P(=O)(OCH₃)(OCH₂-cyclobutyl) |
| IAa.1057 | F | —P(=O)(OCH₃)(OCH₂-cyclopentyl) |
| IAa.1058 | F | —P(=O)(OCH₃)(OCH₂-cyclohexyl) |
| IAa.1059 | F | —P(=O)(OCH₃)(O-phenyl) |
| IAa.1060 | F | —P(=O)(OCH₃)(OCH₂-phenyl) |
| IAa.1061 | F | —P(=O)(OCH₃)(O-oxetan-3-yl) |
| IAa.1062 | F | —P(=O)(OCH₃)(O-tetrahydrofuran-2-yl) |
| IAa.1063 | F | —P(=O)(OCH₃)(O-tetrahydrofuran-3-yl) |
| IAa.1064 | F | —P(=O)(OCH₃)(O-tetrahydropyran-2-yl) |
| IAa.1065 | F | —P(=O)(OCH₃)(O-tetrahydropyran-3-yl) |
| IAa.1066 | F | —P(=O)(OCH₃)(O-tetrahydropyran-4-yl) |
| IAa.1067 | F | —P(=O)(OCH₃)(OCH₂-oxiran-2-yl) |
| IAa.1068 | F | —P(=O)(OCH₃)(OCH₂-oxetan-3-yl) |
| IAa.1069 | F | —P(=O)(OCH₃)(OCH₂-tetrahydrofuran-2-yl) |
| IAa.1070 | F | —P(=O)(OCH₃)(OCH₂-tetrahydrofuran-3-yl) |
| IAa.1071 | F | —P(=O)(OCH₃)(OCH₂-pyrrolidin-1-yl) |
| IAa.1072 | F | —P(=O)(OCH₃)[OCH₂-(2-pyrrolidon-1-yl)] |
| IAa.1073 | F | —P(=O)(OCH₃)(OCH₂-tetrahydropyran-2-yl) |
| IAa.1074 | F | —P(=O)(OCH₃)(OCH₂-tetrahydropyran-3-yl) |
| IAa.1075 | F | —P(=O)(OCH₃)(OCH₂-tetrahydropyran-4-yl) |
| IAa.1076 | F | —P(=O)(OCH₃)(OCH₂-piperidin-1-yl) |
| IAa..1077 | F | —P(=O)(OCH₃)(OCH₂-morpholin-4-yl) |
| IAa.1078 | F | —P(=O)(OC₂H₅)[O-(n-C₃H₇)] |
| IAa.1079 | F | —P(=O)(OC₂H₅)[OCH(CH₃)₂] |
| IAa.1080 | F | —P(=O)(OC₂H₅)[O-(n-C₄H₉)] |
| IAa.1081 | F | —P(=O)(OC₂H₅)[OCH₂—CH(CH₃)₂] |
| IAa.1082 | F | —P(=O)(OC₂H₅)[OCH(CH₃)—C₂H₅] |
| IAa.1083 | F | —P(=O)(OC₂H₅)(OCH₂—CF₃) |
| IAa.1084 | F | —P(=O)(OC₂H₅)(OCH₂—CH₂—OH) |
| IAa.1085 | F | —P(=O)(OC₂H₅)(OCH₂—CH₂—CN) |
| IAa.1086 | F | —P(=O)(OC₂H₅)(OCH₂—CH₂—OCH₃) |
| IAa.1087 | F | —P(=O)(OC₂H₅)(OCH₂—CH₂—OC₂H₅) |
| IAa.1088 | F | —P(=O)(OC₂H₅)(OCH₂—CH₂—OCF₃) |
| IAa.1089 | F | —P(=O)(OC₂H₅)(OCH₂—CH₂—OCH₂—CH=CH₂) |
| IAa.1090 | F | —P(=O)(OC₂H₅)(OCH₂—CH₂—OCH₂—C≡CH) |
| IAa.1091 | F | —P(=O)(OC₂H₅)(OCH₂—CH₂—O-cyclopentyl) |
| IAa.1092 | F | —P(=O)(OC₂H₅)(OCH₂—CH₂—NH₂) |
| IAa.1093 | F | —P(=O)(OC₂H₅)(OCH₂—CH₂—NH—CH₃) |
| IAa.1094 | F | —P(=O)(OC₂H₅)[OCH₂—CH₂—N(CH₃)₂] |
| IAa.1095 | F | —P(=O)(OC₂H₅)(OCH₂—CH₂—SCH₃) |
| IAa.1096 | F | —P(=O)(OC₂H₅)(OCH₂—CH₂—SC₂H₅) |
| IAa.1097 | F | —P(=O)(OC₂H₅)(OCH₂—CH₂—SCF₃) |
| IAa.1098 | F | —P(=O)(OC₂H₅)(OCH₂—CH₂—SCH₂—CH=CH₂) |
| IAa.1099 | F | —P(=O)(OC₂H₅)(OCH₂—CH₂—SCH₂—C≡CH) |
| IAa.1100 | F | —P(=O)(OC₂H₅)(OCH₂—CH₂—SO—CH₃) |
| IAa.1101 | F | —P(=O)(OC₂H₅)(OCH₂—CH₂—SO—C₂H₅) |
| IAa.1102 | F | —P(=O)(OC₂H₅)(OCH₂—CH₂—SO₂—CH₃) |
| IAa.1103 | F | —P(=O)(OC₂H₅)(OCH₂—CH₂—SO₂—C₂H₅) |
| IAa.1104 | F | —P(=O)(OC₂H₅)(OCH₂—CH₂—SO₂—CH₃) |
| IAa.1105 | F | —P(=O)(OC₂H₅)(OCH₂—CH₂—SO₂—C₂H₅) |
| IAa.1106 | F | —P(=O)(OC₂H₅)(OCH₂—CH=CH₂) |
| IAa.1107 | F | —P(=O)(OC₂H₅)(OCH₂—CH=CH—CH₃) |
| IAa.1108 | F | —P(=O)(OC₂H₅)(OCH₂—CH₂—CH=CH₂) |
| IAa.1109 | F | —P(=O)(OC₂H₅)(OCH₂—CH=CH—Cl) |
| IAa.1110 | F | —P(=O)(OC₂H₅)(OCH₂—C≡CH) |
| IAa.1111 | F | —P(=O)(OC₂H₅)[OCH(CH₃)—C≡CH] |
| IAa.1112 | F | —P(=O)(OC₂H₅)(OCH₂—CO—OCH₃) |
| IAa.1113 | F | —P(=O)(OC₂H₅)(OCH₂—CO—OC₂H₅) |
| IAa.1114 | F | —P(=O)(OC₂H₅)[OCH(CH₃)—CO—OCH₃] |
| IAa.1115 | F | —P(=O)(OC₂H₅)[OCH(CH₃)—CO—OC₂H₅] |
| IAa.1116 | F | —P(=O)(OC₂H₅)(OCH₂—CO—NH₂) |
| IAa.1117 | F | —P(=O)(OC₂H₅)(OCH₂—CO—NH—CH₃) |
| IAa.1118 | F | —P(=O)(OC₂H₅)[OCH₂—CO—N(CH₃)₂] |
| IAa.1119 | F | —P(=O)(OC₂H₅)[OCH(CH₃)—CO—NH₂] |
| IAa.1120 | F | —P(=O)(OC₂H₅)[OCH(CH₃)—CO—NH—CH₃] |
| IAa.1121 | F | —P(=O)(OC₂H₅)[OCH(CH₃)—CO—N(CH₃)₂] |
| IAa.1122 | F | —P(=O)(OC₂H₅)(O-cyclopropyl) |
| IAa.1123 | F | —P(=O)(OC₂H₅)(O-cyclobutyl) |
| IAa.1124 | F | —P(=O)(OC₂H₅)(O-cyclopentyl) |
| IAa.1125 | F | —P(=O)(OC₂H₅)(O-cyclohexyl) |
| IAa.1126 | F | —P(=O)(OC₂H₅)(OCH₂-cyclopropyl) |
| IAa.1127 | F | —P(=O)(OC₂H₅)(OCH₂-cyclobutyl) |
| IAa.1128 | F | —P(=O)(OC₂H₅)(OCH₂-cyclopentyl) |
| IAa.1129 | F | —P(=O)(OC₂H₅)(OCH₂-cyclohexyl) |
| IAa.1130 | F | —P(=O)(OC₂H₅)(O-phenyl) |
| IAa.1131 | F | —P(=O)(OC₂H₅)(OCH₂-phenyl) |
| IAa.1132 | F | —P(=O)(OC₂H₅)(O-oxetan-3-yl) |
| IAa.1133 | F | —P(=O)(OC₂H₅)(O-tetrahydrofuran-2-yl) |
| IAa.1134 | F | —P(=O)(OC₂H₅)(O-tetrahydrofuran-3-yl) |
| IAa.1135 | F | —P(=O)(OC₂H₅)(O-tetrahydropyran-2-yl) |
| IAa.1136 | F | —P(=O)(OC₂H₅)(O-tetrahydropyran-3-yl) |
| IAa.1137 | F | —P(=O)(OC₂H₅)(O-tetrahydropyran-4-yl) |
| IAa.1138 | F | —P(=O)(OC₂H₅)(OCH₂-oxiran-2-yl) |
| IAa.1139 | F | —P(=O)(OC₂H₅)(OCH₂-oxetan-3-yl) |
| IAa.1140 | F | —P(=O)(OC₂H₅)(OCH₂-tetrahydrofuran-2-yl) |
| IAa.1141 | F | —P(=O)(OC₂H₅)(OCH₂-tetrahydrofuran-3-yl) |
| IAa.1142 | F | —P(=O)(OC₂H₅)(OCH₂-pyrrolidin-1-yl) |
| IAa.1143 | F | —P(=O)(OC₂H₅)[OCH₂-(2-pyrrolidon-1-yl)] |
| IAa.1144 | F | —P(=O)(OC₂H₅)(OCH₂-tetrahydropyran-2-yl) |
| IAa.1145 | F | —P(=O)(OC₂H₅)(OCH₂-tetrahydropyran-3-yl) |
| IAa.1146 | F | —P(=O)(OC₂H₅)(OCH₂-tetrahydropyran-4-yl) |
| IAa.1147 | F | —P(=O)(OC₂H₅)(OCH₂-piperidin-1-yl) |
| IAa.1148 | F | —P(=O)(OC₂H₅)(OCH₂-morpholin-4-yl) |
| IAa.1149 | F | —P(=O)(1,2-phenylenedioxy) |
| IAa.1150 | F | —P(=O)(O—CH₂—CH₂—O) |
| IAa.1151 | F | —P(=O)[O—CH(CH₃)—CH₂—O] |
| IAa.1152 | F | —P(=O)[O—CH(CH₃)—CH(CH₃)—O] |
| IAa.1153 | F | —P(=O)[O—CH(COOCH₃)—CH(COOCH₃)—O] |
| IAa.1154 | F | —P(=O)(O—CH₂—CH₂—CH₂—O) |
| IAa.1155 | F | —P(=O)[O—CH₂—C(CH₃)₂—CH₂—O] |
| IAa.1156 | F | —P(=O)(O—CH₂—CH₂—CH₂—CH₂—O) |
| IAa.1157 | F | —P(=S)(OH)₂ |
| IAa.1158 | F | —P(=S)(OCH₃)₂ |
| IAa.1159 | F | —P(=S)(OC₂H₅)₂ |
| IAa.1160 | F | —P(=S)[O-(n-C₃H₇)]₂ |
| IAa.1161 | F | —P(=S)[O-(n-C₄H₉)]₂ |
| IAa.1162 | F | —P(=S)(O—CH₂—CH₂—CH₂—O) |
| IAa.1163 | F | —P(=O)(NH₂)₂ |
| IAa.1164 | F | —P(=O)(NH—CH₃)₂ |
| IAa.1165 | F | —P(=O)[N(CH₃)₂]₂ |

TABLE 1-continued

IAa

[Structure: 6-(trifluoromethyl)-1-methyl-3-[2-R⁴-4-chloro-5-(CH₂—CH₂—P(=Y¹)(Y²R¹)(Y³R²))phenyl]pyrimidine-2,4-dione]

| No. | R⁴ | —P(=Y¹)(Y²R¹)(Y³R²) |
|---|---|---|
| IAa.1166 | F | —P(=O)(NH—C₂H₅)₂ |
| IAa.1167 | F | —P(=O)[N(C₂H₅)₂]₂ |
| IAa.1168 | F | —P(=O)(NH—CH₂—CH=CH₂)₂ |
| IAa.1169 | F | —P(=O)(NH—CH₂—C≡CH)₂ |
| IAa.1170 | F | —P(=O)(NH-cyclopropyl)₂ |
| IAa.1171 | F | —P(=O)(NH—CH₂-cyclopentyl)₂ |
| IAa.1172 | F | —P(=O)(NH-phenyl)₂ |
| IAa.1173 | F | —P(=O)(NH—CH₂-phenyl)₂ |
| IAa.1174 | F | —P(=O)(pyrrolidin-1-yl)₂ |
| IAa.1175 | F | —P(=O)(2-methoxycarbonylpyrrolidin-1-yl)₂ |
| IAa.1176 | F | —P(=O)(NH—CH₂—CO—OCH₃)₂ |
| IAa.1177 | F | —P(=O)[N(CH₃)—CH₂—CO—OCH₃]₂ |
| IAa.1178 | F | —P(=O)(NH—CH₂—CO—OC₂H₅)₂ |
| IAa.1179 | F | —P(=O)[N(CH₃)—CH₂—CO—OC₂H₅]₂ |
| IAa.1180 | F | —P(=O)[NH—CH(CH₃)—CO—OCH₃]₂ |
| IAa.1181 | F | —P(=O)(OH)(NH₂) |
| IAa.1182 | F | —P(=O)(OH)(NH—CH₃) |
| IAa.1183 | F | —P(=O)(OH)[N(CH₃)₂] |
| IAa.1184 | F | —P(=O)(OH)(NH—C₂H₅) |
| IAa.1185 | F | —P(=O)(OH)[N(C₂H₅)₂] |
| IAa.1186 | F | —P(=O)(OH)(NH—CH₂—CH=CH₂) |
| IAa.1187 | F | —P(=O)(OH)(NH—CH₂—C≡CH) |
| IAa.1188 | F | —P(=O)(OH)(NH-cyclopropyl) |
| IAa.1189 | F | —P(=O)(OH)(NH—CH₂-cyclopentyl) |
| IAa.1190 | F | —P(=O)(OH)(NH-phenyl) |
| IAa.1191 | F | —P(=O)(OH)(NH—CH₂-phenyl) |
| IAa.1192 | F | —P(=O)(OH)(pyrrolidin-1-yl) |
| IAa.1193 | F | —P(=O)(OH)(2-methoxycarbonylpyrrolidin-1-yl) |
| IAa.1194 | F | —P(=O)(OH)(NH—CH₂—CO—OCH₃) |
| IAa.1195 | F | —P(=O)(OH)[N(CH₃)—CH₂—CO—OCH₃] |
| IAa.1196 | F | —P(=O)(OH)(NH—CH₂—CO—OC₂H₅) |
| IAa.1197 | F | —P(=O)(OH)[N(CH₃)—CH₂—CO—OC₂H₅] |
| IAa.1198 | F | —P(=O)(OH)[NH—CH(CH₃)—CO—OCH₃] |
| IAa.1199 | F | —P(=O)(OCH₃)(NH₂) |
| IAa.1200 | F | —P(=O)(OCH₃)(NH—CH₃) |
| IAa.1201 | F | —P(=O)(OCH₃)[N(CH₃)₂] |
| IAa.1202 | F | —P(=O)(OCH₃)(NH—C₂H₅) |
| IAa.1203 | F | —P(=O)(OCH₃)[N(C₂H₅)₂] |
| IAa.1204 | F | —P(=O)(OCH₃)(NH—CH₂—CH=CH₂) |
| IAa.1205 | F | —P(=O)(OCH₃)(NH—CH₂—C≡CH) |
| IAa.1206 | F | —P(=O)(OCH₃)(NH-cyclopropyl) |
| IAa.1207 | F | —P(=O)(OCH₃)(NH—CH₂-cyclopentyl) |
| IAa.1208 | F | —P(=O)(OCH₃)(NH-phenyl) |
| IAa.1209 | F | —P(=O)(OCH₃)(NH—CH₂-phenyl) |
| IAa.1210 | F | —P(=O)(OCH₃)(pyrrolidin-1-yl) |
| IAa.1211 | F | —P(=O)(OCH₃)(2-methoxycarbonylpyrrolidin-1-yl) |
| IAa.1212 | F | —P(=O)(OCH₃)(NH—CH₂—CO—OCH₃) |
| IAa.1213 | F | —P(=O)(OCH₃)[N(CH₃)—CH₂—CO—OCH₃] |
| IAa.1214 | F | —P(=O)(OCH₃)(NH—CH₂—CO—OC₂H₅) |
| IAa.1215 | F | —P(=O)(OCH₃)[N(CH₃)—CH₂—CO—OC₂H₅] |
| IAa.1216 | F | —P(=O)(OCH₃)[NH—CH(CH₃)—CO—OCH₃] |
| IAa.1217 | F | —P(=O)(OC₂H₅)(NH₂) |
| IAa.1218 | F | —P(=O)(OC₂H₅)(NH—CH₃) |
| IAa.1219 | F | —P(=O)(OC₂H₅)[N(CH₃)₂] |
| IAa.1220 | F | —P(=O)(OC₂H₅)(NH—C₂H₅) |
| IAa.1221 | F | —P(=O)(OC₂H₅)[N(C₂H₅)₂] |
| IAa.1222 | F | —P(=O)(OC₂H₅)(NH—CH₂—CH=CH₂) |
| IAa.1223 | F | —P(=O)(OC₂H₅)(NH—CH₂—C≡CH) |
| IAa.1224 | F | —P(=O)(OC₂H₅)(NH-cyclopropyl) |
| IAa.1225 | F | —P(=O)(OC₂H₅)(NH—CH₂-cyclopentyl) |
| IAa.1226 | F | —P(=O)(OC₂H₅)(NH-phenyl) |
| IAa.1227 | F | —P(=O)(OC₂H₅)(NH—CH₂-phenyl) |
| IAa.1228 | F | —P(=O)(OC₂H₅)(pyrrolidin-1-yl) |
| IAa.1229 | F | —P(=O)(OC₂H₅)(2-methoxycarbonylpyrrolidin-1-yl) |
| IAa.1230 | F | —P(=O)(OC₂H₅)(NH—CH₂—CO—OCH₃) |
| IAa.1231 | F | —P(=O)(OC₂H₅)[N(CH₃)—CH₂—CO—OCH₃] |
| IAa.1232 | F | —P(=O)(OC₂H₅)(NH—CH₂—CO—OC₂H₅) |
| IAa.1233 | F | —P(=O)(OC₂H₅)[N(CH₃)—CH₂—CO—OC₂H₅] |
| IAa.1234 | F | —P(=O)(OC₂H₅)[NH—CH(CH₃)—CO—OCH₃] |
| IAa.1235 | F | —P(=O)[N(CH₃)₂](OCH₃) |
| IAa.1236 | F | —P(=O)[N(CH₃)₂](OC₂H₅) |
| IAa.1237 | F | —P(=O)[N(CH₃)₂][O-(n-C₃H₇)] |
| IAa.1238 | F | —P(=O)[N(CH₃)₂][OCH(CH₃)₂] |
| IAa.1239 | F | —P(=O)[N(CH₃)₂][O-(n-C₄H₉)] |
| IAa.1240 | F | —P(=O)[N(CH₃)₂](OCH₂—CH=CH₂) |
| IAa.1241 | F | —P(=O)[N(CH₃)₂](OCH₂—C≡CH) |
| IAa.1242 | F | —P(=O)[N(CH₃)₂](O-cyclohexyl) |
| IAa.1243 | F | —P(=O)[N(CH₃)₂](OCH₂-cyclohexyl) |
| IAa.1244 | F | —P(=O)[N(CH₃)₂](O-phenyl) |
| IAa.1245 | F | —P(=O)[N(CH₃)₂](OCH₂-phenyl) |
| IAa.1246 | F | —P(=O)[N(CH₃)₂](O-tetrahydrofuran-2-yl) |
| IAa.1247 | F | —P(=O)[N(CH₃)₂](OCH₂-oxetan-3-yl) |
| IAa.1248 | F | —P(=O)[N(CH₃)₂](OCH₂—CF₃) |
| IAa.1249 | F | —P(=O)[N(CH₃)₂](OCH₂—CO—OCH₃) |
| IAa.1250 | F | —P(=O)[N(CH₃)₂](OCH₂—CO—OC₂H₅) |
| IAa.1251 | F | —P(=O)(NH—CH₂—CH₂—O) |
| IAa.1252 | F | —P(=O)(NH—CH₂—CH₂—NH) |
| IAa.1253 | F | —P(=O)[N(CH₃)—CH₂—CH₂—N(CH₃)] |
| IAa.1254 | F | —P(=O)(NH—CH₂—CH₂—CH₂—O) |
| IAa.1255 | F | —P(=O)(NH—CH₂—CH₂—CH₂—NH) |
| IAa.1256 | F | —P(=O)[N(CH₃)—CH₂—CH₂—CH₂—N(CH₃)] |
| IAa.1257 | F | —P(=O)(O—CH₂—CH(CH₃)—CH₂—O) |
| IAa.1258 | F | —P(=O)[NH—CH₂—CH₂—CH₂—N(CH₃)] |
| IAa.1259 | F | —P(=O)[N(CH₃)—CH₂—C(CH₃)₂—CH₂—N(CH₃)] |
| IAa.1260 | F | —P(=O)[NH—CH₂—CH₂—CH₂—CH₂—O] |
| IAa.1261 | F | —P(=O)[NH—CH₂—CH₂—CH₂—CH₂—NH] |
| IAa.1262 | F | —P(=S)(NH₂)₂ |
| IAa.1263 | F | —P(=S)(NH—CH₃)₂ |
| IAa.1264 | F | —P(=S)[N(CH₃)₂]₂ |
| IAa.1265 | F | —P(=S)(NH—C₂H₅)₂ |
| IAa.1266 | F | —P(=S)[N(C₂H₅)₂]₂ |
| IAa.1267 | F | —P(=S)(NH—CH₂—CH₂—CH₂—O) |
| IAa.1268 | F | —P(=S)(NH—CH₂—CH₂—CH₂—NH) |
| IAa.1269 | F | —P(=S)[N(CH₃)—CH₂—CH₂—CH₂—N(CH₃)] |
| IAa.1270 | F | —P(=O)(SCH₃)₂ |
| IAa.1271 | F | —P(=O)(SC₂H₅)₂ |
| IAa.1272 | F | —P(=O)[S-(n-C₃H₇)]₂ |
| IAa.1273 | F | —P(=O)[SCH(CH₃)₂]₂ |
| IAa.1274 | F | —P(=O)[S-(n-C₄H₉)]₂ |
| IAa.1275 | F | —P(=O)(SCH₂—CH=CH₂)₂ |
| IAa.1276 | F | —P(=O)(S-phenyl)₂ |
| IAa.1277 | F | —P(=O)(SCH₂-phenyl)₂ |
| IAa.1278 | F | —P(=O)(SCH₂—CO—OCH₃)₂ |
| IAa.1279 | F | —P(=O)(SCH₂—CO—OC₂H₅)₂ |
| IAa.1280 | F | —P(=O)(S—CH₂—CH₂—CH₂—S) |
| IAa.1281 | F | —P(=O)(S—CH₂—CH₂—CH₂—O) |
| IAa.1282 | F | —P(=S)(SCH₃)₂ |
| IAa.1283 | F | —P(=S)(SC₂H₅)₂ |
| IAa.1284 | F | —P(=S)[S-(n-C₃H₇)]₂ |
| IAa.1285 | F | —P(=S)[S-n-C₄H₉)]₂ |
| IAa.1286 | F | —P(=S)(S—CH₂—CH₂—CH₂—S) |

TABLE 1-continued

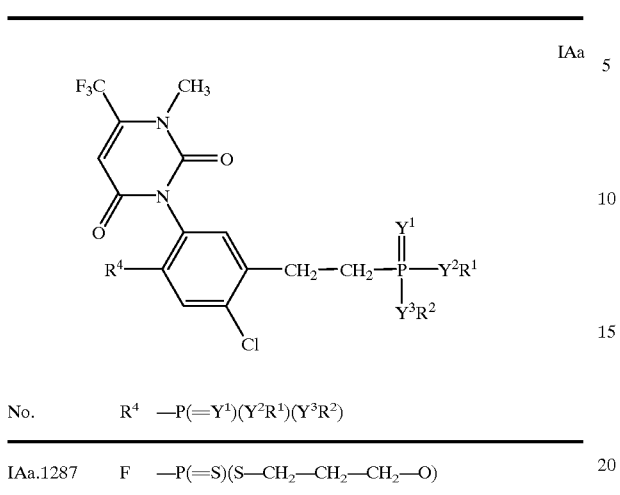
IAa

| No. | R⁴ | —P(=Y¹)(Y²R¹)(Y³R²) |
|---|---|---|
| IAa.1287 | F | —P(=S)(S—CH₂—CH₂—CH₂—O) |

Further especially preferred aromatic phosphonic acid derivatives are those of the formulae IAb-IAn, IBa-IBn, ICa-ICn, IDa-IDn, IEa-IEn, IFa-IFn, IGa-IGn, IHa-IHn, IKa-IKn, ILa-ILn, IMa-IMn and INa-INn, in particular the compounds IAb.1–IAb.1287, which differ from the corresponding compounds IAa.1–IAa.1287 only in that Eth is —CH₂—CH(Cl)—:

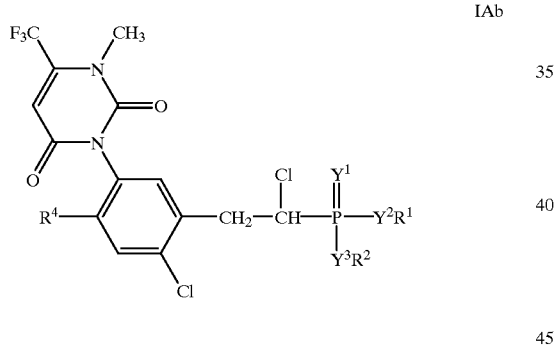
IAb the compounds IAc.1–IAc.1287, which differ from the corresponding compounds IAa.1–IAa.1287 only in that Eth is —CH₂—CH(Br)—:

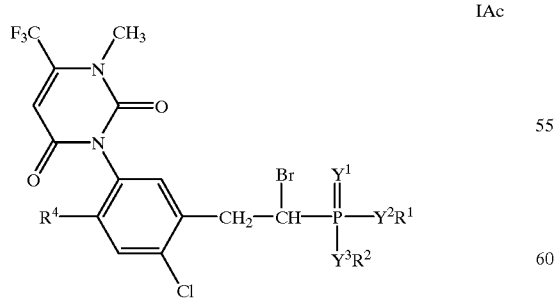
IAc the compounds IAd.1–IAd.1287, which differ from the corresponding compounds IAa.1–IAa.1287 only in that Eth is —CH₂—CH(CN)—:

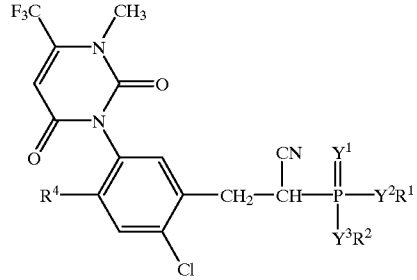
IAd the compounds IAe.1–IAe.1287, which differ from the corresponding compounds IAa.1–IAa.1287 only in that Eth is —CH₂—CH(CH₃ )—:

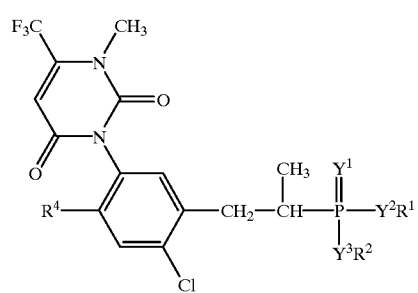
IAe the compounds IAf.1–IAf.1287, which differ from the corresponding compounds IAa.1–IAa.1287 only in that Eth is —CH₂—CH(COOCH₃ )—:

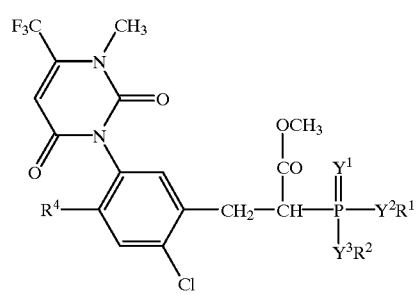
IAf the compounds IAg.1–IAg.1287, which differ from the corresponding compounds IAa.1–IAa.1287 only in that Eth is 1,2-ethenediyl:

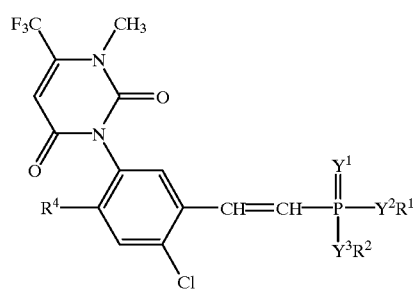
IAg the compounds IAh.1–IAh.1287, which differ from the corresponding compounds IAa.1–IAa.1287 only in that Eth is —CH=C(Cl)—:

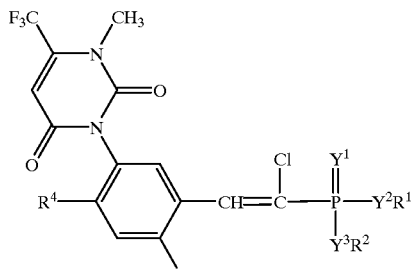
IAh the compounds IAi.1-IAi.1287, which differ from the corresponding compounds IAa.1–IAa.1287 only in that Eth is —CH=C(Br)—:

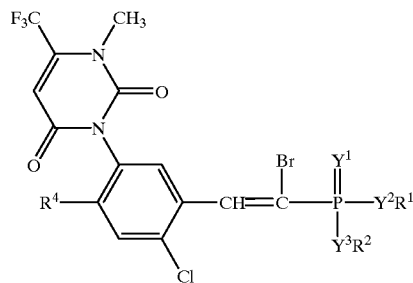
IAi the compounds IAj.1–IAj.1287, which differ from the corresponding compounds IAa.1–IAa.1287 only in that Eth is —CH=C(CN)—:

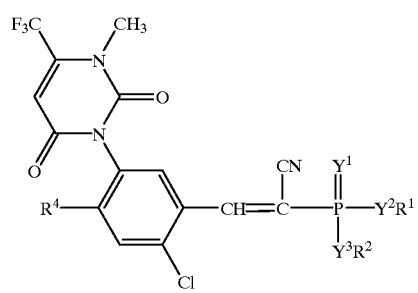
IAj the compounds IAk.1–IAk.1287, which differ from the corresponding compounds IAa.1–IAa.1287 only in that Eth is —CH=C(CH$_3$)—:

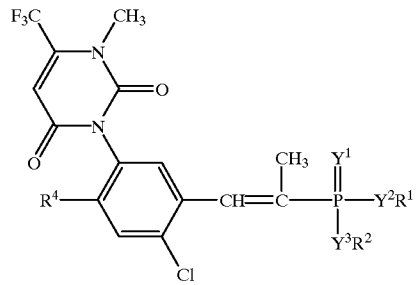
IAk the compounds IAm.1–IAm.1287, which differ from the corresponding compounds IAa.1–IAa.1287 only in that Eth is —CH=C(COOCH$_3$)—:

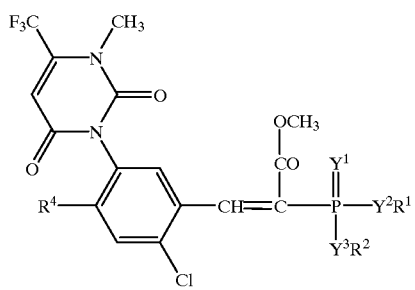
IAm the compounds IAn.1–IAn.1287, which differ from the corresponding compounds IAa.1–IAa.1287 only in that Eth is —C≡C—:

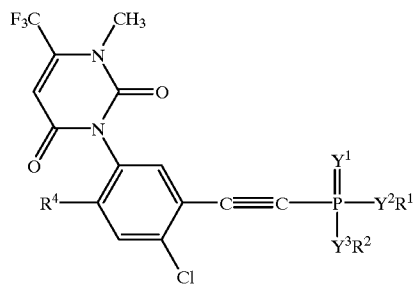
IAn the compounds IBa.430–IBa.1287, which differ from the corresponding compounds IAa.430–IAa.1287 only in that R$^5$ is the heterocycle Φ$^2$ where R$^{10}$=methyl, R$^{11}$=difluoromethoxy and R$^{12}$=chlorine:

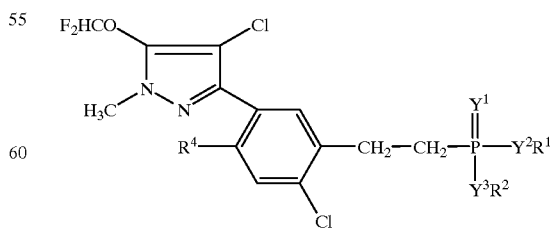
IBa the compounds IBb.430–IBb.1287, which differ from the corresponding compounds IAa.430–IAa.1287 only in that Eth is —CH$_2$—CH(Cl)— and R$^5$ is the heterocycle Φ$^2$ where R$^{10}$=methyl, R$^{11}$=difluoromethoxy and R$^{12}$=chlorine:

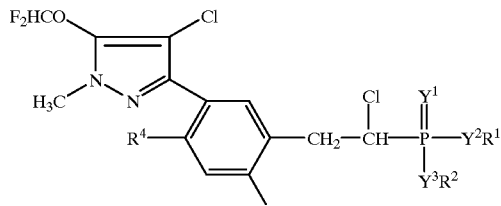

IBb the compounds IBc.430–IBc.1287, which differ from the corresponding compounds IAa.430–IAa.1287 only in that Eth is —CH$_2$—CH(Br)— and R$^5$ is the heterocycle Φ$^2$ where R$^{10}$=methyl, R$^{11}$=difluoromethoxy and R$^{12}$=chlorine:

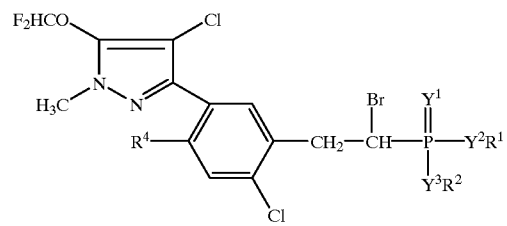

IBc the compounds IBd.430–IBd.1287, which differ from the corresponding compounds IAa.430–IAa.1287 only in that Eth is —CH$_2$—CH(CN)— and R$^5$ is the heterocycle Φ$^2$ where R$^{10}$=methyl, R$^{11}$=difluoromethoxy and R$^{12}$=chlorine:

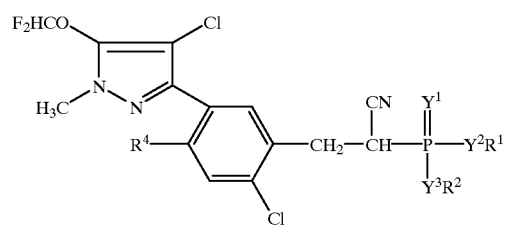

IBd the compounds IBe.430–IBe.1287, which differ from the corresponding compounds IAa.430–IAa.1287 only in that Eth is —CH$_2$—CH(CH$_3$)— and R$^5$ is the heterocycle Φ$^2$ where R$^{10}$=methyl, R$^{11}$=difluoromethoxy and R$^{12}$=chlorine:

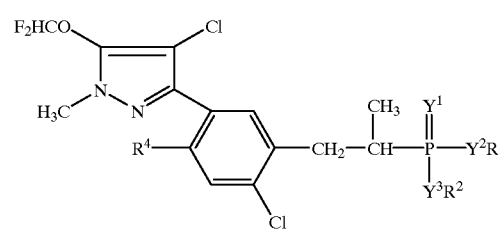

IBe the compounds IBf.430–IBf.1287, which differ from the corresponding compounds IAa.430–IAa.1287 only in that Eth is —CH$_2$—CH(COOCH$_3$)— and R$^5$ is the heterocycle Φ$^2$ where R$^{10}$=methyl, R$^{11}$=difluoromethoxy and R$^{12}$=chlorine:

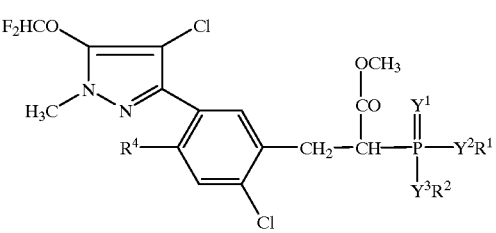

IBf the compounds IBg.430–IBg.1287, which differ from the corresponding compounds IAa.430–IAa.1287 only in that Eth is 1,2-ethenediyl and R$^5$ is the heterocycle Φ$^2$ where R$^{10}$=methyl, R$^{11}$=difluoromethoxy and R$^{12}$=chlorine:

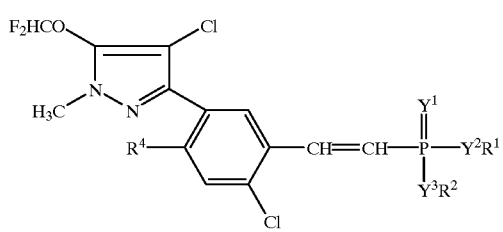

IBg the compounds IBh.430–IBh.1287, which differ from the corresponding compounds IAa.430–IAa.1287 only in that Eth is —CH=C(Cl)— and R$^5$ is the heterocycle Φ$^2$ where R$^{10}$=methyl, R$^{11}$=difluoromethoxy and R$^{12}$=chlorine:

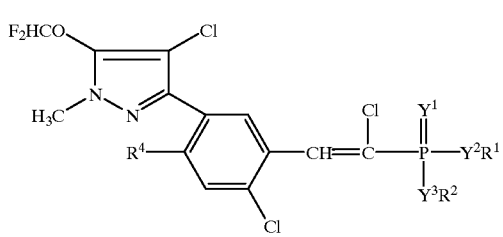

IBh the compounds IBi.430–IBi.1287, which differ from the corresponding compounds IAa.430–IAa.1287 only in that Eth is —CH=C(Br)— and R$^5$ is the heterocycle Φ$^2$ where R$^{10}$=methyl, R$^{11}$=difluoromethoxy and R$^{12}$=chlorine:

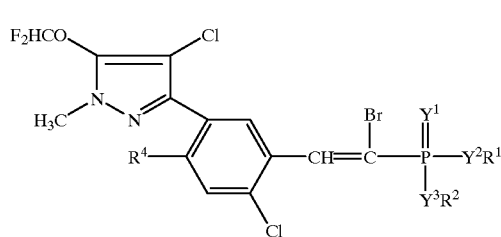

IBi the compounds IBj.430–IBj.1287, which differ from the corresponding compounds IAa.430–IAa.1287 only in that Eth is —CH=C(CN)— and $R^5$ is the heterocycle $\Phi^2$ where $R^{10}$=methyl, $R^{11}$=difluoromethoxy and $R^{12}$=chlorine:

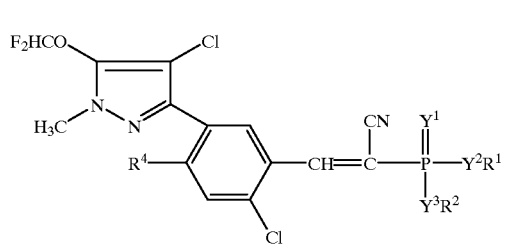

IBj the compounds IBk.430–IBk.1287, which differ from the corresponding compounds IAa.430–IAa.1287 only in that Eth is —CH=C(CH$_3$)— and $R^5$ is the heterocycle $\Phi^2$ where $R^{10}$=methyl, $R^{11}$=difluoromethoxy and $R^{12}$=chlorine:

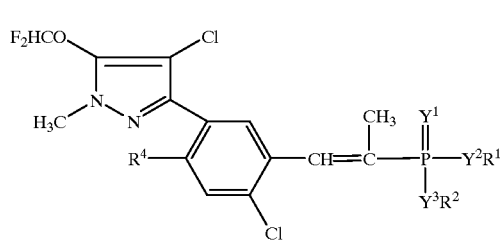

IBk the compounds IBm.430–IBm.1287, which differ from the corresponding compounds IAa.430–IAa.1287 only in that Eth is —CH=C(COOCH$_3$)— and $R^5$ is the heterocycle $\Phi^2$ where $R^{10}$=methyl, $R^{11}$=difluoromethoxy and $R^{12}$=chlorine:

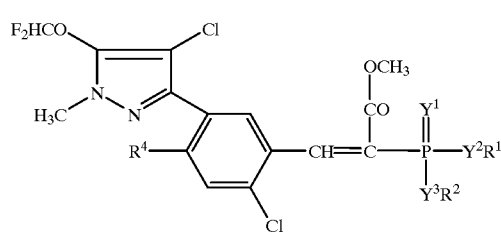

IBm the compounds IBn.430–IBn.1287, which differ from the corresponding compounds IAa.430–IAa.1287 only in that Eth is —C≡C— and $R^5$ is the heterocycle $\Phi^2$ where $R^{10}$=methyl, $R^{11}$=difluoromethoxy and $R^{12}$=chlorine:

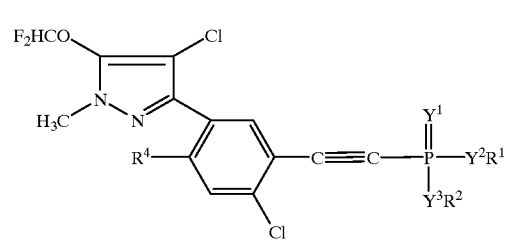

IBn the compounds ICa.430–ICa.1287, which differ from the corresponding compounds IAa.430–IAa.1287 only in that $R^5$ is the heterocycle $\Phi^2$ where $R^{10}$=methyl, $R^{11}$=trifluoromethyl and $R^{12}$=chlorine:

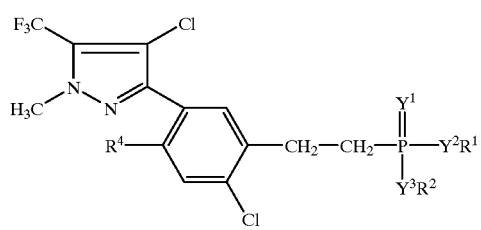

ICa the compounds ICb.430–ICb.1287, which differ from the corresponding compounds IAa.430–IAa.1287 only in that Eth is —CH$_2$—CH(Cl)— and $R^5$ is the heterocycle $\Phi^2$ where $R^{10}$=methyl, $R^{11}$=trifluoromethyl and $R^{12}$=chlorine:

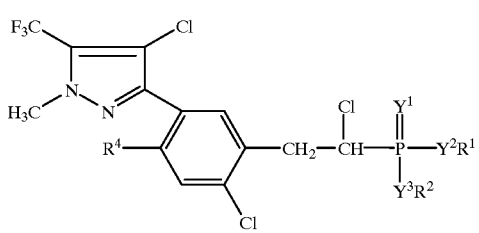

ICb the compounds ICc.430–ICc.1287, which differ from the corresponding compounds IAa.430–IAa.1287 only in that Eth is —CH$_2$—CH(Br)— and $R^5$ is the heterocycle $\Phi^2$ where $R^{10}$=methyl, $R^{11}$=trifluoromethyl and $R^{12}$=chlorine:

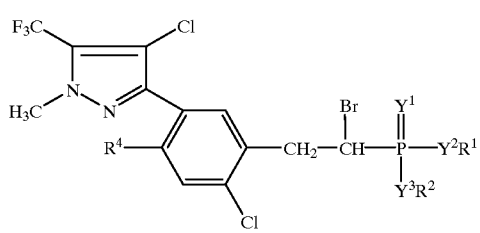

ICc the compounds ICd.430–ICd.1287, which differ from the corresponding compounds IAa.430–IAa.1287 only in that Eth is —CH$_2$—CH(CN)— and $R^5$ is the heterocycle $\Phi^{42}$ where $R^{10}$=methyl, $R^{11}$=trifluoromethyl and $R^{12}$=chlorine:

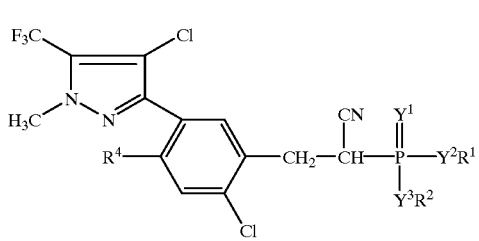
ICd

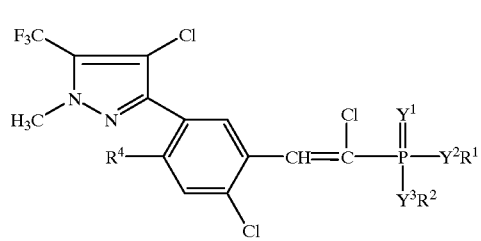
ICh the compounds ICe.430–ICe.1287, which differ from the corresponding compounds IAa.430–IAa.1287 only in that Eth is —CH$_2$—CH(CH$_3$)— and R$^5$ is the heterocycle Φ$^2$ where R$^{10}$=methyl, R$^{11}$=trifluoromethyl and R$^{12}$=chlorine:

the compounds ICi.430–ICi.287, which differ from the corresponding compounds IAa.430–IAa.1287 only in that Eth is —CH=C(Br)— and R$^5$ is the heterocycle Φ$^2$ where R$^{10}$=methyl, R$^{11}$=trifluoromethyl and R$^{12}$=chlorine:

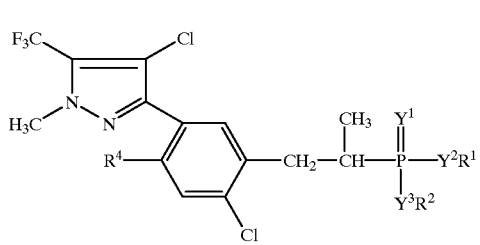
ICe

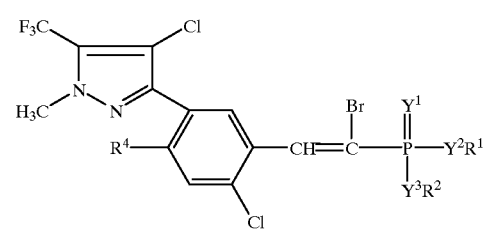
ICi the compounds ICf.430–ICf.1287, which differ from the corresponding compounds IAa.430–IAa.1287 only in that Eth is —CH$_2$—CH(COOCH$_3$)— and R$^5$ is the heterocycle Φ$^{42}$ where R$^{10}$=methyl, R$^{11}$=trifluoromethyl and R$^{12}$=chlorine:

the compounds ICj.430–ICj.1287, which differ from the corresponding compounds IAa.430–IAa.1287 only in that Eth is —CH=C(CN)— and R$^5$ is the heterocycle Φ$^2$ where R$^{10}$=methyl, R$^{11}$=trifluoromethyl and R$^{12}$=chlorine:

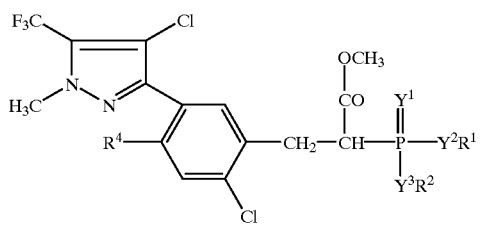
ICf

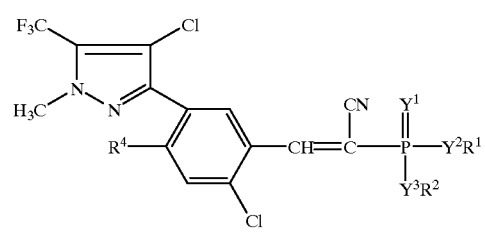
ICj the compounds ICg.430–ICg.1287, which differ from the corresponding compounds IAa.430–IAa.1287 only in that Eth is 1,2-ethenediyl and R$^5$ is the heterocycle Φ$^2$ where R$^{10}$=methyl, R$^{11}$=trifluoromethyl and R$^{12}$=chlorine:

the compounds ICk.430–ICk.1287, which differ from the corresponding compounds IAa.430–IAa.1287 only in that Eth is —CH=C(CH$_3$)— and R$^5$ is the heterocycle Φ$^2$ where R$^{10}$=methyl, R$^{11}$=trifluoromethyl and R$^{12}$=chlorine:

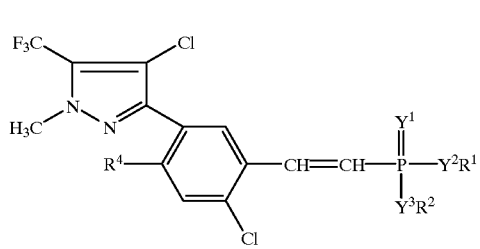
ICg

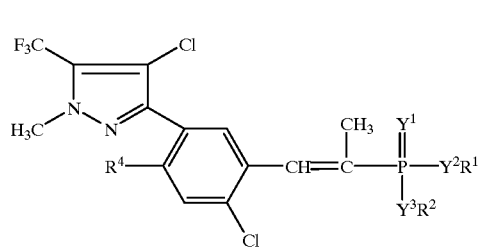
ICk the compounds ICh.430–ICh.1287, which differ from the corresponding compounds IAa.430–IAa.1287 only in that Eth is —CH=C(Cl)— and R$^5$ is the heterocycle Φ$^2$ where R$^{10}$=methyl, R$^{11}$=trifluoromethyl and R$^{12}$=chlorine:

the compounds ICm.430–ICm.1287, which differ from the corresponding compounds IAa.430–IAa.1287 only in that Eth is —CH=C(COOCH$_3$)— and R$^5$ is the heterocycle Φ$^2$ where R$^{10}$=methyl, R$^{11}$=trifluoromethyl and R$^{12}$=chlorine:

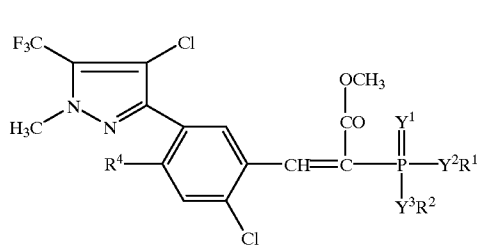

ICm

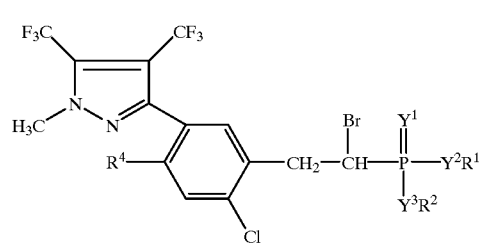

IDc the compounds ICn.430–ICn.1287, which differ from the corresponding compounds IAa.430–IAa.1287 only in that Eth is —C≡C— and $R^5$ is the heterocycle $\Phi^2$ where $R^{10}$=methyl, $R^{11}$=trifluoromethyl and $R^{12}$=chlorine:

the compounds IDd.430–IDd.1287, which differ from the corresponding compounds IAa.430–IAa.1287 only in that Eth is —CH$_2$—CH(CN)— and $R^5$ is the heterocycle $\Phi^2$ where $R^{10}$=methyl, and $R^{11}$ and $R^{12}$=trifluoromethyl:

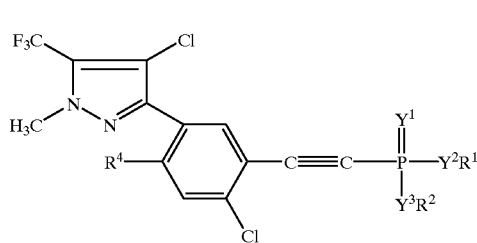

ICn

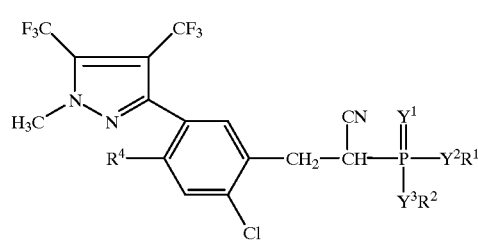

IDd the compounds IDa.430–IDa.1287, which differ from the corresponding compounds IAa.430–IAa.1287 only in that $R^5$ is the heterocycle $\Phi^2$ where $R^{10}$=methyl, and $R^{11}$ and $R^{12}$=trifluoromethyl:

the compounds IDe.430–IDe.1287, which differ from the corresponding compounds IAa.430–IAa.1287 only in that Eth is —CH$_2$—CH(CH$_3$)— and $R^5$ is the heterocycle $\Phi^2$ where $R^{10}$=methyl, and $R^{11}$ and $R^{12}$=trifluoromethyl:

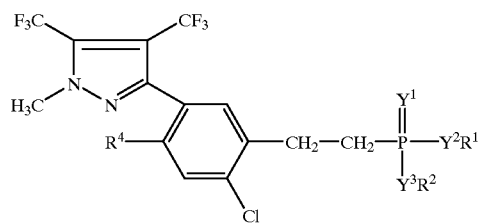

IDa

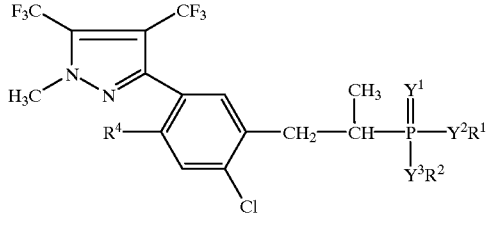

IDe the compounds IDb.430–IDb.1287, which differ from the corresponding compounds IAa.430–IAa.1287 only in that Eth is —CH$_2$—CH(Cl)— and $R^5$ is the heterocycle $\Phi^2$ where $R^{10}$=methyl, and $R^{11}$ and $R^{12}$=trifluoromethyl:

the compounds IDf.430–IDf.1287, which differ from the corresponding compounds IAa.430–IAa.1287 only in that Eth is —CH$_2$—CH(COOCH$_3$)— and $R^5$ is the heterocycle $\Phi^2$ where $R^{10}$=methyl, and $R^{11}$ and $R^{12}$=trifluoromethyl:

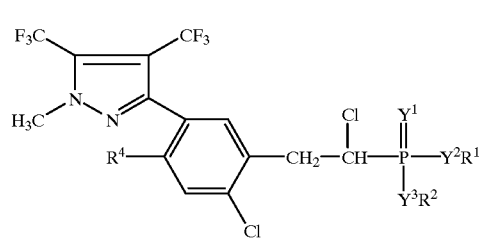

IDb

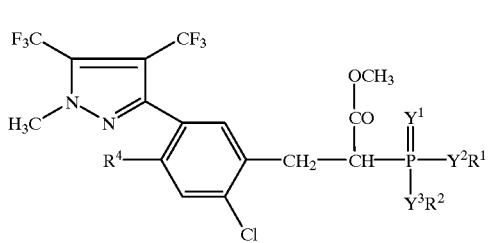

IDf the compounds IDc.430–IDc.1287, which differ from the corresponding compounds IAa.430–IAa.1287 only in that Eth is —CH$_2$—CH(Br)— and $R^5$ is the heterocycle $\Phi^2$ where $R^{10}$=methyl, and $R^{11}$ and $R^{12}$=trifluoromethyl:

the compounds IDg.430–IDg.1287, which differ from the corresponding compounds IAa.430–IAa.1287 only in that Eth is 1,2-ethenediyl and $R^5$ is the heterocycle $\Phi^2$ where $R^{10}$=methyl, and $R^{11}$ and $R^{12}$=trifluoromethyl:

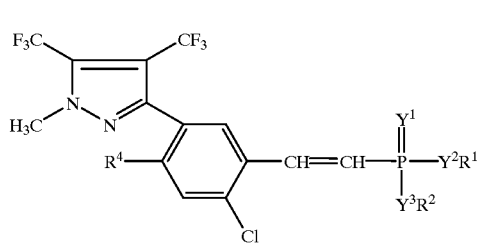

IDg the compounds IDh.430–IDh.1287, which differ from the corresponding compounds IAa.430–IAa.1287 only in that Eth is —CH=C(Cl)— and $R^5$ is the heterocycle $\Phi^2$ where $R^{10}$=methyl, and $R^{11}$ and $R^{12}$=trifluoromethyl:

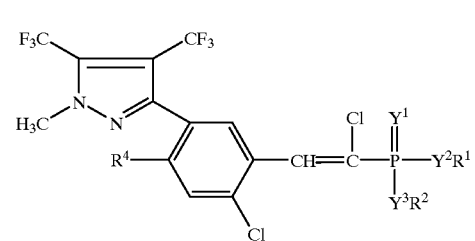

IDh the compounds IDi.430–IDi.1287, which differ from the corresponding compounds IAa.430–IAa.1287 only in that Eth is —CH=C(Br)— and $R^5$ is the heterocycle $\Phi^2$ where $R^{10}$=methyl, and $R^{11}$ and $R^{12}$=trifluoromethyl stehen:

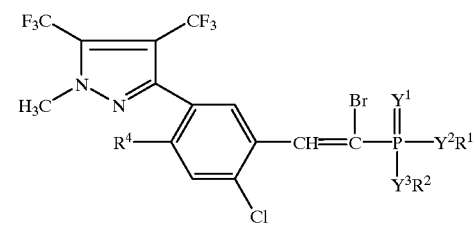

IDi the compounds IDj.430–IDj.1287, which differ from the corresponding compounds IAa.430–IAa.1287 only in that Eth is —CH=C(CN)— and $R^5$ is the heterocycle $\Phi^2$ where $R^{10}$=methyl, and $R^{11}$ and $R^{12}$=trifluoromethyl:

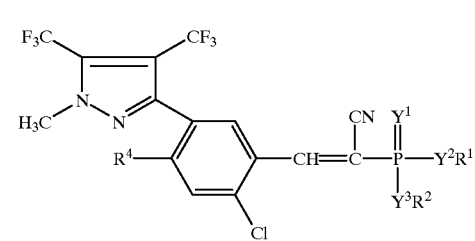

IDj the compounds IDk.430–IDk.1287, which differ from the corresponding compounds IAa.430–IAa.1287 only in that Eth is —CH=C(CH$_3$)— and $R^5$ is the heterocycle $\Phi^2$ where $R^{10}$=methyl, and $R^{11}$ and $R^{12}$=trifluoromethyl:

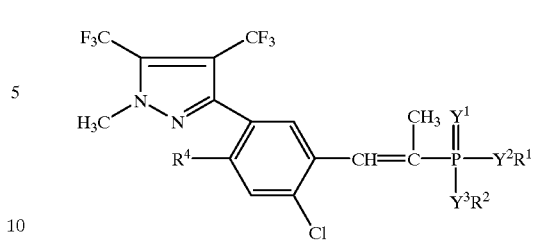

IDk the compounds IDm.430–IDm.1287, which differ from the corresponding compounds IAa.430–IAa.1287 only in that Eth is —CH=C(COOCH$_3$)— and $R^5$ is the heterocycle $\Phi^2$ where $R^{10}$=methyl, and $R^{11}$ and $R^{12}$=trifluoromethyl:

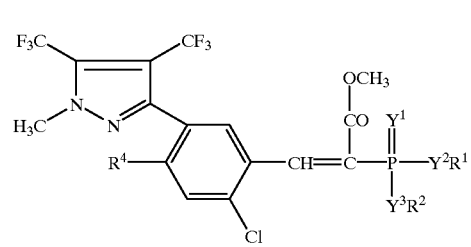

IDm the compounds IDn.430–IDn.1287, which differ from the corresponding compounds IAa.430–IAa.1287 only in that Eth is —C≡C— and $R^5$ is the heterocycle $\Phi^2$ where $R^{10}$=methyl, and $R^{11}$ and $R^{12}$=trifluoromethyl:

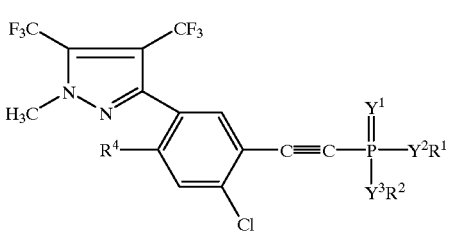

IDn the compounds IEa.1–IEa.1287, which differ from the corresponding compounds IAa.1–IAa.1287 only in that $R^5$ is the heterocycle $\Phi^3$ where $Y^4$=oxygen, and $R^{13}$ and $R^{14}$ together=a tetramethylene chain:

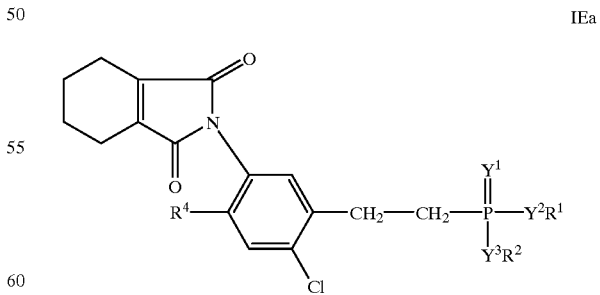

IEa the compounds IEb.1–IEb.1287, which differ from the corresponding compounds IAa.1–IAa.1287 only in that Eth is —CH$_2$—CH(Cl)— and $R^5$ is the heterocycle $\Phi^3$ where $Y^4$=oxygen, and $R^{13}$ and $R^{14}$ together=a tetramethylene chain:

IEb

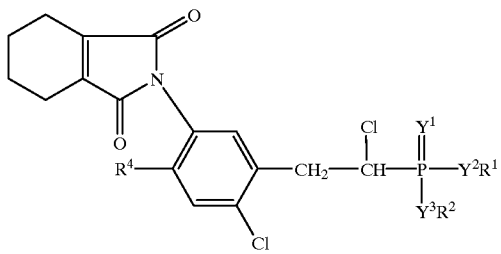

the compounds IEc.1–IEc.1287, which differ from the corresponding compounds IAa.1–IAa.1287 only in that Eth is —CH$_2$—CH(Br)— and R$^5$ is the heterocycle Φ$^3$ where Y$^4$=oxygen, and R$^{13}$ and R$^{14}$ together=a tetramethylene chain:

IEc

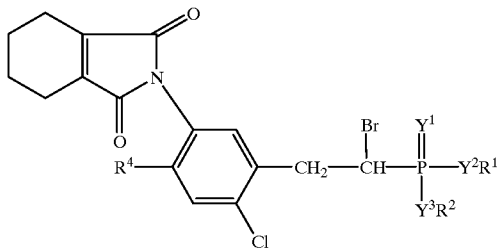

the compounds IEd.1–IEd.1287, which differ from the corresponding compounds IAa.1–IAa.1287 only in that Eth is —CH$_2$—CH(CN)— and R$^5$ is the heterocycle Φ$^3$ where Y$^4$=oxygen, and R$^{13}$ and R$^{14}$ together=a tetramethylene chain:

IEd

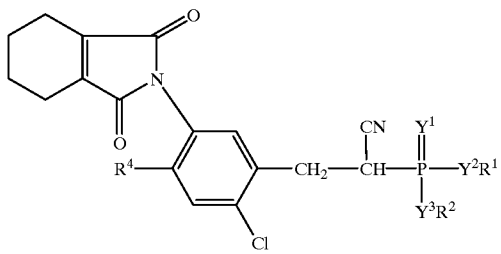

the compounds IEe.1–IEe.1287, which differ from the corresponding compounds IAa.1–IAa.1287 only in that Eth is —CH$_2$—CH(CH$_3$)— and R$^5$ is the heterocycle Φ$^3$ where Y$^4$=oxygen, and R$^{13}$ and R$^{14}$ together=a tetramethylene chain:

IEe

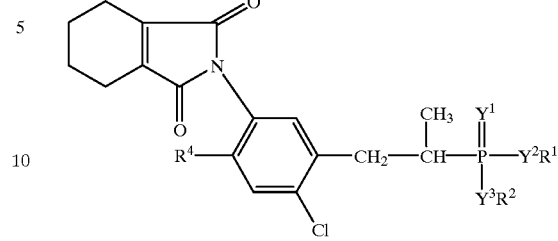

the compounds IEf.1–IEf.1287, which differ from the corresponding compounds IAa.1–IAa.1287 only in that Eth is —CH$_2$—CH(COOCH$_3$)— and R$^5$ is the heterocycle Φ$^3$ where Y$^4$=oxygen, and R$^{13}$ and R$^{14}$ together=a tetramethylene chain:

IEf

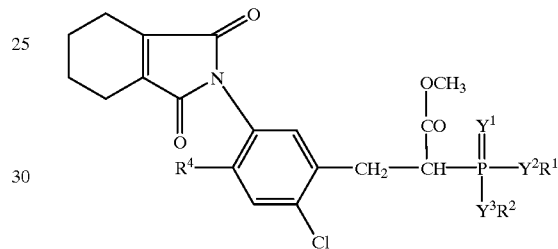

the compounds IEg.1–IEg.1287, which differ from the corresponding compounds IAa.1–IAa.1287 only in that Eth is 1,2-ethenediyl and R$^5$ is the heterocycle Φ$^3$ where Y$^4$=oxygen, and R$^{13}$ and R$^{14}$ together=a tetramethylene chain:

IEg

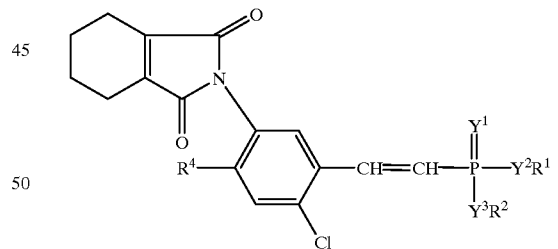

the compounds IEh.1–IEh.1287, which differ from the corresponding compounds IAa.1–IAa.1287 only in that Eth is —CH=C(Cl)— and R$^5$ is the heterocycle Φ$^3$ where Y$^4$=oxygen, and R$^{13}$ and R$^{14}$ together=a tetramethylene chain:

IEh

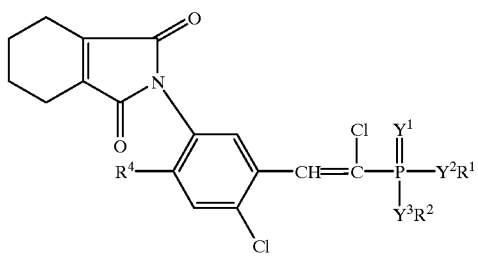

the compounds IEi.1–IEi.1287, which differ from the corresponding compounds IAa.1–IAa.1287 only in that Eth is —CH═C(Br)— and $R^5$ is the heterocycle $\Phi^3$ where $Y^4$=oxygen, and $R^{13}$ and $R^{14}$ together=a tetramethylene chain:

IEi

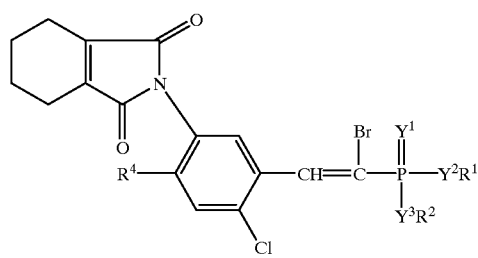

the compounds IEj.1–IEj.1287, which differ from the corresponding compounds IAa.1–IAa.1287 only in that Eth is —CH═C(CN)— and $R^5$ is the heterocycle $\Phi^3$ where $Y^4$=oxygen, and $R^{13}$ and $R^{14}$ together=a tetramethylene chain:

IEj

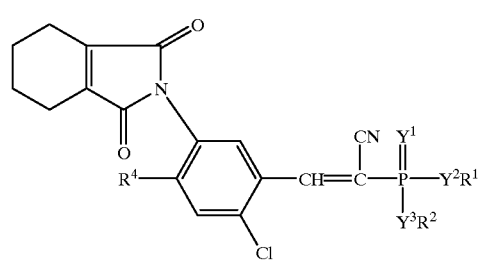

the compounds IEk.1–IEk.1287, which differ from the corresponding compounds IAa.1–IAa.1287 only in that Eth is —CH═C(CH$_3$)— and $R^5$ is the heterocycle $\Phi^3$ where $Y^4$=oxygen, and $R^{13}$ and $R^{14}$ together=a tetramethylene chain:

IEk

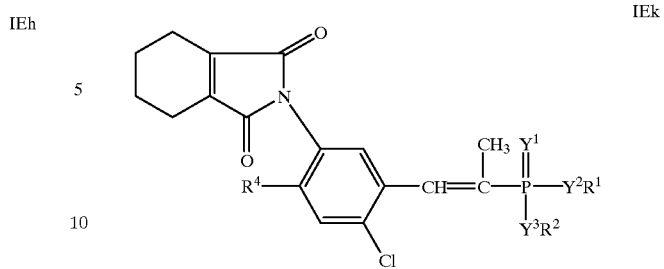

the compounds IEm.1–IEm.1287, which differ from the corresponding compounds IAa.1–IAa.1287 only in that Eth is —CH═C(COOCH$_3$)— and $R^5$ is the heterocycle $\Phi^3$ where $Y^4$=oxygen, and $R^{13}$ and $R^{14}$ together=a tetramethylene chain:

IEm

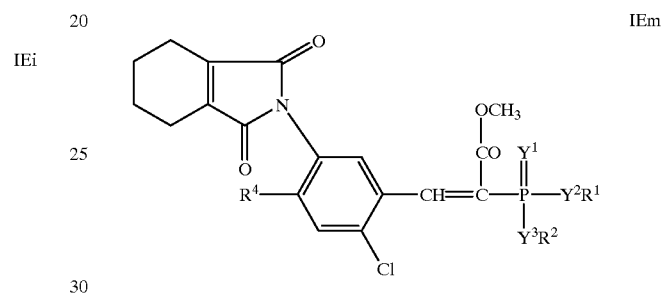

the compounds IEn.1–IEn.1287, which differ from the corresponding compounds IAa.1–IAa.1287 only in that Eth is —C≡C— and $R^5$ is the heterocycle $\Phi^3$ where $Y^4$=oxygen, and $R^{13}$ and $R^{14}$ together=a tetramethylene chain:

IEn

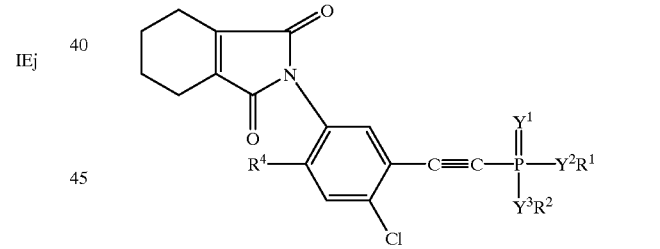

the compounds IFa.1–IFa.1287, which differ from the corresponding compounds IAa.1–IAa.1287 only in that $R^5$ is the heterocycle $\Phi^3$ where $Y^4$=oxygen, and $R^{13}$ and $R^{14}$=methyl:

IFa

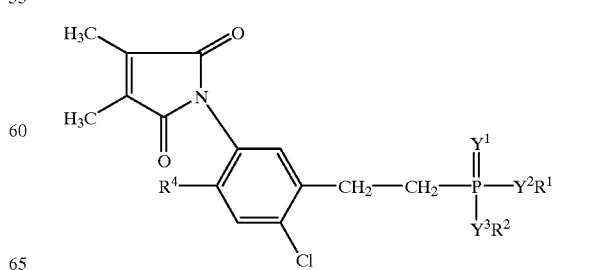

the compounds IFb.1–IFb.1287, which differ from the corresponding compounds IAa.1–IAa.1287 only in that Eth is —CH$_2$—CH(Cl)— and R$^5$ is the heterocycle Φ$^3$ where Y$^4$=oxygen, and R$^{13}$ and R$^{14}$=methyl:

IFb

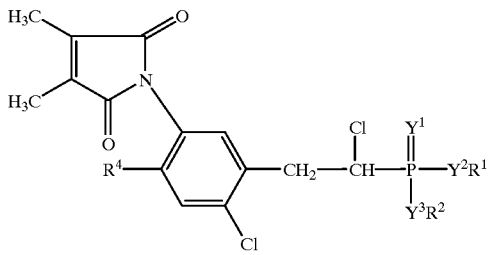

the compounds IFc.1–IFc.1287, which differ from the corresponding compounds IAa.1–IAa.1287 only in that Eth is —CH$_2$—CH(Br)— and R$^5$ is the heterocycle Φ$^3$ where Y$^4$=oxygen, and R$^{13}$ and R$^{14}$=methyl:

IFc

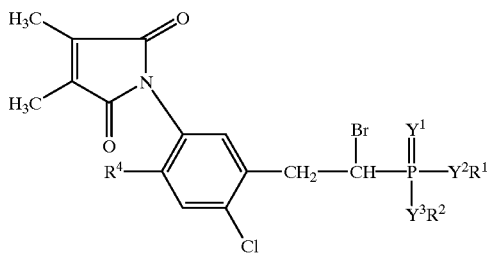

the compounds IFd.1–IFd.1287, which differ from the corresponding compounds IAa.1–IAa.1287 only in that Eth is —CH$_2$—CH(CN)— and R$^5$ is the heterocycle Φ$^3$ where Y$^4$=oxygen, and R$^{13}$ and R$^{14}$=methyl:

IFd

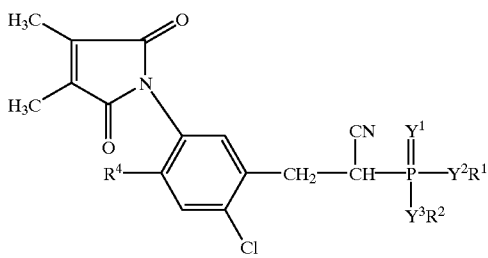

the compounds IFe.1–IFe.1287, which differ from the corresponding compounds IAa.1–IAa.1287 only in that Eth is —CH$_2$—CH(CH$_3$)— and R$^5$ is the heterocycle Φ$^3$ where Y$^4$=oxygen, and R$^{13}$ and R$^{14}$=methyl:

IFe

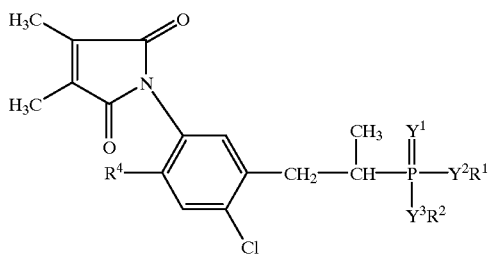

the compounds IFf.1–IFf.1287, which differ from the corresponding compounds IAa.1–IAa.1287 only in that Eth is —CH$_2$—CH(COOCH$_3$)— and R$^5$ is the heterocycle Φ$^3$ where Y$^4$=oxygen, and R$^{13}$ and R$^{14}$=methyl:

IFf

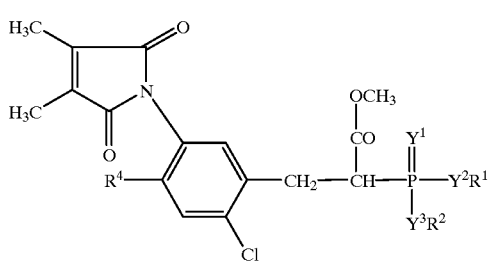

the compounds IFg.1–IFg.1287, which differ from the corresponding compounds IAa.1–IAa.1287 only in that Eth is 1,2-ethenediyl and R$^5$ is the heterocycle Φ$^3$ where Y$^4$=oxygen, and R$^{13}$ and R$^{14}$=methyl:

IFg

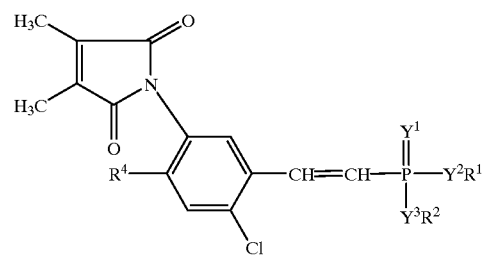

the compounds IFh.1–IFh.1287, which differ from the corresponding compounds IAa.1–IAa.1287 only in that Eth is —CH=C(Cl)— and R$^5$ is the heterocycle Φ$^3$ where Y$^4$=oxygen, and R$^{13}$ and R$^{14}$=methyl:

IFh

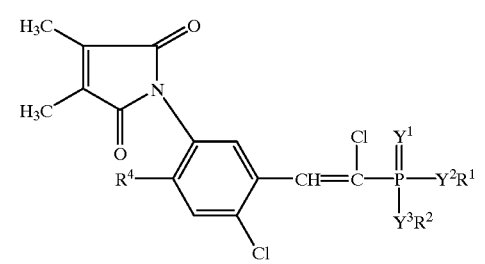

the compounds IFi.1–IFi.1287, which differ from the corresponding compounds IAa.1–IAa.1287 only in that Eth is —CH=C(Br)— and $R^5$ is the heterocycle $\Phi^3$ where $Y^4$=oxygen, and $R^{13}$ and $R^{14}$=methyl:

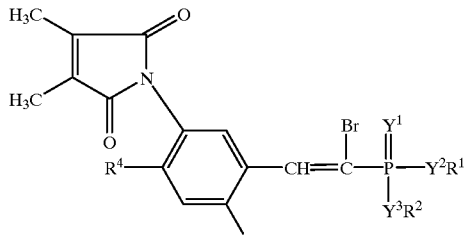

IFi the compounds IFj.1–IFj.1287, which differ from the corresponding compounds IAa.1–IAa.1287 only in that Eth is —CH=C(CN)— and $R^5$ is the heterocycle $\Phi^3$ where $Y^4$=oxygen, and $R^{13}$ and $R^{14}$=methyl:

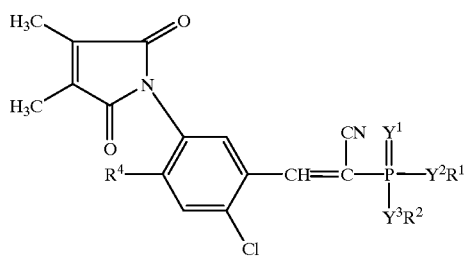

IFj the compounds IFk.1–IFk.1287, which differ from the corresponding compounds IAa.1–IAa.1287 only in that Eth is —CH=C(CH$_3$)— and $R^5$ is the heterocycle $\Phi^3$ where $Y^4$=oxygen, and $R^{13}$ and $R^{14}$=methyl:

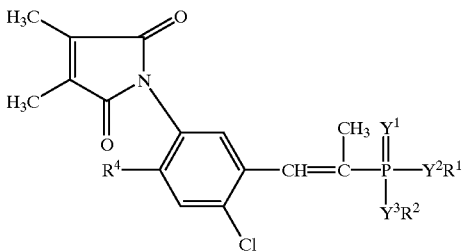

IFk the compounds IFm.1–IFm.1287, which differ from the corresponding compounds IAa.1–IAa.1287 only in that Eth is —CH=C(COOCH$_3$)— and $R^5$ is the heterocycle $\Phi^3$ where $Y^4$=oxygen, and $R^{13}$ and $R^{14}$=methyl:

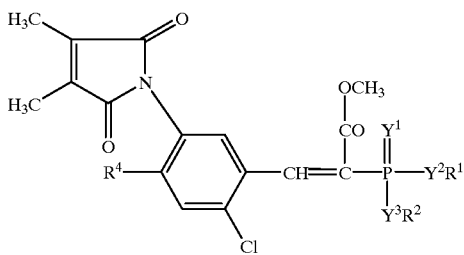

IFm the compounds IFn.1–IFn.1287, which differ from the corresponding compounds IAa.1–IAa.1287 only in that Eth is —C≡C— and $R^5$ is the heterocycle $\Phi^3$ where $Y^4$=oxygen, and $R^{13}$ and $R^{14}$=methyl:

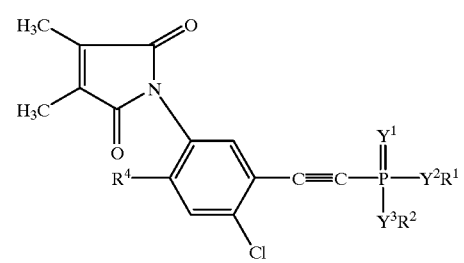

IFn the compounds IGa.1–IGa.1287, which differ from the corresponding compounds IAa.1–IAa.1287 only in that $R^5$ is the heterocycle $\Phi^4$ where $R^{15}$ and $R^{16}$ together= tetramethylene chain and $R^{17}$=chlorine:

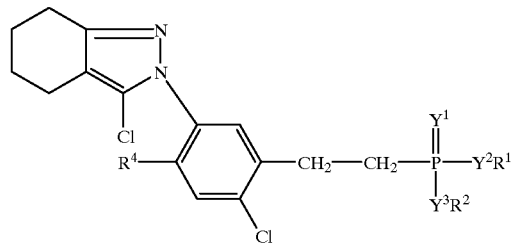

IGa the compounds IGb.1–IGb.1287, which differ from the corresponding compounds IAa.1–IAa.1287 only in that Eth is —CH$_2$—CH(Cl)— and $R^5$ is the heterocycle $\Phi^4$ where $R^{15}$ and $R^{16}$ together=tetramethylene chain and $R^{17}$=chlorine:

IGb

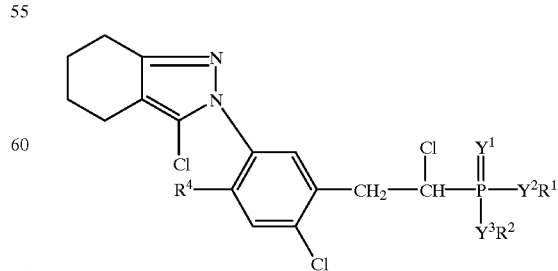

the compounds IGc.1–IGc.1287, which differ from the corresponding compounds IAa.1–IAa.1287 only in that Eth is —CH$_2$—CH(Br)— and R$^5$ is the heterocycle Φ$^4$ where R$^{15}$ and R$^{16}$ together=tetramethylene chain and R$^{17}$=chlorine:

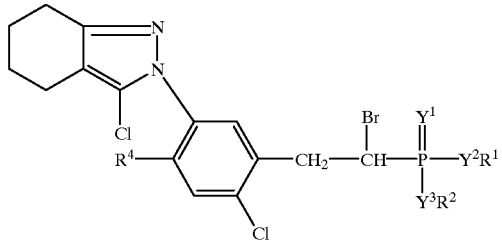

IGc the compounds IGd.1–IGd.1287, which differ from the corresponding compounds IAa.1–IAa.1287 only in that Eth is —CH$_2$—CH(CN)— and R$^5$ is the heterocycle Φ$^4$ where R$^{15}$ and R$^{16}$ together=tetramethylene chain and R$^{17}$=chlorine:

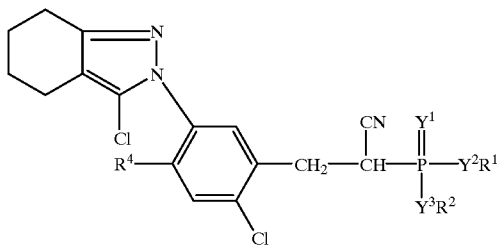

IGd the compounds IGe.1–IGe.1287, which differ from the corresponding compounds IAa.1–IAa.1287 only in that Eth is —CH$_2$—CH(CH$_3$)— and R$^5$ is the heterocycle Φ$^4$ where R$^{15}$ and R$^{16}$ together=tetramethylene chain and R$^{17}$=chlorine:

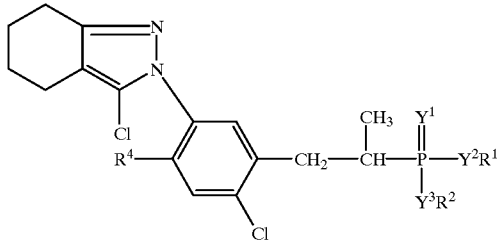

IGe the compounds IGf.1–IGf.1287, which differ from the corresponding compounds IAa.1–IAa.1287 only in that Eth is —CH$_2$—CH(COOCH$_3$)— and R$^5$ is the heterocycle Φ$^4$ where R$^{15}$ and R$^{16}$ together=tetramethylene chain and R$^{17}$=chlorine:

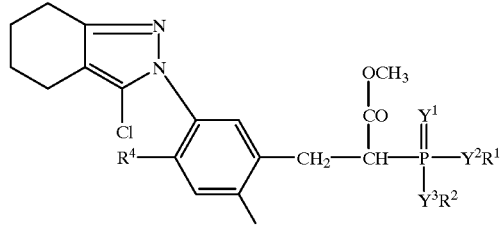

IGf the compounds IGg.1–IGg.1287, which differ from the corresponding compounds IAa.1–IAa.1287 only in that Eth is 1,2-ethenediyl and R$^5$ is the heterocycle Φ$^4$ where R$^{15}$ and R$^{16}$ together=tetramethylene chain and R$^{17}$=chlorine:

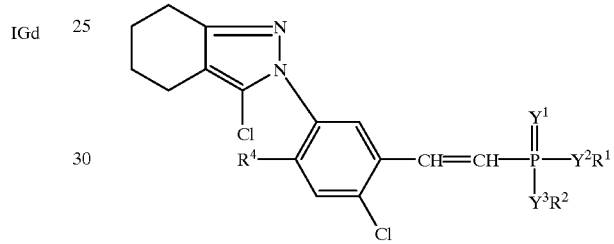

IGg the compounds IGh.1–IGh.1287, which differ from the corresponding compounds IAa.1–IAa.1287 only in that Eth is —CH=C(Cl)— and R$^5$ is the heterocycle Φ$^4$ where R$^{15}$ and R$^{16}$ together=tetramethylene chain and R$^{17}$=chlorine:

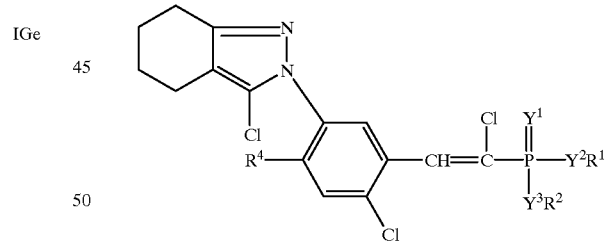

IGh the compounds IGi.1–IGi.1287, which differ from the corresponding compounds IAa.1–IAa.1287 only in that Eth is —CH=C(Br)— and R$^5$ is the heterocycle Φ$^{44}$ where R$^{15}$ and R$^{16}$ together=tetramethylene chain and R$^{17}$=chlorine:

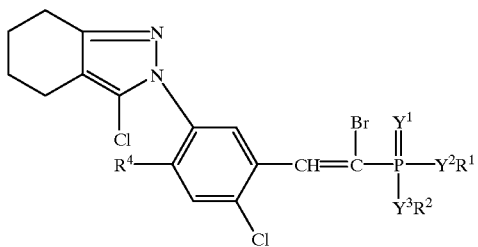

the compounds IGj.1–IGj.1287, which differ from the corresponding compounds IAa.1–IAa.1287 only in that Eth is —CH=C(CN)— and $R^5$ is the heterocycle $\Phi^4$ where $R^{15}$ and $R^{16}$ together=tetramethylene chain and $R^{17}$=chlorine:

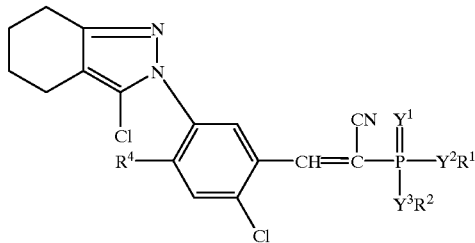

the compounds IGk.1–IGk.1287, which differ from the corresponding compounds IAa.1–IAa.1287 only in that Eth is —CH=C(CH$_3$)— and $R^5$ is the heterocycle $\Phi^4$ where $R^{15}$ and $R^{16}$ together=tetramethylene chain and $R^{17}$=chlorine:

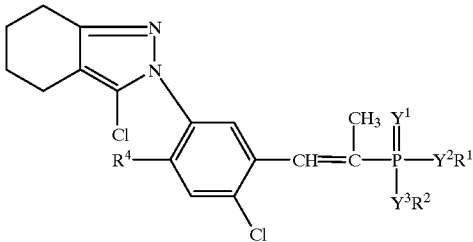

the compounds IGm.1–IGm.1287, which differ from the corresponding compounds IAa.1–IAa.1287 only in that Eth is —CH=C(COOCH$_3$)— and $R^5$ is the heterocycle $\Phi^4$ where $R^{15}$ and $R^{16}$ together=tetramethylene chain and $R^{17}$=chlorine:

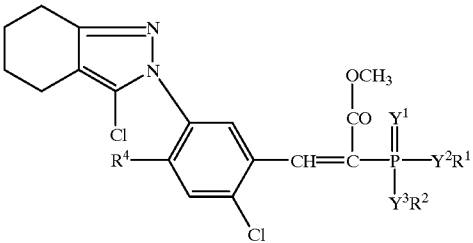

the compounds IGn.1–IGn.1287, which differ from the corresponding compounds IAa.1–IAa.1287 only in that Eth is —C≡C— and $R^5$ is the heterocycle $\Phi^4$ where $R^{15}$ and $R^{16}$ together=tetramethylene chain and $R^{17}$=chlorine:

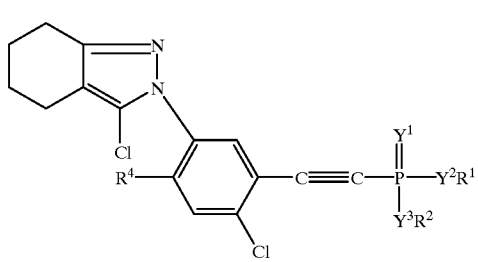

the compounds IHa.1–IHa.1287, which differ from the corresponding compounds IAa.1–IAa.1287 only in that $R^5$ is the heterocycle $\Phi^5$ where $R^{18}$=chlorine, $R^{19}$=difluoromethyl and $R^{20}$=methyl:

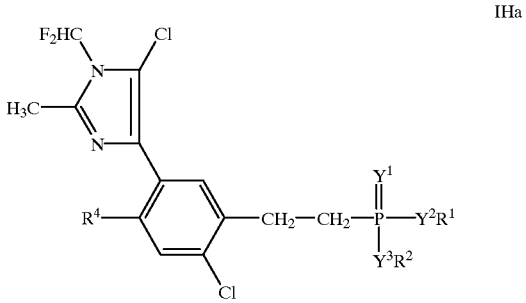

the compounds IHb.1–IHb.1287, which differ from the corresponding compounds IAa.1–IAa.1287 only in that Eth is —CH$_2$—CH(Cl)— and $R^5$ is the heterocycle $\Phi^5$ where $R^{18}$=chlorine, $R^{19}$=difluoromethyl and $R^{20}$=methyl:

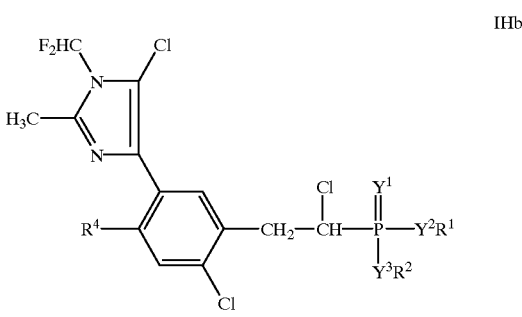

the compounds IHc.1–IHc.1287, which differ from the corresponding compounds IAa.1–IAa.1287 only in that Eth is —CH$_2$—CH(Br)— and $R^5$ is the heterocycle $\Phi^5$ where $R^{18}$=chlorine, $R^{19}$=difluoromethyl and $R^{20}$=methyl:

IHc

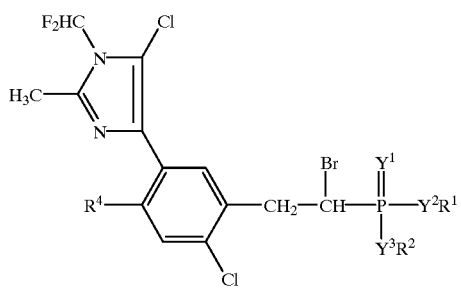

the compounds IHd.1–IHd.1287, which differ from the corresponding compounds IAa.1–IAa.1287 only in that Eth is —CH$_2$—CH(CN)— and R$^5$ is the heterocycle Φ$^5$ where R$^{18}$=chlorine, R$^{19}$=difluoromethyl and R$^{20}$=methyl:

IHd

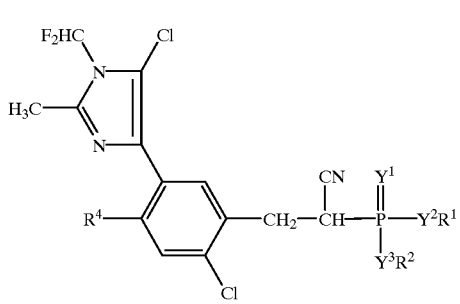

the compounds IHe.1–IHe.1287, which differ from the corresponding compounds IAa.1–IAa.1287 only in that Eth is —CH$_2$—CH(CH$_3$)— and R$^5$ is the heterocycle Φ$^5$ where R$^{18}$ =chlorine, R$^{19}$=difluoromethyl and R$^{20}$=methyl:

IHe

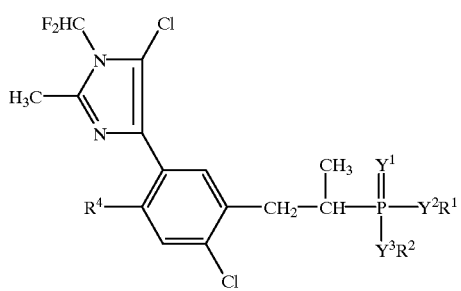

the compounds IHf.1–IHf.1287, which differ from the corresponding compounds IAa.1–IAa.1287 only in that Eth is —CH$_2$—CH(COOCH$_3$)— and R$^5$ is the heterocycle Φ$^5$ where R$^{18}$=chlorine, R$^{19}$=difluoromethyl and R$^{20}$=methyl:

IHf

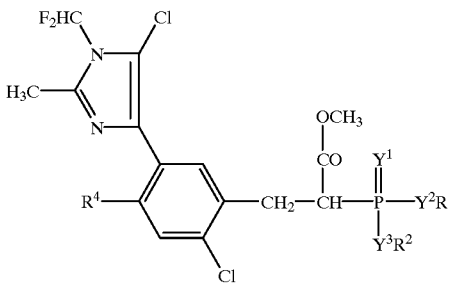

the compounds IHg.1–IHg.1287, which differ from the corresponding compounds IAa.1–IAa.1287 only in that Eth is 1,2-ethenediyl and R$^5$ is the heterocycle Φ$^5$ where R$^{18}$=chlorine, R$^{19}$=difluoromethyl and R$^{20}$=methyl:

IHg

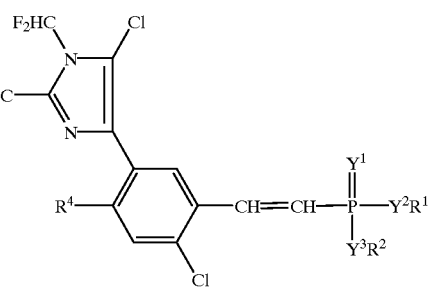

the compounds IHh.1–IHh.1287, which differ from the corresponding compounds IAa.1–IAa.1287 only in that Eth is —CH=C(Cl)— and R$^5$ is the heterocycle Φ$^5$ where R$^{18}$=chlorine, R$^{19}$=difluoromethyl and R$^{20}$=methyl:

IHh

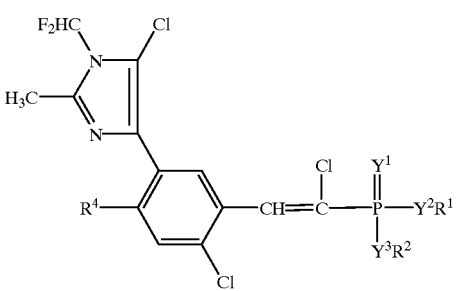

the compounds IHi.1–IHi.1287, which differ from the corresponding compounds IAa.1–IAa.1287 only in that Eth is —CH=C(Br)— and R$^5$ is the heterocycle Φ$^5$ where R$^{18}$=chlorine, R$^{19}$=difluoromethyl and R$^{20}$=methyl:

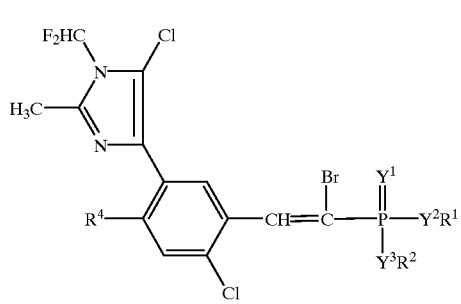
IHi

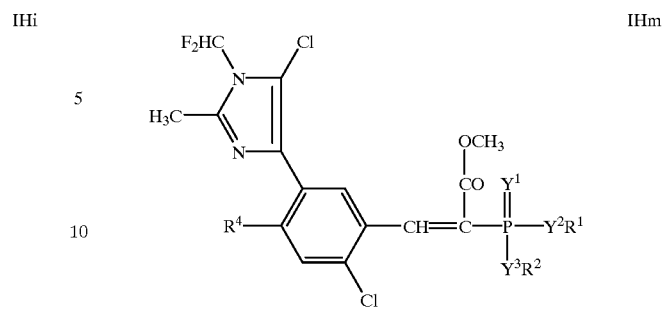
IHm the compounds IHj.1–IHj.1287, which differ from the corresponding compounds IAa.1–IAa.1287 only in that Eth is —CH=C(CN)— and $R^5$ is the heterocycle $\Phi^{45}$ where $R^{18}$=chlorine, $R^{19}$=difluoromethyl and $R^{20}$=methyl:

the compounds IHn.1–IHn.1287, which differ from the corresponding compounds IAa.1–IAa.1287 only in that Eth is —C≡C— and $R^5$ is the heterocycle $\Phi^5$ where $R^{18}$=chlorine, $R^{19}$=difluoromethyl and $R^{20}$=methyl:

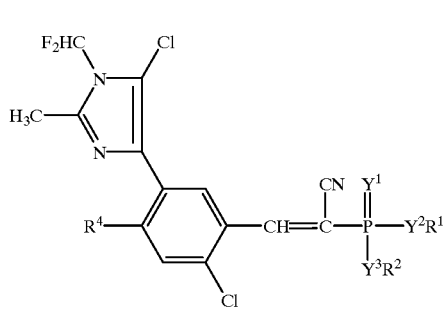
IHj

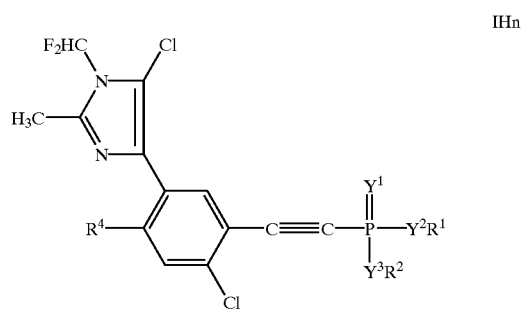
IHn the compounds IHk.1–IHk.1287, which differ from the corresponding compounds IAa.1–IAa.1287 only in that Eth is —CH=C(CH$_3$)— and $R^5$ is the heterocycle $\Phi^5$ where $R^{18}$=chlorine, $R^{19}$=difluoromethyl and $R^{20}$=methyl:

the compounds IKa.1–IKa.1287, which differ from the corresponding compounds IAa.1–IAa.1287 only in that $R^5$ is the heterocycle $\Phi^7$ where $Y^7$=oxygen, and $R^{23}$ and $R^{24}$ together=tetramethylene chain:

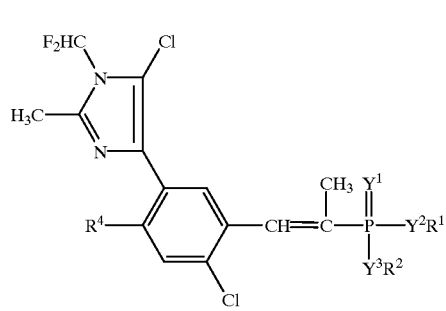
IHk

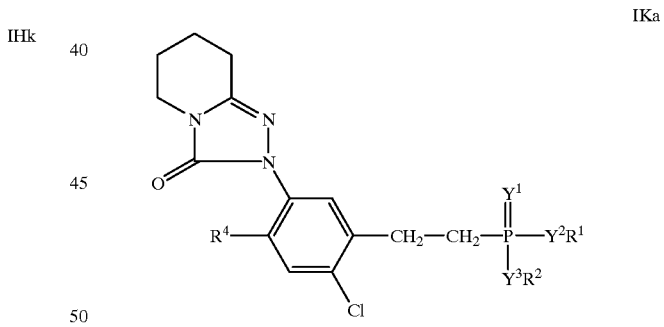
IKa the compounds IHm.1–IHm.1287, which differ from the corresponding compounds IAa.1–IAa.1287 only in that Eth is —CH=C(COOCH$_3$)— and $R^5$ is the heterocycle $\Phi^5$ where $R^{18}$=chlorine, $R^{19}$=difluoromethyl and $R^{20}$=methyl:

the compounds IKb.1–IKb.1287, which differ from the corresponding compounds IAa.1–IAa.1287 only in that Eth is —CH$_2$—CH(Cl)— and $R^5$ is the heterocycle $\Phi^7$ where $Y^7$=oxygen, and $R^{23}$ and $R^{24}$ together=tetramethylene chain:

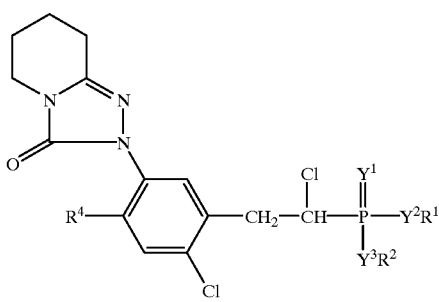

IKb the compounds IKc.1–IKc.1287, which differ from the corresponding compounds IAa.1–IAa.1287 only in that Eth is —CH$_2$—CH(Br)— and R$^5$ is the heterocycle Φ$^7$ where Y$^7$=oxygen, and R$^{23}$ and R$^{24}$ together=tetramethylene chain:

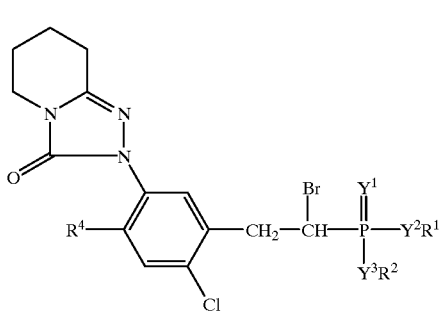

IKc the compounds IKd.1–IKd.1287, which differ from the corresponding compounds IAa.1–IAa.1287 only in that Eth is —CH$_2$—CH(CN)— and R$^5$ is the heterocycle Φ$^7$ where Y$^7$=oxygen, and R$^{23}$ and R$^{24}$ together=tetramethylene chain:

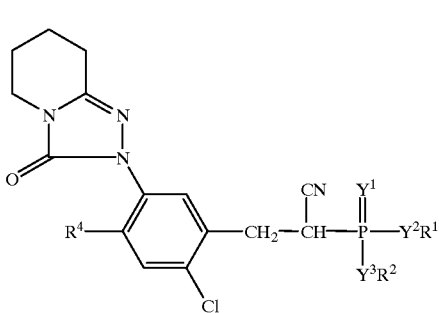

IKd the compounds IKe.1–IKe.1287, which differ from the corresponding compounds IAa.1–IAa.1287 only in that Eth is —CH$_2$—CH(CH$_3$)— and R$^5$ is the heterocycle Φ$^7$ where Y$^7$=oxygen, and R$^{23}$ and R$^{24}$ together=tetramethylene chain:

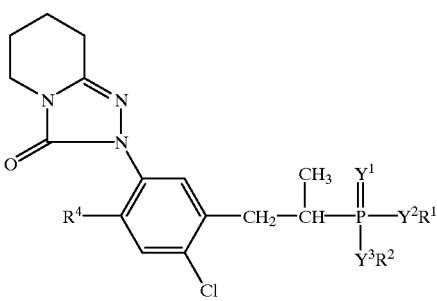

IKe the compounds IKf.1–IKf.1287, which differ from the corresponding compounds IAa.1–IAa.1287 only in that Eth is —CH$_2$—CH(COOCH$_3$)— and R$^5$ is the heterocycle Φ$^7$ where Y$^7$=oxygen, and R$^{23}$ and R$^{24}$ together=tetramethylene chain:

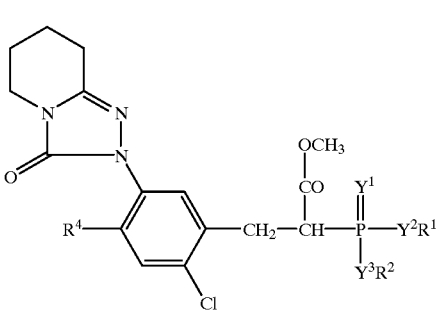

IKf the compounds IKg.1–IKg.1287, which differ from the corresponding compounds IAa.1–IAa.1287 only in that Eth is 1,2-ethenediyl and R$^5$ is the heterocycle Φ$^7$ where Y$^7$=oxygen, and R$^{23}$ and R$^{24}$ together=tetramethylene chain:

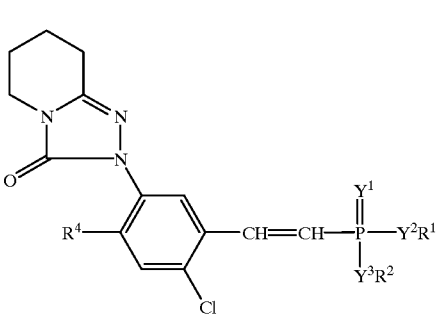

IKg the compounds IKh.1–IKh.1287, which differ from the corresponding compounds IAa.1–IAa.1287 only in that Eth is —CH=C(Cl)— and R$^5$ is the heterocycle Φ$^7$ where Y$^7$=oxygen, and R$^{23}$ and R$^{24}$ together=tetramethylene chain:

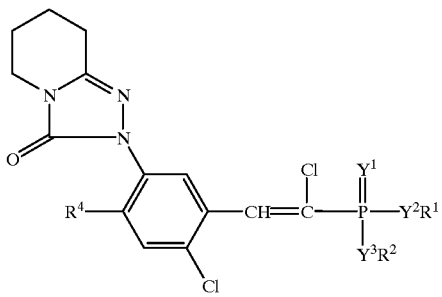

IKh the compounds IKi.1–IKi.1287, which differ from the corresponding compounds IAa.1–IAa.1287 only in that Eth is —CH=C(Br)— and $R^5$ is the heterocycle $\Phi^7$ where $Y^7$=oxygen, and $R^{23}$ and $R^{24}$ together=tetramethylene chain:

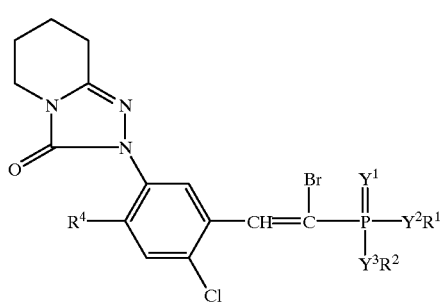

IKi the compounds IKj.1–IKj.1287, which differ from the corresponding compounds IAa.1–IAa.1287 only in that Eth is —CH=C(CN)— and $R^5$ is the heterocycle $\Phi^7$ where $Y^7$=oxygen, and $R^{23}$ and $R^{24}$ together=tetramethylene chain:

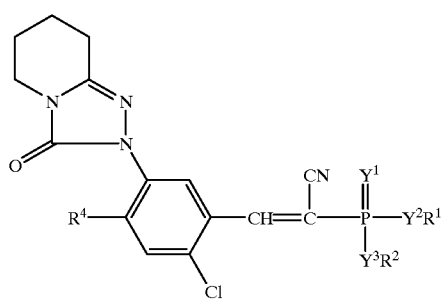

IKj the compounds IKk.1–IKk.1287, which differ from the corresponding compounds IAa.1–IAa.1287 only in that Eth is —CH=C(CH$_3$)— and $R^5$ is the heterocycle $\Phi^7$ where $Y^7$=oxygen, and $R^{23}$ and $R^{24}$ together= tetramethylene chain:

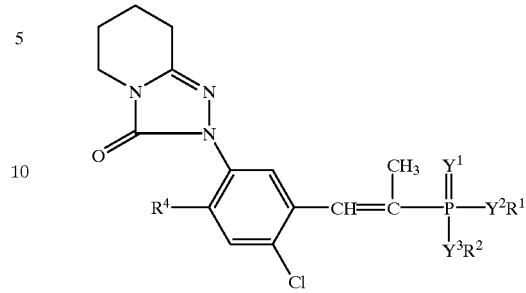

IKk the compounds IKm.1–IKm.1287, which differ from the corresponding compounds IAa.1–IAa.1287 only in that Eth is —CH=C(COOCH$_3$)— and $R^5$ is the heterocycle $\Phi^7$ where $Y^7$=oxygen, and $R^{23}$ and $R^{24}$ together= tetramethylene chain:

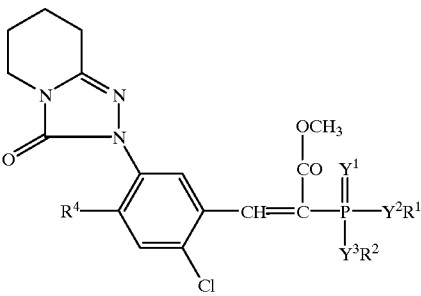

IKm the compounds IKn.1–IKn.1287, which differ from the corresponding compounds IAa.1–IAa.1287 only in that Eth is —C≡C— and $R^5$ is the heterocycle $\Phi^7$ where $Y^7$=oxygen, and $R^{23}$ and $R^{24}$ together=tetramethylene chain:

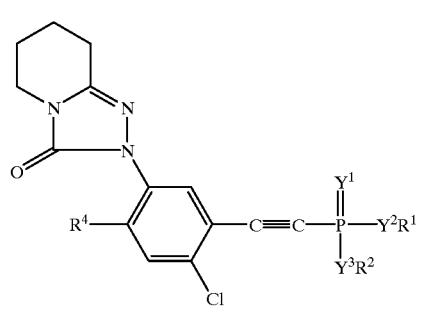

IKn the compounds ILa.1–ILa.1287, which differ from the corresponding compounds IAa.1–IAa.1287 only in that $R^5$ is the heterocycle $\Phi^{20}$ where $R^{50}$=methyl, $R^{51}$=trifluoromethyl and $R^{52}$=hydrogen:

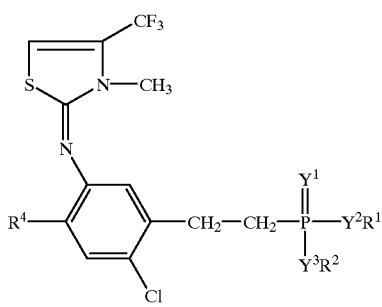

IIa

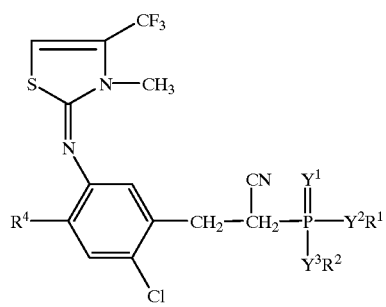

IId the compounds IIb.1–IIb.1287, which differ from the corresponding compounds IAa.1–IAa.1287 only in that Eth is —CH$_2$—CH(Cl)— and R$^5$ is the heterocycle Φ$^{20}$ where R$^{50}$=methyl, R$^{51}$=trifluoromethyl and R$^{52}$=hydrogen:

the compounds IIe.1–IIe.1287, which differ from the corresponding compounds IAa.1–IAa.1287 only in that Eth is —CH$_2$—CH(CH$_3$)— and R$^5$ is the heterocycle Φ$^{20}$ where R$^{50}$=methyl, R$^{51}$=trifluoromethyl and R$^{52}$=hydrogen:

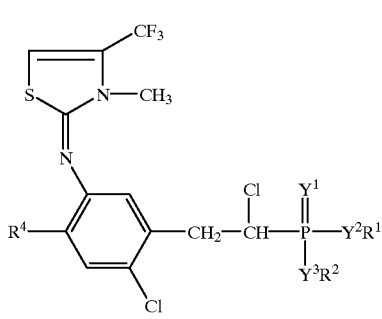

IIb

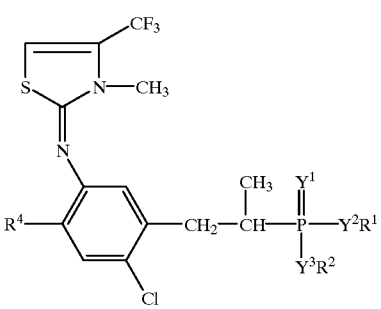

IIe the compounds IIc.1–IIc.1287, which differ from the corresponding compounds IAa.1–IAa.1287 only in that Eth is —CH$_2$—CH(Br)— and R$^5$ is the heterocycle Φ$^{20}$ where R$^{50}$=methyl, R$^{51}$=trifluoromethyl and R$^{52}$=hydrogen:

the compounds IIf.1–IIf.1287, which differ from the corresponding compounds IAa.1–IAa.1287 only in that Eth is —CH$_2$—CH(COOCH$_3$)— and R$^5$ is the heterocycle Φ$^{20}$ where R$^{50}$=methyl, R$^{51}$=trifluoromethyl and R$^{52}$=hydrogen:

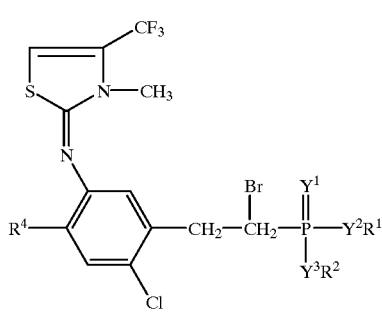

IIc

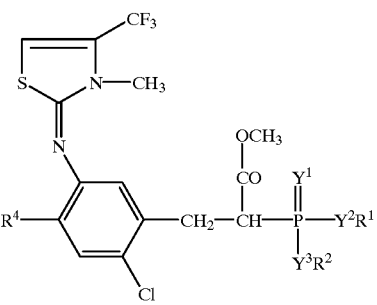

IIf the compounds IId.1–IId.1287, which differ from the corresponding compounds IAa.1–IAa.1287 only in that Eth is —CH$_2$—CH(CN)— and R$^5$ is the heterocycle Φ$^{20}$ where R$^{50}$=methyl, R$^{51}$=trifluoromethyl and R$^{52}$=hydrogen:

the compounds IIg.1–IIg.1287, which differ from the corresponding compounds IAa.1–IAa.1287 only in that Eth is 1,2-ethenediyl and R$^5$ is the heterocycle Φ$^{20}$ where R$^{50}$=methyl, R$^{51}$=trifluoromethyl and R$^{52}$=hydrogen:

ILg

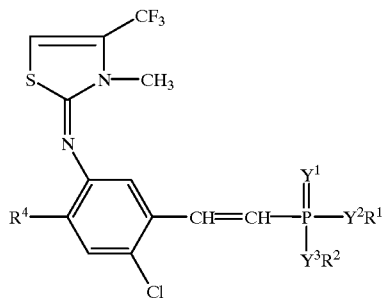

the compounds ILh.1–ILh.1287, which differ from the corresponding compounds IAa.1–IAa.1287 only in that Eth is —CH═C(Cl)— and $R^5$ is the heterocycle $\Phi^{20}$ where $R^{50}$=methyl, $R^{51}$=trifluoromethyl and $R^{52}$=hydrogen:

ILh

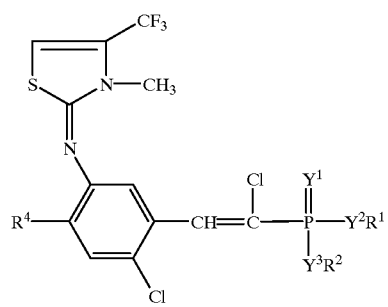

the compounds ILi.1–ILi.1287, which differ from the corresponding compounds IAa.1–IAa.1287 only in that Eth is —CH═C(Br)— and $R^5$ is the heterocycle $\Phi^{20}$ where $R^{50}$=methyl, $R^{51}$=trifluoromethyl and $R^{52}$=hydrogen:

ILi

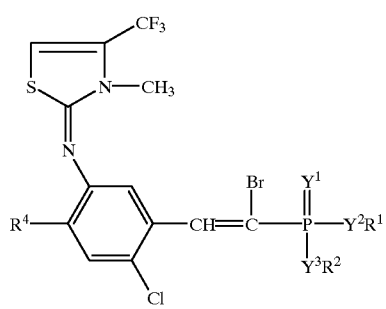

the compounds ILj.1–ILj.1287, which differ from the corresponding compounds IAa.1–IAa.1287 only in that Eth is —CH═C(CN)— and $R^5$ is the heterocycle $\Phi^{20}$ where $R^{50}$=methyl, $R^{51}$=trifluoromethyl and $R^{52}$=hydrogen:

ILj

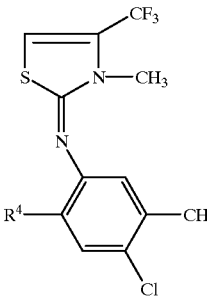

the compounds ILk.1–ILk.1287, which differ from the corresponding compounds IAa.1–IAa.1287 only in that Eth is —CH═C(CH$_3$)— and $R^5$ is the heterocycle $\Phi^{20}$ where $R^{50}$=methyl, $R^{51}$=trifluoromethyl and $R^{52}$=hydrogen:

ILk

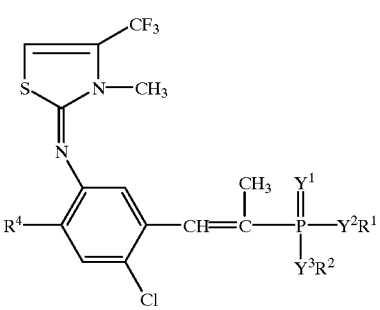

the compounds ILm.1–ILm.1287, which differ from the corresponding compounds IAa.1–IAa.1287 only in that Eth is —CH═C(COOCH$_3$)— and $R^5$ is the heterocycle $\Phi^{20}$ where $R^{50}$=methyl, $R^{51}$=trifluoromethyl and $R^{52}$=hydrogen:

ILm

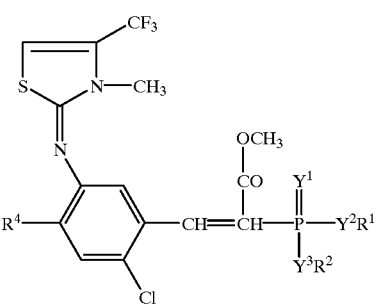

the compounds ILn.1–ILn.1287, which differ from the corresponding compounds IAa.1–IAa.1287 only in that Eth is —C≡C— and $R^5$ is the heterocycle $\Phi^{20}$ where $R^{50}$=methyl, $R^{51}$=trifluoromethyl and $R^{52}$=hydrogen:

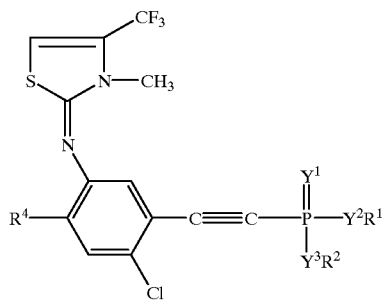

ILn

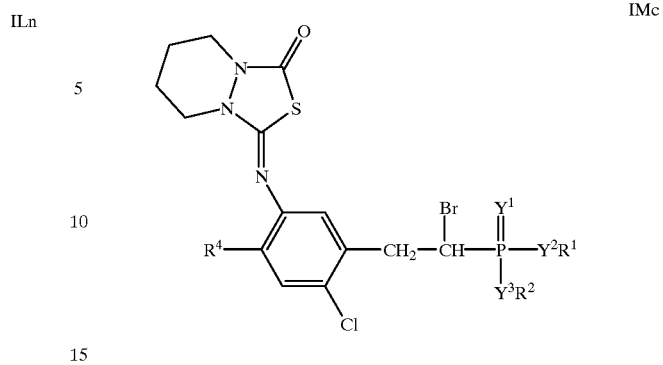

IMc the compounds IMa.1–IMa.1287, which differ from the corresponding compounds IAa.1–IA.1287 only in that $R^5$ is the heterocycle $\Phi^{21}$ where $Z^3$ and $Z^4$=nitrogen, and $R^{53}$ and $R^{54}$ together=tetramethylene chain:

the compounds IMd.1–IMd.1287, which differ from the corresponding compounds IAa.1–IAa.1287 only in that Eth is —$CH_2$—CH(CN)— and $R^5$ is the heterocycle $\Phi^{21}$ where $Z^3$ and $Z^4$=nitrogen, and $R^{53}$ and $R^{54}$ together=tetramethylene chain:

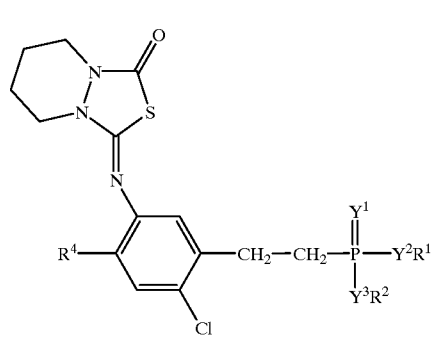

IMa

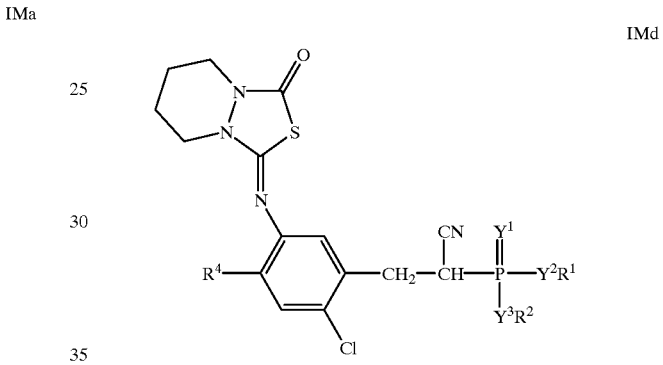

IMd the compounds IMb.1–IMb.1287, which differ from the corresponding compounds IAa.1–IAa.1287 only in that Eth is —$CH_2$—CH(Cl)— and $R^5$ is the heterocycle $\Phi^{21}$ where $Z^3$ and $Z^4$ nitrogen, and $R^{53}$ and $R^{54}$ together=tetramethylene chain:

the compounds IMe.1–IMe.1287, which differ from the corresponding compounds IAa.1–IAa.1287 only in that Eth is —$CH_2$—CH($CH_3$)— and $R^5$ is the heterocycle $\Phi^{21}$ where $Z^3$ and $Z^4$=nitrogen, and $R^{53}$ and $R^{54}$ together=tetramethylene chain:

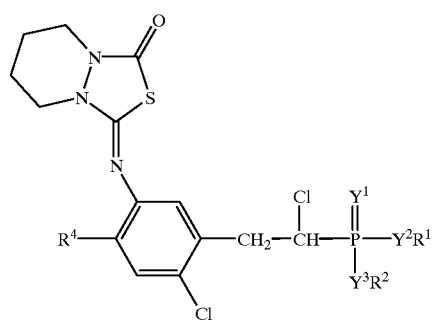

IMb

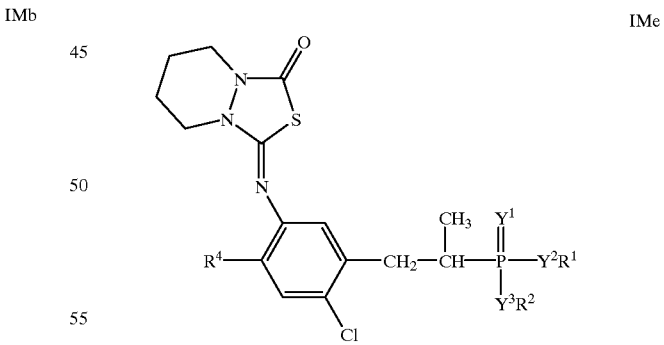

IMe the compounds IMc.1–IMc.1287, which differ from the corresponding compounds IAa.1–IAa.1287 only in that Eth is —$CH_2$—CH(Br)— and $R^5$ is the heterocycle $\Phi^{21}$ where $Z^3$ and $Z^4$=nitrogen, and $R^{53}$ and $R^{54}$ together=tetramethylene chain:

the compounds IMf.1–IMf.1287, which differ from the corresponding compounds IAa.1–IAa.1287 only in that Eth is —$CH_2$—CH($COOCH_3$)— and $R^5$ is the heterocycle $\Phi^{21}$ where $Z^3$ and $Z^4$=nitrogen, and $R^{53}$ and $R^{54}$ together=tetramethylene chain:

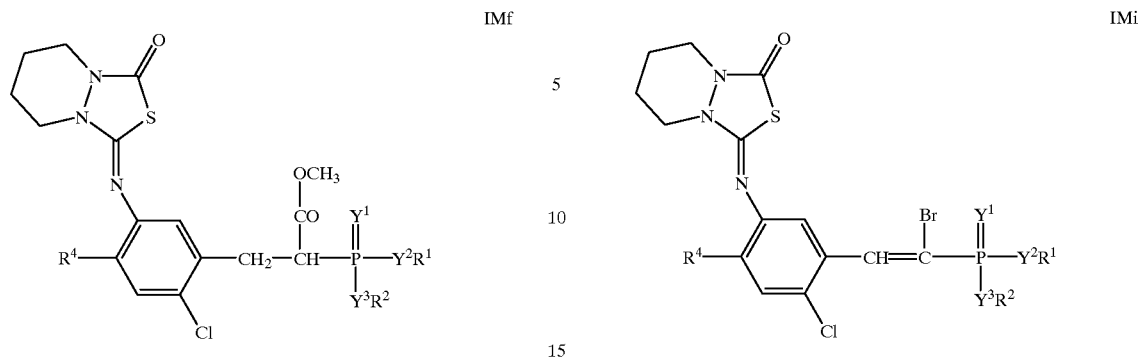

the compounds IMg.1–IMg.1287, which differ from the corresponding compounds IAa.1–IAa.1287 only in that Eth is 1,2-ethenediyl and $R^5$ is the heterocycle $\Phi^{21}$ where $Z^3$ and $Z^4$=nitrogen, and $R^{53}$ and $R^{54}$ together=tetramethylene chain:

the compounds IMj.1–IMj.1287, which differ from the corresponding compounds IAa.1–IAa.1287 only in that Eth is —CH=C(CN)— and $R^5$ is the heterocycle $\Phi^{21}$ where $Z^3$ and $Z^4$=nitrogen, and $R^{53}$ and $R^{54}$ together=tetramethylene chain:

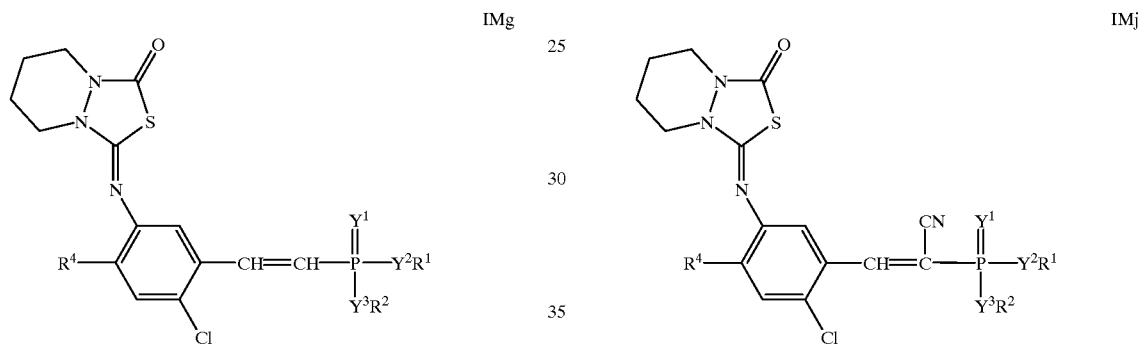

the compounds IMh.1–IMh.1287, which differ from the corresponding compounds IAa.1–IAa.1287 only in that Eth is —CH=C(Cl)— and $R^5$ is the heterocycle $\Phi^{21}$ where $Z^3$ and $Z^4$=nitrogen, and $R^{53}$ and $R^{54}$ together=tetramethylene chain:

the compounds IMk.1–IMk.1287, which differ from the corresponding compounds IAa.1–IAa.1287 only in that Eth is —CH=C(CH$_3$)— and $R^5$ is the heterocycle $\Phi^{21}$ where $Z^3$ and $Z^4$=nitrogen, and $R^{53}$ and $R^{54}$ together=tetramethylene chain:

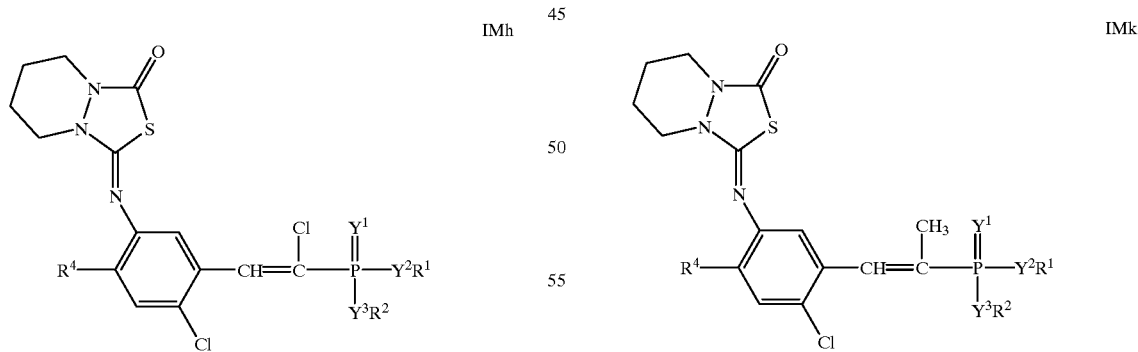

the compounds IMi.1–IMi.1287, which differ from the corresponding compounds IAa.1–IAa.1287 only in that Eth is —CH=C(Br)— and $R^5$ is the heterocycle $\Phi^{21}$ where $Z^3$ and $Z^4$=nitrogen, and $R^{53}$ and $R^{54}$ together=tetramethylene chain:

the compounds IMm.1–IMm.1287, which differ from the corresponding compounds IAa.1–IAa.1287 only in that Eth is —CH=C(COOCH$_3$)— and $R^5$ is the heterocycle $\Phi^{21}$ where $Z^3$ and $Z^4$=nitrogen, and $R^{53}$ and $R^{54}$ together=tetramethylene chain:

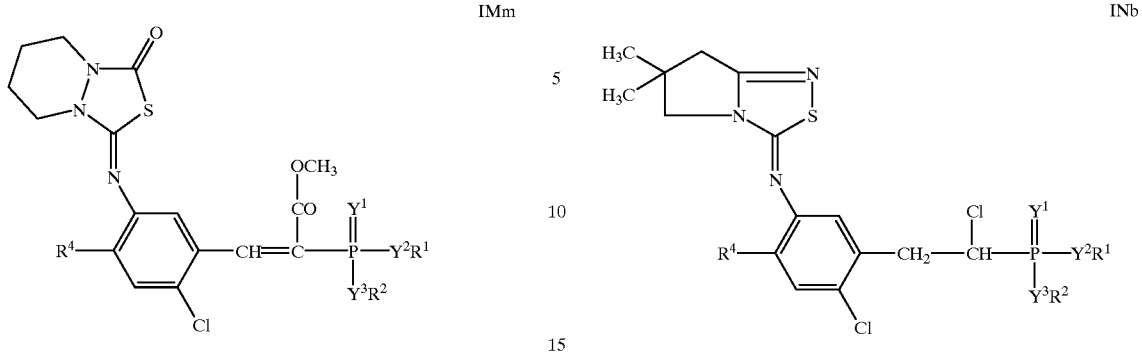

the compounds IMn.1–IMn.1287, which differ from the corresponding compounds IAa.1–IAa.1287 only in that Eth is —C≡C— and $R^5$ is the heterocycle $\Phi^{21}$ where $Z^3$ and $Z^4$=nitrogen, and $R^{53}$ and $R^{54}$ together= tetramethylene chain:

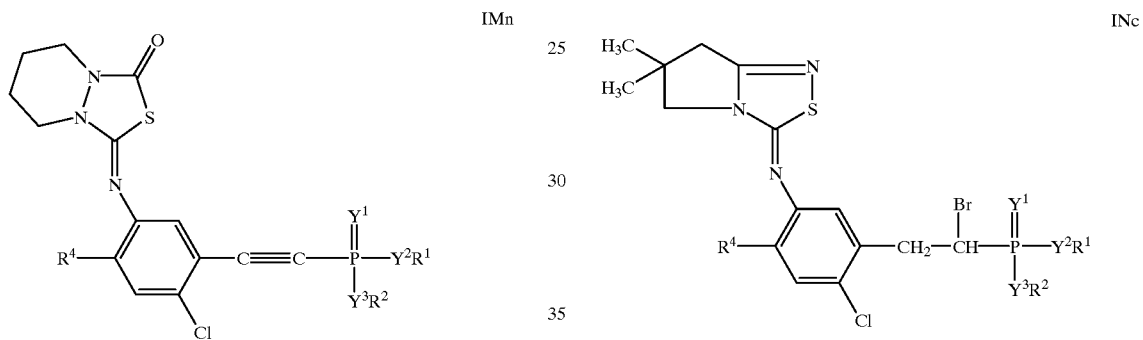

the compounds INa.1–INa.1287, which differ from the corresponding compounds IAa.1–IAa.1287 only in that $R^5$ is the heterocycle $\Phi^{22}$ where $R^{55}$ and $R^{56}$ together=2,2-dimethylpropane-1,3-diyl chain:

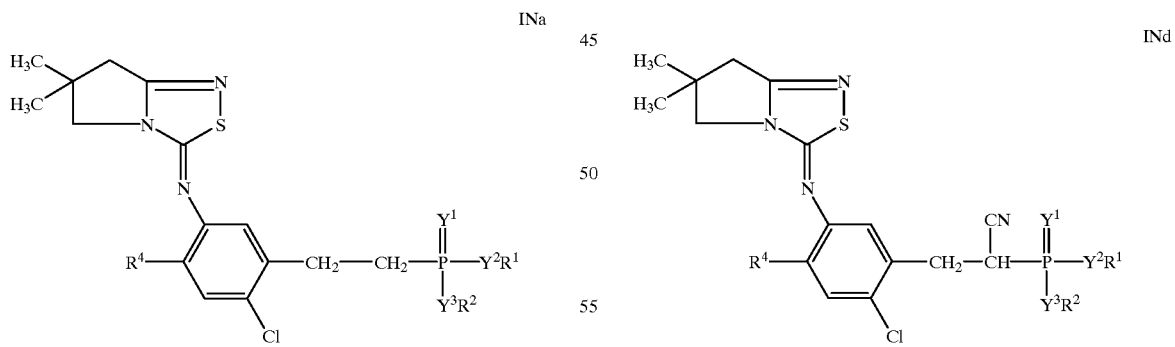

the compounds INb.1–INb.1287, which differ from the corresponding compounds IAa.1–IAa.1287 only in that Eth is —CH$_2$—CH(Cl)— and $R^5$ is the heterocycle $\Phi^{22}$ where $R^{55}$ and $R^{56}$ together 2,2-dimethylpropane-1,3-diyl chain:

the compounds INc.1–INc.1287, which differ from the corresponding compounds IAa.1–IAa.1287 only in that Eth is —CH$_2$—CH(Br)— and $R^5$ is the heterocycle $\Phi^{22}$ where $R^{55}$ and $R^{56}$ together=2,2-dimethylpropane-1,3-diyl chain:

the compounds INd.1–INd.1287, which differ from the corresponding compounds IAa.1–IAa.1287 only in that Eth is —CH$_2$—CH(CN)— and $R^5$ is the heterocycle $\Phi^{22}$ where $R^{55}$ and $R^{56}$ together=2,2-dimethylpropane-1,3-diyl chain:

the compounds INe.1–INe.1287, which differ from the corresponding compounds IAa.1–IAa.1287 only in that Eth is —CH$_2$—CH(CH$_3$)— and $R^5$ is the heterocycle $\Phi^{22}$ where $R^{55}$ and $R^{56}$ together=2,2-dimethylpropane-1,3-diyl chain:

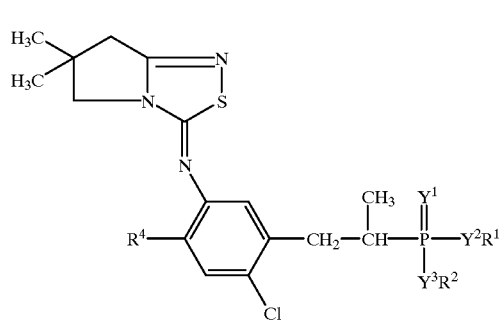

INe the compounds INf.1–INf.1287, which differ from the corresponding compounds IAa.1–IAa.1287 only in that Eth is —CH$_2$—CH(COOCH$_3$)— and R$^5$ is the heterocycle Φ$^{22}$ where R$^{55}$ and R$^{56}$ together=2,2-dimethylpropane-1,3-diyl chain:

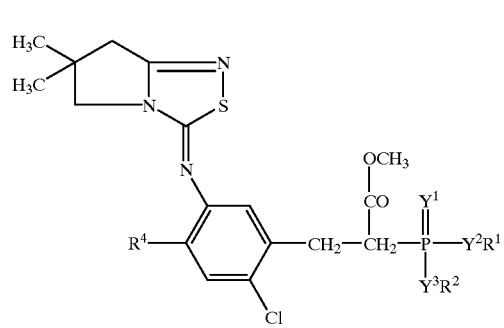

INf the compounds INg-1–INg.1287, which differ from the corresponding compounds IAa.1–IAa.1287 only in that Eth is 1,2-ethenediyl and R$^5$ is the heterocycle Φ$^{22}$ where R$^{55}$ and R$^{56}$ together=2,2-dimethylpropane-1,3-diyl chain:

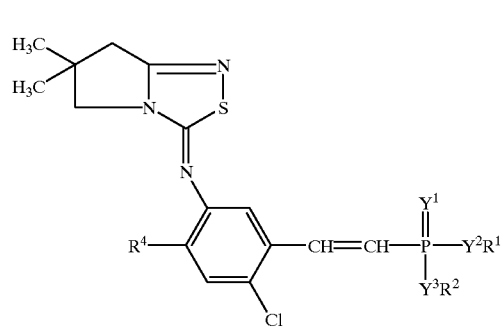

INg the compounds INh.1–INh.1287, which differ from the corresponding compounds IAa.1–IAa.1287 only in that Eth is —CH=C(Cl)— and R$^5$ is the heterocycle Φ$^{22}$ where R$^{55}$ and R$^{56}$ together=2,2-dimethylpropane-1,3-diyl chain:

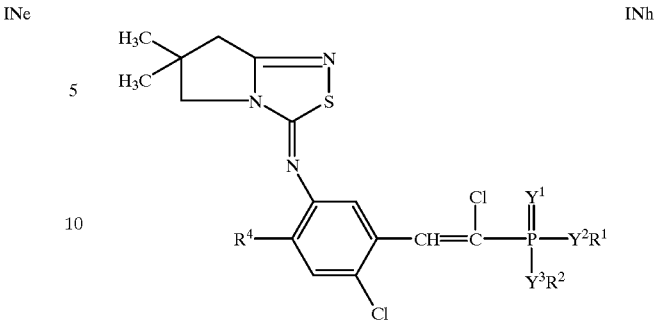

INh the compounds INi.1–INi.1287, which differ from the corresponding compounds IAa.1–IAa.1287 only in that Eth is —CH=C(Br)— and R$^5$ is the heterocycle Φ$^{22}$ where R$^{55}$ and R$^{56}$ together=2,2-dimethylpropane-1,3-diyl chain:

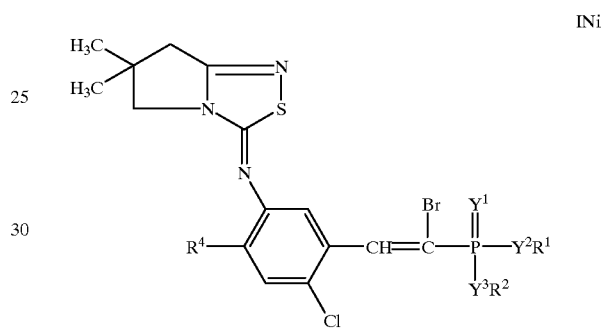

INi the compounds INj.1–INj.1287, which differ from the corresponding compounds IAa.1–IAa.1287 only in that Eth is —CH=C(CN)— and R$^5$ is the heterocycle Φ$^{22}$ where R$^{55}$ and R$^{56}$ together=2,2-dimethylpropane-1,3-diyl chain:

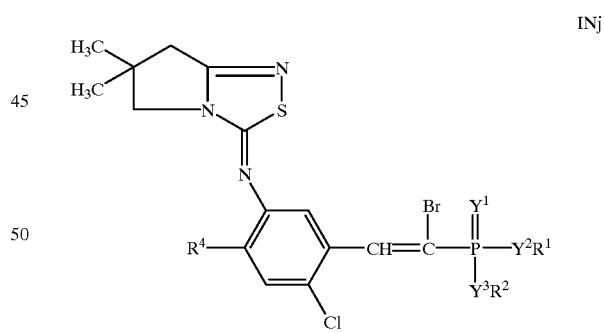

INj the compounds INk.1–INk.1287, which differ from the corresponding compounds IAa.1–IAa.1287 only in that Eth is —CH=C(CH$_3$)— and R$^5$ is the heterocycle Φ$^{22}$ where R$^{55}$ and R$^{56}$ together=2,2-dimethylpropane-1,3-diyl chain:

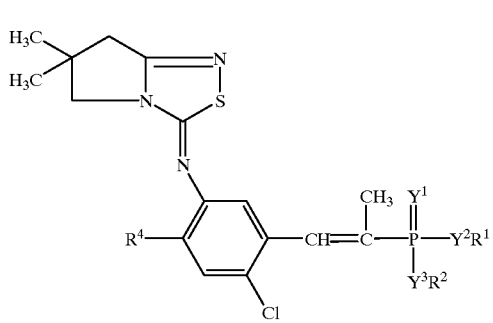

INk the compounds INm.1–INm.1287, which differ from the corresponding compounds IAa.1–IAa.1287 only in that Eth is —CH=C(COOCH$_3$)— and R$^5$ is the heterocycle Φ$^{22}$ where R$^{55}$ and R$^{56}$ together=2,2-dimethylpropane-1, 3-diyl chain:

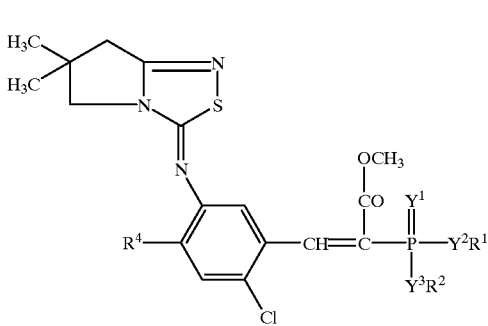

INm the compounds INn.1–INn.1287, which differ from the corresponding compounds IAa.1–IAa.1287 only in that Eth is —C≡C— and R$^5$ is the heterocycle Φ$^{22}$ where R$^{55}$ and R$^{56}$ together=2,2-dimethylpropane-1,3-diyl chain:

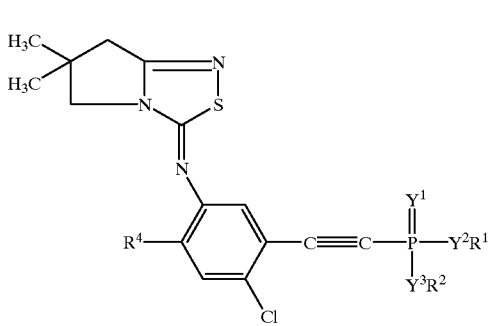

INn

The substituted aromatic phosphonic acid derivatives of the formula I are obtainable by a variety of routes, in particular by one of the following processes:

A) linkage of the phosphonyl group to the aromatic ring

A.1) by diazotizing anilines II and reacting the resulting diazonium salts with vinyl- or alkynylphosphonic acid derivatives III by the Meerwein method {cf, for example, Org. Reactions 11 (1960), chapter 3, pp. 189–260 and Kogyo Kagaku Zasshi 67(12) (1964), 2093–2095}:

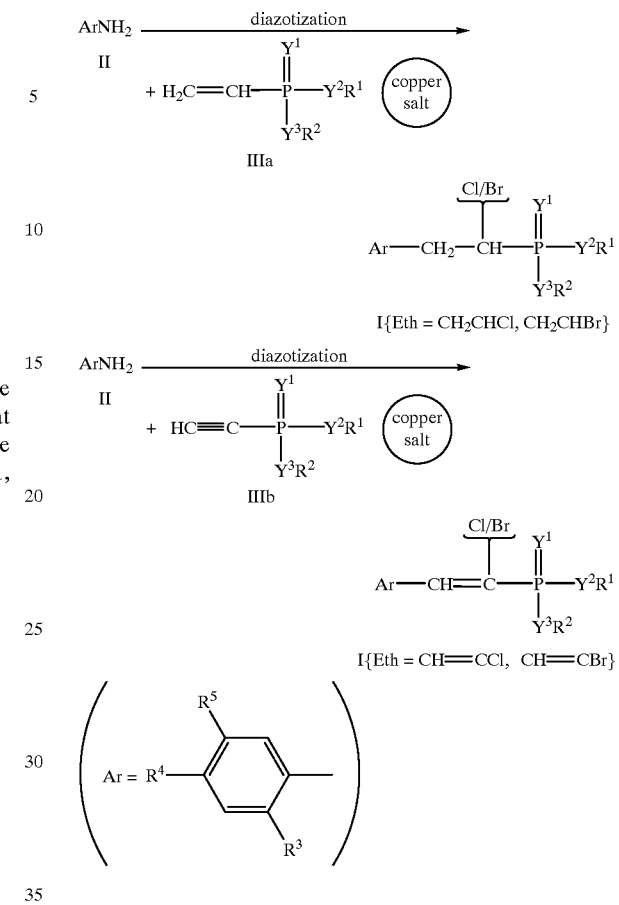

In this method, the aniline of the formula II, which is either known from the literature or can be synthesized similarly to anilines known from the literature, is first converted into the corresponding diazonium cation in a manner known per se, and this is then reacted completely with IIIa or IIIb in the presence of a copper salt.

The diazonium salt is generally obtained by reacting the aniline II with a nitrite, such as sodium nitrite and potassium nitrite, in an aqueous acid solution, e.g. in aqueous hydrofluoric acid, hydrochloric acid, hydrobromic acid, sulfuric acid or tetrafluoroboric acid. The nitrite is normally employed in approximately equimolar amounts or in an excess of up to approximately five times the molar amount based on the amount of aniline II.

The resulting solution of the diazonium salt, or the diazonium salt isolated therefrom, is then reacted with a solution or suspension of the vinyl- or alkynylphosphonic acid derivative IIIa/IIIb in the presence of a copper salt, such as copper(I) bromide, copper(II) bromide, copper(I) chloride and copper(II) chloride.

Examples of suitable solvents are water, acetonitrile, ketones such as acetone, diethyl ketone and methyl ethyl ketone, ethers such as diethyl ether and tetrahydrofuran, and furthermore alcohols such as methanol or ethanol.

The vinyl- or alkynylphosphonic acid derivatives IIIa/IIIb and the copper halide are normally used in approximately equimolar amounts or in an excess of up to approximately 30 times the molar amount based on the aniline II. However, it is possible to employ a lesser or catalytic amount of the copper halide.

As a rule, the diazotization and the reaction of the diazonium salt with IIIa/IIIb are carried out at from (–100) to 50° C., preferably (–20) to +30° C.

One process variant consists in an addition to a solution or suspension of the aniline II, of the vinyl or alkynylphosphonic acid derivative IIIa/IIIb and of the copper halide in an anhydrous system, e.g. in glacial acetic acid/chlorohydrocarbon, absolute methanol or ethanol, in an ether such as tetrahydrofuran and dioxane or in acetonitrile or acetone, a nitrous ester such as tert-butyl nitrite and isopentyl nitrite. what has been said above regarding the reaction temperature and the ratios of the reactants also applies here.

A.2) by means of a Heck reaction (see, for example, B. A. Burini, S. Cacchi, P. Pace, B. R. Pietroni, Synlett 1995, 677):

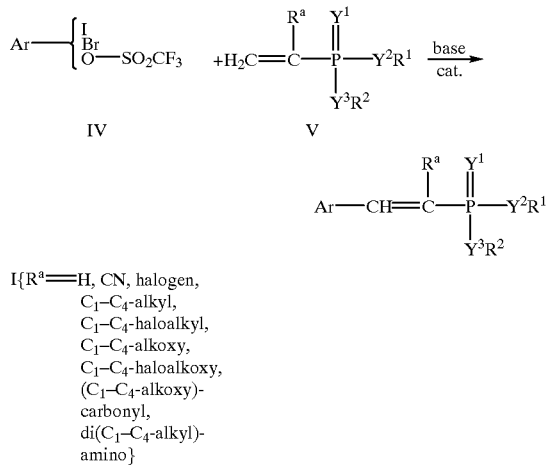

I{$R^a$=H, CN, halogen,
$C_1$–$C_4$-alkyl,
$C_1$–$C_4$-haloalkyl,
$C_1$–$C_4$-alkoxy,
$C_1$–$C_4$-haloalkoxy,
($C_1$–$C_4$-alkoxy)-carbonyl,
di($C_1$–$C_4$-alkyl)-amino}

As regards the definition of Ar, see Process A.1); cat. is a transition-metal catalyst, preferably a palladium(II) compound such as palladium acetate.

As a rule, the reaction is carried out in an inert organic solvent, in particular in dimethylformamide or tetrahydrofuran.

Examples of suitable bases are carbonates such as potassium carbonate, acetates such as sodium acetate and tertiary amines such as triethylamine.

The reaction is generally carried out at from 0° C. to the boiling point of the reaction mixture, preferably at 50 to 100° C.

A.3) by means of Knoevenagel condensation of aromatic aldehydes VIa or ketones VIb with phosphonic acid derivatives VII:

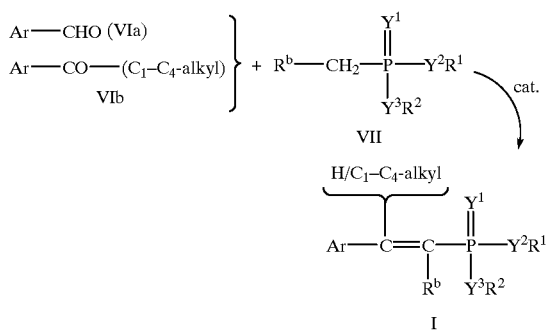

As regards the definition of Ar, see process A.1);
$R^b$ is cyano, $C_1$–$C_4$-alkoxy or ($C_1$–$C_4$-alkoxy)carbonyl (VIIa=VII where $R^b$=CN; VIIb=VII where $R^b$=alkoxy); cat. is a catalyst, e.g. piperidine/acetic acid, sodium methanolate, sodium ethanolate, titanium tetrachloride/N-methylmorpholine, or chlorotri(isopropoxy)titanium/triethylamine.

The process is normally carried out in an inert organic solvent, e.g. in an aromatic hydrocarbon such as toluene, a lower alcohol such as methanol and ethanol, or in a chlorinated hydrocarbon such as dichloromethane.

The reaction temperature is generally at from 0° C. to the boiling point of the reaction mixture.

If desired, the water which is freed during the reaction can be removed by means of azeotropic distillation. In this case, the process is preferably carried out in an aromatic hydrocarbon such as benzene, toluene and the xylenes at the respective boiling point of the reaction mixture. {See, for example, S. Abdallah-El Ayoubi, F. Texier-Boullet, J. Hamelin, Synthesis 1994, 258; D. Danion, R. Carrie, Tetrahedron Lett. 1968, 4537; F. Texier-Boullet, A. Foucaud, Tetrahedron Lett. 21 (1980), 2161; S. Patai, A. Schwartz, J. Org. Chem. 25 (1960), 1232; J. M. McIntosh, R. A. Sieler, Can. J. Chem. 56 (1978), 226; M. T. Reetz, R. Peter, M. v. Itzstein, Chem. Ber. 120 (1987) 121; K. A. Petrov, V. A. Chauzov, S. V. Agafonov, N. V. Pazhitnova, J. Gen. Chem. USSR 50 (1980), 1225}.

Those aromatic aldehydes VIa or ketones VIb which are not already known can be prepared in a manner known per se.

A.4) by means of Wittig-Horner olefination {cf., for example, B. M. G. T. Lowen, M. R. Almond, J. Org. Chem 59 (1994) 4548; P. Teulade, P. Savignac, E. E. Aboujaoude, S. Lietge, N. Collignon, J. Organomet. Chem. 304 (1986), 283; G. M. Parratt, J. Chem. Soc., Perkin Trans. 1 (1986), 1417; B. Costisella, I. Keitel H. Gross, Tetrahedron 37 (1981), 1227}:

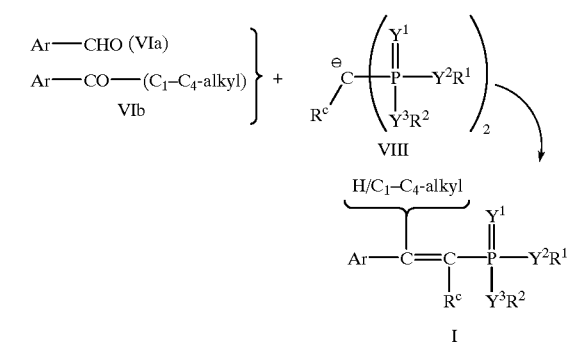

As regards the definition of Ar, see process A.1);
$R^c$ is hydrogen, halogen, $C_1$–$C_4$-alkyl or di($C_1$–$C_4$-alkyl) amino (VIIIa=VIII where $R^c$=H;
VIIIb=VIII where $R^c$=halogen; VIIIc=VIII where $R^c$=alkyl).

The process is normally carried out in an inert organic solvent, e.g. in an aromatic hydrocarbon such as toluene, a halogenated hydrocarbon such as dichloromethane or an ether such as diethyl ether, tetrahydrofuran, dioxane and 1,2-dimethoxyethane.

The anion VIII can be obtained, for example, by deprotonating the corresponding methanediphosphonic acid derivative with a strong base such as lithium diisopropylamide, sodium hydride and n-butyllithium.

The reaction is generally carried out at from (−100)° C. to the boiling point of the reaction mixture, preferably at from (−78) to +30° C.

A. 5) by means of Wittig olefination {see, in this context, for example GB-A 12 43 214}:

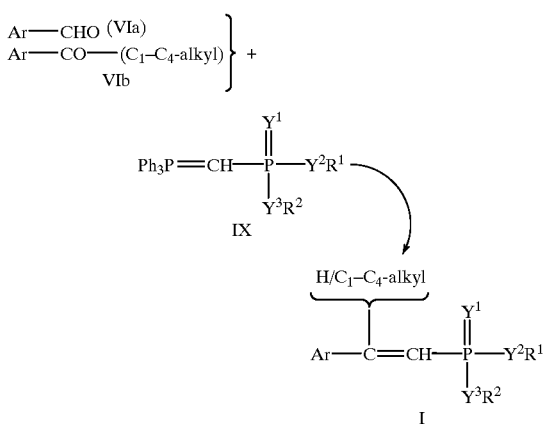

As regards the definition of Ar, see process A.1);
Ph is the phenyl group.

The process is normally carried out in an inert organic solvent, e.g. in an aromatic hydrocarbon such as toluene, a halogenated hydrocarbon such as dichloromethane or an ether such as diethyl ether, tetrahydrofuran, dioxane and 1,2-dimethoxyethane.

The reaction is generally carried out at from (–100)° C. to the boiling point of the reaction mixture, preferably at from 20 to 60° C.

A.6) by means of Peterson olefination {see, in this context, for example O. I. Kolodyazhnyi, D. B. Golokhov, J. Gen. Chem. USSR 57 (1987), 2353; F. A. Carey, A. S. Court, J. Org. Chem. 37 (1972), 939}:

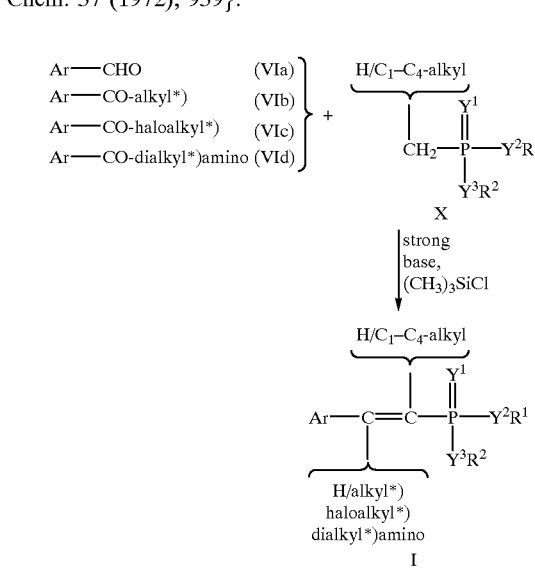

*)each $C_1$–$C_4$

The process is normally carried out in an inert organic solvent, e.g. in an aromatic hydrocarbon such as toluene or an ether such as diethyl ether, tetrahydrofuran, dioxane and 1,2-dimethoxyethane.

Examples of suitable strong bases are lithium diisopropylamide, sodium hydride or butyllithium.

In general, the reaction is carried out at from (–100)° C. to the boiling point of the reaction mixture, preferably at from (–70) to +30° C.

Preferably, X is first reacted with chlorotrimethylsilane in the presence of a strong base, and only then is the reaction product treated with a compound VIa to VId. As a rule, the base is used in an excess, approximately 2 to 5 times, in particular approximately 2 times, the molar amount based on the amount of X. Chlorotrimethylsilane is expediently employed in an approximately equimolar amount based on the amount of X.

Those aromatic aldehydes VIa, ketones VIb and VIc and the N,N-dialkylbenzamides VId which are not already known can be prepared in a manner known per se.

A.7) by means of subjecting a styryl halide XI to a coupling reaction with a trialkyl phosphite XII or a dialkyl phosphite XIII {cf. in this context, for example, R. S. Gross, S. Mehdi, J. R. McCarthy, Tetrahedron Lett. 34 (1993), 7197; G. Axelrad, S. Laosooksathit, R. Engel, J. Org. Chem. 46 (1981), 5200}:

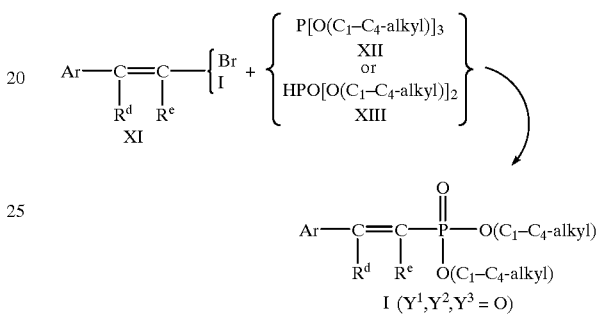

As regards the definition of Ar, see process A.1);
$R^d$ and $R^e$ are hydrogen, halogen or $C_1$–$C_4$-alkyl.

The process is normally carried out in an inert organic solvent, preferably in an aromatic hydrocarbon such as toluene or an ether such as tetrahydrofuran.

The reaction of XI with a trialkyl phosphite XII is advantageously carried out in the presence of copper(I) bromide or copper(I) chloride.

The reaction of XI with a dialkyl phosphite XIII is advantageously carried out in the presence of a transition-metal catalyst, preferably a palladium(II) compound, such as dichlorobis(triphenylphosphine)palladium, and, if desired, in the presence of a base, e.g. triethylamine.

The reaction is generally carried out at from (–100)° C. to the boiling point of the reaction mixture, preferably at approximately +25° C.

Those styryl halides XI and phosphorus compounds XII and XIII which are not already known can be prepared in a manner known per se.

A.8) by reacting a phenylacetylene XIV
  with a trialkyl phosphite XII or
  in succession with phosphorus pentachloride and an alcohol, mercaptan or amine ($HY^2R^1$/$HY^3R^2$) in the presence of a base
  {cf. in this context, for example, C. E. Griffin, T. D. Mitchell, J. Org. Chem. 30 (1965), 1935; A. Meisters, J. M. Swan, Aust. J. Chem. 18 (1965), 155; L. Maier, Synth. Inorg. Met. Org. Chem. 3 (1973), 329; A. A. Petrov, J. Gen. Chem. USSR 41 (1971) 1670}:

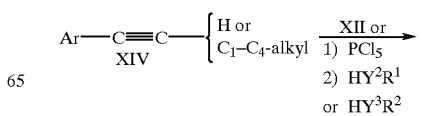

-continued

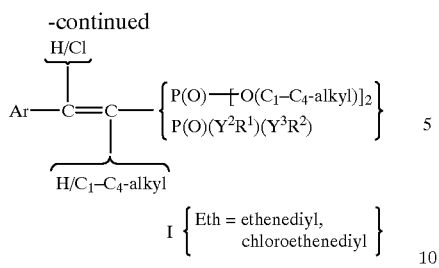

I { Eth = ethenediyl, chloroethenediyl }

As regards the definition of Ar, see process A.1).

XIV is preferably reacted with XII in the absence of a solvent at from 20° C. to the boiling point of the trialkyl phosphite XII, in particular at the boiling point of the reaction mixture.

Suitable bases for reacting the phenylacetylene XIV with $PC_{15}$ and $(HY^2R^1/HY^3R^2)$ are, in particular, tertiary amines such as pyridine and triethylamine.

XIV is preferably reacted with $PCl_5$ at from 50 to 200° C., in contrast to the subsequent reaction with $(HY^2R^1/HY^3R^2)$, where the reaction temperature is from $(-100)°$ C. to the boiling point of the reaction mixture.

Those phenylacetylenes XIV and the alcohols, mercaptans and amines $(HY^2R^1/HY^3R^2)$ which are not already known can be prepared in a manner known per se.

A.9) by reacting benzylidenetriphenylphosphoranes XV with a perfluoroalkanecarboxylic anhydride and subsequently with a lithium dialkyl phosphite in a manner known per se {cf. in this context, for example, Y. Shen, Q. Liao, W. Qiu, J. Chem. Soc., Perkin Trans 1, 695 (1990)}:

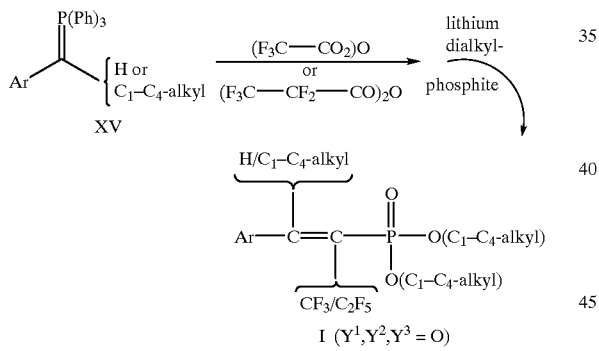

As regards the definition of Ar, see process A.1);
Ph is the phenyl group.

Suitable solvents/diluents for XV are, in particular, aromatic hydrocarbons, such as toluene and ethers such as tetrahydrofuran.

The reaction can generally be carried out at from $(-100)°$ C. to the boiling point of the reaction mixture, preferably at from $(-78)$ to $+25°$ C.

Those benzylidenetriphenylphosphoranes XV which are not already known can be prepared in a manner known per se.

A.10) by alkylating a phosphonic acid derivative XVI with a 3-pyridylbenzyl halide XVII in a manner known per se in the presence of a strong base {cf. in this context, for example, G. M. Blackburn, M. J. Parratt, J. Chem. Soc., Perkin Trans 1 (1986), 1425; G. M. Kosolapoff, J. S. Powell, J. Am. Chem. Soc. 72 (1950), 4198; R. M. Keenan et al., J. Med. Chem. 35 (1992), 3858; H. Ahlbrecht, W. Farnung, Synthesis 336 (1977); E. D'Incan, J. Seyden-Penne, Synthesis, 516 (1975); S. Hanessian, Y. L. Bennani, D. Delorme, Tetrahedron Lett. 31 (1990), 6461}:

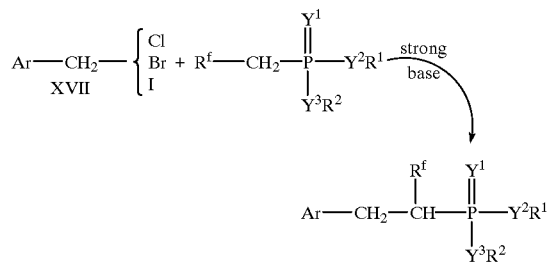

I{X = ethanediyl; cyano, halogen-, $C_1$–$C_4$-alkyl-, ($C_1$–$C_4$-alkoxy)carbonyl- or di-($C_1$–$C_4$-alkyl)amino- subst. ethanediyl}

As regards the definition of Ar, see process A.1;
$R^f$ is hydrogen, cyano, halogen, $C_1$–$C_4$-alkyl, ($C_1$–$C_4$-alkoxy)carbonyl or di($C_1$–$C_4$-alkyl)amino (XVIa=XVI where $R^f$=CN; XVIb=XVI where $R^f$=alkyl).

Examples of suitable strong bases are sodium hydroxide, butyllithium and lithium diisopropylamide.

The process is usually carried out in an inert organic solvent, preferably in an aromatic hydrocarbon such as toluene or a cyclic ether such as tetrahydrofuran.

The process is generally carried out at from $(-100)°$ C. to the boiling point of the reaction mixture, preferably from $(-78)°$ C. to 25° C.

Those phosphonic acid derivatives XVI and benzyl halides XVII which are not already known can be prepared in a manner known per se.

A.11) by reacting phenylacetaldehydes XVIII with dialkyl phosphites XIII, if desired in the presence of ammonia or of a primary or secondary amine {cf. in this context, for example, M. E. Chalmers, G. M. Kosolapoff, J. Am. Chem. Soc. 75 (1953), 5278; C. Li, C. Yuan, Tetrahedron Lett. 34 (1993), 1515}:

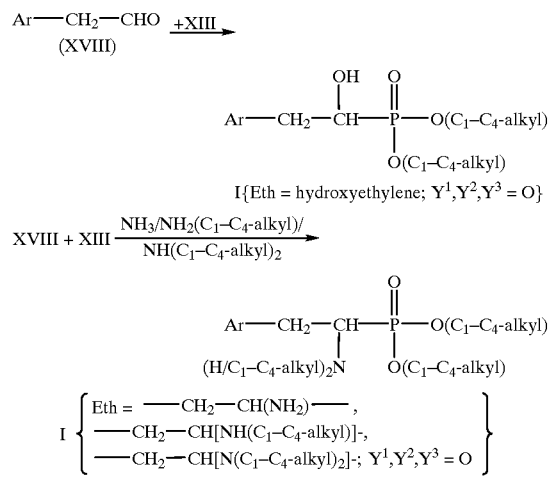

As regards the definition of Ar, see process A.1).

Examples of suitable solvents are water, the lower alcohols such as methanol, ethers such as tetrahydrofuran and diethyl ether, and pyridine.

The process is generally carried out at from $(-100)°$ C. to the boiling point of the reaction mixture, preferably from 20 to 50° C.

Those phenylacetaldehydes XVIII which are not already known can be prepared in a manner known per se.

A.12) by reacting alkyl halides XIX with trialkyl phosphites XII in a manner known per se following Arbuzov's method {see in this context, for example, A. Y. Garner, E. C. Chapin, P. M. Scanlon, J. Org. Chem. 24 (1959), 532}:

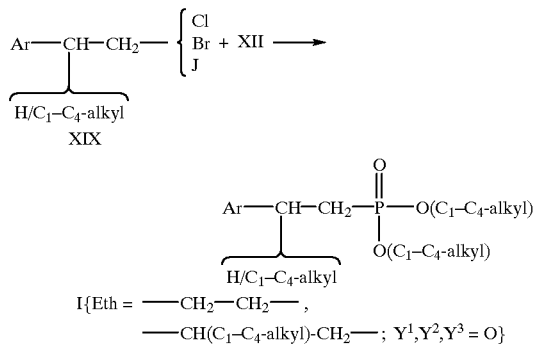

As regards the definition of Ar, see process A.1).

The reaction is preferably carried out in the absence of a solvent, suitable reaction temperatures being from 0° C. to the boiling point of the trialkyl phosphite XII, preferably from 20 to 150° C.

Those alkyl halides XIX which are not already known can be prepared in a manner known per se.

A.13) by reacting an aldehyde VIa with a trichloromethanephosphonic acid derivative XXVI in the presence of an alkyllithium compound XXVII

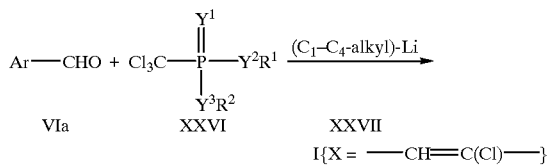

As regards the definition of Ar, see process A.1).

Normally, the trichloromethanephosphonic acid derivative XXVI is first reacted with the alkyllithium compound XXVII in an inert organic solvent, for example an ether such as tetrahydrofuran or a hydrocarbon such as n-hexane. The process is generally carried out between the melting point and the boiling point of the reaction mixture, preferably at from (−80) to (−50)° C.

The reaction product is then reacted with the aldehyde VIa—preferably without prior work-up—, the reaction temperature preferably being raised to approximately +20° C.

B) Derivatization of substituted aromatic phosphoric acid derivatives of the formula I:

As regards the reaction procedure and the ratios of the reactants, reference may be made, for example, to HoubenWeyl, Methoden der Organischen Chemie [Methods in Organic Chemistry], Georg Thieme Verlag, Stuttgart, Vol. 12/1, 4th Edition 1963, p. 387 et seq., 407 et seq. and 557 et seq.; Vol. E2 1982, p. 300 et seq. and 419 et seq.

B.1) Hydrogenation of substituted aromatic phosphonic acid derivatives I where Eth is ethene-1,2-diyl or a halogen-substituted ethane-1,2-diyl bridge {cf., for example, C. N. Robinson, P. K. Li. J. F. Addison, J. Org. Chem. 37 (1972), 2939; G. T. Lowen, M. R. Almond, J. Org. Chem. 59 (1994), 4548}:

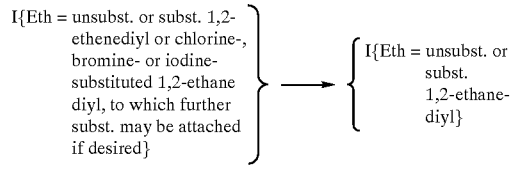

As regards the definition of Ar, see process A.1).

The hydrogenation is carried out either using hydrogen in the presence of a catalyst customary for this purpose, such as palladium or platinum on active charcoal or Raney nickel, at from 0 to 150° C. and a hydrogen pressure of approximately 1 to 200 bar, or using a metal hydride such as sodium borohydride and lithium aluminum hydride, at from 0° C. to the boiling point of the reaction mixture.

Examples of solvents which are suitable for the hydrogenation using hydrogen are water, the lower alcohols, such as methanol and ethanol, ethers such as diethyl ether and tetrahydrofuran or esters such as ethyl acetate.

When reacting the starting compound with a metal hydride, the process is preferably carried out in an inert organic solvent, in particular an ether such as diethyl ether and tetrahydrofuran.

B.2) Hydrolysis of substituted aromatic phosphonic acid derivatives I, conversion of the process products into phosphonyl halides, and reaction thereof with nucleophiles:

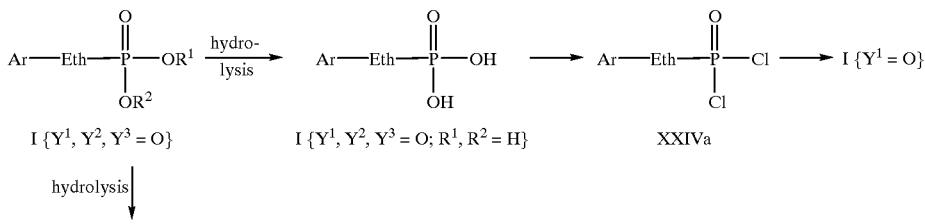

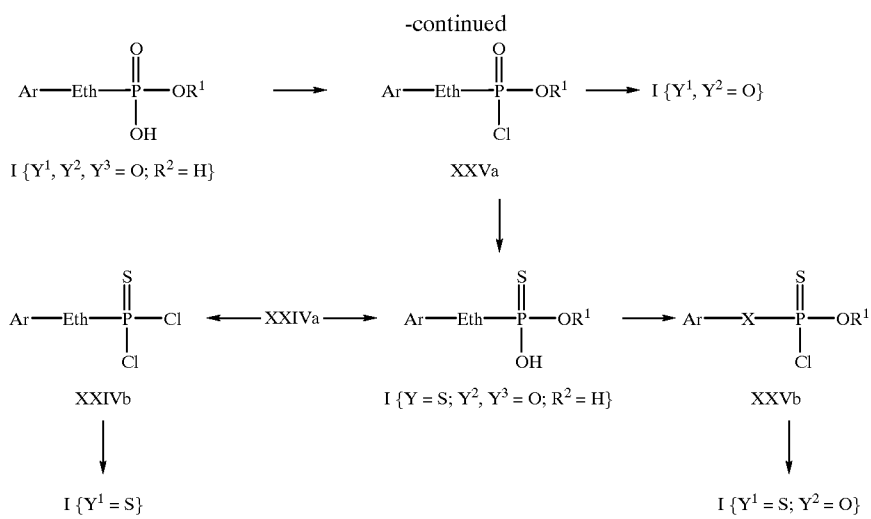

As regards the definition of Ar, see process A.1).

In this process, the substituted aromatic phosphonic acid derivatives I are first cleaved hydrolytically (acidic or basic) or, in the event that $R^1$ and/or $R^2$ is a benzyl or allyl radical, also hydrogenolytically to give phosphonic acids and phosphonic monoesters I. If desired, the cleavage can also be carried out by means of reaction with a tri($C_1$–$C_4$-alkyl)silyl halide, such as chlorotrimethylsilane, iodotrimethylsilane, or a mixture of chlorotrimethylsilane and an alkali metal iodide.

The cleaved products can then be converted into the corresponding phosphonylmono- or -dichlorides XXIVa and XXVa by reacting them with a halogenating agent such as oxalyl chloride, thionyl chloride or phosphorus pentachloride.

If desired, the phosphonyl dichlorides XXIVa can be sulfurized in a manner known per se using a sulfurizing agent, such as phosphorus(V) sulfide and 2,4-bis(4-methoxyphenyl)-1,3,2,4-dithiadiphosphetane-2,4-dithione ("Lawesson's reagent") to give thionophosphonyl dichlorides XXIVb. As regards suitable solvents, temperature and ratios, mention may be made of what has been said in DE-A 19 504 188 under process D).

Finally, other substituted aromatic phosphonic acid derivatives I are accessible by reacting XXIV and XXV with nucleophiles $HY^2R^1$ or $HY^3R^2$.

The phosphonic acid monoester chlorides XXVa can be converted into the thionophosphonic acid monoesters XXVb, for example by reaction with sodium hydrogen sulfide.

B.3) Elimination of hydrogen halide from compounds I where Eth=—$CH_2$—CH(halogen)— or —CH=C(halogen)—:

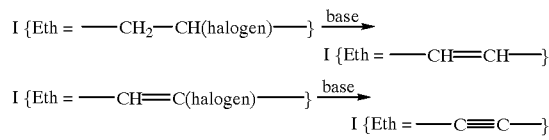

The process is normally carried out in water or an inert organic solvent, e.g. an alcohol such as ethanol, an ether such as diethyl ether, tetrahydrofuran and dioxane, or an aprotic solvent such as acetonitrile, dimethylformamide and dimethyl sulfoxide.

Examples of suitable bases are alkali metal hydroxides, alkali metal carbonates, alkali metal hydrides, alkyllithium compounds such as butyllithium, or organic amines such as triethylamine, 1,4-diazabicyclo[2.2.2.]-octane (DABCO) and 1,8-diazabicyclo[5.4.0.]undec-7-ene (DBU).

As a rule, the reaction is carried out at from (−100)° C. to the boiling point of the reaction mixture, preferably at from 20 to 100° C.

C) Synthesis of the heterocycles $R^5$:

C.1) Synthesis of the triazolopyridine ring

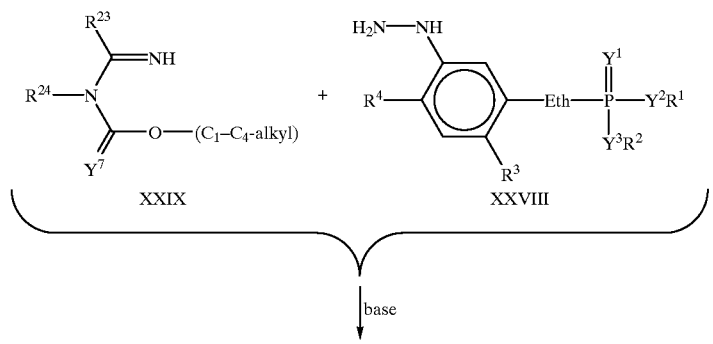

-continued

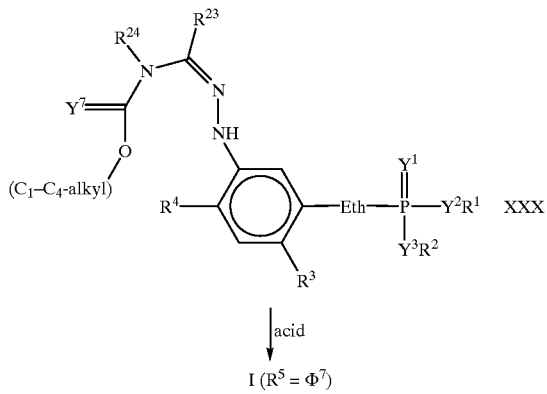

In this process, an amidine of the formula XXIX or an acid addition salt thereof (for example the hydrochloride, hydrobromide or hydrogen sulfate thereof) is reacted with a phenylhydrazine of the formula XXVIII or an acid addition salt thereof (for example the hydrochloride, hydrobromide or hydrogen sulfate thereof) in the presence of a base, for example an alkali metal acetate, alkali metal hydrogen carbonate, alkali metal carbonate or alkali metal hydroxide or a tertiary amine such as triethylamine.

As a rule, the reaction is carried out in an inert organic solvent, e.g. an ether such as tetrahydrofuran, an alcohol such as ethanol, or an aprotic solvent such as dimethylformamide, acetonitrile or dimethyl sulfoxide.

As a rule, the reaction is carried out between the melting point and the boiling point of the reaction mixture, preferably at from 0 to 50° C.

The reaction product XXX is then cyclized in an inert organic solvent, e.g. a hydrocarbon such as toluene or n-hexane, an ether such as tetrahydrofuran, an alcohol such as ethanol, a carboxylic acid such as acetic acid, or an aprotic solvent such as dimethylformamide, acetonitrile or dimethyl sulfoxide, in the presence of an acid, for example acetic or hydrochloric acid.

Again, the cyclization is carried out between the melting point and the boiling point of the reaction mixture, preferably at from 0 to 150° C.

C.1.1) Preparation of the phenylhydrazines XXVIII from anilines of the formula XXXI:

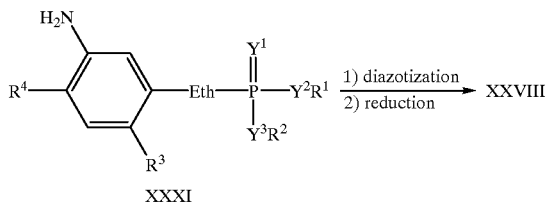

In this process, the aniline XXXI is first diazotized. In this context, reference may be made to the information given above for A.1).

The resulting diazonium salt is reacted with a reducing agent, for example a tin(II) compound such as tin(II) chloride in an inert solvent/diluent, e.g. a hydrocarbon such as toluene or n-hexane, an ether such as tetrahydrofuran, an alcohol such as ethanol, an acid such as acetic acid and hydrochloric acid, an aprotic solvent such as dimethylformamide, acetonitrile and dimethyl sulfoxide, or in water. The reaction is carried out between the melting point and the boiling point of the reaction mixture, preferably at from 0 to 150° C.

Especially preferred phenylhydrazines of the formula XXVIII are listed in Table 2 below.

TABLE 2

XXVIII

| No. | $R^3$ | $R^4$ | -Eth-P($=Y^1$)($Y^2R^1$)($Y^3R^2$) |
|---|---|---|---|
| XXVIII.1 | Cl | H | —$CH_2$—$CH_2$—P($=$O)($OCH_3$)$_2$ |
| XXVIII.2 | Cl | Cl | —$CH_2$—$CH_2$—P($=$O)($OCH_3$)$_2$ |
| XXVIII.3 | Cl | F | —$CH_2$—$CH_2$—P($=$O)($OCH_3$)$_2$ |
| XXVIII.4 | Cl | H | —$CH_2$—$CH_2$—P($=$O)($OC_2H_5$)$_2$ |
| XXVIII.5 | Cl | Cl | —$CH_2$—$CH_2$—P($=$O)($OC_2H_5$)$_2$ |
| XXVIII.6 | Cl | F | —$CH_2$—$CH_2$—P($=$O)($OC_2H_5$)$_2$ |
| XXVIII.7 | Cl | H | —$CH_2$—CH(Cl)—P($=$O)($OCH_3$)$_2$ |
| XXVIII.8 | Cl | Cl | —$CH_2$—CH(Cl)—P($=$O)($OCH_3$)$_2$ |
| XXVIII.9 | Cl | F | —$CH_2$—CH(Cl)—P($=$O)($OCH_3$)$_2$ |
| XXVIII.10 | Cl | H | —$CH_2$—CH(Cl)—P($=$O)($OC_2H_5$)$_2$ |
| XXVIII.11 | Cl | Cl | —$CH_2$—CH(Cl)—P($=$O)($OC_2H_5$)$_2$ |
| XXVIII.12 | Cl | F | —$CH_2$—CH(Cl)—P($=$O)($OC_2H_5$)$_2$ |
| XXVIII.13 | Cl | H | —$CH_2$—CH(Br)—P($=$O)($OCH_3$)$_2$ |
| XXVIII.14 | Cl | Cl | —$CH_2$—CH(Br)—P($=$O)($OCH_3$)$_2$ |
| XXVIII.15 | Cl | F | —$CH_2$—CH(Br)—P($=$O)($OCH_3$)$_2$ |
| XXVIII.16 | Cl | H | —$CH_2$—CH(Br)—P($=$O)($OC_2H_5$)$_2$ |
| XXVIII.17 | Cl | Cl | —$CH_2$—CH(Br)—P($=$O)($OC_2H_5$)$_2$ |
| XXVIII.18 | Cl | F | —$CH_2$—CH(Br)—P($=$O)($OC_2H_5$)$_2$ |
| XXVIII.19 | Cl | H | —$CH_2$—CH(CN)—P($=$O)($OCH_3$)$_2$ |
| XXVIII.20 | Cl | Cl | —$CH_2$—CH(CN)—P($=$O)($OCH_3$)$_2$ |
| XXVIII.21 | Cl | F | —$CH_2$—CH(CN)—P($=$O)($OCH_3$)$_2$ |
| XXVIII.22 | Cl | H | —$CH_2$—CH(CN)—P($=$O)($OC_2H_5$)$_2$ |
| XXVIII.23 | Cl | Cl | —$CH_2$—CH(CN)—P($=$O)($OC_2H_5$)$_2$ |
| XXVIII.24 | Cl | F | —$CH_2$—CH(CN)—P($=$O)($OC_2H_5$)$_2$ |
| XXVIII.25 | Cl | H | —CH=CH—P($=$O)($OCH_3$)$_2$ |
| XXVIII.26 | Cl | Cl | —CH=CH—P($=$O)($OCH_3$)$_2$ |
| XXVIII.27 | Cl | F | —CH=CH—P($=$O)($OCH_3$)$_2$ |
| XXVIII.28 | Cl | H | —CH=CH—P($=$O)($OC_2H_5$)$_2$ |
| XXVIII.29 | Cl | Cl | —CH=CH—P($=$O)($OC_2H_5$)$_2$ |
| XXVIII.30 | Cl | F | —CH=CH—P($=$O)($OC_2H_5$)$_2$ |
| XXVIII.31 | Cl | H | —CH=C(Cl)—P($=$O)($OCH_3$)$_2$ |
| XXVIII.32 | Cl | Cl | —CH=C(Cl)—P($=$O)($OCH_3$)$_2$ |
| XXVIII.33 | Cl | F | —CH=C(Cl)—P($=$O)($OCH_3$)$_2$ |
| XXVIII.34 | Cl | H | —CH=C(Cl)—P($=$O)($OC_2H_5$)$_2$ |
| XXVIII.35 | Cl | Cl | —CH=C(Cl)—P($=$O)($OC_2H_5$)$_2$ |
| XXVIII.36 | Cl | F | —CH=C(Cl)—P($=$O)($OC_2H_5$)$_2$ |
| XXVIII.37 | Cl | H | —CH=C(Br)—P($=$O)($OCH_3$)$_2$ |
| XXVIII.38 | Cl | Cl | —CH=C(Br)—P($=$O)($OCH_3$)$_2$ |
| XXVIII.39 | Cl | F | —CH=C(Br)—P($=$O)($OCH_3$)$_2$ |

TABLE 2-continued

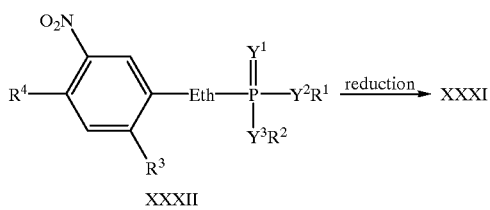

XXVIII

| No. | R³ | R⁴ | -Eth-P(=Y¹)(Y²R¹)(Y³R²) |
|---|---|---|---|
| XXVIII.40 | Cl | H | —CH=C(Br)—P(=O)(OC$_2$H$_5$)$_2$ |
| XXVIII.41 | Cl | Cl | —CH=C(Br)—P(=O)(OC$_2$H$_5$)$_2$ |
| XXVIII.42 | Cl | F | —CH=C(Br)—P(=O)(OC$_2$H$_5$)$_2$ |
| XXVIII.43 | Cl | H | —CH=C(CN)—P(=O)(OCH$_3$)$_2$ |
| XXVIII.44 | Cl | Cl | —CH=C(CN)—P(=O)(OCH$_3$)$_2$ |
| XXVIII.45 | Cl | F | —CH=C(CN)—P(=O)(OCH$_3$)$_2$ |
| XXVIII.46 | Cl | H | —CH=C(CN)—P(=O)(OC$_2$H$_5$)$_2$ |
| XXVIII.47 | Cl | Cl | —CH=C(CN)—P(=O)(OC$_2$H$_5$)$_2$ |
| XXVIII.48 | Cl | F | —CH=C(CN)—P(=O)(OC$_2$H$_5$)$_2$ |

C.1.2) Preparation of the anilines XXXI by reducing nitrobenzene derivatives XXXII:

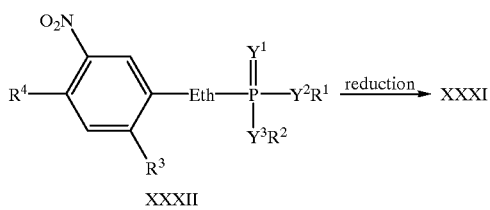

XXXII

The reduction can be carried out with a metal such as iron, zinc or tin under acidic reaction conditions, or with a complex hydride such as lithiumaluminum hydride and sodium borohydride, examples of solvents being water, alcohols such as methanol, ethanol and isopropanol, or ethers such as diethyl ether, methyl tert-butyl ether, dioxane, tetrahydrofuran and ethylene glycol dimethyl ether, depending on the chosen reducing agent.

If the reduction is carried out with a metal, this is preferably performed in the absence of a solvent in an inorganic acid, in particular in concentrated or dilute hydrochloric acid, or in an organic acid such as acetic acid. However, it is also possible to admix an inert solvent, e.g. one of those mentioned above, with the acid.

The amount of acid is not critical. In order to reduce the starting compound as completely as possible, it is expedient to use at least an equivalent amount of acid.

The reaction temperature is generally at from (−30) to 200° C., preferably at 0 to 80° C.

The nitro group of the compounds XXXII may also be hydrogenated catalytically using hydrogen. Examples of catalysts which are suitable for this purpose are Raney nickel, palladium-on-charcoal, palladium oxide, platinum and platinum oxide, an amount of catalyst of from 0.05 to 10.0 mol % based on the compound to be reduced generally being sufficient.

The process is either carried out in the absence of a solvent or in an inert solvent or diluent, e.g. in acetic acid, a mixture of acetic acid and water, ethyl acetate, ethanol, or in toluene.

After the catalyst has been removed, the reaction solution can be worked up as usual to give the product.

The hydrogenation can be carried out under atmospheric pressure or under elevated pressure.

Especially preferred anilines XXXI are listed in Table 3 below.

TABLE 3

XXXI

| No. | R³ | R⁴ | -Eth-P(=Y¹)(Y²R¹)(Y³R²) |
|---|---|---|---|
| XXXI.1 | Cl | H | —CH$_2$—CH$_2$—P(=O)(OCH$_3$)$_2$ |
| XXXI.2 | Cl | Cl | —CH$_2$—CH$_2$—P(=O)(OCH$_3$)$_2$ |
| XXXI.3 | Cl | F | —CH$_2$—CH$_2$—P(=O)(OCH$_3$)$_2$ |
| XXXI.4 | Cl | H | —CH$_2$—CH$_2$—P(=O)(OC$_2$H$_5$)$_2$ |
| XXXI.5 | Cl | Cl | —CH$_2$—CH$_2$—P(=O)(OC$_2$H$_5$)$_2$ |
| XXXI.6 | Cl | F | —CH$_2$—CH$_2$—P(=O)(OC$_2$H$_5$)$_2$ |
| XXXI.7 | Cl | H | —CH$_2$—CH(Cl)—P(=O)(OCH$_3$)$_2$ |
| XXXI.8 | Cl | Cl | —CH$_2$—CH(Cl)—P(=O)(OCH$_3$)$_2$ |
| XXXI.9 | Cl | F | —CH$_2$—CH(Cl)—P(=O)(OCH$_3$)$_2$ |
| XXXI.10 | Cl | H | —CH$_2$—CH(Cl)—P(=O)(OC$_2$H$_5$)$_2$ |
| XXXI.11 | Cl | Cl | —CH$_2$—CH(Cl)—P(=O)(OC$_2$H$_5$)$_2$ |
| XXXI.12 | Cl | F | —CH$_2$—CH(Cl)—P(=O)(OC$_2$H$_5$)$_2$ |
| XXXI.13 | Cl | H | —CH$_2$—CH(Br)—P(=O)(OCH$_3$)$_2$ |
| XXXI.14 | Cl | Cl | —CH$_2$—CH(Br)—P(=O)(OCH$_3$)$_2$ |
| XXXI.15 | Cl | F | —CH$_2$—CH(Br)—P(=O)(OCH$_3$)$_2$ |
| XXXI.16 | Cl | H | —CH$_2$—CH(Br)—P(=O)(OC$_2$H$_5$)$_2$ |
| XXXI.17 | Cl | Cl | —CH$_2$—CH(Br)—P(=O)(OC$_2$H$_5$)$_2$ |
| XXXI.18 | Cl | F | —CH$_2$—CH(Br)—P(=O)(OC$_2$H$_5$)$_2$ |
| XXXI.19 | Cl | H | —CH$_2$—CH(CN)—P(=O)(OCH$_3$)$_2$ |
| XXXI.20 | Cl | Cl | —CH$_2$—CH(CN)—P(=O)(OCH$_3$)$_2$ |
| XXXI.21 | Cl | F | —CH$_2$—CH(CN)—P(=O)(OCH$_3$)$_2$ |
| XXXI.22 | Cl | H | —CH$_2$—CH(CN)—P(=O)(OC$_2$H$_5$)$_2$ |
| XXXI.23 | Cl | Cl | —CH$_2$—CH(CN)—P(=O)(OC$_2$H$_5$)$_2$ |
| XXXI.24 | Cl | F | —CH$_2$—CH(CN)—P(=O)(OC$_2$H$_5$)$_2$ |
| XXXI.25 | Cl | H | —CH=CH—P(=O)(OCH$_3$)$_2$ |
| XXXI.26 | Cl | Cl | —CH=CH—P(=O)(OCH$_3$)$_2$ |
| XXXI.27 | Cl | F | —CH=CH—P(=O)(OCH$_3$)$_2$ |
| XXXI.28 | Cl | H | —CH=CH—P(=O)(OC$_2$H$_5$)$_2$ |
| XXXI.29 | Cl | Cl | —CH=CH—P(=O)(OC$_2$H$_5$)$_2$ |
| XXXI.30 | Cl | F | —CH=CH—P(=O)(OC$_2$H$_5$)$_2$ |
| XXXI.31 | Cl | H | —CH=C(Cl)—P(=O)(OCH$_3$)$_2$ |
| XXXI.32 | Cl | Cl | —CH=C(Cl)—P(=O)(OCH$_3$)$_2$ |
| XXXI.33 | Cl | F | —CH=C(Cl)—P(=O)(OCH$_3$)$_2$ |
| XXXI.34 | Cl | H | —CH=C(Cl)—P(=O)(OC$_2$H$_5$)$_2$ |
| XXXI.35 | Cl | Cl | —CH=C(Cl)—P(=O)(OC$_2$H$_5$)$_2$ |
| XXXI.36 | Cl | F | —CH=C(Cl)—P(=O)(OC$_2$H$_5$)$_2$ |
| XXXI.37 | Cl | H | —CH=C(Br)—P(=O)(OCH$_3$)$_2$ |
| XXXI.38 | Cl | Cl | —CH=C(Br)—P(=O)(OCH$_3$)$_2$ |
| XXXI.39 | Cl | F | —CH=C(Br)—P(=O)(OCH$_3$)$_2$ |
| XXXI.40 | Cl | H | —CH=C(Br)—P(=O)(OC$_2$H$_5$)$_2$ |
| XXXI.41 | Cl | Cl | —CH=C(Br)—P(=O)(OC$_2$H$_5$)$_2$ |
| XXXI.42 | Cl | F | —CH=C(Br)—P(=O)(OC$_2$H$_5$)$_2$ |
| XXXI.43 | Cl | H | —CH=C(CN)—P(=O)(OCH$_3$)$_2$ |
| XXXI.44 | Cl | Cl | —CH=C(CN)—P(=O)(OCH$_3$)$_2$ |
| XXXI.45 | Cl | F | —CH=C(CN)—P(=O)(OCH$_3$)$_2$ |
| XXXI.46 | Cl | H | —CH=C(CN)—P(=O)(OC$_2$H$_5$)$_2$ |
| XXXI.47 | Cl | Cl | —CH=C(CN)—P(=O)(OC$_2$H$_5$)$_2$ |
| XXXI.48 | Cl | F | —CH=C(CN)—P(=O)(OC$_2$H$_5$)$_2$ |

C.1.3) Preparation of the nitrobenzene derivatives XXXII:

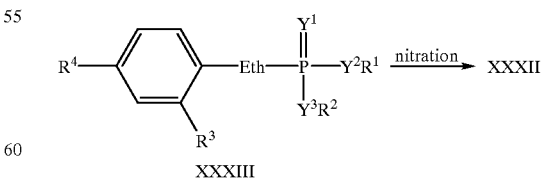

XXXIII

Examples of suitable nitrating reagents are nitric acid in various concentrations, also concentrated and fuming nitric acid, mixtures of sulfuric acid and nitric acid, acetyl nitrates and alkyl nitrates.

The reaction can be carried out either in the absence of a solvent in an excess of the nitrating reagent or in an inert solvent or diluent, suitable examples being water, mineral acids, organic acids, halohydrocarbons such as methylene chloride, anhydrides such as acetic anhydride, and mixtures of these solvents.

Starting compound XXXIII and nitrating reagent are expediently employed in approximately equimolar amounts; however, to optimize conversion of the starting compound it may be advantageous to use the nitrating reagent in an excess of up to approximately 10 times the molar amount. If the reaction is carried out without solvent in the nitrating reagent, the latter is present in an even larger excess.

The reaction temperature is normally at from (−100) to 200° C., preferably (−30) to +50° C.

Especially preferred nitro compounds of the formula XXXII are listed in Table 4 below.

TABLE 4

| No. | $R^3$ | $R^4$ | -Eth-P(=$Y^1$)($Y^2R^1$)($Y^3R^2$) |
|---|---|---|---|
| XXXII.1 | Cl | H | —$CH_2$—$CH_2$—P(=O)($OCH_3$)$_2$ |
| XXXII.2 | Cl | Cl | —$CH_2$—$CH_2$—P(=O)($OCH_3$)$_2$ |
| XXXII.3 | Cl | F | —$CH_2$—$CH_2$—P(=O)($OCH_3$)$_2$ |
| XXXII.4 | Cl | H | —$CH_2$—$CH_2$—P(=O)($OC_2H_5$)$_2$ |
| XXXII.5 | Cl | Cl | —$CH_2$—$CH_2$—P(=O)($OC_2H_5$)$_2$ |
| XXXII.6 | Cl | F | —$CH_2$—$CH_2$—P(=O)($OC_2H_5$)$_2$ |
| XXXII.7 | Cl | H | —$CH_2$—CH(Cl)—P(=O)($OCH_3$)$_2$ |
| XXXII.8 | Cl | Cl | —$CH_2$—CH(Cl)—P(=O)($OCH_3$)$_2$ |
| XXXII.9 | Cl | F | —$CH_2$—CH(Cl)—P(=O)($OCH_3$)$_2$ |
| XXXII.10 | Cl | H | —$CH_2$—CH(Cl)—P(=O)($OC_2H_5$)$_2$ |
| XXXII.11 | Cl | Cl | —$CH_2$—CH(Cl)—P(=O)($OC_2H_5$)$_2$ |
| XXXII.12 | Cl | F | —$CH_2$—CH(Cl)—P(=O)($OC_2H_5$)$_2$ |
| XXXII.13 | Cl | H | —$CH_2$—CH(Br)—P(=O)($OCH_3$)$_2$ |
| XXXII.14 | Cl | Cl | —$CH_2$—CH(Br)—P(=O)($OCH_3$)$_2$ |
| XXXII.15 | Cl | F | —$CH_2$—CH(Br)—P(=O)($OCH_3$)$_2$ |
| XXXII.16 | Cl | H | —$CH_2$—CH(Br)—P(=O)($OC_2H_5$)$_2$ |
| XXXII.17 | Cl | Cl | —$CH_2$—CH(Br)—P(=O)($OC_2H_5$)$_2$ |
| XXXII.18 | Cl | F | —$CH_2$—CH(Br)—P(=O)($OC_2H_5$)$_2$ |
| XXXII.19 | Cl | H | —$CH_2$—CH(CN)—P(=O)($OCH_3$)$_2$ |
| XXXII.20 | Cl | Cl | —$CH_2$—CH(CN)—P(=O)($OCH_3$)$_2$ |
| XXXII.21 | Cl | F | —$CH_2$—CH(CN)—P(=O)($OCH_3$)$_2$ |
| XXXII.22 | Cl | H | —$CH_2$—CH(CN)—P(=O)($OC_2H_5$)$_2$ |
| XXXII.23 | Cl | Cl | —$CH_2$—CH(CN)—P(=O)($OC_2H_5$)$_2$ |
| XXXII.24 | Cl | F | —$CH_2$—CH(CN)—P(=O)($OC_2H_5$)$_2$ |
| XXXII.25 | Cl | H | —CH=CH—P(=O)($OCH_3$)$_2$ |
| XXXII.26 | Cl | Cl | —CH=CH—P(=O)($OCH_3$)$_2$ |
| XXXII.27 | Cl | F | —CH=CH—P(=O)($OCH_3$)$_2$ |
| XXXII.28 | Cl | H | —CH=CH—P(=O)($OC_2H_5$)$_2$ |
| XXXII.29 | Cl | Cl | —CH=CH—P(=O)($OC_2H_5$)$_2$ |
| XXXII.30 | Cl | F | —CH=CH—P(=O)($OC_2H_5$)$_2$ |
| XXXII.31 | Cl | H | —CH=C(Cl)—P(=O)($OCH_3$)$_2$ |
| XXXII.32 | Cl | Cl | —CH=C(Cl)—P(=O)($OCH_3$)$_2$ |
| XXXII.33 | Cl | F | —CH=C(Cl)—P(=O)($OCH_3$)$_2$ |
| XXXII.34 | Cl | H | —CH=C(Cl)—P(=O)($OC_2H_5$)$_2$ |
| XXXII.35 | Cl | Cl | —CH=C(Cl)—P(=O)($OC_2H_5$)$_2$ |
| XXXII.36 | Cl | F | —CH=C(Cl)—P(=O)($OC_2H_5$)$_2$ |
| XXXII.37 | Cl | H | —CH=C(Br)—P(=O)($OCH_3$)$_2$ |
| XXXII.38 | Cl | Cl | —CH=C(Br)—P(=O)($OCH_3$)$_2$ |
| XXXII.39 | Cl | F | —CH=C(Br)—P(=O)($OCH_3$)$_2$ |
| XXXII.40 | Cl | H | —CH=C(Br)—P(=O)($OC_2H_5$)$_2$ |
| XXXII.41 | Cl | Cl | —CH=C(Br)—P(=O)($OC_2H_5$)$_2$ |
| XXXII.42 | Cl | F | —CH=C(Br)—P(=O)($OC_2H_5$)$_2$ |
| XXXII.43 | Cl | H | —CH=C(CN)—P(=O)($OCH_3$)$_2$ |
| XXXII.44 | Cl | Cl | —CH=C(CN)—P(=O)($OCH_3$)$_2$ |
| XXXII.45 | Cl | F | —CH=C(CN)—P(=O)($OCH_3$)$_2$ |
| XXXII.46 | Cl | H | —CH=C(CN)—P(=O)($OC_2H_5$)$_2$ |

TABLE 4-continued

| No. | $R^3$ | $R^4$ | -Eth-P(=$Y^1$)($Y^2R^1$)($Y^3R^2$) |
|---|---|---|---|
| XXXII.47 | Cl | Cl | —CH=C(CN)—P(=O)($OC_2H_5$)$_2$ |
| XXXII.48 | Cl | F | —CH=C(CN)—P(=O)($OC_2H_5$)$_2$ |

C.1.4) Preparation of the aromatic phosphonic acid derivatives XXXIII where Eth is —CH=C(Cl)—:

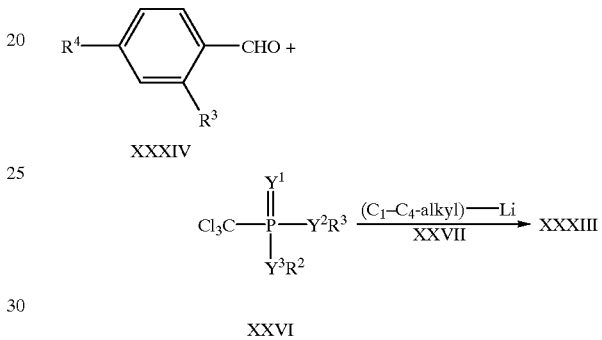

As regards this reaction, reference may be made to the information given above under A.13).

Especially preferred aromatic phosphonic acid derivatives of the formula XXXIIIa (=XXXIII where $R^{4'}$; $R^4$=halogen) are listed in Table 5 below.

TABLE 5

| No. | $R^3$ | $R^4$ | -Eth-P(=$Y^1$)($Y^2R^1$)($Y^3R^2$) |
|---|---|---|---|
| XXXIII.1 | Cl | Cl | —$CH_2$—$CH_2$—P(=O)($OCH_3$)$_2$ |
| XXXIII.2 | Cl | F | —$CH_2$—$CH_2$—P(=O)($OCH_3$)$_2$ |
| XXXIII.3 | Cl | Cl | —$CH_2$—$CH_2$—P(=O)($OC_2H_5$)$_2$ |
| XXXIII.4 | Cl | F | —$CH_2$—$CH_2$—P(=O)($OC_2H_5$)$_2$ |
| XXXIII.5 | Cl | Cl | —$CH_2$—CH(Cl)—P(=O)($OCH_3$)$_2$ |
| XXXIII.6 | Cl | F | —$CH_2$—CH(Cl)—P(=O)($OCH_3$)$_2$ |
| XXXIII.7 | Cl | Cl | —$CH_2$—CH(Cl)—P(=O)($OC_2H_5$)$_2$ |
| XXXIII.8 | Cl | F | —$CH_2$—CH(Cl)—P(=O)($OC_2H_5$)$_2$ |
| XXXIII.9 | Cl | Cl | —$CH_2$—CH(Br)—P(=O)($OCH_3$)$_2$ |
| XXXIII.10 | Cl | F | —$CH_2$—CH(Br)—P(=O)($OCH_3$)$_2$ |
| XXXIII.11 | Cl | Cl | —$CH_2$—CH(Br)—P(=O)($OC_2H_5$)$_2$ |
| XXXIII.12 | Cl | F | —$CH_2$—CH(Br)—P(=O)($OC_2H_5$)$_2$ |
| XXXIII.13 | Cl | Cl | —$CH_2$—CH(CN)—P(=O)($OCH_3$)$_2$ |
| XXXIII.14 | Cl | F | —$CH_2$—CH(CN)—P(=O)($OCH_3$)$_2$ |
| XXXIII.15 | Cl | Cl | —$CH_2$—CH(CN)—P(=O)($OC_2H_5$)$_2$ |
| XXXIII.16 | Cl | F | —$CH_2$—CH(CN)—P(=O)($OC_2H_5$)$_2$ |
| XXXIII.17 | Cl | Cl | —CH=CH—P(=O)($OCH_3$)$_2$ |
| XXXIII.18 | Cl | F | —CH=CH—P(=O)($OCH_3$)$_2$ |
| XXXIII.19 | Cl | Cl | —CH=CH—P(=O)($OC_2H_5$)$_2$ |
| XXXIII.20 | Cl | F | —CH=CH—P(=O)($OC_2H_5$)$_2$ |
| XXXIII.21 | Cl | Cl | —CH=C(Cl)—P(=O)($OCH_3$)$_2$ |
| XXXIII.22 | Cl | F | —CH=C(Cl)—P(=O)($OCH_3$)$_2$ |

TABLE 5-continued

XXXIIIa

| No. | $R^3$ | $R^4$ | -Eth-P(=$Y^1$)($Y^2R^1$)($Y^3R^2$) |
|---|---|---|---|
| XXXIII.23 | Cl | Cl | —CH=C(Cl)—P(=O)(OC$_2$H$_5$)$_2$ |
| XXXIII.24 | Cl | F | —CH=C(Cl)—P(=O)(OC$_2$H$_5$)$_2$ |
| XXXIII.25 | Cl | Cl | —CH=C(Br)—P(=O)(OCH$_3$)$_2$ |
| XXXIII.26 | Cl | F | —CH=C(Br)—P(=O)(OCH$_3$)$_2$ |
| XXXIII.27 | Cl | Cl | —CH=C(Br)—P(=O)(OC$_2$H$_5$)$_2$ |
| XXXIII.28 | Cl | F | —CH=C(Br)—P(=O)(OC$_2$H$_5$)$_2$ |
| XXXIII.29 | Cl | Cl | —CH=C(CN)—P(=O)(OCH$_3$)$_2$ |
| XXXIII.30 | Cl | F | —CH=C(CN)—P(=O)(OCH$_3$)$_2$ |
| XXXIII.31 | Cl | Cl | —CH=C(CN)—P(=O)(OC$_2$H$_5$)$_2$ |
| XXXIII.32 | Cl | F | —CH=C(CN)—P(=O)(OC$_2$H$_5$)$_2$ |

C.2) Synthesis of the thiazole ring

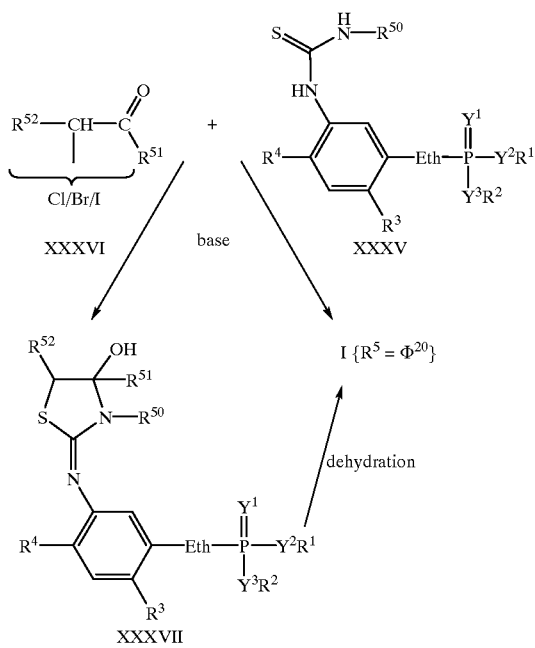

In this process, a thiourea derivative of the formula XXXV is reacted with a ketone of the formula XXXVI in the presence of a base, for example an alkali metal acetate, alkali metal hydrogen carbonate, alkali metal carbonate, alkali metal hydroxide or a tertiary amine such as triethylamine.

The process is normally carried out in an inert solvent/diluent, e.g. in a hydrocarbon such as toluene and n-hexane, an ether such as tetrahydrofuran, or in an aprotic solvent such as dimethylformamide, acetonitrile and dimethyl sulfoxide.

The reaction is carried out between the melting point and the boiling point of the reaction mixture, preferably at from 0 to 150° C.

This process results in the direct formation of either the compounds of the formula I where $R^5$=$\Phi^{20}$ or alcohols of the formula XXXVII which can be dehydrated in the customary manner to give I, for example by azeotropic distillation with a suitable entraining agent, e.g. toluene or xylene, or by reaction with catalytic amounts of a strong acid such as hydrochloric acid, sulfuric acid and toluenesulfonic acid, or by esterification with a carboxylic acid chloride, sulfonic acid chloride, carboxylic anhydride or sulfonic anhydride and treatment with a base, for example an alkali metal acetate, alkali metal hydrogen carbonate, alkali metal carbonate, alkali metal hydroxide or a tertiary amine such as triethylamine and pyridine.

C.2.1) Preparation of the thiourea derivatives XXXV by reaction of isocyanates XXXVIII with anilines XXXI:

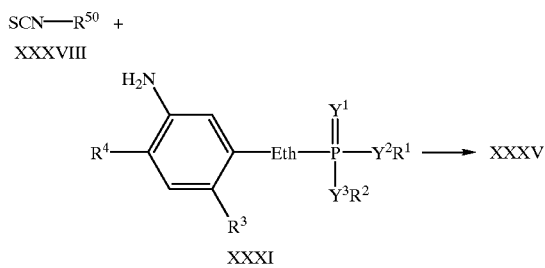

Examples of suitable solvents/diluents are hydrocarbons such as toluene and n-hexane, halogenated hydrocarbons such as dichloromethane, ethers such as tetrahydrofuran, alcohols such as ethanol, aprotic solvents such as dimethylformamide, acetonitrile and dimethyl sulfoxide.

The reaction is generally carried out between the melting point and the boiling point of the reaction mixture, preferably at from 0 to 150° C.

Especially preferred thiourea derivatives of the formula XXXV are listed in Table 6 below.

TABLE 6

XXXV

| No. | $R^3$ | $R^4$ | $R^{50}$ | -Eth-P(=$Y^1$)($Y^2R^1$)($Y^3R^2$) |
|---|---|---|---|---|
| XXXV.1 | Cl | H | CH$_3$ | —CH$_2$—CH$_2$—P(=O)(OCH$_3$)$_2$ |
| XXXV.2 | Cl | Cl | CH$_3$ | —CH$_2$—CH$_2$—P(=O)(OCH$_3$)$_2$ |
| XXXV.3 | Cl | F | CH$_3$ | —CH$_2$—CH$_2$—P(=O)(OCH$_3$)$_2$ |
| XXXV.4 | Cl | H | CH$_3$ | —CH$_2$—CH$_2$—P(=O)(OC$_2$H$_5$)$_2$ |
| XXXV.5 | Cl | Cl | CH$_3$ | —CH$_2$—CH$_2$—P(=O)(OC$_2$H$_5$)$_2$ |
| XXXV.6 | Cl | F | CH$_3$ | —CH$_2$—CH$_2$—P(=O)(OC$_2$H$_5$)$_2$ |
| XXXV.7 | Cl | H | CH$_3$ | —CH$_2$—CH(Cl)—P(=O)(OCH$_3$)$_2$ |
| XXXV.8 | Cl | Cl | CH$_3$ | —CH$_2$—CH(Cl)—P(=O)(OCH$_3$)$_2$ |
| XXXV.9 | Cl | F | CH$_3$ | —CH$_2$—CH(Cl)—P(=O)(OCH$_3$)$_2$ |
| XXXV.10 | Cl | H | CH$_3$ | —CH$_2$—CH(Cl)—P(=O)(OC$_2$H$_5$)$_2$ |
| XXXV.11 | Cl | Cl | CH$_3$ | —CH$_2$—CH(Cl)—P(=O)(OC$_2$H$_5$)$_2$ |
| XXXV.12 | Cl | F | CH$_3$ | —CH$_2$—CH(Cl)—P(=O)(OC$_2$H$_5$)$_2$ |
| XXXV.13 | Cl | H | CH$_3$ | —CH$_2$—CH(Br)—P(=O)(OCH$_3$)$_2$ |
| XXXV.14 | Cl | Cl | CH$_3$ | —CH$_2$—CH(Br)—P(=O)(OCH$_3$)$_2$ |
| XXXV.15 | Cl | F | CH$_3$ | —CH$_2$—CH(Br)—P(=O)(OCH$_3$)$_2$ |
| XXXV.16 | Cl | H | CH$_3$ | —CH$_2$—CH(Br)—P(=O)(OC$_2$H$_5$)$_2$ |
| XXXV.17 | Cl | Cl | CH$_3$ | —CH$_2$—CH(Br)—P(=O)(OC$_2$H$_5$)$_2$ |
| XXXV.18 | Cl | F | CH$_3$ | —CH$_2$—CH(Br)—P(=O)(OC$_2$H$_5$)$_2$ |
| XXXV.19 | Cl | H | CH$_3$ | —CH$_2$—CH(CN)—P(=O)(OCH$_3$)$_2$ |
| XXXV.20 | Cl | Cl | CH$_3$ | —CH$_2$—CH(CN)—P(=O)(OCH$_3$)$_2$ |
| XXXV.21 | Cl | F | CH$_3$ | —CH$_2$—CH(CN)—P(=O)(OCH$_3$)$_2$ |
| XXXV.22 | Cl | H | CH$_3$ | —CH$_2$—CH(CN)—P(=O)(OC$_2$H$_5$)$_2$ |
| XXXV.23 | Cl | Cl | CH$_3$ | —CH$_2$—CH(CN)—P(=O)(OC$_2$H$_5$)$_2$ |
| XXXV.24 | Cl | F | CH$_3$ | —CH$_2$—CH(CN)—P(=O)(OC$_2$H$_5$)$_2$ |

TABLE 6-continued

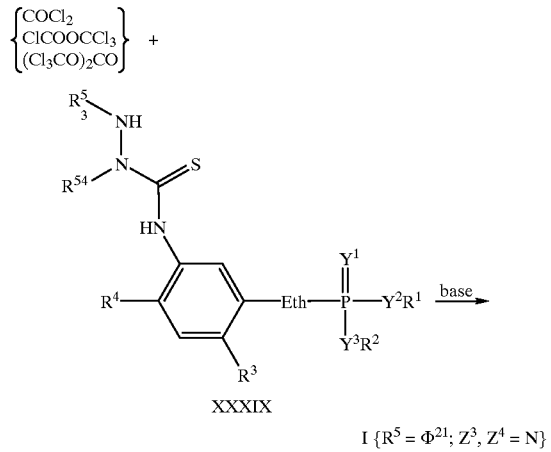

XXXV

| No. | $R^3$ | $R^4$ | $R^{50}$ | -Eth-P(=Y$^1$)(Y$^2$R$^1$)(Y$^3$R$^2$) |
|---|---|---|---|---|
| XXXV.25 | Cl | H  | CH$_3$ | —CH=CH—P(=O)(OCH$_3$)$_2$ |
| XXXV.26 | Cl | Cl | CH$_3$ | —CH=CH—P(=O)(OCH$_3$)$_2$ |
| XXXV.27 | Cl | F  | CH$_3$ | —CH=CH—P(=O)(OCH$_3$)$_2$ |
| XXXV.28 | Cl | H  | CH$_3$ | —CH=CH—P(=O)(OC$_2$H$_5$)$_2$ |
| XXXV.29 | Cl | Cl | CH$_3$ | —CH=CH—P(=O)(OC$_2$H$_5$)$_2$ |
| XXXV.30 | Cl | F  | CH$_3$ | —CH=CH—P(=O)(OC$_2$H$_5$)$_2$ |
| XXXV.31 | Cl | H  | CH$_3$ | —CH=C(Cl)—P(=O)(OCH$_3$)$_2$ |
| XXXV.32 | Cl | Cl | CH$_3$ | —CH=C(Cl)—P(=O)(OCH$_3$)$_2$ |
| XXXV.33 | Cl | F  | CH$_3$ | —CH=C(Cl)—P(=O)(OCH$_3$)$_2$ |
| XXXV.34 | Cl | H  | CH$_3$ | —CH=C(Cl)—P(=O)(OC$_2$H$_5$)$_2$ |
| XXXV.35 | Cl | Cl | CH$_3$ | —CH=C(Cl)—P(=O)(OC$_2$H$_5$)$_2$ |
| XXXV.36 | Cl | F  | CH$_3$ | —CH=C(Cl)—P(=O)(OC$_2$H$_5$)$_2$ |
| XXXV.37 | Cl | H  | CH$_3$ | —CH=C(Br)—P(=O)(OCH$_3$)$_2$ |
| XXXV.38 | Cl | Cl | CH$_3$ | —CH=C(Br)—P(=O)(OCH$_3$)$_2$ |
| XXXV.39 | Cl | F  | CH$_3$ | —CH=C(Br)—P(=O)(OCH$_3$)$_2$ |
| XXXV.40 | Cl | H  | CH$_3$ | —CH=C(Br)—P(=O)(OC$_2$H$_5$)$_2$ |
| XXXV.41 | Cl | Cl | CH$_3$ | —CH=C(Br)—P(=O)(OC$_2$H$_5$)$_2$ |
| XXXV.42 | Cl | F  | CH$_3$ | —CH=C(Br)—P(=O)(OC$_2$H$_5$)$_2$ |
| XXXV.43 | Cl | H  | CH$_3$ | —CH=C(CN)—P(=O)(OCH$_3$)$_2$ |
| XXXV.44 | Cl | Cl | CH$_3$ | —CH=C(CN)—P(=O)(OCH$_3$)$_2$ |
| XXXV.45 | Cl | F  | CH$_3$ | —CH=C(CN)—P(=O)(OCH$_3$)$_2$ |
| XXXV.46 | Cl | H  | CH$_3$ | —CH=C(CN)—P(=O)(OC$_2$H$_5$)$_2$ |
| XXXV.47 | Cl | Cl | CH$_3$ | —CH=C(CN)—P(=O)(OC$_2$H$_5$)$_2$ |
| XXXV.48 | Cl | F  | CH$_3$ | —CH=C(CN)—P(=O)(OC$_2$H$_5$)$_2$ |

C.3) Synthesis of the thiazolopyridazine ring

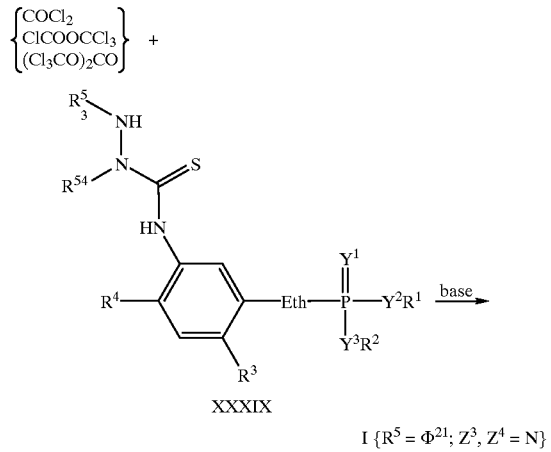

In this process, a thiosemicarbazide derivative of the formula XXXIX is reacted with phosgene, diphosgene or triphosgene in the presence of a base—for example an alkali metal hydrogen carbonate, alkali metal carbonate, alkali metal hydroxide or a tertiary amine such as triethylamine or pyridine.

The process is normally carried out in an inert solvent/diluent, e.g. in a hydrocarbon such as toluene or n-hexane, a halogenated hydrocarbon such as dichloromethane, an ether such as tetrahydrofuran, or in an aprotic solvent such as dimethylformamide, acetonitrile and dimethyl sulfoxide.

The reaction is carried out between the melting point and the boiling point of the reaction mixture, preferably at from 0 to 150°.

C.3.1) Preparation of the thiosemicarbazide derivatives XXXIX by reacting hydrazines XLI with isothiocyanates XL:

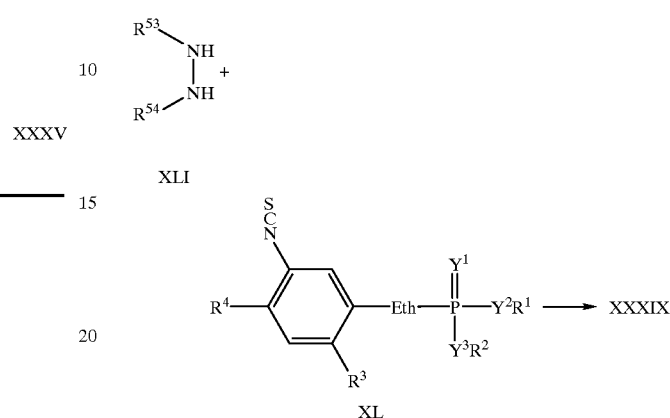

Examples of suitable solvents/diluents are hydrocarbons such as toluene and n-hexane, halogenated hydrocarbons such as dichloromethane, ethers such as tetrahydrofuran, alcohols such as ethanol or aprotic solvents such as dimethylformamide, acetonitrile and dimethyl sulfoxide.

The reaction is generally carried out between the melting point and the boiling point of the reaction mixture, preferably at from 0 to 150°.

Especially preferred thiosemicarbazide derivatives of the formula XXXIX are listed in Table 7 below.

TABLE 7

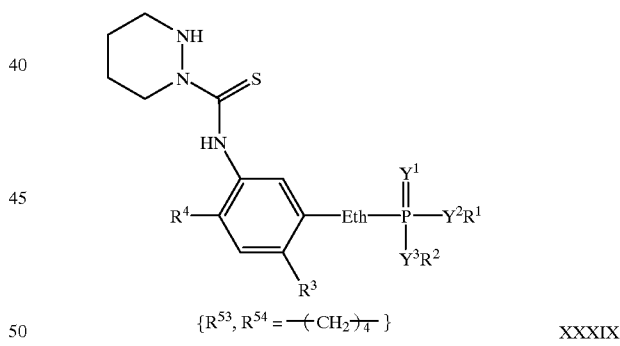

$\{R^{53}, R^{54} = -(CH_2)_4-\}$

XXXIX

| No. | $R^3$ | $R^4$ | -Eth-P(=Y$^1$)(Y$^2$R$^1$)(Y$^3$R$^2$) |
|---|---|---|---|
| XXXIX.1  | Cl | H  | —CH$_2$—CH$_2$—P(=O)(OCH$_3$)$_2$ |
| XXXIX.2  | Cl | Cl | —CH$_2$—CH$_2$—P(=O)(OCH$_3$)$_2$ |
| XXXIX.3  | Cl | F  | —CH$_2$—CH$_2$—P(=O)(OCH$_3$)$_2$ |
| XXXIX.4  | Cl | H  | —CH$_2$—CH$_2$—P(=O)(OC$_2$H$_5$)$_2$ |
| XXXIX.5  | Cl | Cl | —CH$_2$—CH$_2$—P(=O)(OC$_2$H$_5$)$_2$ |
| XXXIX.6  | Cl | F  | —CH$_2$—CH$_2$—P(=O)(OC$_2$H$_5$)$_2$ |
| XXXIX.7  | Cl | H  | —CH$_2$—CH(Cl)—P(=O)(OCH$_3$)$_2$ |
| XXXIX.8  | Cl | Cl | —CH$_2$—CH(Cl)—P(=O)(OCH$_3$)$_2$ |
| XXXIX.9  | Cl | F  | —CH$_2$—CH(Cl)—P(=O)(OCH$_3$)$_2$ |
| XXXIX.10 | Cl | H  | —CH$_2$—CH(Cl)—P(=O)(OC$_2$H$_5$)$_2$ |
| XXXIX.11 | Cl | Cl | —CH$_2$—CH(Cl)—P(=O)(OC$_2$H$_5$)$_2$ |
| XXXIX.12 | Cl | F  | —CH$_2$—CH(Cl)—P(=O)(OC$_2$H$_5$)$_2$ |
| XXXIX.13 | Cl | H  | —CH$_2$—CH(Br)—P(=O)(OCH$_3$)$_2$ |
| XXXIX.14 | Cl | Cl | —CH$_2$—CH(Br)—P(=O)(OCH$_3$)$_2$ |
| XXXIX.15 | Cl | F  | —CH$_2$—CH(Br)—P(=O)(OCH$_3$)$_2$ |
| XXXIX.16 | Cl | H  | —CH$_2$—CH(Br)—P(=O)(OC$_2$H$_5$)$_2$ |
| XXXIX.17 | Cl | Cl | —CH$_2$—CH(Br)—P(=O)(OC$_2$H$_5$)$_2$ |

TABLE 7-continued

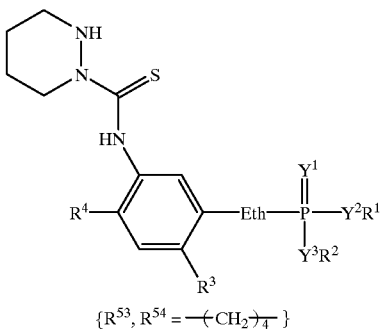

{$R^{53}$, $R^{54}$ = —(CH$_2$)$_4$—}  XXXIX

| No. | $R^3$ | $R^4$ | -Eth-P(=Y$^1$)(Y$^2$R$^1$)(Y$^3$R$^2$) |
|---|---|---|---|
| XXXIX.18 | Cl | F | —CH$_2$—CH(Br)—P(=O)(OC$_2$H$_5$)$_2$ |
| XXXIX.19 | Cl | H | —CH$_2$—CH(CN)—P(=O)(OCH$_3$)$_2$ |
| XXXIX.20 | Cl | Cl | —CH$_2$—CH(CN)—P(=O)(OCH$_3$)$_2$ |
| XXXIX.21 | Cl | F | —CH$_2$—CH(CN)—P(=O)(OCH$_3$)$_2$ |
| XXXIX.22 | Cl | H | —CH$_2$—CH(CN)—P(=O)(OC$_2$H$_5$)$_2$ |
| XXXIX.23 | Cl | Cl | —CH$_2$—CH(CN)—P(=O)(OC$_2$H$_5$)$_2$ |
| XXXIX.24 | Cl | F | —CH$_2$—CH(CN)—P(=O)(OC$_2$H$_5$)$_2$ |
| XXXIX.25 | Cl | H | —CH=CH—P(=O)(OCH$_3$)$_2$ |
| XXXIX.26 | Cl | Cl | —CH=CH—P(=O)(OCH$_3$)$_2$ |
| XXXIX.27 | Cl | F | —CH=CH—P(=O)(OCH$_3$)$_2$ |
| XXXIX.28 | Cl | H | —CH=CH—P(=O)(OC$_2$H$_5$)$_2$ |
| XXXIX.29 | Cl | Cl | —CH=CH—P(=O)(OC$_2$H$_5$)$_2$ |
| XXXIX.30 | Cl | F | —CH=CH—P(=O)(OC$_2$H$_5$)$_2$ |
| XXXIX.31 | Cl | H | —CH=C(Cl)—P(=O)(OCH$_3$)$_2$ |
| XXXIX.32 | Cl | Cl | —CH=C(Cl)—P(=O)(OCH$_3$)$_2$ |
| XXXIX.33 | Cl | F | —CH=C(Cl)—P(=O)(OCH$_3$)$_2$ |
| XXXIX.34 | Cl | H | —CH=C(Cl)—P(=O)(OC$_2$H$_5$)$_2$ |
| XXXIX.35 | Cl | Cl | —CH=C(Cl)—P(=O)(OC$_2$H$_5$)$_2$ |
| XXXIX.36 | Cl | F | —CH=C(Cl)—P(=O)(OC$_2$H$_5$)$_2$ |
| XXXIX.37 | Cl | H | —CH=C(Br)—P(=O)(OCH$_3$)$_2$ |
| XXXIX.38 | Cl | Cl | —CH=C(Br)—P(=O)(OCH$_3$)$_2$ |
| XXXIX.39 | Cl | F | —CH=C(Br)—P(=O)(OCH$_3$)$_2$ |
| XXXIX.40 | Cl | H | —CH=C(Br)—P(=O)(OC$_2$H$_5$)$_2$ |
| XXXIX.41 | Cl | Cl | —CH=C(Br)—P(=O)(OC$_2$H$_5$)$_2$ |
| XXXIX.42 | Cl | F | —CH=C(Br)—P(=O)(OC$_2$H$_5$)$_2$ |
| XXXIX.43 | Cl | H | —CH=C(CN)—P(=O)(OCH$_3$)$_2$ |
| XXXIX.44 | Cl | Cl | —CH=C(CN)—P(=O)(OCH$_3$)$_2$ |
| XXXIX.45 | Cl | F | —CH=C(CN)—P(=O)(OCH$_3$)$_2$ |
| XXXIX.46 | Cl | H | —CH=C(CN)—P(=O)(OC$_2$H$_5$)$_2$ |
| XXXIX.47 | Cl | Cl | —CH=C(CN)—P(=O)(OC$_2$H$_5$)$_2$ |
| XXXIX.48 | Cl | F | —CH=C(CN)—P(=O)(OC$_2$H$_5$)$_2$ |

C.3.2) Preparation of the isothiocyanates XL by reacting anilines of the formula XXXI with thiophosgene in the presence of a base:

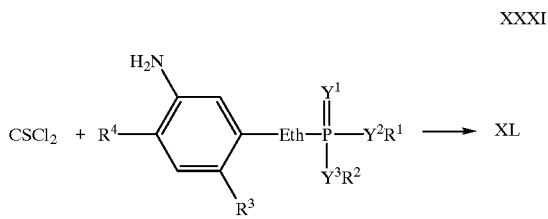

XXXI

Examples of suitable diluents/solvents are hydrocarbons such as toluene and n-hexane, halogenated hydrocarbons such as dichloromethane, ethers such as tetrahydrofuran, or aprotic solvents such as dimethylformamide, acetonitrile and dimethyl sulfoxide.

Suitable bases are mainly the alkali metal acetates, alkali metal hydrogen carbonates, alkali metal carbonates, alkali metal hydroxides or tertiary amines such as triethylamine and pyridine.

The reaction is carried out between the melting point and the boiling point of the reaction mixture, preferably at from 0 to 150°.

Especially preferred isothiocyanates of the formula XL are listed in Table 8 below.

TABLE 8

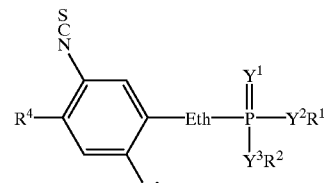

XL

| No. | $R^3$ | $R^4$ | -Eth-P(=Y$^1$)(Y$^2$R$^1$)(Y$^3$R$^2$) |
|---|---|---|---|
| XL.1 | Cl | H | —CH$_2$—CH$_2$—P(=O)(OCH$_3$)$_2$ |
| XL.2 | Cl | Cl | —CH$_2$—CH$_2$—P(=O)(OCH$_3$)$_2$ |
| XL.3 | Cl | F | —CH$_2$—CH$_2$—P(=O)(OCH$_3$)$_2$ |
| XL.4 | Cl | H | —CH$_2$—CH$_2$—P(=O)(OC$_2$H$_5$)$_2$ |
| XL.5 | Cl | Cl | —CH$_2$—CH$_2$—P(=O)(OC$_2$H$_5$)$_2$ |
| XL.6 | Cl | F | —CH$_2$—CH$_2$—P(=O)(OC$_2$H$_5$)$_2$ |
| XL.7 | Cl | H | —CH$_2$—CH(Cl)—P(=O)(OCH$_3$)$_2$ |
| XL.8 | Cl | Cl | —CH$_2$—CH(Cl)—P(=O)(OCH$_3$)$_2$ |
| XL.9 | Cl | F | —CH$_2$—CH(Cl)—P(=O)(OCH$_3$)$_2$ |
| XL.10 | Cl | H | —CH$_2$—CH(Cl)—P(=O)(OC$_2$H$_5$)$_2$ |
| XL.11 | Cl | Cl | —CH$_2$—CH(Cl)—P(=O)(OC$_2$H$_5$)$_2$ |
| XL.12 | Cl | F | —CH$_2$—CH(Cl)—P(=O)(OC$_2$H$_5$)$_2$ |
| XL.13 | Cl | H | —CH$_2$—CH(Br)—P(=O)(OCH$_3$)$_2$ |
| XL.14 | Cl | Cl | —CH$_2$—CH(Br)—P(=O)(OCH$_3$)$_2$ |
| XL.15 | Cl | F | —CH$_2$—CH(Br)—P(=O)(OCH$_3$)$_2$ |
| XL.16 | Cl | H | —CH$_2$—CH(Br)—P(=O)(OC$_2$H$_5$)$_2$ |
| XL.17 | Cl | Cl | —CH$_2$—CH(Br)—P(=O)(OC$_2$H$_5$)$_2$ |
| XL.18 | Cl | F | —CH$_2$—CH(Br)—P(=O)(OC$_2$H$_5$)$_2$ |
| XL.19 | Cl | H | —CH$_2$—CH(CN)—P(=O)(OCH$_3$)$_2$ |
| XL.20 | Cl | Cl | —CH$_2$—CH(CN)—P(=O)(OCH$_3$)$_2$ |
| XL.21 | Cl | F | —CH$_2$—CH(CN)—P(=O)(OCH$_3$)$_2$ |
| XL.22 | Cl | H | —CH$_2$—CH(CN)—P(=O)(OC$_2$H$_5$)$_2$ |
| XL.23 | Cl | Cl | —CH$_2$—CH(CN)—P(=O)(OC$_2$H$_5$)$_2$ |
| XL.24 | Cl | F | —CH$_2$—CH(CN)—P(=O)(OC$_2$H$_5$)$_2$ |
| XL.25 | Cl | H | —CH=CH—P(=O)(OCH$_3$)$_2$ |
| XL.26 | Cl | Cl | —CH=CH—P(=O)(OCH$_3$)$_2$ |
| XL.27 | Cl | F | —CH=CH—P(=O)(OCH$_3$)$_2$ |
| XL.28 | Cl | H | —CH=CH—P(=O)(OC$_2$H$_5$)$_2$ |
| XL.29 | Cl | Cl | —CH=CH—P(=O)(OC$_2$H$_5$)$_2$ |
| XL.30 | Cl | F | —CH=CH—P(=O)(OC$_2$H$_5$)$_2$ |
| XL.31 | Cl | H | —CH=C(Cl)—P(=O)(OCH$_3$)$_2$ |
| XL.32 | Cl | Cl | —CH=C(Cl)—P(=O)(OCH$_3$)$_2$ |
| XL.33 | Cl | F | —CH=C(Cl)—P(=O)(OCH$_3$)$_2$ |
| XL.34 | Cl | H | —CH=C(Cl)—P(=O)(OC$_2$H$_5$)$_2$ |
| XL.35 | Cl | Cl | —CH=C(Cl)—P(=O)(OC$_2$H$_5$)$_2$ |
| XL.36 | Cl | F | —CH=C(Cl)—P(=O)(OC$_2$H$_5$)$_2$ |
| XL.37 | Cl | H | —CH=C(Br)—P(=O)(OCH$_3$)$_2$ |
| XL.38 | Cl | Cl | —CH=C(Br)—P(=O)(OCH$_3$)$_2$ |
| XL.39 | Cl | F | —CH=C(Br)—P(=O)(OCH$_3$)$_2$ |
| XL.40 | Cl | H | —CH=C(Br)—P(=O)(OC$_2$H$_5$)$_2$ |
| XL.41 | Cl | Cl | —CH=C(Br)—P(=O)(OC$_2$H$_5$)$_2$ |
| XL.42 | Cl | F | —CH=C(Br)—P(=O)(OC$_2$H$_5$)$_2$ |
| XL.43 | Cl | H | —CH=C(CN)—P(=O)(OCH$_3$)$_2$ |
| XL.44 | Cl | Cl | —CH=C(CN)—P(=O)(OCH$_3$)$_2$ |
| XL.45 | Cl | F | —CH=C(CN)—P(=O)(OCH$_3$)$_2$ |
| XL.46 | Cl | H | —CH=C(CN)—P(=O)(OC$_2$H$_5$)$_2$ |
| XL.47 | Cl | Cl | —CH=C(CN)—P(=O)(OC$_2$H$_5$)$_2$ |
| XL.48 | Cl | F | —CH=C(CN)—P(=O)(OC$_2$H$_5$)$_2$ |

C.4) Synthesis of the pyrrolothiadiazole ring

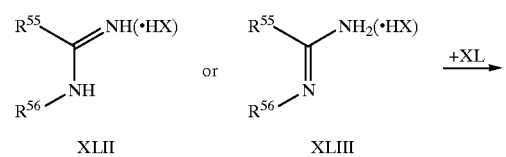

XLII        XLIII

-continued

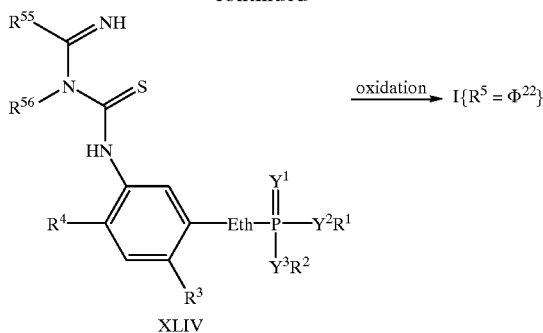

XLIV

X is the anion of the acid, preferably a chloride, bromide, hydrogen sulfate or ½ sulfate ion.

In this process, an isothiocyanate of the formula XL is reacted with an amidine of the formula XLII or XLIII.

The process is normally carried out in an inert solvent/diluent, e.g. in a hydrocarbon such as toluene and n-hexane, a halogenated hydrocarbon such as dichloromethane, an ether such as tetrahydrofuran, an alcohol such as ethanol, or in an aprotic solvent such as dimethylformamide, acetonitrile and dimethyl sulfoxide.

Alternatively, XL can also be reacted with an acid addition salt of the amidine XLII or XLIII (for example with hydrochloric or sulfuric acid). In this case, the process is carried out in the presence of a base, for example an alkali metal acetate, alkali metal hydrogen carbonate, alkali metal carbonate, alkali metal hydroxide or a tertiary amine such as triethylamine or pyridine.

The reaction products of the formula XLIV are then oxidized in one of the solvents mentioned for the preparation of XLIV, preferably using a halogen such as chlorine or bromine.

Both the conversion of XL into XLIV and the oxidation of XLIV are generally carried out between the melting point and the boiling point of the reaction mixture in question, preferably at from 0 to 150° C.

C.5) Synthesis of the uracil ring by reacting an isocyanate of the formula XLV with an aminoacrylic acid derivative of the formula XLVI in the presence of a strong base:

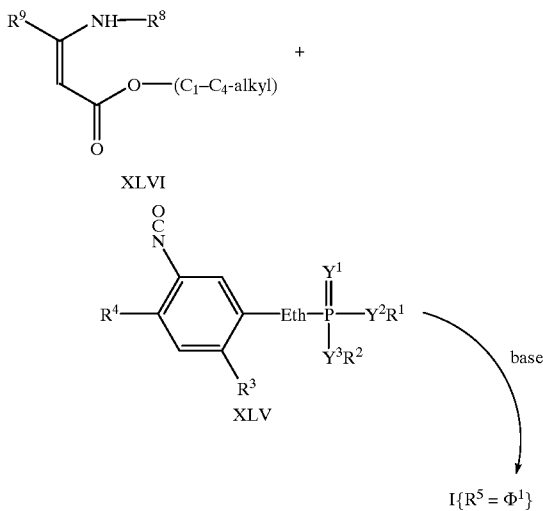

Examples of suitable solvents/diluents are hydrocarbons such as toluene and n-hexane, halogenated hydrocarbons such as dichloromethane, ethers such as tetrahydrofuran or aprotic solvents such as dimethylformamide, acetonitrile and dimethyl sulfoxide.

Suitable bases are mainly the alkali metal hydrides, alkali metal alkoxides, alkali metal amides, alkali metal hydroxides or alkyllithium compounds such as butyllithium.

The reaction is generally carried out between the melting point and the boiling point of the reaction mixture, preferably at from 0 to 150° C.

Those process products I where $R^5$ is $\Phi^1$ and $R^8$ is hydrogen can subsequently be alkylated or aminated in the presence of a base:

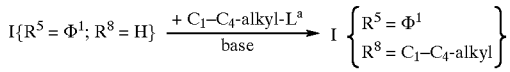

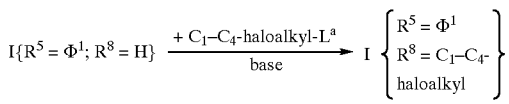

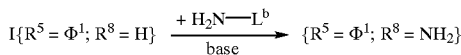

$L^a$ is a customary leaving group, in particular halide, triflate, tosylate or mesylate;

$L^b$ is a customary leaving group, in particular halide, hydrogen sulfate, mono- or dinitrophenoxy, i.e., for example, chloroamine, hydroxylamine-O-sulfuric acid or 2,4-dinitrophenoxyamine.

The solvents mentioned for the synthesis of the uracil ring are likewise suitable here.

Examples of useful bases are the alkali metal acetates, alkali metal hydrogen carbonates, alkali metal carbonates and alkali metal hydroxides, and tertiary amines such as triethylamine and pyridine.

The reaction is generally carried out between the melting point and the boiling point of the reaction mixture, preferably at from 0 to 150° C.

C.5.1) Preparation of the isocyanates XLV by reacting anilines of the formula XXXI with phosgene, diphosgene or triphosgene in the presence of a base:

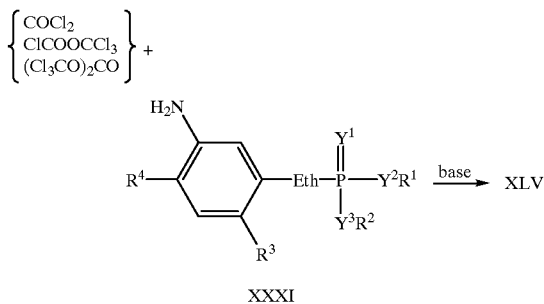

XXXI

Examples of suitable solvents/diluents are hydrocarbons such as toluene and n-hexane, halogenated hydrocarbons such as dichloromethane, ethers such as tetrahydrofuran and aprotic solvents such as dimethylformamide, acetonitrile and dimethyl sulfoxide.

Suitable bases are mainly the alkali metal acetates, alkali metal hydrogen carbonates, alkali metal carbonates, alkali metal hydroxides or tertiary amines such as triethylamine and pyridine.

The reaction is generally carried out between the melting point and the boiling point of the reaction mixture, preferably at from 0 to 150° C.

C.6) Synthesis of a cyclic imide ring by reacting an aniline of the formula XXXI with an anhydride of the formula XLVII or XLIII in the presence of an acid:

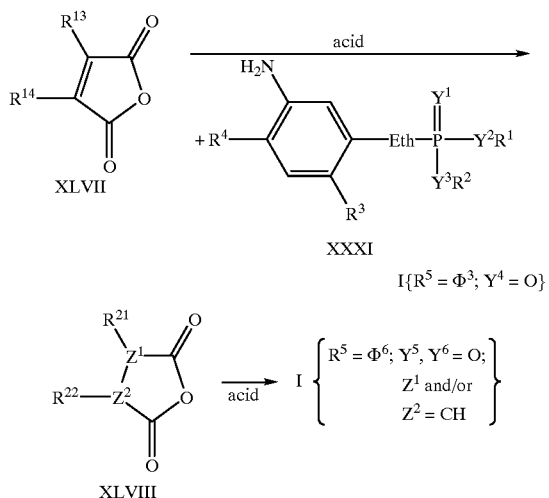

Examples of suitable acids are mineral acids such as hydrochloric acid, sulfuric acid and phosphoric acid, carboxylic acids such as acetic acid or sulfonic acids such as benzene- and toluenesulfonic acid.

The process is normally carried out in an inert solvent/diluent, for example in a hydrocarbon such as toluene or n-hexane, a halogenated hydrocarbon such as dichloromethane, an ether such as tetrahydrofuran, an alcohol such as ethanol, a carboxylic acid such as acetic acid, or in an aprotic solvent such as dimethylformamide, acetonitrile or dimethyl sulfoxide.

The reaction is carried out between the melting point and the boiling point of the reaction mixture, preferably at from 0 to 150°.

Unless otherwise specified, all processes described above are expediently carried out under atmospheric pressure or under the inherent autogeneous pressure of the reaction mixture in question.

In general, the reactants are employed in a molar ratio of from 0.95:1 to 5:1.

As a rule, the reaction mixtures are worked up by methods known per se, for example by diluting the reaction solution with water followed by isolation of the product by means of filtration, crystallization or solvent extraction, or by removing the solvent, partitioning the residue in a mixture of water and a suitable organic solvent and working up the organic phase to give the product.

The substituted aromatic phosphonic acid derivatives I can be obtained from their preparation as isomer mixtures which, however, can be separated into the pure isomers, if desired, by the methods customary for this purpose, such as crystallization or chromatography, also on an optically active adsorbate. Pure optically active isomers can be prepared advantageously from suitable optically active starting materials.

Agriculturally useful salts of the compounds I can be formed by reaction with a base of the cation in question, preferably an alkali metal hydroxide or alkali metal hydride, or by reaction with an acid of the anion in question, preferably of hydrochloric acid, hydrobromic acid, sulfuric acid, phosphoric acid or nitric acid.

Salts of I whose metal ion is not an alkali metal ion can also be prepared in the customary manner by double decomposition of the alkali metal salt in question, and ammonium, phosphonium, sulfonium and sulfoxonium salts using ammonia, phosphonium hydroxide, sulfonium hydroxide or sulfoxonium hydroxide.

The compounds I and their agriculturally useful salts, both as isomer mixtures and in the form of the pure isomers, are suitable as herbicides. The herbicidal compositions comprising I are capable of effecting very good vegetation control on non-crop areas, especially at high rates of application. In crops such as wheat, rice, maize, soybeans and cotton, they are active against broad-leaved weeds and grass weeds without damaging the crop plants to a substantial extent. This effect is observed especially at low rates of application.

Depending on the application method in question, the compounds I, or the herbicidal compositions comprising them, can also be employed in a further number of crop plants for eliminating undesirable plants. Suitable crops are for example the following:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spec., *Manihot esculenta, Medicago sativa,* Musa spec., *Nicotiana tabacum* (*N. rustica*), *Olea europaea, Oryza sativa, Phaseolus lunatus, Phaseolus vulgaris, Picea abies,* Pinus spec., *Pisum sativum, Prunus avium, Prunus persica, Pyrus communis, Ribes sylvestre, Ricinus communis, Saccharum officinarum, Secale cereale, Solanum tuberosum, Sorghum bicolor* (*S. vulgare*), *Theobroma cacao, Trifolium pratense, Triticum aestivum, Triticum durum, Vicia faba, Vitis vinifera* and *Zea mays.*

In addition, the compounds I can also be used in crops which tolerate the action of herbicides as a result of breeding, including genetic engineering methods.

Moreover, the substituted aromatic phosphonic acid derivatives I are also suitable for desiccating and/or defoliating plants.

As desiccants, they are especially suitable for desiccating the aerial parts of crop plants such as potatoes, oilseed rape, sunflowers and soybeans. This allows completely mechanical harvesting of these important crop plants.

Also of economic interest is to facilitate harvesting, which is made possible by concentrating, over a period of time, dehiscence, or reducing the adherence to the tree, in citrus fruit, olives or other species of pomaceous fruit, stone fruit and nuts. The same mechanism, i.e. promotion of the formation of abscission tissue between fruit or leaf and shoot of the plants, is also important for readily controllable defoliation of useful plants, in particular cotton.

Moreover, shortening the period within which the individual cotton plants mature results in an improved fiber quality after harvesting.

The compounds I or the compositions comprising them can be used for example in the form of directly sprayable aqueous solutions, powders, suspensions, also highly concentrated aqueous, oily or other suspensions or dispersions, emulsions, oil dispersions, pastes, dusts, materials for spreading or granules, by means or is spraying, atomizing, dusting, spreading or pouring. The use forms depend on the intended aims; in any case, they should guarantee the finest possible distribution of the active ingredients according to the invention.

Suitable inert auxiliaries are mainly: mineral oil fractions of medium to high boiling point, such as kerosene and diesel oil, furthermore coal tar oils and oils of vegetable or animal origin, aliphatic, cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines, such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the substrates, as such or dissolved in an oil or solvent, can be homogenized in water by means of a wetting agent, tackifier, dispersant or emulsifier. Alternatively, it is possible to prepare concentrates comprising active substance, wetting agent, tackifier, dispersant or emulsifier and, if desired, solvent or oil, which are suitable for dilution with water.

Suitable surfactants are the alkali metal salts, alkaline earth metal salts and ammonium salts of aromatic sulfonic acids, e.g. ligno-, phenol-, naphthalene- and dibutylnaphthalenesulfonic acid, and of fatty acids, alkyl- and alkylarylsulfonates, of alkyl sulfates, lauryl ethyl sulfates and fatty alcohol sulfates, and the salts of sulfated hexa-, hepta- and octadecanols and of fatty alcohol glycol ethers; condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl polyglycol ether, tributylphenyl polyglycol ether, alkylaryl polyether alcohols, isotridecyl alcohol, fatty alcohol/ethyleneoxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for spreading and dusts can be prepared by mixing or grinding together the active substances with a solid carrier.

Granules, e.g. coated granules, impregnated granules and homogeneous granules, can be prepared by binding the active ingredients to solid carriers. Solid carriers are mineral earths, such as silicas, silica gels, silicates, talc, kaolin, limestone, lime, chalk, bole, loss, clay, dolomite, diatomaceous earth, calcium sulfate, magnesium sulfate, magnesium oxide, ground synthetic materials, fertilizers, such as ammonium sulfate, ammonium phosphate, ammonium nitrate, ureas, and products of vegetable origin, such as cereal meal, tree bark meal, wood meal and nutshell meal, cellulose powders or other solid carriers.

The concentrations of the active ingredients I in the ready-to-use products can be varied within wide ranges. In general, the formulations comprise approximately from 0.001 to 98% by weight, preferably 0.01 to 95% by weight, of at least one active ingredient. The active ingredients are employed in a purity of from 90% to 100%, preferably 95% to 100% (according to NMR spectrum).

The formulation examples which follow illustrate the preparation of such products:

I. 20 parts by weight of the compound No. IAh.432 are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

II. 20 parts by weight of the compound No. IAh.861 are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

III. 20 parts by weight of the active ingredient No. IBg.861 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

IV. 20 parts by weight of the active ingredient No. ICh.860 are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel and the mixture is ground in a hammer mill. Finely distributing the mixture in 20,000 parts by weight of water gives a spray mixture which comprises 0.1% by weight of the active ingredient.

V. 3 parts by weight of the active ingredient No. ICh.1154 are mixed with 97 parts by weight of finely divided kaolin. This gives a dust which comprises 3% by weight of the active ingredient.

VI. 20 parts by weight of the active ingredient No. IBh.860 are mixed intimately with 2 parts by weight of calcium dodecylbenzenesulfonate, 8 parts by weight of fatty alcohol polyglycol ether, 2 parts by weight of sodium salt of a phenol/urea/formaldehyde condensate and 68 parts by weight of a paraffinic mineral oil. This gives a stable oily dispersion.

VII. 1 part by weight of the compound No. IBh.861 is dissolved in a mixture composed of 70 parts by weight of cyclohexanone, 20 parts by weight of ethoxylated isooctylphenol and 10 parts by weight of ethoxylated castor oil. The resulting mixture can then be diluted with water to the desired concentration of active ingredient. This gives a stable emulsion concentrate.

VIII. 1 part by weight of the compound No. IBh.1154 is dissolved in a mixture composed of 80 parts by weight of cyclohexanone and 20 parts by weight of Wettol® EM 31 (=nonionic emulsifier based on ethoxylated castor oil; BASF AG). The resulting mixture can then be diluted with water to the desired concentration of active ingredient. This gives a stable emulsion concentrate.

The active ingredients I or the herbicidal compositions can be applied pre- or post-emergence. If the active ingredients are less well tolerated by certain crop plants, application techniques may be used in which the herbicidal compositions are sprayed, with the aid of the spraying apparatus, in such a way that they come into as little contact, if any, with the leaves of the sensitive crop plants, while the active ingredients reach the leaves of undesirable plants which grow underneath, or the bare soil surface (post-directed, lay-by).

Depending on the aim of control, the season, the target plants and the growth stage, the application rates of active ingredient I are from 0.001 to 3.0, preferably 0.01 to 1.0, kg of active substance (a.s.) per ha.

To widen the spectrum of action and to achieve synergistic effects, the substituted aromatic phosphonic acid derivatives I may be mixed with a large number of representatives of other herbicidal or growth-regulating active ingredients and applied jointly.

Suitable examples of components in mixtures are 1,2,4-thiadiazoles, 1,3,4-thiadiazoles, amides, aminophosphoric acid and its derivatives, aminotriazoles, anilides, aryloxy-/hetaryloxyalkanoic acids and their derivatives, benzoic acid and its derivatives, benzothiadiazinones, 2-(hetaroyl/aroyl)-1,3-cyclohexanediones, hetaryl-aryl-ketones, benzylisoxazolidinones, meta-$CF_3$-phenyl derivatives, carbamates, quinolinecarboxylic acid and its derivatives, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolcarboxamides and uracils.

It may furthermore be advantageous to apply the compounds I, alone or in combination with other herbicides, together with further crop protection agents, for example with pesticides or with agents for controlling phytopathogenic fungi or bacteria. Also of interest is the miscibility with mineral salt solutions, which are employed for treating nutritional and trace element deficiencies. Non-phytotoxic oils and oil concentrates may also be added.

PREPARATION EXAMPLES

Example 1

Diethyl 2-(2-chloro-5-(4-chloro-5-difluoromethoxy-1-methyl-1H-pyrazol-3-yl)-4-fluorophenyl)vinylphosphonate (No. IBg.861)

1 g (3 mmol) of tetraethyl methanediphosphonate was dissolved in 50 ml of toluene and treated with 80 mg (3.2 mmol) of sodium hydride. After the evolution of gas had ceased, a solution of 1 g (2.9 mmol) of 2-chloro-5-(4-chloro-5-difluoromethoxy-1-methyl-1H-pyrazol-3-yl)-4-fluorobenzaldehyde in 50 ml of toluene was added. The reaction mixture was subsequently stirred for 16 hours at room temperature and then treated with 0.15 l of water. The product of value was extracted from the aqueous phase using 50 ml of toluene. Finally, the combined organic phases, in turn, were washed with water and then dried over magnesium sulfate and concentrated. Yield: 1.1 g.

Precursor 1.1
5-(4-Chloro-2-fluoro-5-methylphenyl)-1,2-dihydro-2-methyl-3H-pyrazol-3-one 34.7 g (0.75 mol) of methylhydrazine were added to a solution of 177 g (0.68 mol) of ethyl 3-(4-chloro-2-fluoro-5-methylphenyl)-3-oxopropionate in 500 ml of diethylene glycol. After 6 hours at 100° C., the mixture was poured into 4 l of water. The solids were subsequently removed and dried. Yield: 133 g; m.p.: 155–156° C.

Precursor 1.2
3-(4-Chloro-2-fluoro-5-methylphenyl)-5-difluoromethoxy-1-methyl-1H-pyrazole Gaseous chlorodifluoromethane was passed for 2 hours into a solution of 133 g (0.55 mol) of 5-(4-chloro-2-fluoro-5-methylphenyl)-1,2-dihydro-2-methyl-3H-pyrazol-3-one and 110 g (2.7 mol) of sodium hydroxide in 1 l of dioxane and 0.5 l of water at room temperature. The reaction solution was then poured into 2 l of water, whereupon the aqueous phase was extracted three times using ethyl acetate. The combined organic phases were dried over magnesium sulfate and then filtered and concentrated. The residue was purified by means of column chromatography on silica gel (eluent: cyclohexane/ethyl acetate=9:1) followed by preparative MPLC on silica gel (identical eluent). Yield: 43 g.

$^1$H NMR (250 MHz; in $CDCl_3$): δ [ppm]=2.37 (s,3H), 3.80 (s,3H), 6.30 (s,1H), 6.57 (t,1H), 7.14 (d,1H), 7.82 (d,1H).

Precursor 1.3
4-Chloro-3-(4-chloro-2-fluoro-5-methylphenyl)-5-difluoromethoxy-1-methyl-1H-pyrazole 22 g (0.16 mol) of sulfuryl chloride were added dropwise to a solution of 43 g (0.15 mol) of 3-(4-chloro-2-fluoro-5-methylphenyl)-5-difluoromethoxy-1-methyl-1H-pyrazole in 250 ml of tetrachloromethane. After the reaction solution had subsequently been stirred for 16 hours, 200 ml of saturated aqueous sodium hydrogen carbonate solution was added dropwise. The organic phase was then separated off, washed using saturated sodium chloride solution, dried over magnesium sulfate, then filtered and finally concentrated. Yield: 46 g.

$^1$H NMR (250 MHz; in $CDCl_3$): δ [ppm]=2.37 (s,3H), 3.84 (s,3H), 6.71 (t,1H), 7.21 (d,1H), 7.40 (d,1H).

Precursor 1.4
4-Chloro-3-(4-chloro-5-dibromomethyl-2-fluorophenyl)-5-difluoromethoxy-1-methyl-1H-pyrazole A solution of 46 g (0.14 mol) of 4-chloro-3-(4-chloro-2-fluoro-5-methylphenyl)-5-difluoromethoxy-1-methyl-1H-pyrazole and 62.9 g (0.35 mol) of N-bromosuccinimide in 2 l of tetrachloromethane was irradiated for 3.5 hours with a 1500 watt high-pressure mercury lamp and a UV lamp. The solids content was subsequently filtered off and washed two more times using tetrachloromethane. The combined filtrates were then concentrated. Yield: 68 g.

$^1$H NMR (270 MHz; in $CDCl_3$): δ [ppm]=3.86 (s,3H), 6.72 (t,1H), 57.05 (s,1H), 7.19 (d,1H), 8.23 (d,1H).

Precursor 1.5
2-Chloro-5-(4-chloro-5-difluoromethoxy-1-methyl-1H-pyrazol-3-yl)-4-fluorobenzaldehyde 68 g (0.14 mol) of 4-chloro-3-(4-chloro-5-dibromomethyl-2-fluorophenyl)-5-difluoromethoxy-1-methyl-1H-pyrazole were dissolved in 200 ml of concentrated sulfuric acid, with ice-cooling, whereupon the mixture was heated at 10° C. until the evolution of gas had ceased. It was then poured into 4 l of ice-water. The mixture was subsequently extracted three times using ethyl acetate. The combined organic phases were washed with water, then dried over magnesium sulfate and finally concentrated. The crude product was purified by means of silica gel column chromatography (eluent: hexane/ethyl acetate=8:1). Yield: 35 g; m.p.: 95–98° C.

Example 2
Diethyl 1-chloro-2-[2-chloro-5-(4-chloro-5-difluoromethoxy-1-methyl-1H-pyrazol-3-yl)-4-fluorophenyl]vinylphosphonate (No. IBh.861)

2 ml of a butyllithium solution (1.6 M in hexane; 3.2 mmol) were added in such a way to a solution, cooled at (−70)° C., of 1.63 g (6.4 mmol) of diethyl trichloromethanephosphonate in 20 ml of tetrahydrofuran that the temperature did not exceed (−65)° C. Stirring was subsequently continued for 1 hour at from (−65) to (−70)° C., whereupon a solution of 1 g (2.9 mmol) of 2-chloro-5-(4-chloro-5-difluoromethoxy-1-methyl-1H-pyrazol-3-yl)-4-fluorobenzaldehyde in 20 ml of tetrahydrofuran was slowly added dropwise. Stirring was continued for 30 minutes, the cooling bath was then removed, and stirring was continued for a further 16 hours, during which process the temperature of the mixture climbed to approximately 20° C. After 5 g of ammonium chloride had been added, the reaction mixture was poured into 50 ml of water.

The product of value was then obtained from the aqueous phase by extracting it twice using in each case 50 ml of methyl tert-butyl ether. The combined organic phases were washed using saturated aqueous sodium chloride solution and water, dried over magnesium sulfate and finally concentrated. The crude product was purified by means of silica gel column chromatography (eluent: hexane/ethyl acetate=4:1). Yield: 0.7 g.

Example 3
Diethyl 2-[2-chloro-4-fluoro-5-(1-methyl-6-trifluoromethyl-2,4-(1H,3H)-pyrimidinedion-3-yl)phenyl] vinylphosphonate (No. IAg.861)

0.12 g (4.7 mmol) of sodium hydride was added to a solution of 1.5 g (5.2 mmol) of tetraethyl methanediphosphonate in 50 ml of toluene. After the evolution of gas had ceased, a solution of 1.5 g (4.3 mmol) of 2-chloro-4-fluoro-5-(1-methyl-6-trifluoromethyl-2,4(1H,3H)-pyrimidinedion-3-yl)benzaldehyde in 50 ml of toluene was added. The mixture was subsequently stirred for a further 16 hours at approximately 20° C. For working-up, the reaction mixture was treated with 0.15 l of water. Residues of the product of value which had remained in the aqueous phase were extracted using 50 ml of toluene. The combined organic phases were subsequently washed with water, dried over magnesium sulfate and finally concentrated. Yield: 1.4 g.

Precursor 3.1
2-Chloro-4-fluoro-5-isocyanatobenzaldehyde (O-methyl)oxime 411.3 g of diphosgene (2.08 mol) were added dropwise to a solution of 383 g (1.89 mol) of 5-amino-2-chloro-4-fluorobenzaldehyde (O-methyl)oxime in 2 l of toluene. The temperature was then slowly raised to 110° C. in the course of approximately 6 hours so that the evolution of gas proceeded in a controlled manner. The mixture was subsequently refluxed for a further 5 hours. The reaction mixture was then left to cool and finally concentrated. Yield: 432 g.

The product was processed without purification.

Precursor 3.2
2-Chloro-4-fluoro-5-(6-trifluoromethyl-2,4(1H,3H)-pyrimidinedion-3-yl)benzaldehyde (O-methyl)oxime A solution of 168.5 g (0.92 mol) of ethyl 3-amino-4,4,4-trifluorocrotonate in 0.1 l of dimethylformamide was added dropwise with ice-cooling to 30.4 g (1.01 mol) of 80% by weight sodium hydride in 0.5 l of dimethylformamide. After one hour at this temperature, the mixture was cooled to (−30) to (−35)° C., and a solution of 210.3 g (0.92 mol) of 2-chloro-4-fluoro-5-isocyanatobenzaldehyde (O-methyl)oxime in 0.15 l of tetrahydrofuran was added dropwise. The reaction mixture was then stirred for 20 hours at approximately 20° C., and 1.5 l of water were subsequently added with ice-cooling. Undissolved matter in the mixture formed was removed and washed using 300 ml of water. The combined filtrates were acidified using dilute hydrochloric acid. The product of value was then extracted from the solution obtained using dichloromethane. The extract was washed with water, dried over sodium sulfate and finally concentrated. Yield: 289 g; m.p.: 176–177° C. (diisopropyl ether/petroleum ether).

Precursor 3.3
2-Chloro-4-fluoro-5-(1-methyl-6-trifluoromethyl-2,4(1H,3H)-pyrimidinedion-3-yl)benzaldehyde (O-methyl)oxime First, 117.1 g (0.85 mol) of potassium carbonate were added to a solution of 281.6 g (0.77 mol) of 2-chloro-4-fluoro-5-(6-trifluoromethyl-2,4(1H,3H)-pyrimidinedion-3-yl)benzaldehyde (O-methyl)oxime in 0.8 l of dimethylformamide, whereupon a solution of 120.2 g of methyl iodide (0.85 mol) in 0.1 l of dimethylformamide was added dropwise in the course of 1 hour. The reaction mixture was subsequently stirred for 20 hours at approximately 20° C., and 0.9 l of water was subsequently added dropwise with ice-cooling. The product of value was extracted from the resulting solution using 1 l of dichloromethane. The extract was washed three times using 300 ml of water, dried over sodium sulfate and finally concentrated. Yield: 241 g; m.p.: 141–142° C. (diisopropyl ether).

Precursor 3.4
2-Chloro-4-fluoro-5-(1-methyl-6-trifluoromethyl-2,4(1H,3H)-pyrimidinedion-3-yl)benzaldehyde 150 ml of a 30% by weight aqueous formaldehyde solution and 150 35 ml of concentrated hydrochloric acid were added dropwise to a solution of 189.9 g (0.50 mol) of 2-chloro-4-fluoro-5-(1-methyl-6-trifluoromethyl-2,4(1H,3H)-pyrimidinedion-3-yl)benzaldehyde (O-methyl)oxime in 0.75 l of glacial acetic acid. The mixture was subsequently refluxed for two hours. After cooling, 0.75 l of water were added, whereupon the solid product of value formed was separated off and washed first with water until the reaction was neutral and then with petroleum ether. Yield: 140 g; m.p.: 175–178° C.

Example 4
Diethyl 1-chloro-2-[2-chloro-4-fluoro-5-(1-methyl-6-trifluoromethyl-2,4(1H,3H)-pyrimidinedion-3-yl)phenyl] vinylphosphonate (No. IAh.861)

3.2 ml of a butyllithium solution (1.5 M in hexane; 4.8 mmol) were added in such a way to a solution, cooled at (−70)° C., of 2.4 g (9.5 mmol) of diethyl trichloromethane phosphonate in 30 ml of tetrahydrofuran that the temperature did not exceed (−65)° C. The mixture was then stirred for 1 hour at from (−65) to (−70)° C., whereupon a solution of 1.5 g (4.3 mmol) of 2-chloro-4-fluoro-5-(1-methyl-6-trifluoromethyl-2,4(1H,3H)-pyrimidinedion-3-yl) benzaldehyde in 20 ml of tetrahydrofuran was slowly added dropwise. 30 minutes later, the cooling bath was removed, and the mixture was allowed to come to room temperature in the course of 16 hours. After 3.6 g of ammonium chloride had been added, the reaction mixture was poured into 20 ml of water. The product was extracted twice from the aqueous phase using in each case 50 ml of methyl tert-butyl ether. The combined organic phases were washed using saturated aqueous sodium chloride solution and water, dried over magnesium sulfate and finally concentrated. The crude product was purified by means of silica gel column chromatography (eluent: hexane/ethyl acetate=4:1). Yield: 0.7 g.

Example 5
Dimethyl 1-chloro-2-(2-chloro-5-(1,3,4,5,6,7-hexahydro-1, 3-dioxo-2H-isoindol-2-yl)phenyl)ethylphosphonate (No. IEb.2)

2.8 g (10 mmol) of 2-chloro-5-(1,3,4,5,6,7-hexahydro-1, 3-dioxo-2H-isoindol-2-yl)aniline were added to a solution of 31.2 g (0.23 mol) of dimethyl vinylphosphonate, 1.6 g (12 mmol) of copper(II) Q. chloride and 1.6 g (16 mmol) of tert-butyl nitrite in 200 ml of acetonitrile. After the reaction mixture had been stirred for 2 hours, 200 ml of methyl tert-butyl ether were added. The organic phase was subsequently washed twice using in each case 50 ml of water and then dried over magnesium sulfate and finally concentrated. The crude product was purified by means of silica gel column chromatography (eluent: first cyclohexane/methyl tert-butyl ether=4:1, then ethyl acetate). Yield: 2.0 g.

Example 6
Dimethyl 1-chloro-2-(2-chloro-5-(5-chloro-1-difluoromethyl-2-methyl-1H-imidazol-4-yl)phenyl)ethylphosphonate (No. IHb.2)

A solution of 42.5 g (0.26 mol) of dimethyl vinylphosphonate, 2.5 g of copper(II) chloride (19 mmol) and 1.7 g (17 mmol) of tert-butyl nitrite in 100 ml of acetonitrile was stirred for 30 minutes, and a solution of 3.8 g (13 mmol) of 2-chloro-5-(5-chloro-1-difluoromethyl-2-methyl-1H-imidazol-4-yl)aniline in 20 ml of acetonitrile was subsequently added. After 1 further hour, the mixture was concentrated, and the residue was then treated with 50 ml of water. The product was extracted from the aqueous phase using 50 ml of ethyl acetate. The organic phase was dried over magnesium sulfate, filtered and finally concentrated. The crude product was purified by means of silica gel column chromatography (eluent: hexane/ethyl acetate=4:1). Yield: 0.8 g.

Precursor 6.1
4(5)-(4-Chlorophenyl)-2-methyl-1H-imidazole 28.6 g (0.65 mol) of acetaldehyde were added dropwise with cooling to 320 ml of 25% by weight aqueous ammonia solution. Then, 86.3 g (0.43 mol) of copper(II) acetate monohydrate and a solution of 46 g (0.22 mol) of 1-(4-chlorophenyl)ethanon-2-yl acetate in 300 ml of dimethylformamide were added successively, whereupon the mixture was heated at 100° C. for 30 minutes. The reaction mixture was subsequently poured into 3 l of ice-water. The solids were filtered off and then taken up in 300 ml of ethanol. Hydrogen sulfide gas was then passed into this solution until saturation was reached, during which process black copper sulfide precipitated. After 5 g of active charcoal had been added, the mixture was stirred for a further 2 hours at reflux temperature, then cooled and filtered, and the filtrate was concentrated. Yield: 31.5 g.

$^1$H NMR (270 MHz; in CDCl$_3$): δ [ppm]=2.41 (s,3H), 7.17 (s,2H), 7.30 (d,2H), 7.61 (d,2H).

Precursor 6.2
4-(4-Chlorophenyl)-1-difluoromethyl-2-methyl-1H-imidazole 45.2 g (0.33 mol) of potassium carbonate were added to a solution of 31.5 g (0.16 mol) of 4(5)-(4-chlorophenyl)-2-methyl-1H-imidazole in 150 ml of dimethylformamide. The mixture was then heated at 90° C. and chlorodifluoromethane gas was passed in for 2 hours. The reaction mixture was subsequently poured into 300 ml of water. The product was extracted three times from the aqueous phase using in each case 300 ml of ethyl acetate, whereupon the combined organic phases were washed with water and saturated aqueous sodium chloride solution, dried over magnesium sulfate and finally concentrated. Yield: 36 g.

$^1$H NMR (270 MHz; in CDCl$_3$): δ [ppm]=2.56 (s,3H), 7.04 (t,1H), 7.35 (m,3H), 7.68 (d,2H).

Precursor 6.3
5-Chloro-4-(4-chlorophenyl)-1-difluoromethyl-2-methyl-1H-imidazole 26.7 g (0.19 mol) of sulfuryl chloride were added dropwise with ice-cooling to a suspension of 24 g (98 mmol) of 4-(4-chlorophenyl)-1-difluoromethyl-2-methyl-1H-imidazole in 200 ml of tetrachloromethane. After the reaction mixture had been stirred for 2 hours, an excess of saturated aqueous sodium hydrogen carbonate solution was added dropwise (still with ice-cooling). The solids were subsequently filtered off. The organic phase was washed with water until neutral, dried over magnesium sulfate and concentrated. The crude product was purified by means of silica gel column chromatography (eluent: hexane/ethyl acetate=8:1). Yield: 7.4 g.

$^1$H NMR (270 MHz; in CDCl$_3$): δ [ppm]=2.60 (s,3H), 7.14 (t,1H), 7.38 (d,2H), 7.84 (d,2H).

Precursor 6.4
5-Chloro-4-(4-chloro-3-nitrophenyl)-1-difluoromethyl-2-methyl-1H-imidazole 8 g (28 mmol) of 5-chloro-4-(4-chlorophenyl)-1-difluoromethyl-2-methyl-1H-imidazole were cooled to (–40)° C., and 100 ml of concentrated nitric acid were added. After 2 hours at (–20)° C., the mixture was poured into ice-water, whereupon the solid product of value was filtered off, washed with water and dried. Yield: 7 g.

$^1$H NMR (270 MHz; in CDCl$_3$): δ [ppm]=2.63 (s,3H), 7.16 (t,1H), 7.59 (d,1H), 8.09 (dd,1H), 8.47 (d,2H).

Precursor 6.5
2-Chloro-5-(5-chloro-1-difluoromethyl-2-methyl-1H-imidazol-4-yl)aniline 7 g (22 mmol) of 5-chloro-4-(4-chloro-3-nitrophenyl)-1-difluoromethyl-2-methyl-1H-imidazole were dissolved in 200 ml of methanol with heating. This solution was added dropwise to a suspension of 3.6 g (65 mmol) of iron powder in 150 ml of glacial acetic acid, stirred at reflux temperature. After 3 hours, the reaction mixture was poured into 500 ml of water. A further 500 ml of ethyl acetate were added to the mixture, whereupon the iron residues were filtered off. The aqueous phase was separated off and mixed with another 500 ml of ethyl acetate. The combined organic phases were washed with water and saturated aqueous sodium chloride solution, dried over magnesium sulfate and finally concentrated. To remove the remaining acetic acid, the crude product was treated with 100 ml of toluene, whereupon the mixture was again concentrated to dryness. Yield: 5.7 g.

$^1$H NMR (270 MHz; in CDCl$_3$): δ [ppm]=2.60 (s,3H), 4.13 (s,2H), 7.12 (t,1H), 7.15–7.35 (m,3H).

Example 7
Dimethyl 1-bromo-2-[2-chloro-4-fluoro-5-(1,3,4,5,6,7-hexahydro-1,3-dioxo-2H-isoindol-2-yl)phenyl]ethylphosphonate (No. IEc.860)

Following the procedure described in Example 5 and using 21.2 g (0.16 mol) of dimethyl vinylphosphonate, 1.8 g (8 mmol) of copper(II) bromide, 1.1 g (11 mmol) of tert-butyl nitrite and 2.0 g (6.8 mmol) of 2-chloro-4-fluoro-5-(1,3,4,5,6,7-hexahydro-1,3-dioxo-2H-isoindol-2-yl) aniline, 0.7 g of the above product of value is obtained.

Example 8
Dimethyl 1-chloro-2-(2-chloro-4-fluoro-5-(1,3,4,5,6,7-hexahydro-1,3-dioxo-2H-isoindol-2-yl)phenyl)ethylphosphonate (No. IEb.860)

Following the procedure described in Example 5 and using 21.2 g (0.16 mol) of dimethyl vinylphosphonate, 1.1 g (8 mmol) of copper(II) chloride, 1.1 g (11 mmol) of tert-butyl nitrite and 2.0 g (6.8 mmol) of 2-chloro-4-fluoro-5-(1,3,4,5,6,7-hexahydro-1,3-dioxo-2H-isoindol-2-yl)aniline, 1.0 g of the above product of value is obtained.

Example 9
Dimethyl 1-chloro-2-[2-chloro-5-(3-chloro-4,5,6,7-tetrahydro-2H-indazol-2-yl)phenyl]ethylphosphonate (No. IGb.2)

Following the procedure described in Example 5 and using 42.4 g (0.31 mol) of dimethyl vinylphosphonate, 2.2 g (16 mmol) of copper(II) chloride, 2.2 g (22 mmol) of tert-butyl nitrite and 4.0 g (14 mmol) of 2-chloro-5-(3-chloro-4,5,6,7-tetrahydro-2H-indazol-2-yl)aniline, 0.8 g of the above product of value is obtained.

Example 10
Dimethyl 1-chloro-2-[2,4-dichloro-5-(4-chloro-5-difluoromethoxy-1-methyl-1H-pyrazol-3-yl)phenyl]ethylphosphonate (No. IBb.431)

Following the procedure described in Example 5 and using 32.6 g (0.24 mol) of dimethyl vinylphosphonate, 3.6 g (26 mmol) of copper(II) chloride, 2.6 g (25 mmol) of tert-butyl nitrite and 13.6 g (24 mmol) of 2,4-dichloro-5-(4-chloro-5-difluoromethoxy-1-methyl-1H-pyrazol-3-yl)aniline, 3.6 g of the above product of value are obtained.

Example 11
Dimethyl 1-chloro-2-(2-chloro-5-(1-methyl-6-trifluoromethyl-2,4(1H,3H)-pyrimidinedion-3-yl)phenyl)ethylphosphonate (No. IAb.2)

Following the procedure described in Example 5 and using 17.9 g (0.13 mol) of dimethyl vinylphosphonate, 0.9 g (7 mmol) of copper(II) chloride, 0.65 g (6.5 mmol) of tert-butyl nitrite and 2.0 g (6.3 mmol) of 2-chloro-5-(1-methyl-6-trifluoromethyl-2,4(1H,3H)-pyrimidinedion-3-yl)aniline, 1.0 g of the above product of value is obtained.

Example 12
Dimethyl 1-chloro-2-(2-chloro-4-fluoro-5-[1-methyl-4,5-di-(trifluoromethyl)-1H-pyrazol-3-yl)phenyl)ethylphosphonate (No. IDb.860)

Following the procedure described in Example 5 and using 13.1 g (96 mmol) of dimethyl vinylphosphonate, 0.7 g (5 mmol) of copper(II) chloride, 0.5 g (5 mmol) of tert-butyl nitrite and 1.2 g (4.6 mmol) of 2-chloro-4-fluoro-5-(1-methyl-4,5-di-(trifluoromethyl)-1H-pyrazol-3-yl)aniline, 0.6 g of the above product of value is obtained.

Example 13
Diethyl 1-chloro-2-[2-chloro-5-(4-chloro-5-difluoromethoxy-1-methyl-1H-pyrazol-3-yl)-4-fluorophenyl]ethylphosphonate (No. IBb.861)

Following the procedure described in Example 5 and using 12.5 g (85 mmol) of diethyl vinylphosphonate, 0.7 g (5 mmol) of copper(II) chloride, 0.5 g (5 mmol) of tert-butyl nitrite and 1.5 g (4.6 mmol) of 2-chloro-4-fluoro-5-(4-chloro-5-difluoromethoxy-1-methyl-1H-pyrazol-3-yl)aniline, 0.6 g of the above product of value is obtained.

Example 14
Diethyl 1-bromo-2-(2-chloro-5-(4-chloro-5-difluoromethoxy-1-methyl-1H-pyrazol-3-yl)-4-fluorophenyl)ethylphosphonate (No. IBc.861)

Following the procedure described in Example 5 and using 12.5 g (85 mmol) of diethyl vinylphosphonate, 1.1 g (5 mmol) of copper(II) bromide, 0.5 g (5 mmol) of tert-butyl nitrite and 1.5 g (4.6 mmol) of 2-chloro-4-fluoro-5-(4-chloro-5-difluoromethoxy-1-methyl-1H-pyrazol-3-yl)aniline, 0.8 g of the above product of value is obtained.

Example 15
Diethyl 2-(2-chloro-5-(4-chloro-1-methyl-5-trifluoromethyl-1H-pyrazol-3-yl)-4-fluorophenyl)vinylphosphonate (No. ICg.861)

Following the procedure described in Example 1 and using 0.45 g (1.5 mmol) of tetraethyl methanediphosphonate, 36 mg (1.5 mmol) of sodium hydride and 0.5 g (1.5 mmol) of 2-chloro-5-(4-chloro-1-methyl-5-trifluoromethyl-IH-pyrazol-3-yl)-4-fluorobenzaldehyde, 0.4 g of the above product of value is obtained.

Example 16
Diethyl 2-(2-chloro-5-(1,3,4,5,6,7-hexahydro-1,3-dioxo-2H-isoindol-2-yl)phenyl)vinylphosphonate (No. IEg.3)

Following the procedure described in Example 1 and using 0.5 g (1.7 mmol) of tetraethyl methanediphosphonate, 40 mg (1.7 mmol) of sodium hydride and 0.5 g (1.7 mmol) of 2-chloro-5-(1,3,4,5,6,7-hexahydro-1,3-dioxo-2H-isoindol-2-yl)benzaldehyde, 0.2 g of the above product of value is obtained.

Example 17
Diethyl 2-(2-chloro-4-fluoro-5-(1,3,4,5,6,7-hexahydro-1,3-dioxo-2H-isoindol-2-yl)phenyl)vinylphosphonate (No. IEg.861)

Following the procedure described in Example 1 and using 0.5 g (1.7 mmol) of tetraethyl methanediphosphonate, 39 mg (1.7 mmol) of sodium hydride and 0.5 g (1.6 mmol) of 2-chloro-4-fluoro-5-(1,3,4,5,6,7-hexahydro-2H-isoindol-2-yl)benzaldehyde, 0.4 g of the above product of value is obtained.

Example 18
Diethyl 2-[2-chloro-5-(3,4-dimethyl-1H-pyrrole-2,5-dion-1-yl)-phenyl]vinylphosphonate (No. IFg.3)

Following the procedure described in Example 1 and using 0.55 g (1.9 mmol) of tetraethyl methanediphosphonate, 45 mg (1.9 mmol) of sodium hydride and 0.5 g (1.9 mmol) of 2-chloro-5-(3,4-dimethyl-1H-pyrrole-2,5-dion-1-yl)benzaldehyde, 0.5 g of the above product of value is obtained. M.p.: 93–94° C.

Example 19
Diethyl 2-(2-chloro-5-(1-methyl-6-trifluoromethyl-2,4(1H,3H)-pyrimidinedion-3-yl)phenyl)vinylphosphonate (No. IAg.3)

Following the procedure described in Example 1 and using 0.73 g (2.5 mmol) of tetraethyl methanediphosphonate, 57 mg (2.4 mmol) of sodium hydride and 0.5 g (1.5 mmol) of 2-chloro-5-(1-methyl-6-trifluoromethyl-2,4(1H,3H)-pyrimidinedion-3-yl)benzaldehyde, 0.4 g of the above product of value is obtained.

Example 20
Diethyl 2-(2,4-dichloro-5-(1-methyl-6-trifluoromethyl-2,4(1H,3H)-pyrimidinedion-3-yl)vinylphosphonate (No. IAg.432)

Following the procedure described in Example 1 and using 0.7 g (2.3 mmol) of tetraethyl methanediphosphonate, 52 mg (2.3 mmol) of sodium hydride and 0.5 g (1.4 mmol) of 2,4-dichloro-5-(1-methyl-6-trifluoromethyl-2,4(1H,3H)-pyrimidinedion-3-yl)-benzaldehyde, 0.5 g of the above product of value is obtained.

Precursor 20.1
2,4-Dichloro-5-isocyanatobenzaldehyde (O-ethyl)oxime 65.3 g (0.28 mol) of 5-amino-2,4-dichlorobenzaldehyde (O-ethyl)-oxime (obtainable by the process given for precursors 28.1–28.3) and 60.9 g (0.31 mol) of diphosgene were reacted in the manner described for precursor 3.1. Yield: 72.9 g.

Precursor 20.2
2,4-Dichloro-5-(6-trifluoromethyl-2,4(1H,3H)-pyrimidinedion-3-yl)benzaldehyde (O-ethyl)oxime 9.2 g (0.31 mol) of sodium hydride, 51.3 g (0.28 mol) of ethyl 3-amino-4,4,4-trifluorocrotonate and 72.6 g (0.28 mol) of 2,4-dichloro-5-isocyanatobenzaldehyde (O-ethyl)oxime were reacted in the manner described for precursor 3.2. Yield: 72.0 g; m.p.: 205–209° C.

Precursor 20.3
2,4-Dichloro-5-(1-methyl-6-trifluoromethyl-2,4(1H,3H)-pyrimidinedion-3-yl)benzaldehyde (O-ethyl)oxime 69.3 g (0.175 mol) of 2,4-dichloro-5-(6-trifluoromethyl-2,4(1H,3H)-pyrimidinedion-3-yl)benzaldehyde (O-ethyl)oxime, 26.6 g (0.19 mol) of potassium carbonate and 27.3 g (0.19 mol) of methyl iodide were reacted in the manner described for precursor 3.3. Yield: 69.0 g; m.p.: 140–143° C.

Precursor 20.4
2,4-Dichloro-5-(1-methyl-6-trifluoromethyl-2,4(1H,3H)-pyrimidinedion-3-yl)benzaldehyde 61.5 g (0.15 mol) of 2,4-dichloro-5-(1-methyl-6-trifluoromethyl-2,4(1H,3H)-pyrimidinedion-3-yl)benzaldehyde (O-ethyl)oxime were reacted in the manner described for precursor 3.4. Yield: 50.0 g; m.p.: 117–120° C.

Example 21
Diphenyl 2-(2-chloro-5-(1,3,4,5,6,7-hexahydro-1,3-dioxo-2H-isoindol-2-yl)phenyl)vinylphosphonate (No. IEg.56)

2.6 g (5.2 mmol) of diphenyl (triphenylphosphoranylidene)methanephosphonate and 1 g (3.4 mmol) of 2-chloro-5-(1,3,4,5,6,7-hexahydro-1,3-dioxo-2H-isoindol-2-yl)benzaldehyde were dissolved in 100 ml of toluene, whereupon the mixture was refluxed for 4 hours. The reaction mixture was subsequently concentrated. The crude product obtained as residue was purified by means of silica gel chromatography (eluent: hexane/ethyl acetate=2:1) followed by crystallization from hexane/ethyl acetate. Yield: 0.8 g.

Example 22
Diethyl 1-chloro-2-(2-chloro-5-(4-chloro-1-methyl-5-trifluoromethyl-1H-pyrazol-3-yl)-4-fluorophenyl)vinylphosphonate (No. ICh.861)

Following the procedure described in Example 2 and using 37.3 g (0.15 mol) of diethyl trichloromethanephosphonate, 42 ml (67 mmol) of a 1.6-molar butyllithium solution and 10 g (29 mmol) of 2-chloro-5-(4-chloro-1-methyl-5-trifluoromethyl-1H-pyrazol-3-yl)-4-fluorobenzaldehyde, 12.8 g of the above product of value are obtained.

Example 23
Diethyl 1-chloro-2-(2-chloro-5-(1,3,4,5,6,7-hexahydro-1,3-dioxo-2H-isoindol-2-yl)phenyl)vinylphosphonate (No. IEh.3)

Following the procedure described in Example 2 and using 4.4 g (17 mmol) of diethyl trichloromethanephosphonate, 5 ml (8 mmol) of a 1.6-molar butyllithium solution and 1 g (3.5 mmol) of 2-chloro-5-(1,3,4,5,6,7-hexahydro-1,3-dioxo-2H-isoindol-2-yl)-benzaldehyde, 0.6 g of the above product of value is obtained.

Example 24
Diethyl 1-chloro-2-(2-chloro-4-fluoro-5-(1,3,4,5,6,7-hexahydro-1,3-dioxo-2H-isoindol-2-yl)phenyl)vinylphosphonate (No. IEh.861)

Following the procedure described in Example 2 and using 4.1 g (16 mmol) of diethyl trichloromethanephosphonate, 5 ml (8 mmol) of a 1.6-molar butyllithium solution and 1 g (3.2 mmol) of 2-chloro-4-fluoro-5(1,3,4,5,617-hexahydro-1,3-dioxo-2H-isoindol-2-yl)benzaldehyde, 0.6 g of the above product of value is obtained.

Example 25
Diethyl 1-chloro-2-(2-chloro-5-(3,4-dimethyl-1H-pyrrole-2,5-dion-1-yl)-phenyl)vinylphosphonate (No. IFh.3)

Following the procedure described in Example 2 and using 4.8 g (19 mmol) of diethyl trichloromethanephosphonate, 5 ml (8 mmol) of a 1.6-molar butyllithium solution and 1 g (3.8 mmol) of 2-chloro-5-(3,4-dimethyl-1H-pyrrole-2,5-dion-1-yl)benzaldehyde, 0.4 g of the above product of value is obtained.

Example 26
Diethyl 1-chloro-2-[2-chloro-5-(1-methyl-6-trifluoromethyl-2,4(1H,3H)-pyrimidinedion-3-yl)phenyl]vinylphosphonate (No. IAh.3)

Following the procedure described in Example 2 and using 4 g (16 mmol) of diethyl trichloromethanephosphonate, 5 ml (8 mmol) of a 1.6-molar butyllithium solution and 0.7 g (2.8 mmol) of 2-chloro-5-(1-methyl-6-trifluoromethyl-2,4(1H,3H)-pyrimidinedion-3-yl)benzaldehyde, 0.5 g of the above product of value is obtained.

Example 27
Diethyl 1-chloro-2-[2,4-dichloro-5-(1-methyl-6-trifluoromethyl-2,4(1H,3H)-pyrimidinedion-3-yl)phenyl]vinylphosphonate (No. IAh.432)

Following the procedure described in Example 2 and using 4 g (16 mmol) of diethyl trichloromethanephosphonate, 5 ml (8 mmol) of a 1.6-molar butyllithium solution and 1 g (2.7 mmol) of 2,4-dichloro-5-(1-methyl-6-trifluoromethyl-2,4(1H,3H)-pyrimidinedion-3-yl)benzaldehyde, 0.3 g of the above product of value is obtained.

Example 28
Diethyl 1-chloro-2-[2,4-dichloro-5-(1,3,4,5,6,7-hexahydro-1,3-dioxo-2H-isoindol-2-yl)phenyl]vinylphosphonate (No. IEh.432)

Following the procedure described in Example 2 and using 1.5 g (6 mmol) of diethyl trichloromethanephosphonate, 1.8 ml (2.9 mmol) of a 1.8-molar butyllithium solution and 0.3 g (0.9 mmol) of 2,4-dichloro-5-(1,3,4,5,6,7-hexahydro-1,3-dioxo-2H-isoindol-2-yl)benzaldehyde, 0.3 g of the above product of value is obtained.

Precursor 28.1
2,4-Dichloro-5-nitrobenzaldehyde

A solution of 125 g of nitric acid in 153 g of sulfuric acid which had been prepared with ice-cooling at (−5)° C. was added dropwise to a solution of 262.5 g (1.5 mol) of 2,4-dichlorobenzaldehyde in 560 ml of sulfuric acid. After the reaction mixture had been stirred for 2 hours at 10° C., it was poured onto 4 kg of ice. The resulting solids were subsequently separated off, washed with water and dissolved in 2 l of dichloromethane. The resulting solution was washed with saturated aqueous sodium hydrogen carbonate solution, then dried over magnesium sulfate and finally concentrated. Yield: 329.5 g; m.p.: 61–63° C.

Precursor 28.2

2,4-Dichloro-5-nitrobenzaldehyde (O-methyl)oxime 93.1 g (0.223 mol) of methoxyamine hydrochloride (20% strength by weight solution in water) were treated with 100 ml of water and 18.7 g (0.223 mol) of sodium hydrogen carbonate. A solution of 44 g (0.2 mol) of 2,4-dichlorobenzaldehyde in 200 ml of toluene were added dropwise to this mixture. The mixture was subsequently heated for 5 hours at 50° C. The organic phase was then separated off. After washing with water and saturated aqueous sodium chloride solution, the resulting crude-product solution was dried over magnesium sulfate and finally concentrated. Yield: 39.2 g; m.p.: 77–79° C.

Precursor 28.3

5-Amino-2,4-dichlorobenzaldehyde (O-methyl)oxime 16.8 g (0.3 mol) of iron powder were dissolved in 130 ml of methanol and 100 ml of acetic acid. A solution of 24.9 g (0.1 mol) of 2,4-dichloro-5-nitrobenzaldehyde (O-methyl)oxime in 100 ml of acetic acid and 100 ml of methanol was added dropwise to this solution at 70° C. The reaction mixture was then heated for 1 hour at 75–80° C., whereupon it was poured onto 3 kg of ice. The product of value was subsequently extracted with 2 l of dichloromethane. The organic phase was dried over magnesium sulfate and finally concentrated. The crude product was purified by stirring with a small amount of pentane. Filtration gave 18.5 g of product of value. M.p.: 129–132° C.

Precursor 28.4

2,4-Dichloro-5-(1,3,4,5,6,7-hexahydro-1,3-dioxo-2H-isoindol-2-yl) benzaldehyde (O-methyl)oxime 18 g (82 mmol) of 5-amino-2,4-dichlorobenzaldehyde (O-methyl)oxime were added to a solution of 12.5 g (82 mmol) of 3,4,5,6-tetrahydrophthalic anhydride in 300 ml of acetic acid, whereupon the mixture was stirred for 15 hours at reflux temperature. The reaction mixture was subsequently poured into 1 l water. The product was then extracted with 300 ml of methyl tert-butyl ether. The extract was washed with saturated aqueous sodium hydrogen carbonate solution, dried over magnesium sulfate and finally concentrated. The residue was purified by means of silica gel chromatography (eluent: hexane/ethyl acetate=4:1). Yield: 20.9 g; m.p.: 122–124° C.

Precursor 28.5

2,4-Dichloro-5-(1,3,4,5,6,7-hexahydro-1,3-dioxo-2H-isoindol-2-yl) benzaldehyde 9 ml of a 37% strength by weight aqueous formaldehyde solution and 9 ml of concentrated hydrochloric acid were added to a solution of 10.6 g (30 mmol) of 2,4-dichloro-5-(1,3,4,5,6,7-hexahydro-1,3-dioxo-2H-isoindol-2-yl) benzaldehyde (O-methyl)oxime in 45 ml of acetic acid. The mixture was subsequently heated for 1 hour at 50–60° C., whereupon the reaction mixture was poured into 300 ml of ice-water. The product was extracted from the resulting mixture using 200 ml of dichloromethane. The extract was dried over magnesium sulfate and then concentrated. The residue was purified by means of silica gel chromatography (eluent: hexane/ethyl acetate=4:1). Yield: 5.2 g; $^1$H NMR (270 MHz; in CDCl$_3$): δ [ppm]=1.85 (s, 4H), 2.45 (s, 4H), 7.67 (s, 1H), 7.81 (s, 1H), 10.40 (s, 1H).

Example 29

Diisopropyl 2-(2-chloro-5-(4-chloro-1-methyl-5-trifluoromethyl-1H-pyrazol-3-yl)-4-fluorophenyl) ethylphosphonate (No. ICa.863)

A suspension of 6 g (11 mmol) of diisopropyl 1-chloro-2-(2-chloro-5-(4-chloro-1-methyl-5-trifluoromethyl-1H-pyrazol-3-yl)-4-fluorophenyl)vinylphosphonate, 1.1 g (13 mmol) of sodium acetate and 50 mg of 5% palladium on active charcoal in 100 ml of ethanol was treated with 5 bar of hydrogen. After the mixture had been stirred for one day, the catalyst was removed by filtration. The filtrate was concentrated. 100 ml of water and 100 ml of ethyl acetate were added to the resulting residue. The organic phase was separated off, dried over magnesium sulfate and finally concentrated. Silica gel chromatography of the residue (eluent: hexane/ethyl acetate=3:1) first gave 0.2 g of the product of value and then 1.5 g of diisopropyl 2-(5-(4-chloro-1-methyl-5-trifluoromethyl-IH-pyrazol-3-yl)-4-fluorophenylJethyl-phosphonate.

Example 30

1-Chloro-2-(2-chloro-5-(4-chloro-1-methyl-5-trifluoromethyl-1H-pyrazol-3-yl)-4-fluorophenyl) vinylphosphonic acid (No. ICh.859)

A solution of 1 g (2 mmol) of diethyl 1-chloro-2-[2-chloro-5-(4-chloro-1-methyl-5-trifluoromethyl-1H-pyrazol-3-yl)-4-fluorophenyl]vinylphosphonate, 0.97 g (5.9 mmol) of potassium iodide and 0.6 g (5.9 mmol) of chlorotrimethylsilane in 20 ml of acetonitrile was heated for 3 hours at 50–60° C. The mixture was subsequently concentrated. The residue was treated with 50 ml of water and 50 ml of ethyl acetate. After the organic phase had been separated off and dried over magnesium sulfate, the mixture was concentrated. Yield: 0.7 g.

Example 31

1-Chloro-2-[2-chloro-5-(4-chloro-5-difluoromethoxy-1-methyl-1H-pyrazol-3-yl)-4-fluorophenyl]vinylphosphonic acid (No. IBh.859)

Following the procedure described in Example 30 and using 11.4 g (22.6 mmol) of diethyl 1-chloro-2-[2-chloro-5-(4-chloro-5-difluoromethoxy-1-methyl-1H-pyrazol-3-yl)-4-fluorophenyl vinylphosphonate, 11.3 g (68 mmol) of potassium iodide and 7.8 g (67 mmol) of chlorotrimethylsilane, 9 g of the above product of value are obtained.

Example 32

1-Chloro-2-[2-chloro-4-fluoro-5-(1-methyl-6-trifluoromethyl-2,4-(1H,3H)pyrimidinedion-3-yl)phenyl] vinylphosphonic acid (No. IAh.859)

Following the procedure described in Example 30 and using 5 g (9.6 mmol) of diethyl 1-chloro-2-[2-chloro-4-fluoro-5-(1-methyl-6-trifluoromethyl-2,4(1H,3H) pyrimidinedion-3-yl)phenyl]vinylphosphonate, 4.8 g (29 mmol) of potassium iodide and 3.1 g (29 mmol) of chlorotrimethylsilane, 4.5 g of the above product of value are obtained.

Example 33

Dimethyl 1-chloro-2-[2-chloro-5-(4-chloro-1-methyl-5-trifluoromethyl-1H-pyrazol-3-yl)-4-fluorophenyl] vinylphosphonate (No. ICh.860)

0.7 g (5.5 mmol) of oxalyl chloride and one drop of dimethylformamide were added to a solution of 0.7 g (1.5 mmol) of 1-chloro-2-[2-chloro-5-(4-chloro-1-methyl-5-trifluoromethyl-1H-pyrazol-3-yl)-4-fluorophenyl] vinylphosphonic acid in 30.ml of dichloromethane. After the evolution of gas had ceased, a solution of 2.3 g (15 mmol) of methanol and 0.6 g (8 mmol) of pyridine in 50 ml of dichloromethane was added dropwise to the resulting mixture. The reaction mixture was stirred for a further 2 hours and subsequently concentrated. The residue was treated with 50 ml of water and 50 ml of ethyl acetate. The organic phase was dried over magnesium sulfate and then concentrated. The crude product was purified by means of siliga gel chromatography (eluent: hexane/ethyl acetate=3:1). Yield: 0.25 g.

Example 34
2-(1-Chloro-2-[2-chloro-5-(4-chloro-1-methyl-5-trifluoromethyl-1H-pyrazol-3-yl)-4-fluorophenyl]vinyl)-2,1,3-phosphadioxan-2-one (No. ICh.1154)

Following the procedure described in Example 33 and using 1 g (2.2 mmol) of 1-chloro-2-[2-chloro-5-(4-chloro-1-methyl-5-trifluoromethyl-1H-pyrazol-3-yl)-4-fluorophenyl]vinylphosphonic acid, 0.7 g (5.5 mmol) of oxalyl chloride, 1.5 g (20 mmol) of 1,3-propanediol and 0.8 g (10 mmol) of pyridine, 0.6 g of the above product of value is obtained.

Example 35
Dimethyl 1-chloro-2-[2-chloro-5-(4-chloro-5-difluoromethoxy-1-methyl-1H-pyrazol-3-yl)-4-fluorophenyl]vinylphosphonate (No. IBh.860)

Following the procedure described in Example 33 and using 0.7 g (1.5 mmol) of 1-chloro-2-[2-chloro-5-(4-chloro-5-difluoromethoxy-1-methyl-1H-pyrazol-3-yl)-4-fluorophenyl]vinylphosphonic acid, 0.7 g (5.5 mmol) of oxalyl chloride, 0.45 g (14 mmol) of methanol and 0.56 g (7.2 mmol) of pyridine, 0.3 g of the above product of value is obtained.

Example 36
2-(1-Chloro-2-[2-chloro-5-(4-chloro-5-difluoromethoxy-1-methyl-1H-pyrazol-3-yl)-4-fluorophenyl]vinyl)-2,1,3-phosphadioxan-2-one (No. IBh.1154)

Following the procedure described in Example 33 and using 0.7 g (1.5 mmol) of 1-chloro-2-[2-chloro-5-(4-chloro-5-difluoromethoxy-1-methyl-1H-pyrazol-3-yl)-4-fluorophenyl]vinylphosphonic acid, 0.7 g (5.5 mmol) of oxalyl chloride, 1 g (14 mmol) of 1,3-propanediol and 0.56 g (7.2 mmol) of pyridine, 0.3 g of the above product of value is obtained.

Example 37
S,S-Diethyl 1-chloro-2-[2-chloro-5-(4-chloro-5-difluoromethoxy-1-methyl-1H-pyrazol-3-yl)-4-fluorophenyl]vinyldithiophosphonate (No. IBh.1271)

Following the procedure described in Example 33 and using 0.8 g (1.8 mmol) of 1-chloro-2-[2-chloro-5-(4-chloro-5-difluoromethoxy-1-methyl-1H-pyrazol-3-yl)-4-fluorophenyl vinylphosphonic acid, 0.5 g (3.9 mmol) of oxalyl chloride, 1.0 g (18 mmol) of ethylmercaptan and 0.7 g (8.8 mmol) of pyridine, 0.5 g of the above product of value is obtained.

Example 38
2-(1-Chloro-2-[2-chloro-5-(4-chloro-5-difluoromethoxy-1-methyl-1H-pyrazol-3-yl)-4-fluorophenyl]vinyl)-1,3-dimethylperhydro-2,1,3-phosphadiazin-2-one (No. IBh.1256)

Following the procedure described in Example 33 and using 0.8 g (1.8 mmol) of 1-chloro-2-[2-chloro-5-(4-chloro-5-difluoromethoxy-1-methyl-1H-pyrazol-3-yl)-4-fluorophenyl]vinylphosphonic acid, 0.5 g (3.9 mmol) of oxalylchloride, 1.8 g (18 mmol) of N,N'-dimethyl-1,3-diaminopropane and 0.7 g (8.8 mmol) of pyridine, 0.34 g of the above product of value is obtained.

Example 39
Dimethyl 1-Chloro-2-[2-chloro-4-fluoro-5-(1-methyl-6-trifluoromethyl-2,4-(1H,3H)pyrimidinedion-3-yl)phenyl]vinylphosphonate (No. IAh.860)

Following the procedure described in Example 33 and using 0.9 g (1.9 mmol) of 1-chloro-2-[2-chloro-4-fluoro-5-(1-methyl-6-trifluoromethyl-2,4 (1H,3H ) pyrimidinedion-3-yl ) phenyl]vinylphosphonic acid, 0.7 g (5.5 mmol) of oxalyl chloride, 0.6 g (19 mmol) of methanol and 0.75 g (9.5 mmol) of pyridine, 0.2 g of the above product of value is obtained.

Example 40
Diisopropyl 1-chloro-2-[2-chloro-4-fluoro-5-(1-methyl-6-trifluoromethyl-2,4-(1H,3H)pyrimidinedion-3-yl)phenyl]vinylphosphonate (No. IAh.863)

0.4 g (15 mmol) of sodium hydride was added to a solution of 5.8 g (15 mmol) of tetraisopropyl chloromethanediphosphonate in 100 ml of tetrahydrofuran. After the mixture had been stirred for 30 minutes, 3.2 g (9 mmol) of 2-chloro-4-fluoro-5-(1-methyl-6-trifluoromethyl-2,4(1H,3H)pyrimidinedion-3-yl)benzaldehyde were added. The mixture was subsequently stirred for 1 hour. The reaction mixture was then treated with 50 ml of water and 50 ml of ethyl acetate. The organic phase was separated off, dried over (magnesium sulfate and finally concentrated. The crude product obtained was purified by means of MPLC on silica gel (eluent: hexane/ethyl acetate=2:1). Yield: 1.1 g.

Example 41
Diisopropyl 1-bromo-2-[2-chloro-4-fluoro-5-(1-methyl-6-trifluoromethyl-2,4-(1H,3H)pyrimidinedion-3-yl)phenyl]vinylphosphonate (No. IAi.863)

Following the procedure described in Example 40 and using 6.5 g (15 mmol) of tetraisopropyl bromomethanediphosphonate, 0.4 g (15 mmol) of sodium hydride and 3.2 g (9 mmol) of 2-chloro-4-fluoro-5-(1-methyl-6-trifluoromethyl-2,4(1H,3H)pyrimidinedion-3-yl) benzaldehyde, 2.6 g of the above product of value are obtained.

Example 42
Diethyl 2-[2-chloro-4-fluoro-5-(1-methyl-6-trifluoromethyl-2,4(1H,3H)pyrimidinedion-3-yl)phenyl]-1-cyanovinylphosphonate (No. IAj.861)

A solution of 1.6 g (9 mmol) of diethyl cyanomethanephosphonate, 3.2 g (9 mmol) of 2-chloro-4-fluoro-5-(1-methyl-6-trifluoromethyl-2,4(1H,3H) pyrimidinedion-3-yl)benzaldehyde, 0.6 ml of acetic acid and 0.18 ml of piperidine in 60 ml of toluene was refluxed for 6 hours, whereupon the mixture was concentrated. The crude product obtained was purified by silica gel chromatography (eluent: hexane/ethyl acetate=1:1). Yield: 1.8 g.

Example 43
Diethyl 1-[2-chloro-4-fluoro-5-(1-methyl-6-trifluoromethyl-2,4(1H,3H)pyrimidinedion-3-yl)phenyl] prop-1-en-2-ylphosphonate (No. IAk.861)

A solution of 10 ml (20 mmol) of a 2-molar solution of lithium diisopropylamide in 50 ml of tetrahydrofuran was cooled to (−60)° C. and at this temperature treated with 1.5 g (9 mmol) of diethyl ethanephosphonate, whereupon the mixture was stirred for 15 minutes. The mixture was subsequently cooled to (−70)° C., and 1 g (9.5 mmol) of chlorotrimethylsilane was added at this temperature. After the mixture had been stirred for a further 15 minutes, it was heated to (−20)° C. and treated with 3.2 g (9 mmol) of 2-chloro-4-fluoro-5-(1-methyl-6-trifluoromethyl-2,4(1H, 3H)pyrimidinedion-3-yl)benzaldehyde. Stirring was then continued for 2 hours at room temperature. For working-up, the reaction mixture was treated with 10 ml of dilute hydrochloric acid. The product was extracted with ethyl acetate. Finally, the ethyl acetate phase was separated off, dried over magnesium sulfate and concentrated. The crude product was purified by means of MPLC on silica gel (eluent: hexane/ethyl acetate=1:2). Yield: 0.2 g.

Example 44

Diethyl 1-chloro-2-[2-chloro-4-fluoro-5-(5,6,7,8-tetrahydro-1,2,4-triazolo[4,3-a]pyridine-3(2H)-on-2-yl)phenyl]vinylphosphonate (No. IKh.861)

1.4 g (16.8 mmol) of sodium acetate were added to a solution of 2 g (5.6 mmol) of diethyl 1-chloro-2-(2-chloro-4-fluoro-5-hydrazinophenyl)vinylphosphonate in 50 ml of acetonitrile.

After the mixture had been stirred for 30 minutes, it was cooled to 0° C. and treated with 1.1 g (5.6 mmol) of methyl 2-iniinopiperidine-1-carboxylate hydrochloride. The reaction mixture was subsequently stirred for 3 hours. It was then treated with 50 ml of water and 50 ml of ethyl acetate. The organic phase was separated off, dried over magnesium sulfate and finally concentrated.

The residue, which contained methyl 2-[2-(4-chloro-2-fluoro-5-[2-chloro-(2-diethylphosphoryl)vinyl]phenyl)hydrazin-1-ylidene]piperidine-1-carboxylate, was dissolved in 50 ml of toluene and then treated with 0.1 ml of acetic acid. The mixture was subsequently refluxed for 2 hours and then concentrated. The crude product obtained was purified by means of silica gel chromatography (eluent: ethyl acetate). Yield: 0.3 g.

Precursor 44.1

Diethyl 1-chloro-2-(2-chloro-4-fluorophenyl)vinylphosphonate (No. XXXIII.24)

462 ml (0.74 mol) of a 1.6-molar butyllithium solution (in hexane) were added to a solution, cooled to (−70)° C., of 408 g (1.6 mol) of diethyl trichloromethanephosphonate in 1.5 l of tetrahydrofuran, whereupon the mixture was stirred for 1 hour at (−70)° C. 51 g (0.32 mol) of 2-chloro-4-fluorobenzaldehyde (dissolved in 200 ml of tetrahydrofuran) were subsequently added dropwise to the mixture. The reaction mixture was then allowed to come to approximately 20° C., at which temperature it was treated with 10 ml of water. Finally, the mixture was concentrated (under a high vacuum during the last phase). To purify the crude product, it was suspended in 50 ml of hexane, and the solids were filtered off. Concentration of the filtrate gave 47.5 g of the product of value.

$^1$H NMR (270 MHz; in CDCl$_3$): δ [ppm]=1.20–1.40 (m,6H), 4.10–4.30 (m,4H), 6.95–7.20 (m,2H), 7.45–7.95 (m,2H).

Precursor 44.2

Diethyl 1-chloro-2-(2-chloro-4-fluoro-5-nitrophenyl)vinylphosphonate (No. XXXII.36)

47.5 g (0.16 mol) of diethyl 1-chloro-2-(2-chloro-4-fluorophenyl)vinylphosphonate were dissolved in 320 ml of concentrated nitric acid at (−40)° C., whereupon the mixture was stirred for 1 hour. The reaction mixture was subsequently stirred into 2.5 l of ice-water. The product was then extracted with dichloromethane. The organic phase was washed with saturated aqueous sodium chloride solution, dried over magnesium sulfate and finally concentrated. The crude product was purified by means of MPLC on silica gel (eluent: hexane/ethyl acetate=2:1). Yield: 33 g; $^1$H NMR (270 MHz; in CDCl$_3$): δ [ppm]=1.30–1.45 (m,6H), 4.10–4.30 (m,4H), 7.35–7.85 (m,2H), 8.30–8.70 (m,1H).

Precursor 44.3

Diethyl 1-chloro-2-(5-amino-2-chloro-4-fluorophenyl)vinylphosphonate (No. XXXI.36)

17.5 g (47 mmol) of diethyl 1-chloro-2-(2-chloro-4-fluoro-5-nitrophenyl)vinylphosphonate were added at 60–65° C. to a suspension of 13.1 g (0.24 mol) of iron powder in 40 ml of ethanol and 88 ml of acetic acid, whereupon the mixture was stirred for 2 hours at reflux temperature. The mixture was subsequently treated with 200 ml of ethyl acetate. The resulting suspension was filtered through a Kieselguhr bed. The filtrate was then concentrated. The residue was dissolved in 200 ml of ethyl acetate. The organic phase was then washed with water, dried over magnesium sulfate and finally concentrated. Yield: 14.8 g; $^1$H NMR (270 MHz; in CDCl$_3$): δ [ppm]=1.41 (t,6H), 3.90 (s,2H), 4.20 (m,4H), 7.09 (d,1H), 7.37 (d,1H), 7.80 (d,1H).

Precursor 44.4

Diethyl 1-chloro-2-(2-chloro-4-fluoro-5-hydrazinophenyl)vinylphosphonate (No. XXVIII.36)

2.5 g (7.3 mmol) of diethyl 1-chloro-2-(5-amino-2-chloro-4-fluorophenyl)vinylphosphonate were dissolved in 13.1 g of concentrated hydrochloric acid by briefly heating to 60° C. The resulting solution was cooled to 0° C. and treated with a solution of 0.5 g (7.3 mmol) of sodium nitrite in 1.5 ml of water. After the mixture had been stirred for 1 hour, a solution of 4.15 g (18.4 mmol) of tin(II) chloride dihydrate in 2.6 ml of concentrated hydrochloric acid was added dropwise. The mixture was subsequently stirred for 2 hours at approximately 20° C. It was then diluted with 100 ml of water. The solids were filtered off. The filtrate was rendered alkaline by adding 50% strength sodium hydroxide solution. The product was extracted from the aqueous phase using three portions of 50 ml of dichloromethane. The combined organic phases were washed with water, dried over magnesium sulfate and finally concentrated. Yield: 2 g; $^1$H NMR (270 MHz; in CDCl$_3$): δ [ppm]=1.40 (t,6H), 3.60 (s,2H), 4.22 (m,4H), 5.48 (s,1H), 7.07 (d,1H), 7.73 (d,1H), 7.85 (d,1H).

Example 45

Diethyl 1-chloro-2-(2-chloro-4-fluoro-5-[(3-methyl-4-trifluoromethyl-2(3H)-thiazolylidene)amino]phenyl)vinylphosphonate (No. ILh.861)

0.3 g (3.5 mmol) of sodium acetate and 0.6 g (2.9 mmol) of 3-bromo-1,1,1-trifluoroacetone were added to a solution of 1.2 g (2.9 mmol) of diethyl 1-chloro-2-(2-chloro-4-fluoro-5-[(methylaminothiocarbonyl)amino]phenyl)vinylphosphonate in 50 ml of toluene, whereupon the mixture was refluxed for 1 week. The reaction mixture was then washed with water, dried over magnesium sulfate and concentrated. The crude product was purified by means of silica gel chromatography (eluent: hexane/ethyl acetate=1:1). Yield: 0.2 g.

Precursor 45.1

Diethyl 1-chloro-2-(2-chloro-4-fluoro-5-[(methylaminothiocarbonyl)amino]phenyl)vinylphosphonate (No. XXXV.36)

1.2 g (16.4 mmol) of methyl isothiocyanate were added to a solution of 3 g (8.7 mmol) of diethyl 1-chloro-2-(5-amino-2-chloro-4-fluorophenyl)vinylphosphonate in 50 ml of ethanol. After the mixture had been stirred for 8 hours at reflux temperature, it was concentrated. The crude product was purified by means of silica gel chromatography (eluent: hexane/ethyl acetate=1:1). Yield: 1.3 g; $^1$H NMR (270 MHz; in CDCl$_3$): δ (ppm]=1.41 (t,6H), 3.15 and 3.17 (2s, together 3H), 4.22 (m,4H), 6.40 (s,1H), 7.29 (d,1H), 7.60 (s,1H), 7.81 (d,1H), 8.16 (s,1H).

Example 46

Diethyl 1-chloro-2-(2-chloro-4-fluoro-5-((tetrahydro-3-oxo-1H,3H-[1,3,4]-thiadiazolof3,4-a]pyridazin-1-ylidene)amino)phenyl)vinylphosphonate (No. IMh.861)

2.2 g (28 mmol) of pyridine and 1.4 g (7 mmol) of diphosgene were added to a solution of 3.3 g (7 mmol) of diethyl 1-chloro-2-(2-chloro-4-fluoro-5-((hexahydropyridazin-1-ylthiocarbonyl)-amino)phenyl)vinylphosphonate in 100 ml of dichloromethane, whereupon the mixture was stirred for 1 hour. The reaction mixture was subsequently washed with water, dried over magnesium sulfate and concentrated. The crude product was purified by means of silica gel chromatography (eluent: hexane/ethyl acetate=1:2). Yield: 1 g.

Precursor 46.1

Diethyl 1-chloro-2-(2-chloro-4-fluoro-5-isothiocyanatophenyl)-vinylphosphonate (No. XL.36)

1.1 g (9.7 mmol) of thiophosgene and a solution of 3 g (8.7 mmol) of diethyl 1-chloro-2-(5-amino-2-chloro-4-fluorophenyl)vinylphosphonate in 15 ml of dichloromethane were added to a solution of 1.6 g (19 mmol) of sodium hydrogen carbonate in 10 ml of water and 10 ml of dichloromethane, whereupon the mixture was stirred for 5 hours. The reaction mixture was subsequently washed with water, dried over magnesium sulfate and concentrated. Yield: 3 g;

$^1$H NMR (270 MHz; in CDCl$_3$): δ [ppm]=1.40 (t,6H), 4.22 (m,4H), 7.30 (d,1H), 7.74 (d,1H), 7.78 (d,1H).

Precursor 46.2

Diethyl 1-chloro-2-(2-chloro-4-fluoro-5[(hexahydropyridazin-1-yl-thiocarbonyl)amino]phenyl)vinylphosphonate (No. XXXIXa.36)

A solution of 3 g (8.7 mmol) of diethyl 1-chloro-2-(2-chloro-4-fluoro-5-isothiocyanatophenyl)vinylphosphonate in 20 ml of tetrahydrofuran was added to a solution of 0.8 g (9.3 mmol) of hexahydropyridazine in 20 ml of tetrahydrofuran, whereupon the mixture was stirred for 16 hours. The reaction mixture was then concentrated. The residue was treated with 50 ml of ethyl acetate. Finally, the organic phase was washed with water, dried over magnesium sulfate and concentrated. Yield: 3.3 g. The crude product was further reacted without further purification.

Example 47

Diethyl 1-chloro-2-(2-chloro-5-[(6,7-dihydro-6,6-dimethyl-3H,5H-pyrrolo-[2,1-c][1,2,4]thiadiazol-3-ylidene)amino]-4-fluorophenyl)vinylphosphonate (No. INh.861)

10.5 g (26.4 mmol) of a 10% strength by weight sodium hydroxide solution were added at 0–5° C. to a solution of 1.3 g (8.8 mmol) of 5-amino-3,4-dihydro-3,3-dimethyl-2H-pyrrole hydrochloride in 50 ml of dichloromethane. After the mixture had been stirred for one hour, it was treated with 2.5 g (6.5 mmol) of diethyl 1-chloro-2-(2-chloro-4-fluoro-5-isothiocyanatophenyl)vinylphosphonate. The reaction mixture was subsequently stirred for 3 hours and then cooled to (−20)° C. and treated with 1.2 g (6.9 mmol) of bromine.

In order to react all reactants as completely as possible, stirring was continued for 16 hours at approximately 20° C. Finally, the organic phase was separated off, dried over magnesium sulfate and concentrated. The crude product was purified by means of silica gel chromatography (eluent: hexane/ethyl acetate=1:1). Yield: 1.7 g.

Example 48

Diisopropyl 1-bromo-2-[2-chloro-5-(4-chloro-5-difluoromethoxy-1-methyl-1H-pyrazol-3-yl)-4-fluorophenyl]vinylphosphonate (No. IBi.863) and diisopropyl 2-[2-chloro-5-(4-chloro-5-difluoromethoxy-1-methyl-1H-pyrazol-3-yl)-4-fluorophenyl]-ethynylphosphonate (No. IBn.863)

Following the procedure described in Example 40 and using 3.4 g (8 mmol) of tetraisopropyl bromomethanediphosphonate, 0.2 g (8 mmol) of sodium hydride and 1.6 g (4 mmol) of 2-chloro-5-(4-chloro-5-difluoromethoxy-1-methyl-1H-pyrazol-3-yl)-4-fluorobenzaldehyde, a crude product is obtained whose silica gel chromatography first revealed 0.5 g of diisopropyl 1-bromo-2-[2-chloro-5-(4-chloro-5-difluoromethoxy-1-methyl-1H-pyrazol-3-yl)-4-fluorophenyl]vinylphosphonate followed by 0.4 g of diisopropyl 2-[2-chloro-5-(4-chloro-5-difluoromethoxy-1-methyl-1H-pyrazol-3-yl)-4-fluorophenyl]ethynylphosphonate.

Example 49

Diethyl 2-[2-chloro-5-(4-chloro-5-difluoromethoxy-1-methyl-1H-pyrazol-3-yl)-4-fluorophenyl]-1-cyanoethylphosphonate (No. IBd.861)

0.66 g (3.7 imol) of diethyl cyanomethanephosphonate was added to a suspension of 80 mg (3.4 mmol) of sodium hydride in 50 ml of tetrahydrofuran. After the mixture had been stirred for 10 minutes, it was treated with 1 g (2.5 mmol) of 2-chloro-5-(4-chloro-5-difluoromethoxy-1-methyl-1H-pyrazol-3-yl)-4-fluorobenzyl bromide. The mixture was subsequently stirred for 16 hours. The reaction mixture was subsequently concentrated. The residue was treated with 100 ml of water and 100 ml of ethyl acetate. After the phases had been mixed, the organic phase was separated off, dried over magnesium sulfate and concentrated. The crude product was purified by silica gel chromatography (eluent: hexane/ethyl acetate=4:1). Yield: 0.7 g.

Example 50

Methyl 3-[2-chloro-5-(4-chloro-5-difluoromethoxy-1-methyl-1H-pyrazol-3-yl)-4-fluorophenyl]-2-(diethylphosphoryl)propionate (No. IBf.861)

Following the procedure described in Example 49 and using 80 mg (3.4 mmol) of sodium hydride, 0.78 g (3.7 mmol) of methyl diethylphosphorylacetate and 1 g (2.5 mmol) of 2-chloro-5-(4-chloro-5-difluoromethoxy-1-methyl-1H-pyrazol-3-yl)-4-fluorobenzyl bromide, 0.7 g of the desired product of value were obtained.

In addition to the substances described above, further aromatic phosphonic acid derivatives of the formula I which were, or can be, prepared in a similar manner are listed in Tables 9–20 below:

TABLE 9

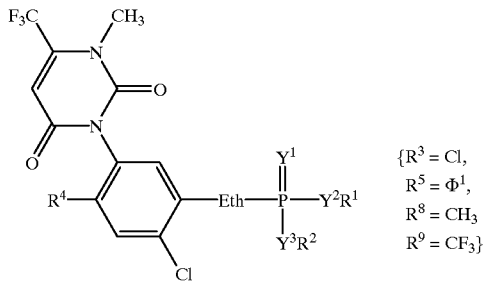

{R³ = Cl, R⁵ = Φ¹, R⁸ = CH₃, R⁹ = CF₃}

IA

| No. | R⁴ | -Eth- | —P(=Y¹)(Y²R¹)(Y³R²) | M.p./¹H NMR (δ in [ppm])/MS [m/z] |
|---|---|---|---|---|
| IAb.2 | H | —CH₂—CH(Cl)— | —P(=O)(OCH₃)₂ | 3.13 (dt, 1H), 3.56 (s, 3H), 3.66 (ddd, 1H), 3.83 (d, 3H), 3.90 (d, 3H), 4.28 (dt, 1H), 6.37 (s, 1H), 7.12 (dd, 1H), 7.21 (d, 1H), 7.53 (d, 1H) |
| IAg.3 | H | —CH=CH— | —P(=O)(OC₂H₅)₂ | 96–98° C. |
| IAg.432 | Cl | —CH=CH— | —P(=O)(OC₂H₅)₂ | 150–152° C. |
| IAg.861 | F | —CH=CH— | —P(=O)(OC₂H₅)₂ | 1.37 (t, 6H), 3.57 (s, 3H), 4.16 (quint, 4H), 6.20 (dd, 1H), 6.39 (s, 1H), 7.36 (d, 1H), 7.52 (d, 1H), 7.77 (dd, 1H) |
| IAh.3 | H | —CH=C(Cl)— | —P(=O)(OC₂H₅)₂ | 1.19 and 1.40 (2t, together 6H), 3.54 and 3.56 (2s, together 3H), 4.22 (m, 4H), 6.34 and 6.38 (2s, together 1H), 7.15 and 7.20 (2dd, together 1H), 7.48 and 7.81 (2d, together 1H), 7.50 and 7.90 (2d, together 1H), 7.52 and 7.59 (2d, together 1H) |
| IAh.432 | Cl | —CH=C(Cl)— | —P(=O)(OC₂H₅)₂ | 118–121° C. |
| IAh.859 | F | —CH=C(Cl)— | —P(=O)(OH)₂ | 3.42 (s, 3H), 6.60 (s, 1H), 7.59 (d, 1H), 7.86 (d, 1H), 8.03 (d, 1H) |
| IAh.860 | F | —CH=C(Cl)— | —P(=O)(OCH₃)₂ | 3.59 (s, 3H), 3.87 (d, 6H), 6.39 (s, 1H), 7.40 (d, 1H), 7.87 (d, 1H), 7.92 (d, 1H) |
| IAh.861 | F | —CH=C(Cl)— | —P(=O)(OC₂H₅)₂ | 518 [M]⁺, 483 [M−Cl]⁺ |
| IAh.862 | F | —CH=C(Cl)— | —P(=O)[O-(n-C₃H₇)]₂ | 0.99 (t, 6H), 1.76 (sext, 4H), 3.58 (s, 3H), 4.10 (quint, 4H), 6.38 (s, 1H), 7.39 (d, 1H), 7.86 (d, 1H), 7.93 (d, 1H) |
| IAh.863 | F | —CH=C(Cl)— | —P(=O)[OCH(CH₃)₂]₂ | 1.36 (d, 6H), 1.41 (d, 6H), 3.58 (s, 3H), 4.77 (m, 2H), 6.38 (s, 1H), 7.37 (d, 1H), 7.86 (d, 1H), 7.90 (d, 1H) |
| IAh.864 | F | —CH=C(Cl)— | —P(=O)[O-(n-C₄H₉)]₂ | 0.95 (t, 6H), 1.43 (sext, 4H), 1.72 (quint, 4H), 3.58 (s, 3H), 4.13 (m, 4H), 6.38 (s, 1H), 7.39 (d, 1H), 7.85 (d, 1H), 7.93 (d, 1H) |
| IAh.865 | F | —CH=C(Cl)— | —P(=O)[OCH₂—CH(CH₃)₂]₂ | 0.98 (d, 12H), 2.03 (m, 2H), 3.59 (s, 3H), 3.91 (m, 4H), 6.38 (s, 1H), 7.39 (d, 1H), 7.85 (d, 1H), 7.93 (d, 1H) |
| IAh.866 | F | —CH=C(Cl)— | —P(=O)[OCH(CH₃)—C₂H₅]₂ | 0.95 and 0.98 (2t, together 6H), 1.35 and 1.40 (2d, together 6H), 1.65–1.80 (m, 4H), 3.58 (s, 3H), 4.57 (m, 2H), 6.39 (s, 1H), 7.39 (d, 1H), 7.87 (d, 1H), 7.89 (d, 1H) |
| IAh.867 | F | —CH=C(Cl)— | —P(=O)(OCH₂—CF₃)₂ | 3.57 (s, 3H), 4.50 (m, 4H), 6.38 (s, 1H), 7.42 (d, 1H), 7.94 (d, 1H), 7.96 (d, 1H) |
| IAh.870 | F | —CH=C(Cl)— | —P(=O)(OCH₂—CH₂—OCH₃)₂ | 3.39 (s, 6H), 3.56 (s, 3H), 3.66 (t, 4H), 4.29 (m, 4H), 4.50 (m, 4H), 6.38 (s, 1H), 7.40 (d, 1H), 7.88 (d, 1H), 7.92 (d, 1H) |
| IAh.890 | F | —CH=C(Cl)— | —P(=O)(OCH₂—CH=CH₂)₂ | 3.57 (s, 3H), 4.65 (m, 4H), 5.27 (d, 2H), 5.42 (d, 2H), 5.97 (m, 2H), 6.39 (s, 1H), 7.39 (d, 1H), 7.87 (d, 1H), 7.92 (d, 1H) |
| IAh.894 | F | —CH=C(Cl)— | —P(=O)(OCH₂—C≡CH)₂ | 2.64 (t, 2H), 3.57 (s, 3H), 4.82 (dd, 4H), 6.38 (s, 1H), 7.40 (d, 1H), 7.92 (d, 1H), 7.95 (d, 1H) |
| IAh.896 | F | —CH=C(Cl)— | —P(=O)(OCH₂—CO—OCH₃)₂ | 3.58 (s, 3H), 3.81 (s, 6H), 4.74 (dd, 2H), 4.83 (dd, 2H), 6.38 (s, 1H), 7.39 (d, 1H), 7.84 (d, 1H), 7.86 (d, 1H) |
| IAh.914 | F | —CH=C(Cl)— | —P(=O)(O-phenyl)₂ | 3.58 (s, 3H), 6.38 (s, 1H), 7.15–7.40 (m, 11H), 7.87 (d, 1H), 7.99 (d, 1H) |
| IAh.1154 | F | —CH=C(Cl)— | —P(=O)(O—CH₂—CH₂—CH₂—O) | 2.08 (m, 1H), 2.30 (m, 1H), 3.57 (s, 3H), 4.58 (m, 4H), 6.38 (s, 1H), 7.39 (d, 1H), 7.82 (d, 1H), 7.87 (d, 1H) |
| IAh.1155 | F | —CH=C(Cl)— | —P(=O)(O—CH₂—C(CH₃)₂—CH₂—O) | 530 [M]⁺, 495 [M−Cl]⁺ |
| IAh.1256 | F | —CH=C(Cl)— | —P(=O)[N(CH₃)—CH₂—CH₂—CH₂—N(CH₃)] | 1.90 (m, 1H), 2.20 (m, 1H), 2.68 (d, 6H), 3.16 (m, 2H), 3.35 (m, 2H), 3.58 (s, 3H), 6.39 (s, 1H), 7.37 (d, 1H), 7.77 (d, 1H), 7.84 (d, 1H) |
| IAi.863 | F | —CH=C(Br)— | —P(=O)[OCH(CH₃)₂]₂ | 1.21 (d, 6H), 1.25 (d, 6H), 3.55 (s, 3H), 4.78 (okt, 2H), 6.34 (s, 1H), 7.31 (d, 1H), 7.62 (d, 1H), 7.70 (d, 1H) |
| IAj.861 | F | —CH=C(CN)— | —P(=O)(OC₂H₅)₂ | 1.42 (t, 6H), 3.57 (s, 3H), 4.25 (m, 4H), 6.38 (s, 1H), 7.44 (d, 1H), 8.26 (d, 1H), 8.35 (d, 1H) |
| IAk.861 | F | —CH=C(CH₃)— | —P(=O)(OC₂H₅)₂ | 1.15 and 1.28 (2dt, together 6H), 1.95 and 2.15 (2dd, together 3H), 3.52 and 3.56 (2s, together 3H), 3.90 and 4.10 (2m, together 4H), 6.31 and 6.36 (2s, together 1H), 7.02 and 7.43 (2dd, together 1H), 7.24, 7.30, 7.38 and 7.62 (4d, together 2H) |

TABLE 10

{R³ = Cl, R⁵ = Φ², R¹⁰ = CH₃, R¹¹ = OCHF₂, R¹² = Cl}

IB

| No. | R⁴ | -Eth- | —P(=Y¹)(Y²R¹)(Y³R²) | M.p./¹H NMR (δ in [ppm])/MS [m/z] |
|---|---|---|---|---|
| IBa.861 | F | —CH₂—CH₂— | —P(=O)(OC₂H₅)₂ | 474 [M]⁺, 439 [M−Cl]⁺ |
| IBb.431 | Cl | —CH₂—CH(Cl)— | —P(=O)(OCH₃)₂ | 3.11 (dt, 1H), 3.62 (ddd, 1H), 3.85 (s, 3H), 3.87 (d, 3H), 3.92 (d, 3H), 4.27 (dt, 1H), 6.72 (t, 1H), 7.39 (s, 1H), 7.53 (s, 1H) |
| IBb.860 | F | —CH₂—CH(Cl)— | —P(=O)(OCH₃)₂ | 3.12 (ddd, 1H), 3.64 (ddd, 1H), 3.85 (s, 3H), 3.87 (d, 3H), 3.91 (d, 3H), 4.25 (dt, 1H), 6.71 (t, 1H), 7.26 (d, 1H), 7.51 (d, 1H) |
| IBb.861 | F | —CH₂—CH(Cl)— | —P(=O)(OC₂H₅)₂ | 1.39 (dt, 6H), 3.11 (ddd, 1H), 3.65 (ddd, 1H), 3.84 (s, 3H), 4.20–4.30 (m, 5H), 6.71 (t, 1H), 7.25 (d, 1H), 7.52 (d, 1H) |
| IBc.860 | F | —CH₂—CH(Br)— | —P(=O)(OCH₃)₂ | 3.18 (ddd, 1H), 3.72 (ddd, 1H), 3.84 (s, 3H), 3.87 (d, 3H), 3.92 (d, 3H), 4.21 (dt, 1H), 6.71 (t, 1H), 7.25 (d, 1H), 7.50 (d, 1H) |
| IBc.861 | F | —CH₂—CH(Br)— | —P(=O)(OC₂H₅)₂ | 1.38 (dt, 6H), 3.19 (ddd, 1H), 3.74 (ddd, 1H), 3.85 (s, 3H), 4.10–4.30 (m, 5H), 6.72 (t, 1H), 7.25 (d, 1H), 7.51 (d, 1H) |
| IBd.861 | F | —CH₂—CH(CN)— | —P(=O)(OC₂H₅)₂ | 1.42 (dt, 6H), 3.15 (ddd, 1H), 3.35 (ddd, 1H), 3.46 (ddd, 1H), 3.84 (s, 3H), 4.27 (m, 4H), 6.71 (t, 1H), 7.28 (d, 1H), 7.59 (d, 1H) |
| IBf.861 | F | —CH₂—CH(COOCH₃)— | —P(=O)(OC₂H₅)₂ | 1.36 (t, 6H), 3.25–3.50 (m, 3H), 3.67 (s, 3H), 3.83 (s, 3H), 4.19 (m, 4H), 6.70 (t, 1H), 7.22 (d, 1H), 7.46 (d, 1H) |
| IBg.861 | F | —CH=CH— | —P(=O)(OC₂H₅)₂ | 472 [M]⁺, 437 [M−Cl]⁺ |
| IBh.859 | F | —CH=C(Cl)— | —P(=O)(OH)₂ | resin |
| IBh.860 | F | —CH=C(Cl)— | —P(=O)(OCH₃)₂ | 3.85 (s, 6H), 3.91 (s, 3H), 6.72 (t, 1H), 7.34 (d, 1H), 7.89 (d, 1H), 8.17 (d, 1H) |
| IBh.861 | F | —CH=C(Cl)— | —P(=O)(OC₂H₅)₂ | 1.41 (t, 6H), 3.86 (s, 3H), 4.24 (m, 4H), 6.72 (t, 1H), 7.31 (d, 1H), 7.88 (d, 1H), 8.15 (d, 1H) |
| IBh.862 | F | —CH=C(Cl)— | —P(=O)[O-(n-C₃H₇)]₂ | 1.00 (t, 6H), 1.78 (sext, 4H), 3.85 (s, 3H), 4.11 (quint, 4H), 6.71 (t, 1H), 7.31 (d, 1H), 7.88 (d, 1H), 8.15 (d, 1H) |
| IBh.863 | F | —CH=C(Cl)— | —P(=O)[OCH(CH₃)₂]₂ | 1.39 (d, 6H), 1.42 (d, 6H), 3.85 (s, 3H), 4.79 (okt, 2H), 6.72 (t, 1H), 7.31 (d, 1H), 7.87 (d, 1H), 8.13 (d, 1H) |
| IBh.864 | F | —CH=C(Cl)— | —P(=O)[O-(n-C₄H₉)]₂ | 0.95 (t, 6H), 1.46 (sext, 4H), 1.73 (quint, 4H), 3.85 (s, 3H), 4.16 (quint, 4H), 6.72 (t, 1H), 7.32 (d, 1H), 7.88 (d, 1H), 8.15 (d, 1H) |
| IBh.865 | F | —CH=C(Cl)— | —P(=O)[OCH₂—CH(CH₃)₂]₂ | 0.99 (d, 12H), 2.03 (m, 2H), 3.86 (s, 3H), 3.91 (m, 4H), 6.72 (t, 1H), 7.32 (d, 1H), 7.88 (d, 1H), 8.15 (d, 1H) |
| IBh.866 | F | —CH=C(Cl)— | —P(=O)[OCH(CH₃)—C₂H₅]₂ | 0.97 and 1.00 (2t, together 6H), 1.36 and 1.41 (2d, together 6H), 1.70 (m, 4H), 3.85 (s, 3H), 4.58 (m, 2H), 6.71 (t, 1H), 7.30 (d, 1H), 7.87 (d, 1H), 8.12 (d, 1H) |
| IBh.914 | F | —CH=C(Cl)— | —P(=O)(O-phenyl)₂ | 3.84 (s, 3H), 6.71 (t, 1H), 7.10–7.40 (m, 11H), 8.03 (d, 1H), 8.14 (d, 1H) |
| IBh.1154 | F | —CH=C(Cl)— | —P(=O)(O—CH₂—CH₂—CH₂—O) | 2.10 (m, 1H), 2.30 (m, 1H), 3.86 (s, 3H), 4.60 (m, 4H), 6.75 (t, 1H), 7.31 (d, 1H), 7.84 (d, 1H), 8.13 (d, 1H) |
| IBh.1256 | F | —CH=C(Cl)— | —P(=O)[N(CH₃)—CH₂—CH₂—CH₂—N(CH₃)] | 1.90 (m, 1H), 2.20 (m, 1H), 2.70 (d, 6H), 3.15 (m, 2H), 3.40 (m, 2H), 3.86 (s, 3H), 6.72 (t, 1H), 7.31 (d, 1H), 7.79 (d, 1H), 8.04 (d, 1H) |
| IBh.1271 | F | —CH=C(Cl)— | —P(=O)(SC₂H₅)₂ | 1.44 (t, 6H), 3.02 (dq, 4H), 3.86 (s, 3H), 6.73 (t, 1H), 7.33 (d, 1H), 7.99 (d, 1H), 8.17 (d, 1H) |
| IBi.863 | F | —CH=C(Br)— | —P(=O)[OCH(CH₃)₂]₂ | 1.23 (d, 12H), 3.83 (s, 3H), 4.66 (okt, 2H), 6.71 (t, 1H), 7.23 (d, 1H), 7.74 (d, 1H), 7.77 (d, 1H) |
| IBn.863 | F | —C≡C— | —P(=O)[OCH(CH₃)₂]₂ | 1.43 (m, 12H), 3.86 (s, 3H), 4.84 (m, 2H), 6.72 (t, 1H), 7.31 (d, 1H), 7.82 (d, 1H) |

TABLE 11

{R³ = Cl, R⁵ = Φ², R¹⁰ = CH₃, R¹¹ = CF₃, R¹² = Cl}

Ic

| No. | R⁴ | -Eth- | —P(=Y¹)(Y²R¹)(Y³R²) | M.p./¹H NMR (δ in [ppm])/MS [m/z] |
|---|---|---|---|---|
| ICa.863 | F | —CH₂—CH₂— | —P(=O)(OCH(CH₃)₂)₂ | 504 [M]⁺, 485 [M−F]⁺ 469 [M−Cl]⁺ |
| ICg.861 | F | —CH=CH— | —P(=O)(OC₂H₅)₂ | 1.38 (t, 6H), 4.09 (s, 3H), 4.16 (quint, 4H), 6.29 (t, 1H), 7.29 (d, 1H), 7.78 (d, 1H), 7.83 (dd, 1H) |
| ICh.859 | F | —CH=C(Cl)— | —P(=O)(OH)₂ | resin |
| ICh.860 | F | —CH=C(Cl)— | —P(=O)(OCH₃)₂ | 89–93° C. |
| ICh.861 | F | —CH=C(Cl)— | —P(=O)(OC₂H₅)₂ | 62–65° C. |
| ICh.862 | F | —CH=C(Cl)— | —P(=O)[O-(n-C₃H₇)]₂ | 1.01 (t, 6H), 1.78 (sext, 4H), 4.09 (s, 3H), 4.14 (m, 4H), 7.34 (d, 1H), 7.87 (d, 1H), 8.13 (d, 1H) |
| ICh.863 | F | —CH=C(Cl)— | —P(=O)[OCH(CH₃)₂]₂ | 1.39 (d, 6H), 1.43 (d, 6H), 4.08 (s, 3H), 4.79 (okt, 2H), 7.34 (d, 1H), 7.88 (d, 1H), 8.10 (d, 1H) |
| ICh.864 | F | —CH=C(Cl)— | —P(=O)[O-(n-C₄H₉)]₂ | 0.94 (t, 6H), 1.46 (sext, 4H), 1.73 (quint, 4H), 4.09 (s, 3H), 4.15 (m, 4H), 7.33 (d, 1H), 7.87 (d, 1H), 8.12 (d, 1H) |
| ICh.865 | F | —CH=C(Cl)— | —P(=O)[OCH²—CH(CH₃)₂]₂ | 0.99 (d, 12H), 2.04 (m, 2H), 3.91 (m, 4H), 4.08 (s, 3H), 7.33 (d, 1H), 7.87 (d, 1H), 8.13 (d, 1H) |
| ICh.866 | F | —CH=C(Cl)— | —P(=O)[OCH(CH₃)—C₂H₅]₂ | 0.97 and 1.00 (2t, together 6H), 1.37 and 1.42 (2d, together 6H), 1.70 (m, 4H), 4.09 (s, 3H), 4.58 (m, 2H), 7.33 (d, 1H), 7.89 (d, 1H), 8.09 (d, 1H) |
| ICh.914 | F | —CH=C(Cl)— | —P(=O)(O-phenyl)₂ | 4.08 (s, 3H), 7.10–7.40 (m, 11H), 8.04 (d, 1H), 8.10 (d, 1H) |
| ICh.941 | F | —CH=C(Cl)— | —P(=O)(OH)(OCH₂—CH₂—OH) | 478 [M−H₂O]⁺, 433 [M−H₂O—Cl]⁺ |
| ICh.1154 | F | —CH=C(Cl)— | —P(=O)(O—CH₂—CH₂—CH₂—O) | 112–116° C. |
| ICh.1256 | F | —CH=C(Cl)— | —P(=O)[N(CH₃)—CH₂—CH₂—CH₂—N(CH₃)] | 1.90 (m, 1H), 2.20 (m, 1H), 2.70 (d, 6H), 3.15 (m, 2H), 3.38 (m, 2H), 4.09 (s, 3H), 7.31 (d, 1H), 7.80 (d, 1H), 8.01 (d, 1H) |
| ICh.1271 | F | —CH=C(Cl)— | —P(=O)(SC₂H₅)₂ | 1.44 (t, 6H), 3.03 (dq, 4H), 4.09 (s, 3H), 7.36 (d, 1H), 7.99 (d, 1H), 8.13 (d, 1H) |

TABLE 12

{R³ = Cl, R⁵ = Φ², R¹⁰ = CH₃, R¹¹ = R¹² = CF₃}

ID

| No. | R⁴ | -Eth- | —P(=Y¹)(Y²R¹)(Y³R²) | M.p./¹H NMR (δ in [ppm])/MS [m/z] |
|---|---|---|---|---|
| IDb.860 | F | —CH₂—CH(Cl)— | —P(=O)(OCH₃)₂ | 98–101° C. |

TABLE 13

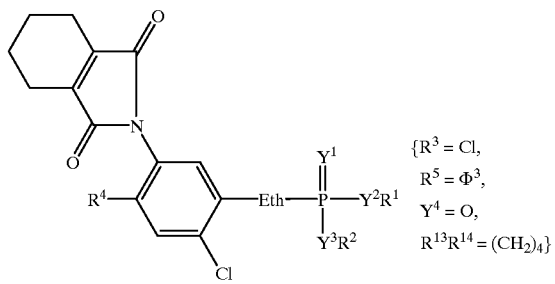

IE

| No. | $R^4$ | -Eth- | —P(=$Y^1$)($Y^2R^1$)($Y^3R^2$) | M.p./$^1$H NMR (δ in [ppm])/MS [m/z] |
|---|---|---|---|---|
| IEb.2 | H | —CH$_2$—CH(Cl)— | —P(=O)(OCH$_3$)$_2$ | 1.84 (s, 4H), 2.44 (s, 4H), 3.11 (dt, 1H), 3.65 (ddd, 1H), 3.88 (d, 3H), 3.91 (d, 3H), 4.37 (dt, 1H), 7.25 (dd, 1H), 7.35 (d, 1H), 7.46 (d, 1H) |
| IEg.3 | H | —CH=CH— | —P(=O)(OC$_2$H$_5$)$_2$ | 1.37 (t, 6H), 1.84 (s, 4H), 2.46 (s, 4H), 4.15 (quint, 4H), 6.19 (t, 1H), 7.35 (dd, 1H), 7.48 (d, 1H), 7.64 (d, 1H), 7.85 (dd, 1H) |
| IEg.56 | H | —CH=CH— | —P(=O)(O-phenyl)$_2$ | 124–126° C. |
| IEh.3 | H | —CH=C(Cl)— | —P(=O)(OC$_2$H$_5$)$_2$ | 114–118° C. |
| IEh.432 | Cl | —CH=C(Cl)— | —P(=O)(OC$_2$H$_5$)$_2$ | 1.40 (t, 6H), 1.86 (s, 4H), 2.47 (s, 4H), 4.20 (m, 4H), 7.64 (d, 1H), 7.85 (s, 1H), 7.86 (s, 1H) |
| IEb.860 | F | —CH$_2$—CH(Cl)— | —P(=O)(OCH$_3$)$_2$ | 1.86 (s, 4H), 2.47 (s, 4H), 3.12 (dt, 1H), 3.62 (ddd, 1H), 3.85 (d, 3H), 3.90 (d, 3H), 4.20 (dt, 1H), 7.25 (d, 1H), 7.32 (d, 1H) |
| IEb.861 | F | —CH$_2$—CH(Cl)— | —P(=O)(OC$_2$H$_5$)$_2$ | 1.36 (m, 6H), 1.83 (s, 4H), 2.45 (s, 4H), 3.07 (dt, 1H), 3.64 (ddd, 1H), 4.14 (dt, 1H), 4.25 (quint, 4H), 7.24 (d, 1H), 7.28 (d, 1H) |
| IEc.860 | F | —CH$_2$—CH(Br)— | —P(=O)(OCH$_3$)$_2$ | 1.82 (s, 4H), 2.40 (s, 4H), 3.17 (dt, 1H), 3.70 (ddd, 1H), 3.80–3.90 (m, 6H), 4.17 (dt, 1H), 7.21 (d, 1H), 7.28 (d, 1H) |
| IEg.861 | F | —CH=CH— | —P(=O)(OC$_2$H$_5$)$_2$ | 1.36 (t, 6H), 1.85 (s, 4H), 2.45 (s, 4H), 4.15 (quint, 4H), 6.21 (t, 1H), 7.32 (d, 1H), 7.49 (d, 1H), 7.78 (dd, 1H) |
| IEh.861 | F | —CH=C(Cl)— | —P(=O)(OC$_2$H$_5$)$_2$ | 134–136° C. |

TABLE 14

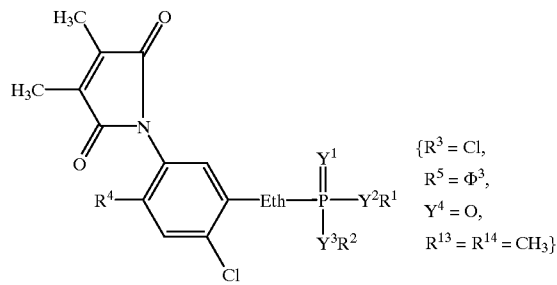

IF

| No. | $R^4$ | -Eth- | —P(=$Y^1$)($Y^2R^1$)($Y^3R^2$) | M.p./$^1$H NMR (δ in [ppm])/MS [m/z] |
|---|---|---|---|---|
| IFg.3 | H | —CH=CH— | —P(=O)(OC$_2$H$_5$)$_2$ | 1.36 (t, 6H), 2.07 (s, 6H), 4.15 (quint, 4H), 6.29 (t, 1H), 7.36 (dd, 1H), 7.49 (d, 1H), 7.64 (d, 1H), 7.84 (dd, 1H) |
| IFh.3 | H | —CH=C(Cl)— | —P(=O)(OC$_2$H$_5$)$_2$ | 124–126° C. |

TABLE 15

{R³ = Cl,
R⁵ = Φ⁴,
R¹⁵R¹⁶ = (CH₂)₄,
R¹⁷ = Cl}

IG

| No. | R⁴ | -Eth- | —P(=Y¹)(Y²R¹)(Y³R²) | M.p./¹H NMR (δ in [ppm])/MS [m/z] |
|---|---|---|---|---|
| IGb.2 | H | —CH₂—CH(Cl)— | —P(=O)(OCH₃)₂ | 1.85 (m, 4H), 2.52 (t, 2H), 2.72 (t, 2H), 3.15 (ddd, 1H), 3.70 (ddd, 1H), 3.92 (d, 3H), 3.95 (d, 3H), 4.30 (dt, 1H), 7.45 (s, 2H), 7.55 (s, 1H) |
| IGb.3 | H | —CH₂—CH(Cl)— | —P(=O)(OC₂H₅)₂ | 1.37 (m, 6H), 1.82 (m, 4H), 2.52 (t, 2H), 2.72 (t, 2H), 3.13 (ddd, 1H), 3.70 (ddd, 1H), 4.20–4.35 (m, 5H), 7.47 (s, 2H), 7.54 (s, 1H) |
| IGb.860 | F | —CH₂—CH(Cl)— | —P(=O)(OCH₃)₂ | 1.82 (m, 4H), 2.51 (t, 2H), 2.71 (t, 2H), 3.11 (ddd, 1H), 3.63 (ddd, 1H), 3.88 (d, 3H), 3.92 (d, 3H), 4.25 (dt, 1H), 7.32 (d, 1H), 7.44 (d, 1H) |

TABLE 16

{R³ = Cl,
R⁵ = Φ⁵,
R¹⁸ = Cl,
R¹⁹ = CHF₂,
R²⁰ = CH₃}

IH

| No. | R⁴ | -Eth- | —P(=Y¹)(Y²R¹)(Y³R²) | M.p./¹H NMR (δ in [ppm])/MS [m/z] |
|---|---|---|---|---|
| IHb.2 | H | —CH₂—CH(Cl)— | —P(=O)(OCH₃)₂ | 2.62 (s, 3H), 3.15 (ddd, 1H), 3.70 (ddd, 1H), 3.88 (d, 3H), 3.94 (d, 3H), 4.34 (dt, 1H), 7.15 (t, 1H), 7.44 (d, 1H), 7.79 (dd, 1H), 7.87 (d, 1H) |

TABLE 17

{R³ = Cl,
R⁵ = Φ⁷,
Y⁷ = O,
R²³R²⁴ = (CH₂)₄}

IK

| No. | R⁴ | -Eth- | —P(=Y¹)(Y²R¹)(Y³R²) | M.p./¹H NMR (δ in [ppm])/MS [m/z] |
|---|---|---|---|---|
| IKh.861 | F | —CH=C(Cl)— | —P(=O)(OC₂H₅)₂ | 1.41 (t, 6H), 1.96 (m, 4H), 2.79 (t, 2H), 3.72 (t, 2H), 4.23 (q, 4H), 7.36 (d, 1H), 7.84 (d, 1H), 8.15 (d, 1H) |

TABLE 18

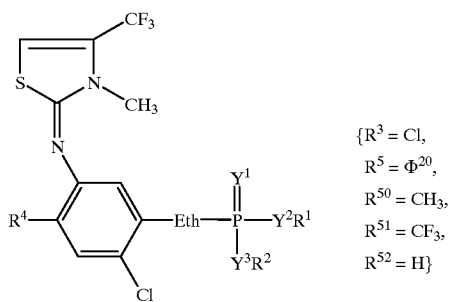

{$R^3$ = Cl, $R^5$ = $\Phi^{20}$, $R^{50}$ = $CH_3$, $R^{51}$ = $CF_3$, $R^{52}$ = H}

IL

| No. | $R^4$ | -Eth- | —P(=$Y^1$)($Y^2R^1$)($Y^3R^2$) | M.p./$^1$H NMR ($\delta$ in [ppm])/MS [m/z] |
|---|---|---|---|---|
| ILh.861 | F | —CH=C(Cl)— | —P(=O)(O$C_2H_5$)$_2$ | 1.40 (t, 6H), 3.57 (s, 3H), 4.22 (m, 4H), 6.58 (s, 1H), 7.24 (d, 1H), 7.69 (d, 1H), 7.86 (d, 1H) |

TABLE 19

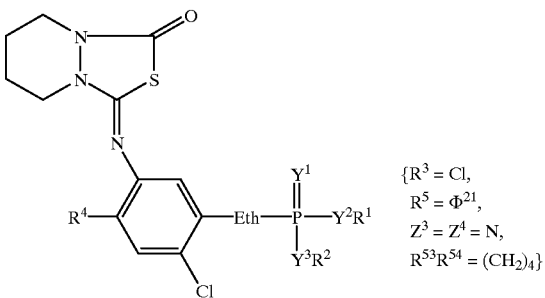

{$R^3$ = Cl, $R^5$ = $\Phi^{21}$, $Z^3$ = $Z^4$ = N, $R^{53}R^{54}$ = (CH$_2$)$_4$}

IM

| No. | $R^4$ | -Eth- | —P(=$Y^1$)($Y^2R^1$)($Y^3R^2$) | M.p./$^1$H NMR ($\delta$ in [ppm])/MS [m/z] |
|---|---|---|---|---|
| IMh.861 | F | —CH=C(Cl)— | —P(=O)(O$C_2H_5$)$_2$ | 1.41 (t, 6H), 1.80–2.00 (m, 4H), 3.75 (t, 2H), 3.84 (t, 2H), 4.22 (m, 4H), 7.24 (d, 1H), 7.57 (d, 1H), 7.84 (d, 1H) |

TABLE 20

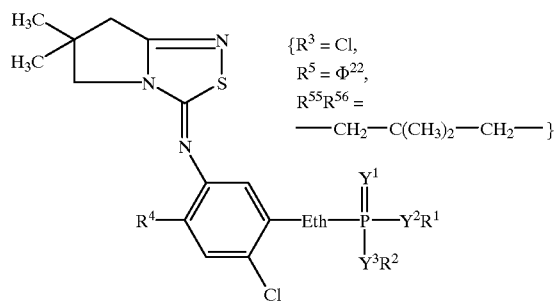

{$R^3$ = Cl, $R^5$ = $\Phi^{22}$, $R^{55}R^{56}$ = —CH$_2$—C(CH$_3$)$_2$—CH$_2$—}

IN

| No. | $R^4$ | -Eth- | —P(=$Y^1$)($Y^2R^1$)($Y^3R^2$) | M.p./$^1$H NMR ($\delta$ in [ppm])/MS [m/z] |
|---|---|---|---|---|
| INh.861 | F | —CH=C(Cl)— | —P(=O)(O$C_2H_5$)$_2$ | 117–120° C. |

Use Examples
(herbicidal activity)

The herbicidal activity of the substituted aromatic phosphonic acid derivatives I was demonstrated by the greenhouse experiments which follow:

The culture containers used were plastic flower pots containing loamy sand with approximately 3.0% of humus as the substrate. The seeds of the test plants were sown separately for each species.

For pre-emergence treatment, the active ingredients, which had been suspended or emulsified in water, were applied by means of finely distributing nozzles directly after sowing. The containers were irrigated gently to promote germination and growth and subsequently covered with translucent plastic hoods until the plants had rooted. This cover causes uniform germination of the test plants unless this was adversely affected by the active ingredients.

For post-emergence treatment, the test plants were first grown to a plant height of 3 to 15 cm, depending on the plant habit, and only then treated with the active ingredients which had been suspended or emulsified in water. The test plants were either sown directly and grown in the same containers, or they were first grown separately as seedlings and transplanted into the test containers a few days prior to treatment. The rate of application for the post-emergence treatment was 15.6, 7.8, 1.9 or 0.9 g of a.s. (active substance)/ha.

Depending on the species, the plants were kept at from 10 to 25° C. or from 20 to 35° C. The test period extended over 2 to 4 weeks. During this time, the plants were tended, and their response to the individual treatments was evaluated.

Evaluation was effected using a scale of from 0 to 100. 100 means no emergence of the plants or complete destruction of at least the aerial parts, and 0 means no damage or normal course of growth.

The plants used in the greenhouse experiments belonged to the following species:

| Scientific name | Common name |
| --- | --- |
| Oryza sativa | rice |
| Abutilon theophrasti | velvet leaf |
| Amaranthus retroflexus | redroot pigweed |
| Chenopodium album | lambsquarters (goosefoot) |
| Galium aparine | catchweed bedstraw |
| Ipomoea subspecies | morning glory |
| Polygonum persicaria | lady's thumb |
| Solanum nigrum | black nightshade |
| Veronica subspecies | speedwell |

At rates of application of 1.9 and 0.9 g of a.s./ha, compound No. IBg.861 applied post-emergence showed a selective herbicidal activity against *Abutilon theophrasti*, *Amaranthus retroflexus* and *Solanum nigrum* in the crop rice, which was only damaged to a minor extent.

Compounds No. IBh.861 and No. IAh.861, applied post-emergence at the same rates of application, showed a very good activity against *Abutilon theophrasti, Amaranthus retroflexus* and *Solanum nigrum.*

At rates of application of 15.6 and 7.8 g of a.S./ha, compounds No. IBg.861, IBh.861 and IAh.861 control *Amaranthus retroflexus, Chenopodium album, Galium aparine* and *Solanum nigrum* better than the comparison compound A, which is known from ASC Symp. Ser. 584 (1995), 90.

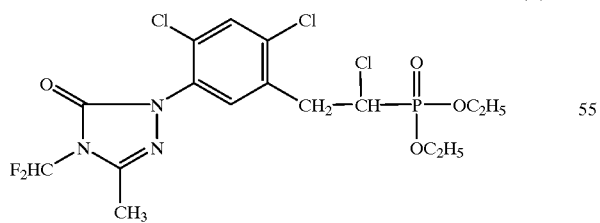

(A)

Use Examples
(desiccant/defoliant activity)

The test plants used were young cotton plants with 4 leaves (without cotyledons) which had been grown under greenhouse conditions (relative humidity 50 to 70%; day/night temperature 27/20° C.).

The young cotton plants were subjected to foliar treatment to drip point with aqueous preparations of the active ingredients (with an addition of 0.15% by weight of the fatty alcohol alkoxylate Plurafac LF® 700[1], based on the spray mixture). The amount of water applied was 1000 l/ha (converted). After 13 days, the number of shed leaves and the degree of defoliation in % were determined.

[1] a low-foam, non-ionic surfactant from BASF AG

No leaves were shed in the untreated control plants.

We claim:

1. A phosphonic acid compound I

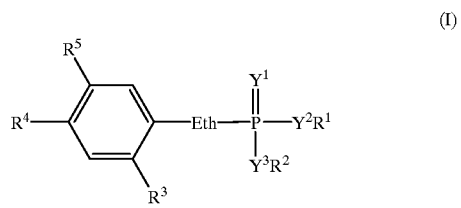

(I)

where the variables have the following meanings:

Eth is 1,2-ethynediyl or an ethane- or ethene-1,2-diyl chain, each of which can be unsubstituted or have attached to it one or two of the following substituents: halogen, cyano, carboxyl, $C_1$–$C_4$-alkyl, $C_1$–$C_4$-haloalkyl, $C_1$–$C_4$-alkoxy, $C_1$–$C_4$-haloalkoxy, ($C_1$–$C_4$-alkoxy)carbonyl and/or di($C_1$–$C_4$-alkyl)amino, it being possible for the ethane-1,2-diyl chain, if desired, additionally to have attached to it a hydroxyl, amino or CL-$C_4$-alkylamino group;

$Y^1$ is oxygen or sulfur;

$Y^2$ is oxygen, sulfur or —N($R^6$)—;

$Y^3$ isg oxygen, sulfur or —N($R^7$)—;

$R^1$, $R^2$, $R^6$ and $R^7$ independently of one another are
hydrogen, $C_1$–$C_6$-alkyl, $C_1$–$C_6$-haloalkyl, hydroxy-$C_1$–$C_4$-alkyl, cyano-$C_1$–$C_4$-alkyl, $C_1$–$C_4$-alkoxy-$C_1$–$C_4$-alkyl, $C_1$–$C_4$-haloalkoxy-$C_1$–$C_4$-alkyl, $C_3$–$C_4$-alkenyloxy-$C_1$–$C_4$-alkyl, $C_3$–$C_4$-alkynyloxy-$C_1$–$C_4$-alkyl, $C_3$–$C_8$-cycloalkoxy-$C_1$–$C_4$-alkyl, amino-$C_1$–$C_4$-alkyl, $C_1$–$C_4$-alkylamino-$C_1$–$C_4$-alkyl, di($C_1$–$C_4$-alkyl)amino-$C_1$–$C_4$-alkyl, $C_1$–$C_4$-alkylthio-$C_1$–$C_4$-alkyl, $C_1$–$C_4$-haloalkylthio-$C_1$–$C_4$-alkyl, $C_1$–$C_4$-alkenylthio-$C_1$–$C_4$-alkyl, $C_3$–$C_4$-alkynylthio-$C_1$–$C_4$-alkyl, $C_1$–$C_4$-alkylsulfinyl-$C_1$–$C_4$-alkyl, $C_1$–$C_4$-haloalkylsulfinyl-$C_1$–$C_4$-alkyl, $C_3$–$C_4$-alkenylsulfinyl-$C_1$–$C_4$-alkyl, $C_3$–$C_4$-alkynylsulfinyl-$C_1$–$C_4$-alkyl, $C_1$–$C_4$-alkylsulfonyl-$C_1$–$C_4$-alkyl, $C_1$–$C_4$-haloalkylsulfonyl-$C_1$–$C_4$-alkyl, $C_3$–$C_4$-alkenylsulfonyl-$C_1$–$C_4$-alkyl, $C_3$–$C_4$-alkynylsulfonyl-$C_1$–$C_4$-alkyl, $C_3$–$C_6$-alkenyl, $C_1$–$C_6$-haloalkenyl, cyano-$C_3$–$C_6$-alkenyl, $C_3$–$C_6$-alkynyl, $C_1$–$C_6$-haloalkynyl, cyano-$C_3$–$C_6$-alkynyl, hydroxycarbonyl-$C_1$–$C_4$-alkyl, ($C_1$–$C_4$-alkoxy) carbonyl-$C_1$–$C_4$-alkyl, ($C_1$–$C_4$-alkylthio) carbonyl-$C_1$–$C_4$-alkyl, aminocarbonyl-$C_1$–$C_4$-alkyl, ($C_1$–$C_4$-alkyl) aminocarbonyl-$C_1$–$C_4$-alkyl, di($C_1$–$C_4$-alkyl) aminocarbonyl-$C_1$–$C_4$-alkyl, $C_3$–$C_8$-cycloalkyl, $C_3$–$C_8$-cycloalkyl-$C_1$–$C_4$-alkyl, phenyl, phenyl-$C_1$–$C_4$-alkyl or and it being possible for all cycloalky and phenyl rings to be unsubstituted or to have attached to them one to four substituents, in each case selected from the group consisting of halogen, cyano, nitro, amino, hydroxyl, carboxyl, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfonyl, $C_1$–$C_4$-haloalkylsulfonyl, ($C_1$–$C_4$-alkyl)carbonyl, ($C_1$–$C_4$-haloalkyl) carbonyl, ($C_1$–$C_4$-alkoxy)carbonyl, ($C_1$–$C_4$-alkyl)carbonyloxy, ($C_1$–$C_4$-haloalkyl) carbonyloxy and di($C_1$–$C_4$-alkyl)amino, or $R^1$ and $R^2$ or $R^1$ and $R^6$ and/or $R^2$ and $R^7$ in each case together form a 1,2-ethanediyl, 1,3-propylene, tetramethylene, pentamethylene or ethyleneoxyethylene chain which, if desired, can be substituted by one to four $C_1$–$C_4$-alkyl and/or one or two ($C_1$–$C_4$-alkoxy) carbonyl groups, or $R^1$ and $R^2$ together are 1,2-phenylene which can be unsubstituted or have attached to it one to three substituents, in each case selected from the group consisting of cyano, nitro, halogen, $C_1$–$C_4$-alkyl, $C_1$–$C_4$-haloalkyl, $C_1$–$C_4$-alkoxy and $C_1$–$C_4$-haloalkoxy;

$R^3$ is cyano, halogen, $C_1$–$C_4$-alkyl, $C_1$–$C_4$-haloalkyl, $C_1$–$C_4$-alkoxy or $C_1$–$C_4$-haloalkoxy;

$R^4$ is hydrogen or halogen;

$R^5$ is one of the following heterocycles $\Phi^1$ to $\Phi^5$, $\Phi^7$ and $\Phi^{20}$ to $\Phi^{22}$:

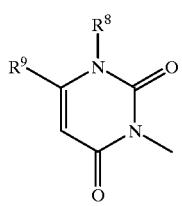

$\Phi^1$

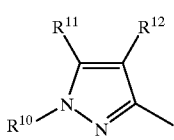

$\Phi^2$

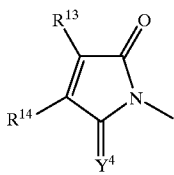

$\Phi^3$

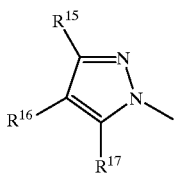

$\Phi^4$

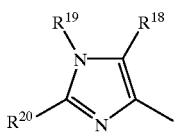

$\Phi^5$

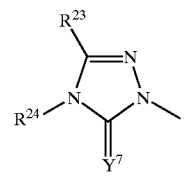

$\Phi^7$

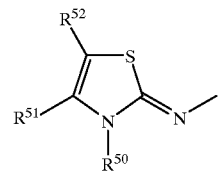

$\Phi^{20}$

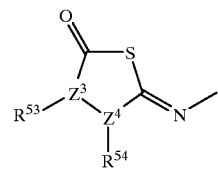

$\Phi^{21}$

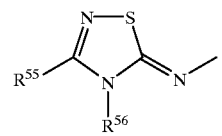

$\Phi^{22}$ where $R^8$ is hydrogen, amino, $C_1$–$C_4$-alkyl or $C_1$–$C_4$-haloalkyl;

$R^9$ is cyano, $C_1$–$C_4$-alkyl, $C_1$–$C_4$-haloalkyl, $C_1$–$C_4$-alkylsulfonyl or $C_1$–$C_4$-haloalkylsulfonyl;

$R^{10}$ is $C_1$–$C_4$-alkyl or $C_1$–$C_4$-haloalkyl;

$R^{11}$ is cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfinyl, $C_1$–$C_4$-haloalkylsulfinyl, $C_1$–$C_4$-alkylsulfonyl or $C_1$–$C_4$-haloalkylsulfonyl, $R^{12}$ is hydrogen, cyano, halogen, $C_1$–$C_4$-alkyl or $C_1$–$C_4$-haloalkyl;

$Y^4$ is oxygen, sulfur or methylene;

$R^{13}$, $R^{14}$ independently of one another are hydrogen or $C_1$–$C_4$-alkyl, or $R^{13}$ and $R^{14}$ together form a tetramethylene bridge;

$R^{15}$ and $R^{16}$ independently of one another are hydrogen, halogen, $C_1$–$C_4$-alkyl or $C_1$–$C_4$-haloalkyl, or $R^{15}$ and $R^{16}$ together form a tetramethylene bridge;

$R^{17}$ is halogen or $C_1$–$C_4$-alkyl;

$R^{18}$ is halogen;

$R^{19}$, $R^{20}$, $R^{55}$ and $R^{56}$ independently of one another are hydrogen, $C_1$–$C_4$-alkyl or $C_1$–$C_4$-haloalkyl, or $R^{55}$ and $R^{56}$ together with the ring atoms linking them are a 5- or 6-membered ring consisting of carbon ring members and the nitrogen ring member to which $R^{56}$ is bonded, which is unsubstituted or substituted by one or two $C_1$–$C_4$-alkyl radicals;

$Y^7$ is oxygen or sulfur;

$Z^3$ and $Z^4$ independently of one another are nitrogen or CH;

$R^{23}$ and $R^{24}$ and/or $R^{53}$ and $R^{54}$ together form a tetramethylene bridge;

$R^{52}$ is hydrogen, $C_1$–$C_4$-alkyl, $C_3$–$C_6$-cycloalkyl or $C_1$–$C_4$-haloalkyl;

$R^{50}$ and $R^{51}$ independently of one another are $C_1$–$C_4$-alkyl, $C_1$–$C_4$-haloalkyl or $C_3$–$C_6$-cycloalkyl or an agriculturally useful salt of a compound I, with the exception of those compounds I where $R^4$ is hydrogen and $R^5$ is $\Phi^2$.

2. The phosphonic acid compound I or a salt thereof as defined in claim 1 where $R^5$ is 1-methyl-6-trifluoromethyl-2,4(1H,3H)-pyrimidinedion-3-yl, 4-chloro-5-difluoromethoxy-1-methyl-1H-pyrazol-3-yl, 4-chloro-1-methyl-5-trifluoromethyl-1H-pyrazol-3-yl, 1-methyl-4,5-di(trifluoromethyl)-1H-pyrazol-3-yl, 1,3,4,5,6,7-hexahydro-1,3-dioxo-2H-isoindol-2-yl, 3,4-dimethyl-1H-pyrrol-2,5-dion-1-yl, 3-chloro-4,5,6,7-tetrahydro-2H-indazol-2-yl, 5-chloro-1-difluoromethyl-2-methyl-1H-imidazol-4-yl, 5,6,7,8-tetrahydro-1,2,4-triazolo[4,3-a]pyridin-3(2H)-on-2-yl, (3-methyl-4-trifluoromethyl-2(3H)-thiazolylidene)amino, (tetrahydro-3-oxo-1H,3H-[1,3,4]thiadiazolo[3,4-a]pyridazin-1-ylidene)amino or (6,7-dihydro-6,6-dimethyl-3H,5H-pyrrolo[2,1-c][1,2,4]thiadiazol-3-ylidene)amino.

3. A herbicidal composition comprising a herbicidally active amount of at least one phosphonic acid compound I or of a salt of I as defined in claim 1 and at least one liquid or solid carrier and optionally at least one surfactant.

4. A composition for the desiccation or defoliation of plants, comprising such an amount of at least one phosphonic acid compound I or of a salt of I as defined in claim 1 that it acts as a desiccant or defoliant, and at least one inert liquid or solid carrier and optionally at least one surfactant.

5. A method of controlling undesirable vegetation, which comprises allowing a herbicidally active amount of at least one phosphonic acid compound I or of a salt of I as defined in claim 1 to act on plants, their environment or on seed.

6. A method of desiccating or defoliating plants, which comprises allowing such an amount of at least one phosphonic acid compound I or of a salt of I as defined in claim 1 to act on plants that it acts as a desiccant or defoliant.

7. The method defined in claim 6, wherein the plants are cotton plants.

8. A phenylhydrazine of the formula XXVIII

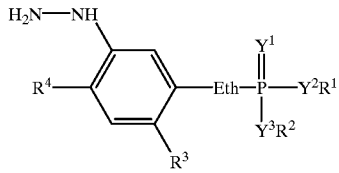

(XXVIII)

where Eth, $Y^1$, $Y^2$, $Y^3$ and $R^1$–$R^4$ have the meanings given in claim 1.

9. An aniline of the formula XXXI

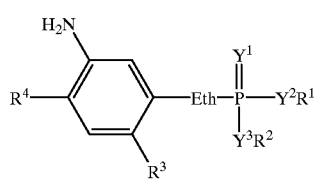

(XXXI)

where Eth, $Y^1$, $Y^2$, $Y^3$ and $R^1$–$R^4$ have the meanings given in claim 1.

10. A nitro compound of the formula XXXII

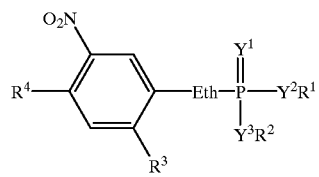

(XXXII)

where Eth, $Y^1$, $Y^2$, $Y^3$ and $R^1$–$R^4$ have the meanings given in claim 1.

11. An aromatic phosphonic acid derivative of the formula XXXIIIEL

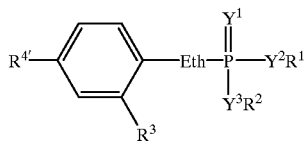

(XXXIIIa)

where Eth, $Y_1$, $Y^2$, $Y^3$ and $R^1$–$R^3$ have the meanings given in claim 1 and $R^{4'}$ is halogen.

12. A thiourea derivative of the formula XXXV

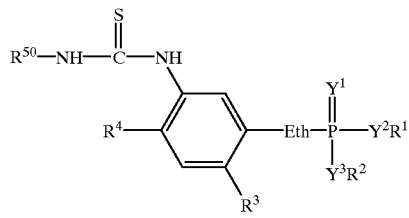

(XXXV)

where Eth, $Y^1$, $Y^2$, $Y^3$, $R^1$–$R^4$ and $R^{50}$ have the meanings given in claim 1.

13. A thiosemicarbazide derivative of the formula XXXIX

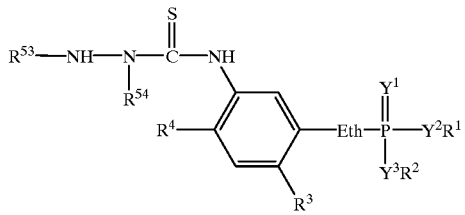

(XXXIX)

where Eth, $Y^1$, $Y^2$, $Y^3$, $R^1$–$R^4$, $R^{53}$ and $R^{54}$ have the meanings given in claim 1.

14. An isothiocyanate of the formula XL

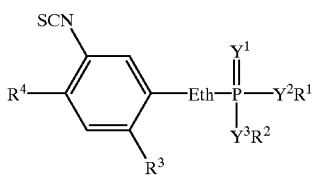
(XL)

where Eth, $Y^1$, $Y^2$, $Y^3$ and $R^1$–$R^4$ have the meanings given in claim 1.

15. An aromatic phosphonic acid compound I

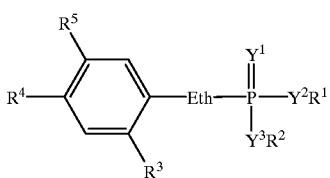
(I)

or a salt thereof where the variables have the following meanings:

Eth is 1,2-ethynediyl or an ethane- or ethene-1,2-diyl chain, each of which can be unsubstituted or have attached to it one or two of the following substituents: halogen, cyano, carboxyl, $C_1$–$C_4$-alkyl, $C_1$–$C_4$-haloalkyl, $C_1$–$C_4$-alkoxy, $C_1$–$C_4$-haloalkoxy, ($C_1$–$C_4$-alkoxy)carbonyl and/or di($C_1$–$C_4$-alkyl)amino, it being possible for the ethane-1,2-diyl chain, if desired, additionally to have attached to it a hydroxyl, amino or ($C_1$–$C_4$-alkylamino group;

$Y^1$-s oxygen or sulfur;

$Y^2$ hs oxygen, sulfur or —N($R^6$)—;

$Y^3$ Ls oxygen, sulfur or —N($R^7$)—;

$R^1$, $R^2$, $R^6$ and $R^7$ independently of one another are hydrogen, $C_1$–$C_6$-alkyl, $C_1$–$C_6$-haloalkyl, hydroxy-$C_1$–$C_4$-alkyl, cyano-$C_1$–$C_4$-alkyl, $C_1$–$C_4$-alkoxy-$C_1$–$C_4$-alkyl, $C_1$–$C_4$-haloalkoxy-$C_1$–$C_4$-alkyl, $C_3$–$C_4$-alkenyloxy-$C_1$–$C_4$-alkyl, $C_3$–$C_4$-alkynyloxy-$C_1$–$C_4$-alkyl, $C_3$–$C_8$-cycloalkoxy-$C_1$–$C_4$-alkyl, amino-$C_1$–$C_4$-alkyl, $C_1$–$C_4$-alkylamino-$C_1$–$C_4$-alkyl, di($C_1$–$C_4$-alkyl)amino-$C_1$–$C_4$-alkyl, $C_1$–$C_4$-alkylthio-$C_1$–$C_4$-alkyl, $C_1$–$C_4$-haloalkylthio-$C_1$–$C_4$-alkyl, $C_3$–$C_4$-alkenylthio-$C_1$–$C_4$-alkyl, $C_3$–$C_4$-alkynylthio-$C_1$–$C_4$-alkyl, $C_1$–$C_4$-alkylsulfinyl-$C_1$–$C_4$-alkyl, $C_1$–$C_4$-haloalkylsulfinyl-($C_1$–$C_4$-alkyl, $C_3$–$C_4$-alkenylsulfinyl-$C_1$–$C_4$-alkyl, $C_3$–$C_4$-alkynylsulfinyl-$C_1$–$C_4$-alkyl, $C_1$–$C_4$-alkylsulfonyl-$C_1$–$C_4$-alkyl, $C_1$–$C_4$-haloalkylsulfonyl-$C_1$–$C_4$-alkyl, $C_3$–$C_4$-alkenylsulfonyl-$C_1$–$C_4$-alkyl, $C_3$–$C_4$-alkynylsulfonyl-$C_1$–$C_4$-alkyl, $C_3$–$C_6$-alkenyl, $C_3$–$C_6$-haloalkenyl, cyano-$C_3$–$C_6$-alkenyl, $C_3$–$C_6$-alkynyl, $C_3$–$C_6$-haloalkynyl, cyano-$C_3$–$C_6$-alkynyl, hydroxycarbonyl$C_1$–$C_4$-alkyl, ($C_1$–$C_4$-alkoxy)carbonyl-$C_1$–$C_4$-alkyl, ($C_1$–$C_4$-alkyl-thio) carbonyl-$C_1$–$C_4$-alkyl, aminocarbonyl-$C_1$–$C_4$-alkyl, ($C_1$–$C_4$-alkyl) aminocarbonyl-$C_1$–$C_4$-alkyl, di($C_1$–$C_4$-alkyl) amino-carbonyl-$C_1$–$C_4$-alkyl, $C_3$–$C_8$-cycloalkyl, $C_3$–$C_8$-cycloalkyl-$C_1$–$C_4$-alkyl, phenyl, phenyl-$C_1$–$C_4$-alkyl, and it being possible for all cycloalkyl and phenyl rings to be unsubstituted or to have attached to them one to four substituents, in each case selected from the group consisting of halogen, cyano, nitro, amino, hydroxyl, carboxyl, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfonyl, $C_1$–$C_4$-haloalkylsulfonyl, ($C_1$–$C_4$-alkyl) carbonyl, ($C_1$–$C_4$-haloalkyl)carbonyl, ($C_1$–$C_4$-alkoxy)carbonyl, ($C_1$–$C_4$-alkyl)carbonyloxy, ($C_1$–$C_4$-haloalkyl) carbonyloxy and di($C_1$–$C_4$-alkyl)amino, or $R^1$ arLd $R^2$ or $R^1$ and $R^6$ and/or $R^2$ and $R^7$ in each case together form a 1,2-ethanediyl, 1,3-propylene, tetramethylene, pentamethylene or ethyleneoxyethylene chain which, if desired, can be substituted by one to four $C_1$–$C_4$-alkyl and/or one or two ($C_1$–$C_4$-alkoxy) carbonyl groups, or $R^1$ and $R^2$ together are 1,2-phenylene which can be unsubstituted or have attached to it one to three substituents, in each case selected from the group consisting of cyano, nitro, halogen, $c_1$–$C_4$-alkyl, $C_1$–$C_4$-haloalkyl, $C_1$–$C_4$-alkoxy and $C_1$–$C_4$-haloalkoxy;

$R^3$ is cyano, halogen, $C_1$–$C_4$-alkyl, $C_1$–$C_4$-haloalkyl, $C_1$–$C_4$-alkoxy or $C_1$–$C_4$-haloalkoxy;

$R^4$ is hydrogen or halogen;

$R^5$ is a heterocycle $\Phi^1$, $\Phi^2$, $\Phi^3$, $\Phi^4$, $\Phi^5$, $\Phi^7$, $\Phi^{20}$, $\Phi^{21}$ or $\Phi^{22}$:

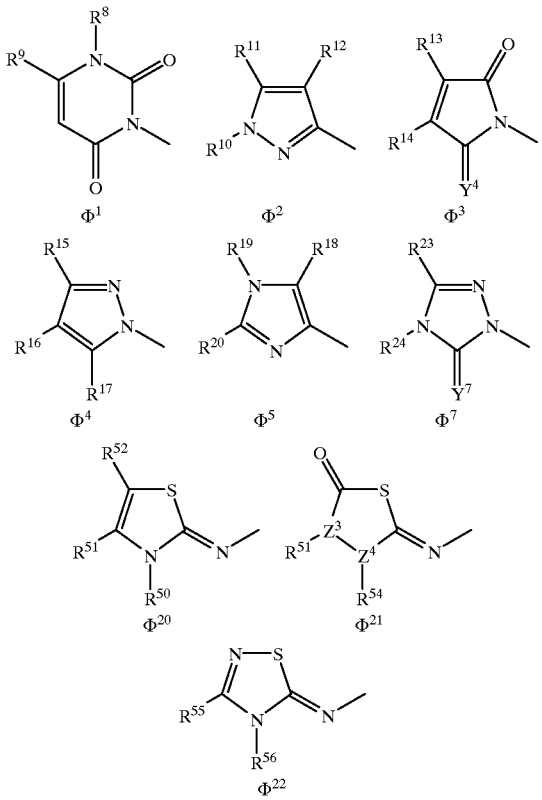

where $R^8$ is hydrogen, amino, $C_1$–$C_4$-alkyl or $C_1$–$C_4$-haloalkyl;

$R^9$ is cyano, $C_1$–$C_4$-alkyl, $C_1$–$C_4$-haloalkyl, $C_1$–$C_4$-alkylsulfonyl or $C_1$–$C_4$-haloalkylsulfonyl;

$R^{10}$ is $C_1$–$C_4$-alkyl or $C_1$–$C_4$-haloalkyl;

$R^{11}$ is cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$- haloalkylthio, $C_1$–$C_4$-alkylsulfinyl, $C_1$–$C_4$-haloalkylsulfinyl, $C_1$–$C_4$-alkylsulfonyl or $C_1$–$C_4$-haloalkylsulfonyl, or $R^{10}$ and $R^{11}$ together form a tetramethylene group which is unsubstituted or substituted by one or two $C_1$–$C_4$-alkyl radicals;

$R^{12}$ is hydrogen, cyano, halogen, $C_1$–$C_4$-alkyl or $C_1$–$C_4$-haloalkyl;

$Y^4$ is oxygen, sulfur or methylene;

$R^{13}$ and $R^{14}$ independently of one another are hydrogen or $C_1$–$C_4$-alkyl, or $R^{13}$ and $R^{14}$ together form a tetramethylene group which is unsubstituted or substituted by one or two halogen and/or $C_1$–$C_4$-alkyl radicals;

$R^{15}$ and $R^{16}$ independently of one another are hydrogen, halogen, $C_1$–$C_4$-alkyl or $C_1$–$C_4$-haloalkyl, or $R^{15}$ and $R^{16}$ together form a tetramethylene group which is unsubstituted or substituted by one or two $C_1$–$C_4$-alkyl radicals;

$R^{17}$ is halogen or $C_1$–$C_4$-alkyl; $R^{18}$ is halogen;

$R^{19}$, $R^{20}$, $R^{55}$ and $R^{56}$ independently of one another are hydrogen, $C_1$–$C_4$-alkyl or $C_1$–$C_4$-haloalkyl, or $R^{55}$ and $R^{56}$ together form a 1.3-propylene group which is unsubstituted or substituted by one or two $C_1$–$C_4$-alkyl or $C_1$–$C_4$-haloalkyl radicals;

$Y^7$ is oxygen or sulfur;

$Z^3$ and $Z^4$ independently of one another are nitrogen or CH;

$R^{23}$ and $R^{24}$ and/or $R^{53}$ and $R^{54}$ together form a tetramethylene group which is unsubstituted or substituted by one or two $C_1$–$C_4$-alkyl radicals;

$R^{52}$ is hydrogen, $C_1$–$C_4$-alkyl, $C_3$–$C_6$-cycloalkyl or $C_1$–$C_4$-haloalkyl;

$R^{50}$ and $R^{51}$ independently of one another are $C_1$–$C_4$-alkyl, $C_1$–$C_4$-haloalkyl or $C_3$–$C_6$-cycloalkyl or an agriculturally useful salt of a compound I, with the exception of those compounds I where $R^4$ is hydrogen and $R^5$ is $\Phi^2$.

16. The aromatic phosphonic acid compound I defined in claim 1, wherein $R^5$ is one of the heterocycles $\Phi^1$, $\Phi^2$, $\Phi^3$, $\Phi^4$, $\Phi^5$, $\Phi^7$, $\Phi^{21}$ and $\Phi^{22}$.

17. The aromatic phosphonic acid compound I defined in claim 1, wherein $R^5$ is one of the heterocycles $\Phi^1$, $\Phi^2$, $\Phi^4$, $\Phi^5$, $\Phi^{20}$, $\Phi^{21}$ and $\Phi^{22}$.

18. The aromatic phosphonic acid compound I defined in claim 1, wherein $R^5$ is one of the heterocycles $\Phi^1$, $\Phi^2$, $\Phi^4$, $\Phi^5$, $\Phi^{21}$ and $\Phi^{22}$.

19. The aromatic phosphonic acid compound I defined in claim 1 wherein $R^5$ is a heterocycle $\Phi^1$, $\Phi^2$ or $\Phi^3$.

20. The aromatic phosphonic acid compound I defined in claim 15 wherein $R^5$ is a heterocycle $\Phi^1$, $\Phi^2$ or $\Phi^3$.

21. The aromatic phosphonic acid compound I defined in claim 1 wherein $R^5$ is a heterocycle $\Phi^1$ or $\Phi^2$.

22. The aromatic phosphonic acid compound I defined in claim 15 wherein $R^5$ is a heterocycle $\Phi^1$ or $\Phi^2$.

23. The aromatic phosphonic acid compound I defined in claim 1 wherein Eth denotes —C≡C—, —CH=CH-, —CH=C(halogen)—, —CH=C(CN)—, —CH=C(CH$_3$)—, —CH=C(CO$_2$CH$_3$)—, —CH2—CH(halogen)—, —CH$_2$—CH(CN)—, —CH$_2$—CH(CH$_3$)— or —CH$_2$—CH(CO$_2$CH$_3$)—.

24. The aromatic phosphonic acid compound I defined in claim 15 wherein Eth denotes —C≡C—, —CH=CH—, —CH=C(halogen)—, —CH=C(CN)—, —CH=C(CH$_3$)—, —CH=C(CO$_2$CH$_3$)—, —CH$_2$—CH(halogen)—, —CH$_2$—CH(CN)—, —CH$_2$—CH(CH$_3$)— or —CH$_2$—CH(CO$_2$CH$_3$)—.

* * * * *

UNITED STATES PATENT AND TRADEMARK OFFICE
CERTIFICATE OF CORRECTION

PATENT NO. : 6,175,007 B1
DATED : January 16, 2001
INVENTOR(S) : Zagar et al.

It is certified that error appears in the above-identified patent and that said Letters Patent is hereby corrected as shown below:

Column 150, claim 1,
Line 31, "CL" should be -- $C_1$ --.
Line 35, "isg" should be -- is --.
Line 45, "$C_1$-$C_4$-alkenylthio" should be -- $C_3$-$C_4$-alkenylthio --.
Line 53, "$C_1$-$C_6$-haloalkenyl" should be -- $C_3$-$C_6$-haloalkenyl --.
Line 54, "$C_1$-$C_6$-haloalkynyl" should be -- $C_3$-$C_6$-haloalkynyl --.
Line 62, "cycloalky" should be -- cycloalkyl --.

Column 154, claim 10,
"-$^1$" should be -- $Y^1$ --.

Column 154, claim 11,
Line 18, "XXXIIIEL" should be -- XXXIII a --.
Line 30, "Elth, $Y_1$," should be -- Eth, $Y^1$, --.

Column 155, claim 15,
Line 36, "($C_1$-$C_4$-" should be -- $C_1$-$C_4$- --.
Line 37, "-s" should be -- is --.
Line 38, "hs" should be -- is --.
Line 39, "Ls" should be -- is --.
Line 51, "($C_1$-$C_4$-" should be -- $C_1$-$C_4$- --.

Column 156, claim 15,
Line 10, "arLd" should be -- and --.
Line 19, "$c_1$-$C_4$-" should be -- $C_1$-$C_4$- --.

UNITED STATES PATENT AND TRADEMARK OFFICE
CERTIFICATE OF CORRECTION

PATENT NO. : 6,175,007 B1
DATED : January 16, 2001
INVENTOR(S) : Zagar et al.

It is certified that error appears in the above-identified patent and that said Letters Patent is hereby corrected as shown below:

Column 157, claim 15,
Line 25, "1.3" should be -- 1,3 --.

Column 158, claim 23,
Line 26, "-CH2-" should be -- $-CH_2-$ --.

Signed and Sealed this

Twenty-third Day of October, 2001

Attest:

*Nicholas P. Godici*

NICHOLAS P. GODICI
*Attesting Officer*   *Acting Director of the United States Patent and Trademark Office*